United States Patent
Hassel et al.

(10) Patent No.: US 12,049,631 B2
(45) Date of Patent: Jul. 30, 2024

(54) APTAMERS FOR TARGETED ACTIVATION OF T CELL-MEDIATED IMMUNITY

(71) Applicant: RHEINISCHE FRIEDRICH-WILHELMS-UNIVERSITAT BONN, Bonn (DE)

(72) Inventors: Silvana Hassel, Troisdorf (DE); Günter Mayer, Bonn (DE); Sven Burgdorf, Swisttal (DE)

(73) Assignee: Rheinische Friedrich-Wilhelms-Universitat Bonn, Bonn (DE)

( * ) Notice: Subject to any disclaimer, the term of this patent is extended or adjusted under 35 U.S.C. 154(b) by 722 days.

(21) Appl. No.: 17/043,784

(22) PCT Filed: Mar. 30, 2019

(86) PCT No.: PCT/IB2019/052641
§ 371 (c)(1),
(2) Date: Sep. 30, 2020

(87) PCT Pub. No.: WO2019/186514
PCT Pub. Date: Oct. 3, 2019

(65) Prior Publication Data
US 2021/0147847 A1 May 20, 2021

Related U.S. Application Data

(60) Provisional application No. 62/650,522, filed on Mar. 30, 2018.

(51) Int. Cl.
*C12N 15/115* (2010.01)
*C12N 5/0784* (2010.01)
*C12N 15/10* (2006.01)

(52) U.S. Cl.
CPC .......... *C12N 15/115* (2013.01); *C12N 5/0639* (2013.01); *C12N 15/1048* (2013.01); *C12N 2310/321* (2013.01); *C12N 2310/322* (2013.01); *C12N 2310/3231* (2013.01); *C12N 2310/3513* (2013.01)

(58) Field of Classification Search
CPC .......... C12N 15/115; C12N 2310/16
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yumane et al. |
| 4,904,582 A | 2/1990 | Tullis |
| 4,948,882 A | 8/1990 | Ruth |
| 4,958,013 A | 8/1990 | Letsinger |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |

(Continued)

FOREIGN PATENT DOCUMENTS

WO WO 2014/011465 1/2014

OTHER PUBLICATIONS

Kaffe et al. Nature Reviews Drug Discovery 9, 537-550 (Year: 2010).*
Yassemnn et al. Pharmaceutics, 955, pp. 1-29 (Year: 2020).*
Agrawal et al., "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos," J Immunol, 2003, 171(10):4984-4989.
Amos et al., "Autoimmunity associated with immunotherapy of cancer," Blood, 2011, 118(3):499-509.
Anassi et al., "Sipuleucel-T (Provenge) Injection," PT, 2011, 36(4):197-202.

(Continued)

*Primary Examiner* — Brian Whiteman
(74) *Attorney, Agent, or Firm* — Kilpatrick Townsend & Stockton LLP

(57) ABSTRACT

Compositions comprising aptamers, and methods of thereof as carrier molecules in cell-mediated immunotherapies, and activation of antigen-specific T-cell responses.

18 Claims, 55 Drawing Sheets

Specification includes a Sequence Listing.

(56) References Cited

U.S. PATENT DOCUMENTS

| | | | |
|---|---|---|---|
| 5,264,562 A | 11/1993 | Matteucci | |
| 5,264,564 A | 11/1993 | Matteucci | |
| 5,272,250 A | 12/1993 | Spielvogel et al. | |
| 5,276,019 A | 1/1994 | Cohen et al. | |
| 5,278,302 A | 1/1994 | Caruthers et al. | |
| 5,286,717 A | 2/1994 | Cohen et al. | |
| 5,292,873 A | 3/1994 | Rokita et al. | |
| 5,317,098 A | 5/1994 | Shizuya et al. | |
| 5,321,131 A | 6/1994 | Agrawal et al. | |
| 5,366,878 A | 11/1994 | Pederson et al. | |
| 5,367,066 A | 11/1994 | Urdea et al. | |
| 5,371,241 A | 12/1994 | Brush | |
| 5,391,723 A | 2/1995 | Priest | |
| 5,399,676 A | 3/1995 | Froehler | |
| 5,403,711 A | 4/1995 | Walder et al. | |
| 5,405,938 A | 4/1995 | Summerton et al. | |
| 5,405,939 A | 4/1995 | Suhadolnik et al. | |
| 5,414,077 A | 5/1995 | Lin et al. | |
| 5,416,203 A | 5/1995 | Letsinger | |
| 5,432,272 A | 7/1995 | Benner | |
| 5,434,257 A | 7/1995 | Matteucci et al. | |
| 5,451,463 A | 9/1995 | Nelson et al. | |
| 5,453,496 A | 9/1995 | Caruthers et al. | |
| 5,455,233 A | 10/1995 | Spielvogel et al. | |
| 5,457,187 A | 10/1995 | Gmeiner et al. | |
| 5,459,255 A | 10/1995 | Cook et al. | |
| 5,466,677 A | 11/1995 | Baxter et al. | |
| 5,470,967 A | 11/1995 | Huie et al. | |
| 5,476,925 A | 12/1995 | Letsinger et al. | |
| 5,484,908 A | 1/1996 | Froehler et al. | |
| 5,486,603 A | 1/1996 | Buhr | |
| 5,489,677 A | 2/1996 | Sanghvi et al. | |
| 5,491,133 A | 2/1996 | Walder et al. | |
| 5,502,177 A | 3/1996 | Matteucci et al. | |
| 5,510,475 A | 4/1996 | Agrawal et al. | |
| 5,512,439 A | 4/1996 | Hornes et al. | |
| 5,512,667 A | 4/1996 | Reed et al. | |
| 5,514,785 A | 5/1996 | Van Ness et al. | |
| 5,519,126 A | 5/1996 | Hecht | |
| 5,525,465 A | 6/1996 | Haralambidis et al. | |
| 5,525,711 A | 6/1996 | Hawkins et al. | |
| 5,536,821 A | 7/1996 | Agrawal et al. | |
| 5,539,082 A | 7/1996 | Nielsen et al. | |
| 5,541,306 A | 7/1996 | Agrawal et al. | |
| 5,541,307 A | 7/1996 | Cook et al. | |
| 5,541,313 A | 7/1996 | Ruth | |
| 5,545,730 A | 8/1996 | Urdea et al. | |
| 5,550,111 A | 8/1996 | Suhadolnik et al. | |
| 5,552,538 A | 9/1996 | Urdea et al. | |
| 5,552,540 A | 9/1996 | Haralambidis | |
| 5,561,225 A | 10/1996 | Maddry et al. | |
| 5,563,253 A | 10/1996 | Agrawal et al. | |
| 5,565,350 A | 10/1996 | Kmiec | |
| 5,565,552 A | 10/1996 | Magda et al. | |
| 5,567,810 A | 10/1996 | Weis et al. | |
| 5,571,799 A | 11/1996 | Tkachuk et al. | |
| 5,574,142 A | 11/1996 | Meyer, Jr. et al. | |
| 5,578,717 A | 11/1996 | Urdea et al. | |
| 5,578,718 A | 11/1996 | Cook et al. | |
| 5,580,731 A | 12/1996 | Chang et al. | |
| 5,585,481 A | 12/1996 | Arnold, Jr. et al. | |
| 5,587,361 A | 12/1996 | Cook et al. | |
| 5,587,371 A | 12/1996 | Sessler et al. | |
| 5,587,469 A | 12/1996 | Cook et al. | |
| 5,591,584 A | 1/1997 | Chang et al. | |
| 5,595,726 A | 1/1997 | Magda et al. | |
| 5,596,086 A | 1/1997 | Matteucci et al. | |
| 5,596,091 A | 1/1997 | Switzer | |
| 5,597,696 A | 1/1997 | Linn et al. | |
| 5,599,923 A | 2/1997 | Sessler et al. | |
| 5,599,928 A | 2/1997 | Hemmi et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,614,617 A | 3/1997 | Cook et al. | |
| 5,618,704 A | 4/1997 | Sanghvi et al. | |
| 5,623,065 A | 4/1997 | Cook et al. | |
| 5,623,070 A | 4/1997 | Cook et al. | |
| 5,625,050 A | 4/1997 | Beaton et al. | |
| 5,633,360 A | 5/1997 | Bischofberger et al. | |
| 5,652,355 A | 7/1997 | Metelev et al. | |
| 5,652,356 A | 7/1997 | Agarwal | |
| 5,663,312 A | 9/1997 | Chaturvedula | |
| 5,677,437 A | 10/1997 | Teng et al. | |
| 5,677,439 A | 10/1997 | Weis et al. | |
| 5,681,941 A | 10/1997 | Cook et al. | |
| 5,688,941 A | 11/1997 | Cook et al. | |
| 5,700,922 A | 12/1997 | Cook | |
| 5,714,331 A | 2/1998 | Buchardt et al. | |
| 5,719,262 A | 2/1998 | Buchardt et al. | |
| 5,750,692 A | 5/1998 | Cook et al. | |
| 2006/0193869 A1* | 8/2006 | Barrat | A61P 43/00 530/352 |

OTHER PUBLICATIONS

Appay et al., "The physiological role of cytotoxic CD4+ T-cells: the holy grail?," Clin Exp Immunol., 2004, 138(1):10-13.

Avci-Adali et al., "Potential capacity of aptamers to trigger immune activation in human blood," PLoS One, 2013, 8(7):e68810, 17 pages.

Avci-Adali et al., "Upgrading SELEX Technology by Using Lambda Exonuclease Digestion for Single-Stranded DNA Generation," Molecules, 2010, 15(1):1-11.

Ballas et al., "Divergent therapeutic and immunologic effects of oligodeoxynucleotides with distinct CpG motifs," J Immunol, 2001, 167(9):4878-4886.

Banchereau et al., "Dendritic cells and the control of immunity," Nature, 1998, 392(6673):245-252.

Banchereau et al., "Dendritic cells as vectors for therapy," Cell, 2001, 106(3):271-274.

Barnden et al., "Defective TCR expression in transgenic mice constructed using cDNA-based alpha- and beta-chain genes under the control of heterologous regulatory elements," Immunol Cell Biol, 1998, 76(1):34-40.

Bauer et al., "Recognition of nucleic acid and nucleic acid analogs by Toll-like receptors 7, 8 and 9," Immunobiology, 2008, 213(3-4)315-328.

Behrens et al., "Helper T cells, dendritic cells and CTL Immunity," Immunol Cell Biol, 2004, 82(1):84-90.

Bercovici et al., "New methods for assessing T-cell responses," Clin Diagn Lab Immunol., 2000, 7(6):859-864.

Berezovski et al., "Aptamer-facilitated biomarker discovery (AptaBiD)," J Am Chem Soc., 2008, 130(28):9137-9143.

Blanchard et al., "Endoplasmic Reticulum Aminopeptidase Associated with Antigen Processing Defines the Composition and Structure of MHC Class I Peptide Repertoire in Normal and Virus-Infected Cells," J Immunol., 2010, 184(6):3033-3042.

Blank, "Next-Generation Analysis of Deep Sequencing Data: Bringing Light into the Black Box of SELEX Experiments," Methods Mol Biol., 2016, 1380:85-95.

Blankenstein et al., "The determinants of tumour immunogenicity," Nat Rev Cancer, 2012, 12(4):307-313.

Bock et al., "Selection of single-stranded DNA molecules that bind and inhibit human thrombin," Nature, 1992, 355(6360):564-566.

Bode et al., "CpG DNA as a vaccine adjuvant," Expert Rev of Vaccines, 2011, 10(4):499-511.

Bol et al., "Dendritic Cell-Based Immunotherapy: State of the Art and Beyond," Clin Cancer Res., 2016, 22(8):1897-1906.

Bonifaz et al., "Efficient targeting of protein antigen to the dendritic cell receptor DEC-205 in the steady state leads to antigen presentation on major histocompatibility complex class I products and peripheral CD8+ T cell tolerance," J Exp Med., 2002, 196(12):1627-1638.

Bonifaz et al., "In vivo targeting of antigens to maturing dendritic cells via the DEC-205 receptor improves T cell vaccination," J Exp Med., 2004, 199(6):815-824.

(56) References Cited

OTHER PUBLICATIONS

Bouchard et al., "Discovery and development of therapeutic aptamers," Annu Rev Pharmacol Toxicol., 2010, 50:237-257.
Bouvier et al., "Accessory proteins and the assembly of human class I MHC molecules: a molecular and structural perspective," Mol Immunol., 2003, 39(12):697-706.
Braasch et al., "Novel antisense and peptide nucleic acid strategies for controlling gene expression," Biochemistry, 2002, 41(14):4503-4510.
Bridonneau et al., "Site-directed selection of oligonucleotide antagonists by competitive elution," Antisense Nucleic Acid Drug Dev., 1991, 9(1):1-11.
Bruno et al., "Development of a Fluorescent Enzyme-Linked DNA Aptamer-Magnetic Bead Sandwich Assay and Portable Fluorometer for Sensitive and Rapid Leishmania Detection in Sandflies," J Fluoresc, 2014, 24(1):267-277.
Bui et al., "Budget Impact of Enzalutamide for Chemotherapy-Naïve Metastatic Castration-Resistant Prostate Cancer," J Manag Care Spec Pharm, 2016, 22(2):163-170.
Burgdorf et al., "Distinct pathways of antigen uptake and intracellular routing in CD4 and CD8 T cell activation," Science, 2007, 316(5824):612-616.
Burgdorf et al., "The mannose receptor mediates uptake of soluble but not of cell-associated antigen for cross-presentation," J Immunol., 2006, 176(11):6770-6776.
Chambers et al., "Costimulatory regulation of T cell function," Curr Opin Cell Biol., 1999, 11(2):203-210.
Chatterjee et al., "Internalization and endosomal degradation of receptor-bound antigens regulate the efficiency of cross presentation by human dendritic cells," Blood, 2012, 120(10):2011-2020.
Cheng et al., "In vivo SELEX for Identification of Brain-penetrating Aptamers," Mol Ther Nucleic Acids, 2013, 2(1):e67, 9 pages.
Cheong et al., "Improved cellular and humoral immune responses in vivo following targeting of HIV Gag to dendritic cells within human anti-human DEC205 monoclonal antibody," Blood, 2010, 116(19):3828-3838.
Cheuk et al., "Role of 4-1BB:4-1BB ligand in cancer immunotherapy," Cancer Gene Ther, 2006, 11(3):215-226.
Chu et al., "Aptamer: toxin conjugates that specifically target prostate tumor cells," Cancer Res, 2006, 66(12):5989-5992.
Colcher et al., "Effects of genetic engineering on the pharmacokinetics of antibodies," Q. J. Nucl. Med., 1999, 43(2):132-139.
Crooke et al., "Pharmacokinetic properties of several novel oligonucleotide analogs in mice," J. Pharmacol. Exp. Tuer., 1996, 277(2):923-937.
Curtsinger et al., "CD8 T cell clonal expansion and development of effector function require prolonged exposure to antigen, costimulation, and signal 3 cytokine," J Immunol., 2003, 171(1):5165-5171.
Curtsinger et al., "Inflammatory cytokines as a third signal for T cell activation," Curr Opin Immunol, 2010, 22(3):333-340.
Da Pieve et al., "PEGylation and Biodistribution of an anti-MUC1 Aptamer in MCF-7 Tumor-Bearing Mice," Bioconjug Chem, 2012, 23(7):1377-1381.
Dangles et al., "Tumor-associated antigen human chorionic gonadotropin beta contains numerous antigenic determinants recognized by in vitro-induced CD8+ and CD4+ T lymphocytes," Cancer Immunol Immunother, 2002, 50:673-681.
Dassie et al., "Systemic administration of optimized aptamer-siRNA chimeras promotes regression of PSMA-expressing tumors," Nat Biotechnol, 2009, 27(9):839-849.
Delamarre et al., "Differential lysosomal proteolysis in antigen-presenting cells determines antigen fate," Science, 2005, 307(5715):1630-1634.
Dhodapkar et al., "Induction of antigen-specific immunity with a vaccine targeting NY-ESO-1 to the dendritic cell receptor DEC-205," Sci Transl Med, 2014, 6(232):232ra251, 10 pages.
Dong et al., "Induction of protective immunity against *Mycobacterium tuberculosis* by delivery of ESX antigens into airway dendritic cells," Mucosal Immunol, 2013, 6(3):522-534.
Drolet et al., "Pharmacokinetics and safety of an anti-vascular endothelial growth factor aptamer (NX1838) following injection into the vitreous humor of rhesus monkeys," Pharm Res, 2000, 17(12):1503-1510.
East et al., "The mannose receptor family," Biochim Biophys Acta, 2002, 1572(2-3):364-386.
Ec.europa.eu, [online], "Public Health—Union Register of Medicinal Products—Union Register of not active medicinal products for human use," 2015, retrieved on Nov. 24, 2020, retrieved from URL<ec.europa.eu/health/documents/community-register/html/h867.htm>, 2 pages.
Ellington et al., "In vitro selection of RNA molecules that bind specific ligands," Nature, 1990, 346(6287):818-822.
Farokhzad et al., "Nanoparticle-aptamer bioconjugates: a new approach for targeting prostate cancer cells," Cancer Res, 2004, 64(21):7668-7672.
Feinberg et al., "Structure of a C-type carbohydrate recognition domain from the macrophage mannose receptor," J Biol Chem, 2000, 275(28):21539-21548.
Figdor et al., "C-type lectin receptors on dendritic cells and Langerhans cells," Nat Rev Immunol, 2002, 2(2):77-84.
Figdor et al., "Dendritic cell immunotherapy: mapping the way," Nat Med, 2004, 10(5):475-480.
Flynn et al., "Immunization with HIV Gag targeted to dendritic cells followed by recombinant New York vaccinia virus induces robust T-cell immunity in nonhuman primates," Proc Nat'l Acad Sci USA, 2011, 108(17):7131-7136.
Fremont et al., "Structures of an MHC class II molecule with covalently bound single peptides," Science, 1996, 272(5264):1001-1004.
Frenz et al., "Antigen presenting cell-selective drug delivery by glycan-decorated nanocarriers," Eur J Pharm Biopharm, 2015, 95(Pt A):13-17.
Gagnon et al., "Endoplasmic reticulum-mediated phagocytosis is a mechanism of entry into macrophages," Cell, 2002, 110(1):119-131.
Gangadhar et al., "Mitigating the toxic effects of anticancer immunotherapy," Nat Rev Clin Oncol, 2014, 11(2):91-99.
Ganji et al., "Aptamers: new arrows to target dendritic cells," Journal of Drug Targeting, 2015, 24(1):1-12.
Gilboa et al., "DC-based cancer vaccines," J Clin Invest, 2007, 117(5):1195-1203.
Gilboa et al., "Use of oligonucleotide aptamer ligands to modulate the function of immune receptors," Clin Cancer Res, 2013, 19(5):1054-1062.
Gold et al., "Aptamer-based multiplexed proteomic technology for biomarker discovery," PLoS One, 2010, 5(12):e15004, 17 pages.
Green et al., "Activation-induced cell death in T cells, " Immunol Rev, 2003, 193:70-81.
Guo et al., "Aptamer-based strategies for stem cell research," Mini Rev Med Chem, 2007, 7(7):701-705.
Haabeth et al., "How Do CD4(+) T Cells Detect and Eliminate Tumor Cells That Either Lack or Express MHC Class II Molecules?," Front Immunol, 2014, 5:174, 13 pages.
Habel, "Aptamers for targeted activation of T cell-mediated immunity," Ph. D. Thesis, Rheinische Friedrich-Wilhelms-Universität Bonn, 2016, 134 pages.
Hahn et al., "Down-modulation of CD4+ T helper type 2 and type 0 cells by T helper type 1 cells via Fas/Fas-ligand interaction," Eur J Immunol, 1995, 25(9):2679-2685.
Hamedani et al., "Capillary Electrophoresis for the Selection of DNA Aptamers Recognizing Activated Protein C," Methods Mol Biol, 2016, 1380:61-75.
Hamedani et al., "Capture and Release (CaR): a simplified procedure for one-tube isolation and concentration of single-stranded DNA during SELEX," Chem Commun (Camb), 2015, 51(6):1135-1138.
Hammerstrom et al., "Cancer immunotherapy: sipuleucel-T and beyond," Pharmacotherapy, 2011, 31(8):813-828.
Harris et al., "Characterization of the Murine Macrophage Mannose Receptor: Demonstration That the Downregulation of Receptor Expression Mediated by Interferon-gamma Occurs at the Level of Transcription," Blood, Nov. 1992, 80(9):2363-2373.

(56) References Cited

OTHER PUBLICATIONS

Hartung et al., "Induction of potent CD8 T cell cytotoxicity by specific targeting of antigen to cross-presenting dendritic cells in vivo via murine or human XCR1," J Immunol, 2015, 194(3):1069-1079.
Heasman, "Morpholino oligos: making sense of antisense?," J. Dev. Biol., 2002, 243(2):209-214.
Heckel et al., "Light regulation of aptamer activity: an anti-thrombin aptamer with caged thymidine nucleobases," J Am Chem Soc, 2005, 127(3):822-823.
Hermann et al., "Adaptive recognition by nucleic acid aptamers," Science, 2000, 287(5454)820-825.
Hicke et al., "Escort aptamers: a delivery service for diagnosis and therapy," J. Clin. Invest., 2000, 106(8):923-928.
Hicke et al., "Tenascin-C aptamers are generated using tumor cells and purified protein," J Biol Chem, 2001, 276(52):48644-48654.
Hogquist et al., "T cell receptor antagonist peptides induce positive selection," Cell, 1994, 76(1):17-27.
Hoption et al., "Dr William Coley and tumour regression: a place in history or in the future," Postgrad Med J, 2003, 79(938):672-680.
Huang et al., "A Time-Efficient, Linear-Space Local Similarity Algorithm," Adv. Appl. Math., 1991, 12:337-357.
Hui et al., "Selection of DNA aptamers against DC-SIGN protein," Mol Cell Biochem, 2007, 306(1-2):71-77.
Huizenga et al., "A DNA aptamer that binds adenosine and ATP," Biochemistry, 1995, 34(2):656-665.
Idoyaga et al., "Comparable T helper 1 (Th1) and CD8 T-cell immunity by targeting HIV gag p24 to CD8 dendritic cells within antibodies to Langerin, DEC205, and Clec9A," Proc Natl Acad Sci USA, 2011, 108(6):2384-2389.
Janeway et al., "Innate immune recognition," Annu Rev Immunol, 2002, 20:197-216.
Kabanov et al., "A new class of antivirals: antisense oligonucleotides combined with a hydrophobic substituent effectively inhibit influenza virus reproduction and synthesis of virus-specific proteins in MDCK cells," Febs Lett., 1990, 259(2):327-330.
Kaisho et al., "Toll-like receptors and their signaling mechanism in innate immunity," Acta Odontol Scand, 2001, 59(3):124-130.
Kantoff et al., "Sipuleucel-T immunotherapy for castration-resistant prostate cancer," N Engl J Med, 2010, 363(5):411-422.
Kastenmuller et al., "Dendritic cell-targeted vaccines—hope or hype?," Nat Rev Immunol, 2014, 14(10):705-711.
Kawai et al., "The role of pattern-recognition receptors in innate immunity: update on Toll-like receptors," Nat Immunol, 2010, 11(5):373-384.
Kim et al., "Prostate cancer cell death produced by the co-delivery of Bcl-xL shRNA and doxorubicin using an aptamer-conjugated polyplex," Biomaterials, 2010, 31(16):4592-4599.
Klein et al., "Autophagy-mediated antigen processing in CD4(+) T cell tolerance and immunity," FEBS Lett, 2010, 584(7):1405-1410.
Kreutz et al., "Targeting dendritic cells—why bother?," Blood, 2013, 121(15):2836-2844.
Ku et al., "Nucleic Acid Aptamers: An Emerging Tool for Biotechnology and Biomedical Sensing," Sensors (Basel), 2015, 15(7):16281-16313.
Labeur et al., "Generation of tumor immunity by bone marrow-derived dendritic cells correlates with dendritic cell maturation stage," J Immunol, 1999, 162(1):168-175.
Lacerra et al., "Restoration of hemoglobin A synthesis in erythroid cells from peripheral blood of thalassemic patients," Proc. Natl. Acad. Sci., 2000, 97(17):9591-9596.
Lakadamyali et al., "Ligands for clathrin-mediated endocytosis are differentially sorted into distinct populations of early endosomes," Cell, 2006, 124(5):997-1009.
Lanzavecchia et al., "Understanding the generation and function of memory T cell subsets," Curr Opin Immunol., 2005, 17(3):326-332.
Lee et al., "Mannose receptor-mediated regulation of serum glycoprotein homeostasis," Science, 2002, 295(5561):1898-1901.
Leggatt et al., "Peptide Dose and/or Structure in Vaccines as a Determinant of T Cell Responses," Vaccines (Basel), 2014, 2(3):537-548.
Lehmann et al., "Direct Delivery of Antigens to Dendritic Cells via Antibodies Specific for Endocytic Receptors as a Promising Strategy for Future Therapies," Vaccines (Basel), 2016, 4(2):8, 32 pages.
Leleux et al., "Engineering immunity: Modulating dendritic cell subsets and lymph node response to direct immune-polarization and vaccine efficacy," J Control Release, 2015, 219:610-621.
Lennarz et al., "An aptamer to the MAP kinase insert region," ACS Chem Biol., 2015, 10(1):320-327.
Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17):6553-6556.
Lim et al., "Macropinocytosis: an endocytic pathway for internalising large gulps," Immunol Cell Biol., 2011, 89(8):836-843.
Linehan et al., "Endogenous ligands of carbohydrate recognition domains of the mannose receptor in murine macrophages, endothelial cells and secretory cells; potential relevance to inflammation and immunity," Eur J Immunol, 2001, 31(6):1857-1866.
Liu et al., "Origin and development of dendritic cells," Immunol Rev, 2010, 234(1):45-54.
Liu et al., "Tumour-associated antigens and their anti-cancer applications," Eur J Cancer Care (Engl), Feb. 7, 2016, vol. 26, 8 pages.
Ludewig et al., "Immunotherapy with dendritic cells directed against tumor antigens shared with normal host cells results in severe autoimmune disease," J Exp Med, 2000, 191(5):795-804.
Lupold et al., "Identification and characterization of nuclease-stabilized RNA molecules that bind human prostate cancer cells via the prostate-specific membrane antigen," Cancer Res, 2002, 62(14):4029-4033.
Lutz et al., "An advanced culture method for generating large quantities of highly pure dendritic cells from mouse bone marrow," J Immunol Methods, 1999, 223(1):77-92.
Lutz et al., "Still Alive and Kicking: In-Vitro-Generated GM-CSF Dendritic Cells!," Immunity, 2016, 44(1):1-2.
Mahnke et al., "The dendritic cell receptor for endocytosis, DEC-205, can recycle and enhance antigen presentation via major histocompatibility complex class II-positive lysosomal compartments," J Cell Biol, 2000, 151(3):673-684.
Makarov et al., "Biomarkers for prostate cancer," Annu Rev Med, 2009, 60:139-151.
Mallikaratchy et al., "A multivalent DNA aptamer specific for the B-cell receptor on human lymphoma and leukemia," Nucleic Acids Res, 2011, 39(6):2458-2469.
Mann et al., "In vitro selection of DNA aptamers binding ethanolamine," Biochem Biophys Res Commun, 2005, 338(4):1928-1934.
Manoharan et al., "Chemical modifications to improve uptake and bioavailability of antisense oligonucleotides," Ann. N.Y. Acad. Sci., 1992, 660:306-309.
Manoharan et al., "Cholic acid-oligonucleotide conjugates for antisense applications," Bioorg. Med. Chem. Let., 1994, 4(8):1053-1060.
Manoharan et al., "Introduction of a lipophilic thioether tether in the minor groove of nucleic acids for antisense applications," Bioorg. Med. Chem. Let., 1993, 3(12):2765-2770.
Manoharan et al., "Lipidic Nucleic Acids," Tetrahedron Lett., 1995, 36(21):3651-3654.
Manoharan et al., "Oligonucleotide Conjugates: Alteration of the Pharmacokinetic Properties of Antisense Agents," Nucleosides & Nucleotides, 1995, 14(3-5):969-973.
Manoharan et al., "Unique gene-silencing and structural properties of 2'-fluoro-modified siRNAs," Angew Chem Int Ed Engl, 2011, 50(10):2284-2288.
Marshall et al., "Cytotoxic CD4 T cells in antiviral immunity," J Biomed Biotechnol, 2011, 2011:954602, 8 pages.
Martinez-Pomares et al., "Carbohydrate-independent recognition of collagens by the macrophage mannose receptor," Eur J Immunol, 2006, 36(5):1074-1082.
Martinez-Pomares, "The mannose receptor," J Leukoc Biol, 2012, 92(6):1177-1186.

(56) References Cited

OTHER PUBLICATIONS

Mayer et al., "Controlling small guanine-nucleotide-exchange factor function through cytoplasmic RNA intramers," Proc Natl Acad Sci USA, 2001, 98(9):4961-4965.

Mayer, "The chemical biology of aptamers," Angew Chem Int Ed Engl., 2009, 48(15):2672-2689.

McFarland et al., "Ovalbumin(323-339) peptide binds to the major histocompatibility complex class III-A(d) protein using two functionally distinct registers," Biochemistry, 1999, 38(50):16663-16670.

McGreal et al., "Divergent roles for C-type lectins expressed by cells of the innate immune system," Mol Immunol, 2004, 41(11):1109-1121.

McNamara et al., "Cell type-specific delivery of siRNAs with aptamer-siRNA chimeras," Nat Biotechnol, 2006, 24(8):1005-1015.

McNamara et al., "Multivalent 4-1BB binding aptamers costimulate CD8+ T cells and inhibit tumor growth in mice," J Clin Invest, 2008, 118(1):376-386.

Mellman et al., "Dendritic cells: specialized and regulated antigen processing machines," Cell, 2001, 106(3):255-258.

Meyer et al., "Cell-specific aptamers as emerging therapeutics," J Nucleic Acids, 2011, 2011:904750, 19 pages.

Mi et al., "In vivo selection of tumor-targeting RNA motifs," Nat Chem Biol., 2010, 6(1):22-24.

Min et al., "Multiple tumor-associated microRNAs modulate the survival and longevity of dendritic cells by targeting YWHAZ and Bcl2 signaling pathways," J Immunol, 2013, 190(5):2437-2446.

Mishra et al., "Improved leishmanicidal effect of phosphorotioate antisense oligonucleotides by LDL-mediated delivery," Biochim. Biophys. Acta, 1995, 1264(2):229-237.

Mitchell et al., "Severe adverse immunologic reaction in a patient with glioblastoma receiving autologous dendritic cell vaccines combined with GM-CSF and dose-intensified temozolomide," Cancer Immunol Res, 2015, 3(4):320-325.

Morelli et al., "Tolerogenic dendritic cells and the quest for transplant tolerance," Nat Rev Immunol, 2007, 7(8):610-621.

Morris et al., "High affinity ligands from in vitro selection: complex targets," Proc Natl Acad Sci USA, 1998, 95(6):2902-2907.

Morse et al., "CDX-1307: a novel vaccine under study as treatment for muscle-invasive bladder cancer," Expert Rev Vaccines, 2011, 10(6):733-742.

Morse et al., "Phase I study utilizing a novel antigen-presenting cell-targeted vaccine with Toll-like receptor stimulation to induce immunity to self-antigens in cancer patients," Clin Cancer Res, 2011, 17(14):4844-4853.

Muller et al., "An exosite-specific ssDNA aptamer inhibits the anticoagulant functions of activated protein C and enhances inhibition by protein C inhibitor," Chem Biol, 2009, 16(4):442-451.

Nair, "Prostate Cancer Immunotherapy by Targeting Dendritic Cells In Vivo Using Receptor-Specific Aptamer Conjugated to Prostate Stem Cell Antigen (PSCA)-Encoding RNA," Aug. 2011, 10 pages.

Nasevicius et al., "Effective targeted gene 'knockdown' in zebrafish," Nat. Genet., 2000, 26(2):216-220.

Needleman et al., "A general method applicable to the search for similarities in the amino acid sequence of two proteins," J. Mol. Biol, 1970, 48(3):443-453.

Ni et al., "Concomitant activation and antigen uptake via human dectin-1 results in potent antigen- specific CD8+ T cell responses," J Immunol, 2010, 185(6):3504-3513.

Nielsen et al., "Sequence-selective recognition of DNA by strand displacement with a thymine-substituted polyamide," Science, 1991, 254(5037):1497-500.

Nimjee et al., "Aptamers: an emerging class of therapeutics," Annu Rev Med, 2005, 56:555-583.

Nino-Castro et al., "The IDO1-induced kynurenines play a major role in the antimicrobial effect of human myeloid cells against Listeria monocytogenes," Innate Immun, 2014, 20(4):401-411.

Nozari et al., "Aptamers for CD Antigens: From Cell Profiling to Activity Modulation," Molecular Therapy Nucleic Acids, 2017, 6:29-44.

Oberhauser et al., "Effective incorporation of 2'-O-methyl-oligoribonucleotides into liposomes and enhanced cell association through modification with thiocholesterol," Nucl. Acids Res., 1992, 20(3):533-538.

Ohlfest et al., "Vaccine injection site matters: qualitative and quantitative defects in CD8 T cells primed as a function of proximity to the tumor in a murine glioma model," J Immunol, 2013, 190(2):613-620.

Ohuchi, "Cell-SELEX Technology," Biores Open Access, 2012, 1(6):265-272.

O'Neill et al., "The history of Toll-like receptors—redefining innate immunity," Nat Rev Immunol, 2013, 13(6):453-460.

Opazo et al., "Modular Assembly of Cell-targeting Devices Based on an Uncommon G-quadruplex Aptamer," Mol Ther Nucleic Acids, 2015, 4(9):e251, 10 pages.

Osorio et al., "Myeloid C-type lectin receptors in pathogen recognition and host defense," Immunity, 2011, 34(5):651-664.

Paludan et al., "Immune sensing of DNA," Immunity, 2013, 38(5):870-880.

Parry et al., "CTLA-4 and PD-1 receptors inhibit T-cell activation by distinct mechanisms," Mol Cell Biol, 2005, 25(21):9543-9553.

Pastor et al., "Targeting 4-1BB costimulation to disseminated tumor lesions with bi-specific oligonucleotide aptamers," Mol Ther, 2011, 19(10):1878-1886.

Patra et al., "2'-Fluoro RNA shows increased Watson-Crick H-bonding strength and stacking relative to RNA: evidence from NMR and thermodynamic data," Angew Chem Int Ed Engl, 2012, 51(47):11863-11866.

PCT International Preliminary Report on Patentability in International Appln. No. PCT/IB2019/052641, dated Oct. 6, 2020, 12 pages.

PCT International Search Report and Written Opinion in International Appln. No. PCT/IB2019/052641, dated Jul. 25, 2019, 18 pages.

PCT Invitation to Pay Additional Fees in International Appln. No. PCT/IB2019/052641, dated Aug. 1, 2019, 14 pages.

Penaloza-Macmaster et al., "Vaccine-elicited CD4 T cells induce immunopathology after chronic LCMV infection," Science, 2015, 347(6219):278-282.

Platt et al., "Mature dendritic cells use endocytic receptors to capture and present antigens," *Proc Nat'l Acad Sci USA,* 2010, 107(9):4287-4292.

Prodeus et al., "Targeting the PD-1/PD-L1 Immune Evasion Axis With DNA Aptamers as a Novel Therapeutic Strategy for the Treatment of Disseminated Cancers," Mol Ther Nucleic Acids, 2015, 4(4):e237, 10 pages.

Quah et al., "Monitoring lymphocyte proliferation in vitro and in vivo with the intracellular fluorescent dye carboxyfluorescein diacetate succinimidyl ester," *Nat Protoc,* 2007, 2(9):2049-2056.

Raddatz et al., "Enrichment of cell-targeting and population-specific aptamers by fluorescence-activated cell sorting," Angew Chem Int Ed Engl, 2008, 47(28):5190-5193.

Raich-Regue et al., "Differential effects of monophosphoryl lipid A and cytokine cocktail as maturation stimuli of immunogenic and tolerogenic dendritic cells for immunotherapy," Vaccine, 2012, 30(2):378-387.

Ramakrishna et al., "Mannose receptor targeting of tumor antigen pmel17 to human dendritic cells directs anti-melanoma T cell responses via multiple HLA molecules," J Immunol, 2004, 172(5):2845-2852.

Rauen et al., "Enhanced cross-presentation and improved CD8+ T cell responses after mannosylation of synthetic long peptides in mice," PLoS One, 2014, 9(8):e103755, 9 pages.

Reff et al., "A review of modifications to recombinant antibodies: attempt to increase efficacy in oncology applications," Critical Reviews in Oncology/Hematology, 2001, 40(1):25-35.

Rhie et al., "Characterization of 2'-fluoro-RNA aptamers that bind preferentially to disease-associated conformations of prion protein and inhibit conversion," J Biol Chem, 2003, 278(41):39697-39705.

Roche et al., "The ins and outs of MHC class II-mediated antigen processing and presentation," Nat Rev Immunol, 2015, 15(4):203-216.

(56) References Cited

OTHER PUBLICATIONS

Roep et al., "Antigen targets of type 1 diabetes autoimmunity," Cold Spring Harb Perspect Med, 2012, 2(4):a007781, 15 pages.
Romani et al., "Targeting skin dendritic cells to improve intradermal vaccination," Curr Top Microbiol Immunol, 2012, 351:113-138.
Rosalia et al., "Dendritic cells process synthetic long peptides better than whole protein, improving antigen presentation and T-cell activation," Eur J Immunol, 2013, 43(10):2554-2565.
Roskrow et al., "Autoimmune disease induced by dendritic cell immunization against leukemia," Leuk Res, 1999, 23(6):549-557.
Rotzschke et al., "Exact prediction of a natural T cell epitope," Eur J Immunol, 1991, 21(11):2891-2894.
Saluja et al., "Targeting human dendritic cells via DEC-205 using PLGA nanoparticles leads to enhanced cross-presentation of a melanoma-associated antigen," Int J Nanomedicine, 2014, 9:5231-5246.
Santulli-Marotto et al., "Multivalent RNA aptamers that inhibit CTLA-4 and enhance tumor immunity," Cancer Res, 2003, 63(21):7483-7489.
Sayers et al., "Vaxjo: a web-based vaccine adjuvant database and its application for analysis of vaccine adjuvants and their uses in vaccine development," J Biomed Biotechnol, 2012, 2012:831486, 13 pages.
Schagger, "Tricine-SDS-PAGE," Nat Protoc, 2006, 1(1):16-22.
Schuette et al., "The ins-and-outs of endosomal antigens for cross-presentation," Curr Opin Immunol, 2014, 26:63-68.
Schutze et al., "Probing the SELEX process with next-generation sequencing," PLoS One, 2011, 6(12):e29604, 10 pages.
Sefah et al., "In vitro selection with artificial expanded genetic information systems," Proc Nat'l Acad Sci USA, 2014, 111(4):1449-1454.
Seliger et al., "The dark side of dendritic ells: development and exploitation of tolerogenic activity that favor tumor outgrowth and immune escape," Front Immunol, 2013, 4:419, 13 pages.
Shamah et al., "Complex target SELEX," Ace Chem Res, 2008, 41(1):130-138.
Shea et al., "Synthesis, hybridization properties and antiviral activity of lipid-oligodeoxynucleotide conjugates," Nucl. Acids Res., 1990, 18(13):3777-3783.
Sommer et al., "The importance of immune gene variability (MHC) in evolutionary ecology and conservation," Front Zool, 2005, 2:16, 18 pages.
Steinman et al., "Tolerogenic dendritic cells," Annu Rev Immunol, 2003, 21:685-711.
Stoltenburg et al., "FluMag-SELEX as an advantageous method for DNA aptamer selection," Anal Bioanal Chem, 2005, 383(1):83-91.
Stoltenburg et al., "SELEX—a (r)evolutionary method to generate high-affinity nucleic acid ligands," Biomol Eng, 2007, 24(4):381-403.
Su et al., "Next-generation sequencing and its applications in molecular diagnostics," Expert Rev Mol Diagn, 2011, 11(3):333-343.
Sun et al., "Oligonucleotide Aptamers: New Tools for Targeted Cancer Therapy," Mol Ther Nucleic Acids, 2014, 3:e182, 14 pages.
Sundaram et al., "Therapeutic RNA aptamers in clinical trials," Eur J Pharm Sci, 2013, 48(1-2):259-271.
Svinarchuk et al., "Inhibition of HIV proliferation in MT-4 cells by antisense oligonucleotide conjugated to lipophilic groups," Biochimie, 1993, 75(1-2):49-54.
Tacken et al., "No advantage of cell-penetrating peptides over receptor-specific antibodies in targeting antigen to human dendritic cells for cross-presentation," J Immunol, 2008, 180(11):7687-7696.
Tang et al., "Selection of aptamers for molecular recognition and characterization of cancer cells," Anal Chem, 2007, 79(13):4900-4907.
Tewari et al., "A cytosolic pathway for MHC class II-restricted antigen processing that is proteasome and TAP dependent," Nat Immunol, 2005, 6(3):287-294.
Thomann et al., "Antitumor activity of liposomal ErbB2/HER2 epitope peptide-based vaccine constructs incorporating TLR agonists and mannose receptor targeting," Biomaterials, 2011, 32(20):4574-4583.
Tolle et al., "A Versatile Approach Towards Nucleobase-Modified Aptamers," Angew Chem Int Ed Engl, 2015, 54(37):10971-4.
Trujillo et al., "Development of the anti-VEGF aptamer to a therapeutic agent for clinical ophthalmology," Clin Ophthalmol, 2007, 1(4):393-402.
Tsuji et al., "Antibody-targeted NY-ESO-1 to mannose receptor or DEC-205 in vitro elicits dual human CD8+ and CD4+ T cell responses with broad antigen specificity," J Immunol, 2011, 186(2):1218-1227.
Tuerk et al., "Systematic evolution of ligands by exponential enrichment: RNA ligands to bacteriophage T4 DNA polymerase," Science, 1990, 249(4968):505-510.
Urban et al., "Targeting Tumor Antigens to Dendritic Cells in Vivo Using Receptor-Specific Aptamers Conjugated to Tumor Antigen," Nucleic Acid Therapeutics, Mary Ann Liebert, Inc. Publishers, US, Sep. 30, 2011, vol. 21, No. 5, A29-A30 (abstract).
Van Vliet et al., "Dendritic cells and C-type lectin receptors: coupling innate to adaptive immune responses," Immunol Cell Biol, 2008, 86(7):580-587.
Vance et al., "Zeptomole detection of C-reactive protein in serum by a nanoparticle amplified surface plasmon resonance imaging aptasensor," Sci Rep, 2014, 4:5129, 7 pages.
Vieira et al., "Modulation of Rab5 and Rab7 recruitment to phagosomes by phosphatidylinositol 3-kinase," Mol Cell Biol, 2003, 23(7):2501-2514.
Vingert et al., "The Shiga toxin B-subunit targets antigen in vivo to dendritic cells and elicits anti-tumor immunity," Eur J Immunol, 2006, 36(5):1124-1135.
Walseng et al., "Major histocompatibility complex class II-peptide complexes internalize using a clathrin- and dynamin-independent endocytosis pathway," J Biol Chem, 2008, 283(21):14717-14727.
Wang et al., "Cyclohexene Nucleic Acids (CeNA): Serum Stable Oligonucleotides that Activate RNase H and Increase Duplex Stability with Complementary RNA," J. Am. Chem. Soc., 2000, 122(36):8595-8602.
Wang et al., "Influence of target concentration and background binding on in vitro selection of affinity reagents," PLoS One, 2012, 7(8):e43940, 8 pages.
Weis et al., "The C-type lectin superfamily in the immune system," Immunol Rev, 1998, 163:19-34.
Wengerter et al., "Aptamer-targeted antigen delivery," Mol Ther, 2014, 22(7):1375-1387.
Wherry, "T cell exhaustion, " Nat Immunol, 2011, 12(6):492-499.
Xiao et al., "Cell-specific internalization study of an aptamer from whole cell selection," Chemistry, 2008, 14(6):1769-1775.
Xing et al., "T-cell tolerance: central and peripheral," Cold Spring Harb Perspect Biol, 2012, 4(6):a006957, 15 pages.
Xue et al., "Transcriptome-based network analysis reveals a spectrum model of human macrophage activation," Immunity, 2014, 40(2):274-288.
Yan et al., "Aptamers and aptamer targeted delivery," RNA Biol, 2009, 6(3):316-320.
Zhang et al., "Aptamers selected by cell-SELEX for application in cancer studies," Bioanalysis, 2010, 2(5):907-918.
Zinchuk et al., "Bridging the gap between qualitative and quantitative colocalization results in fluorescence microscopy studies," Sci Rep, 2013, 3:1365, 5 pages.

\* cited by examiner

Overview on cargo molecules delivered by cell-specific aptamers

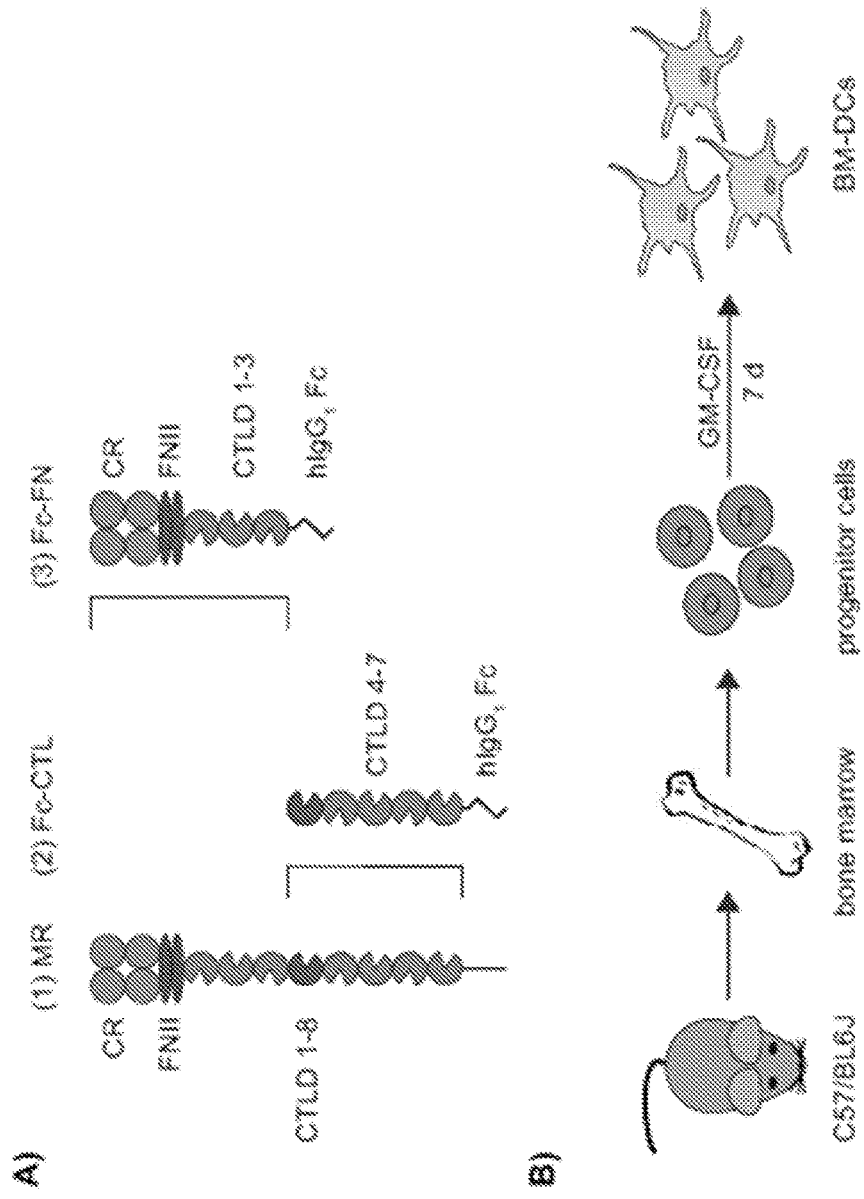
FIG. 11A-B

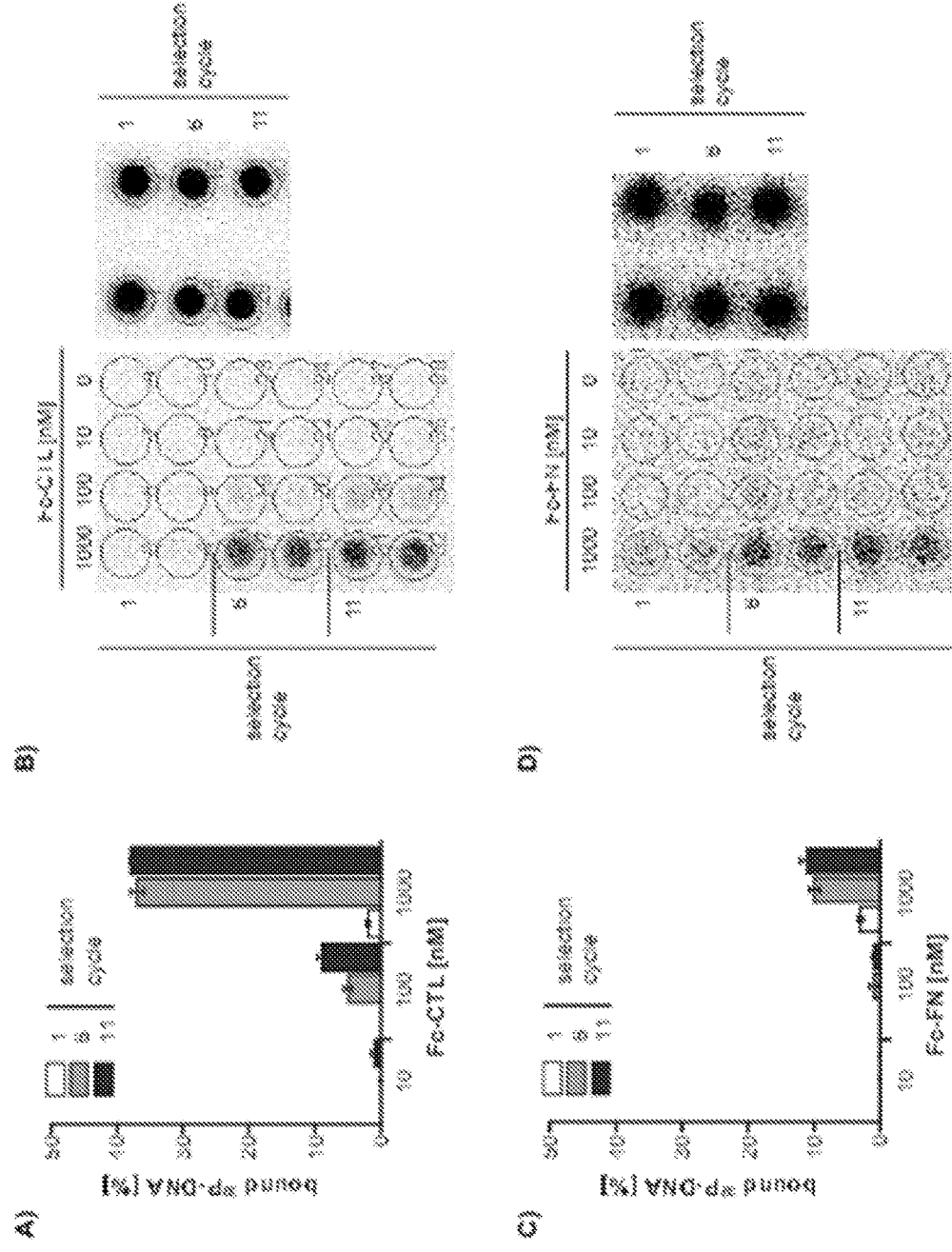
FIG. 12A-D

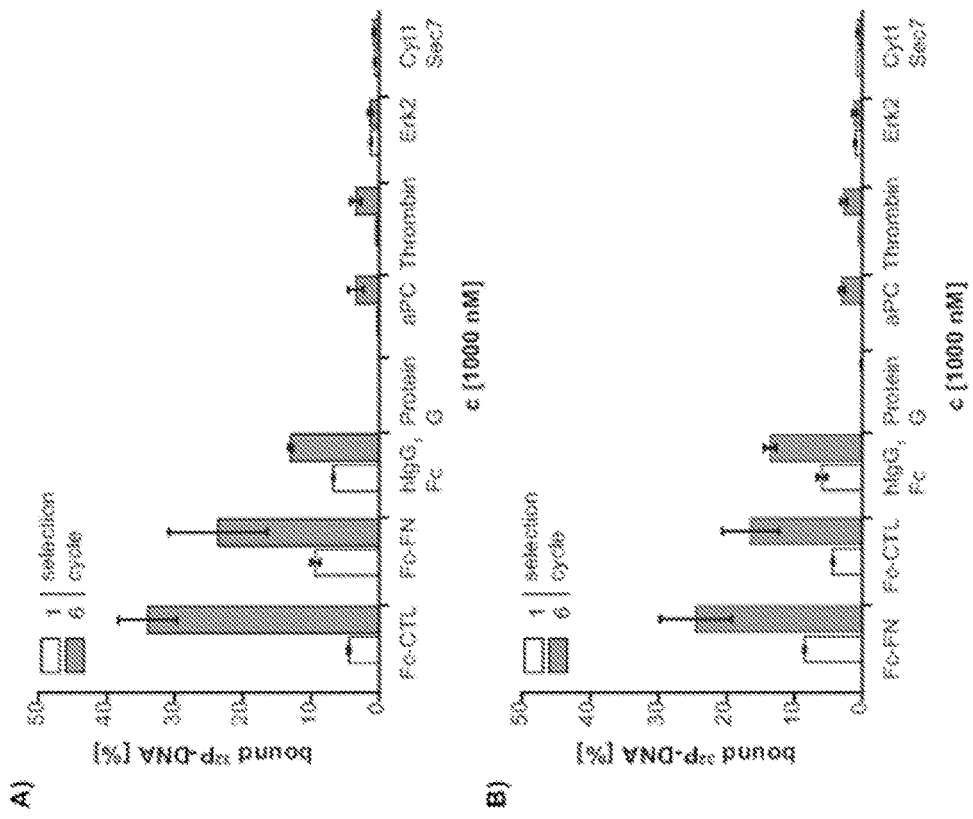
FIG. 13A-B

DNA sequence sharing motifs

A Family 1

```
CTL#5   TGCAATTCTAGCTGACAATGGGGGGGAAGAATGTGGGTGGGTG
CTL#7   CGCAATTCTAGCTGACAATGGGGGGGAAGAATGTGGGTGGGTG
CTL#9   -----------CGAGATGGGGGGGAAGGATGTGGGTGGGTGATCTTCGTTGGGT
CTL#10  ----------------CGTTGTGGGGGAAGATGTGGGTGGGTCTGTTTCAGGAGCA
CTL#13  ----------------------CGTGGGGGGTTGATGAGCATTGGGTGGGAGTTCAGGGTTTGG
```

B Family 2

```
CTL#6   ----------CCGTGGGTGGGTGGGTGGGAATTGGGAGGATGCGGAATTAACTCAGG
CTL#16  CGTACTGATGCCGTGGGTGGGTGGGTACTTTCTTGATTTGGGA
CTL#21  ----------CTGTGGGTGGGGGGATTTGGGGATTCAGGGTAGGTTGTCC
```

FIG. 14A-B

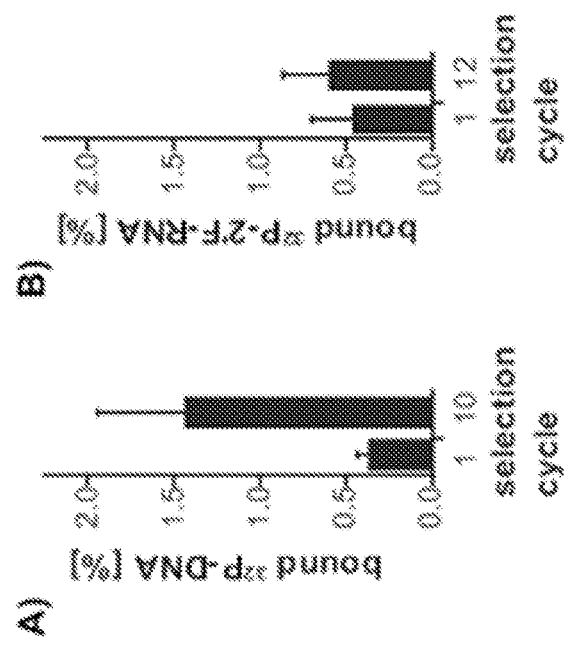
FIG. 17A-B

DNA sequences share sequence similarities

A Family 1

```
D#4   -GTGGGCGGGTTTATATATTCGGTGGTGGTGGGGGTGGTTCTGTT
D#7   CGTGGGTGGGTTTATATTCGGTGGTGGTGGGGGGTGGTACTGTT
D#23  CGTGGGCGGGTTTATATTTGGTGGTGGTGGGGGTGGTACTGTT
D#28  CGTGGGTGGGTTTATATTCGGTGGTGGTGGGGGTGGTACTGTT
```

B Family 2

```
D#2   GCATGTTTGGGTGGGATATTGGCGTGTTTGGGTTGGGACTGCT
D#3   GCATGTTTGGGTGGGATATTGGCCGTGTTTGGGTTGGGACTGCT
D#5   -CGCATTTGGGTGGGATTGTTATTTGGGTCGGGATTGGCAGTT
D#8   -CGCATTTGGGTGGGATTGTTATTTGGGTCGGGATTGGCAGTT
```

Schematic representation of aptamer-targeted delivery of OVA peptides to induce specific T cell-mediated immune responses OVA peptides and thiol-maleimide chemistry were used to synthesize aptamer-peptide conjugates

CD4 cytoxicity is not induced by aptamer-peptide conjugates

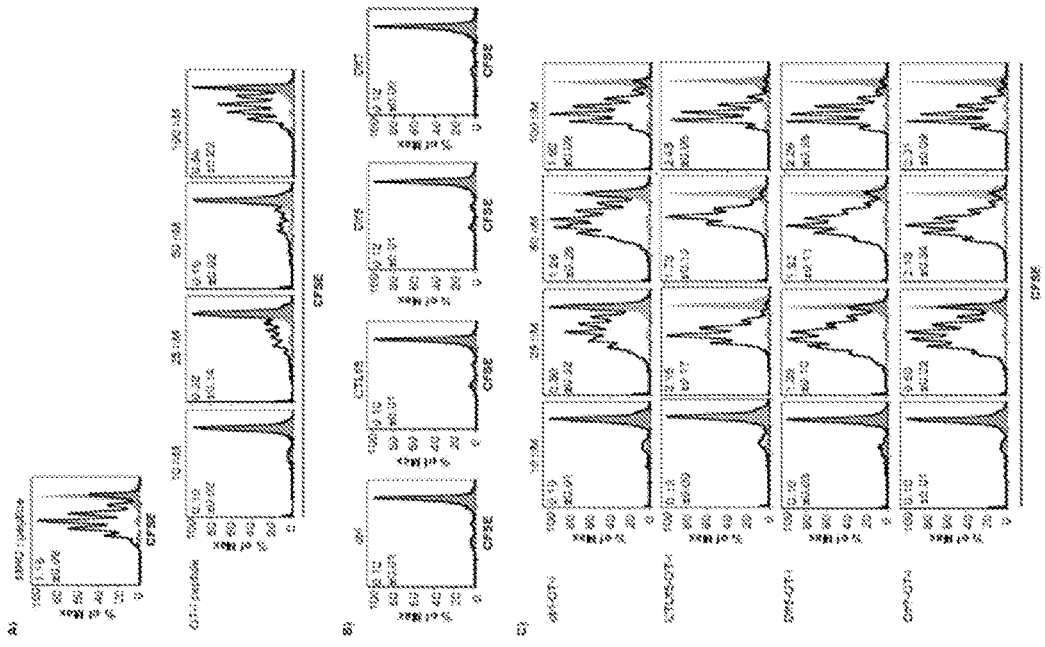
FIG. 35A-C

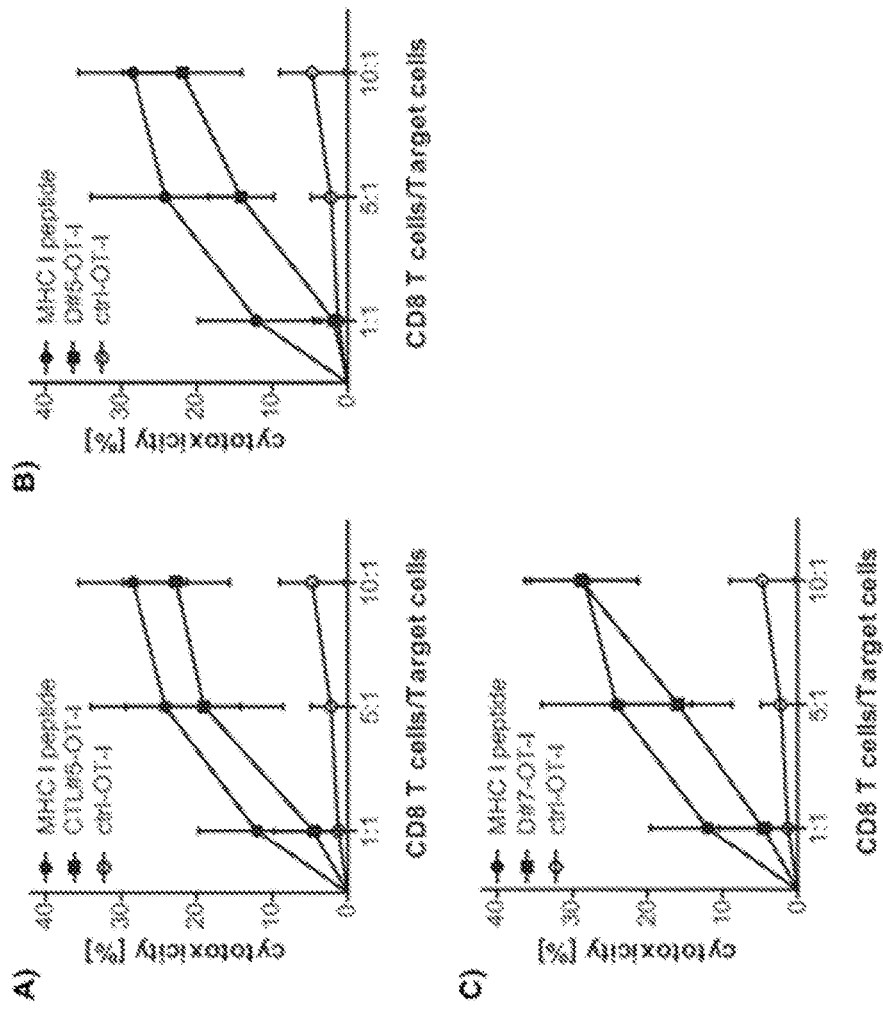
FIG. 36A-C

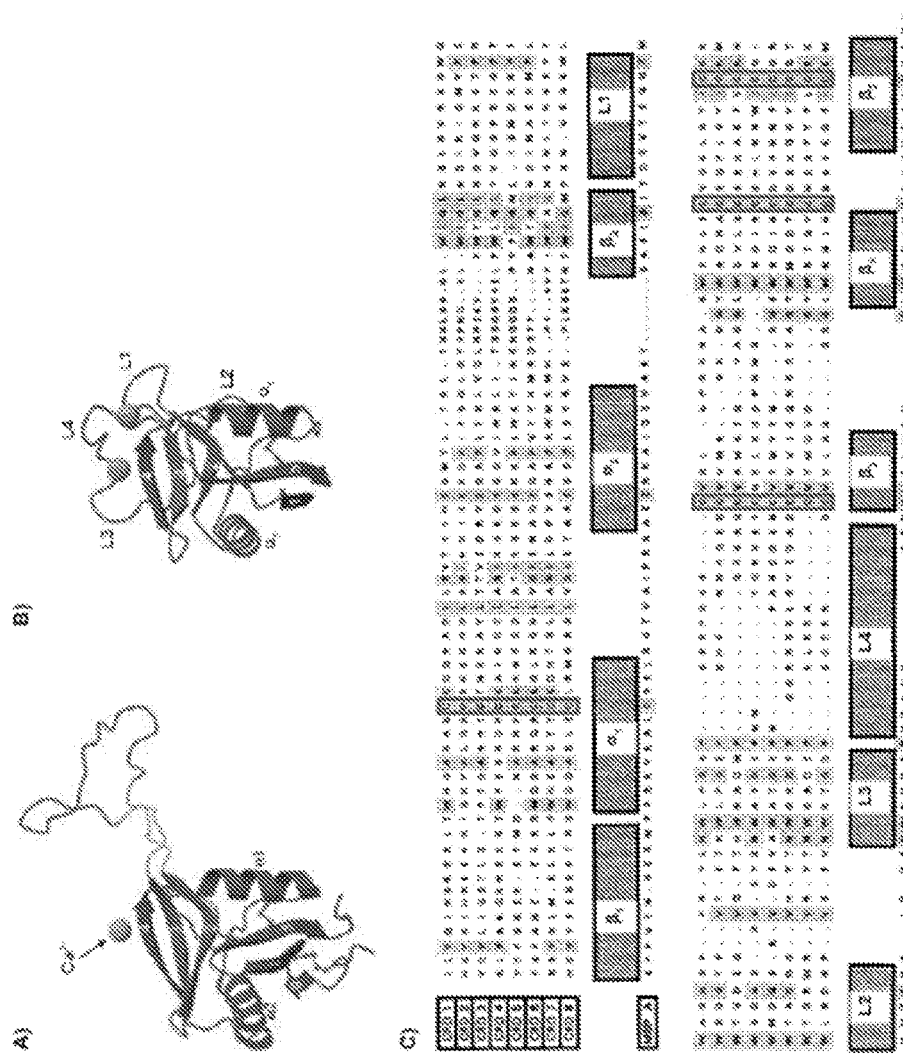
FIG. 37A-C Structure and sequence similarities of the CTLDs of murine MR and rat mannose-binding protein-A

DNA sequences obtained from Fc-FN SELEX

| sequence FN# | DNA-sequence |
|---|---|
| 1 | CGCCCGCCTTACGTCGTTCGGTCTTCGTTGGTGGTTCTTGTCGTG |
| 2 | CCCCCGGAATTCCGTACTTGTATCCGTTCCTTATCTTGTTCGTC |
| 4 | CCACGAGTATTGCTGGGTCCGGCGGGTGGTTTTGTCATGCA |
| 8 | CCGCCCGGATATCGGGTACGTGTTCCTCGTCGTCTTACATTG |
| 9 | CGGGTTCCGTCCGTTAGTCGTGTCGTCGTCGTCCGACTTGG |
| 12 | CGGCATTCGTGTTTTTTGTAACTCGGGGTTGGGTATCGTTG |
| 14 | CCTCGTTCTCTCGTTATCGTATTGTCTTGTTATACTTGTCTTCCTG |
| 15 | CGTGGGCTGGGATTTATTGCGGGTTGTCCTTGTTGTTAGCCT |
| 17 | CTGCTCGTATGTTCTTTGTCTTCCTCCTTATTCATTATTTCCGG |
| 18 | CGCCCATCCGCTCTCTTGTCGTTCTCGTGTCGTGTCTCCCCGG |
| 19 | CGCCCGGAAGGTTGTTGTATTGCGTCGTGAAGGTCGTGANGT |
| 20 | CGGTGCCCGTCGGTTCTTCCTGTCTGTTTCGTCTCTCCTTG |
| 23 | CGCCGGCAGTCGTTCCTTAGCTGGTTTAGCTGGTTACCGTCGGTCG |
| 26 | CCCCCTCTCTTCCTTCTCTCTCGTTCGTTGCTTCCC |

FIG. 38

DNA sequences obtained from Fc-CTL SELEX

| sequence CTL# | DNA-sequence |
|---|---|
| 1 | GCCAGTATTTCATTTCTTCGGCGGCCCGGAATTATGTGG |
| 2 | CAGTCCACCACCGCCACCTGCCAATTTTCGGTCGTTTGTC |
| 3 | CCCGGGTGCGAGTGCCTGTCTGTTGCATGTGGGTAGGGTG |
| 4 | GCGCCCACCCCTTGTTCGTCTGGGCCCACTGGTCCAACCGTG |
| 11 | CGGTACTGTGCGGGCCGCCGGGAAGAACGGCCCCAGGCGT |
| 14 | CCGTCCCTCCGAGGGTGTGCATTTTCCTCGGCCGCCACATGGG |
| 17 | GGACCCGTGGGCCGTTCGGGGTTCGTTTGGGGATATTCCCGGAGTGG |
| 18 | CACTGGAATCGTGTTCCCCCTATACTTTCATTTCGGTCGGACGTCCA |
| 19 | CCAACCCTGGGGGTTGGGGGTTCACTTCATCGTCGTGGGGCC |
| 20 | CGTCCAATCGTCGGGTTTTTCGGGTACTTCGGATCAATCCCCCG |
| 22 | CAGGGGAGCTCGGTTTTTCGGATCAATCCCCCG |

FIG. 39

NGS DNA sequences obtained by cell-SELEX and their NGS frequencies

Consensus sequences and number of sequences of the 15 most abundant NGS patterns

| NGS pattern No. | consensus sequence | number of sequences |
|---|---|---|
| 1 | | 101544 |
| 2 | | 97341 |
| 3 | | 60744 |
| 4 | | 29284 |
| 5 | | 28834 |
| 6 | | 26437 |
| 7 | | 20588 |
| 8 | | 17022 |
| 9 | | 15788 |
| 10 | | 14867 |
| 11 | | 14472 |
| 12 | | 13792 |
| 13 | | 13764 |
| 14 | | 13593 |
| 15 | | 13429 |

Binding of CTL#5 to BM-macrophages

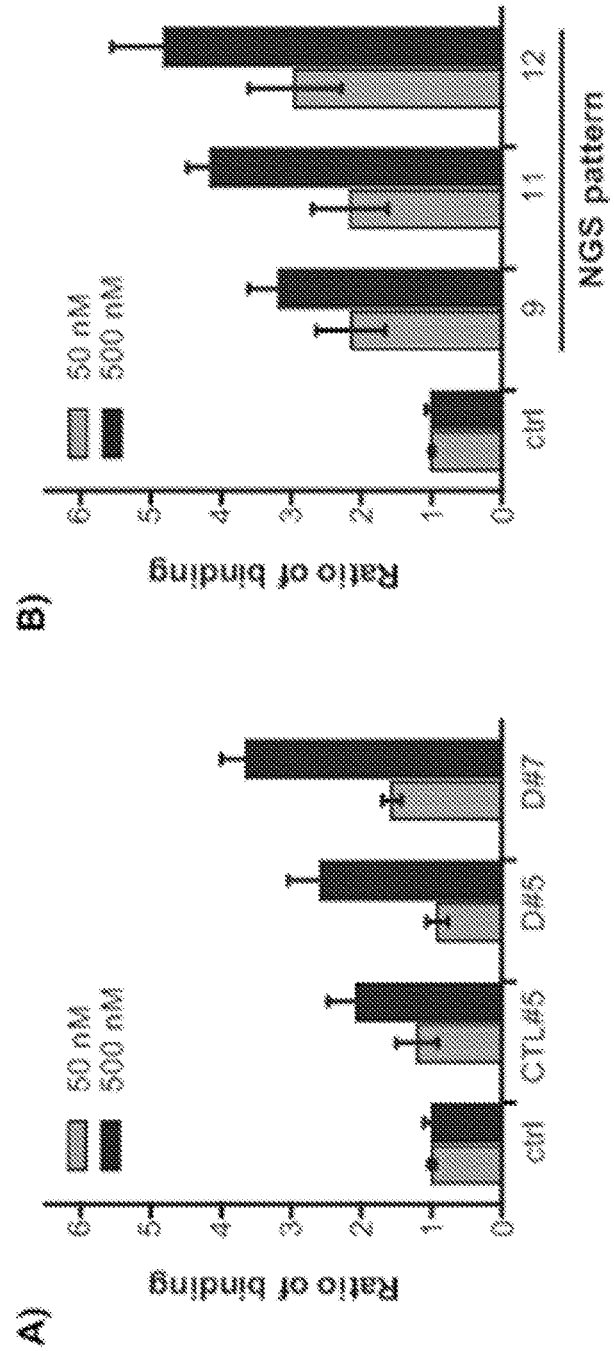
FIG. 49A-B

Binding of BM-DC aptamers to human blood cells
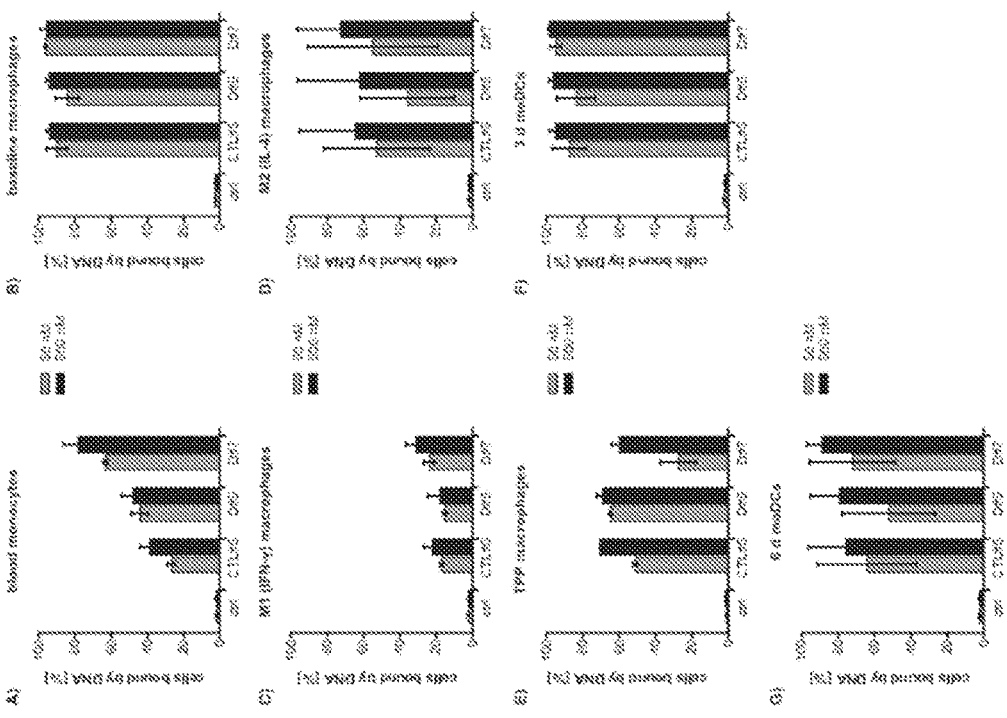
FIG. 50A-F

APTAMER SEQUENCES

| sequence FN# | DNA-sequence | SEQ ID NO. |
|---|---|---|
| 1 | CGGCGGCTTAGGTGGTTGGTTCTTTTGGTGGTTCTTGTGGTG | SEQ ID NO: 1 |
| 2 | CCCCGGAAATTGCGTACTTGTATCGGTCCTTTATCTTGTTGTG | SEQ ID NO: 2 |
| 4 | CCACGAGTATTTGCTGGGTCCTGGTGGCGTGGGTTTTGTGATGCA | SEQ ID NO: 3 |
| 8 | CGGCGCGGGATATGGGGTACGTGTTCTGGTCCTCTTACATTG | SEQ ID NO: 4 |
| 9 | CGGGTTTGCTCTTGGTTAGTGCTTGTGTGTGGTGCGACTTGG | SEQ ID NO: 5 |
| 12 | GGGGATTCTGTTTTTTTTTGTAACTCCGGGTTGGGTATCGTTG | SEQ ID NO: 6 |
| 14 | CCTGTTCTCTGTTTATGTATTGTTTATAGTTGTGTTTCCTG | SEQ ID NO: 7 |
| 15 | CGTGGCTGGGATTTATTGGGGTTGTGGTTTGCTTGTTGTTAGGCT | SEQ ID NO: 8 |
| 17 | CTGGTGTATGTTCTTCTTTGTGTCTCCGCTCGGTTTATTTTTCCGG | SEQ ID NO: 9 |
| 18 | CCCCATGCGCTTCTTGCTCTTGGTCTCGGTCTCCTTGTCCGCCTTG | SEQ ID NO: 10 |
| 19 | GGCGGGAAGGTTTGTGTATTGCGTGGTGAAGGCTCCGTGATGT | SEQ ID NO: 11 |
| 20 | CGGTGGCCGTGGTTTCTTCGTTCGTTGGTTGTGTTTTTCGTCCTTG | SEQ ID NO: 12 |
| 23 | GCGGGGCAGTGTTAAGTCGTTAGGTCGTTTGGTGGTCGTGTGGTGG | SEQ ID NO: 13 |
| 25 | CCCGCTGTGTTCCTTCTGTGATGTTTCGTTCGTTGTTTGCC | SEQ ID NO: 14 |

FIG. 51

APTAMER SEQUENCES

| sequence CTL# | DNA-sequence | |
|---|---|---|
| 1 | GCCAGTATTTGATTTCTTTGGGCGGGGGGAATTTATGTGG | SEQ ID NO:15 |
| 2 | CAGTCCACGAGGGAGGTGGGAATTTTTTGGGTGGTTTTGTC | SEQ ID NO:16 |
| 3 | GCCGGGTGGGAGTGCTCTCTGTTGCATGTGGGTGGTAGCGTG | SEQ ID NO:17 |
| 4 | GGGCCACGCCTTGTTGTGGGCGGGAGTGGTGGGAAAACTACGTG | SEQ ID NO:18 |
| 5 | TGCAATCTAGCTGACAATGGGGGGGAAGAATGTGGGTGGGTG | SEQ ID NO:19 |
| 6 | CCGTGGGTGGGTGGGAATTGGGAGGATGCGGAATTAACTCAGG | SEQ ID NO:20 |
| 7 | CGCAATCTAGCTGACAATGGGGGGGAAGAATGTGGGTGGGTG | SEQ ID NO:21 |
| 9 | CGAGATGGGGGGGAAGGATGTGGGTGGGTGATCTTCGTTGGGT | SEQ ID NO:22 |
| 10 | CGTTGTGGGGGAAGGATGTGGGTGGGTCTGTTTCAGGAGCA | SEQ ID NO:23 |
| 11 | CGGTACTGTGTGGGGTGGGTGGGTCGGAAGAACGCGCCAGGCGT | SEQ ID NO:24 |
| 13 | CGTGGGGGGTTGATGAGCATTGGGTGGGAGTTCAGGGTTTGG | SEQ ID NO:25 |
| 14 | CCGTGCGTGGGAGGGTGTGATTTCCTGGGGTGGGAGCATGGG | SEQ ID NO:26 |
| 16 | CGTACTGATGCGTGGGTGGGTGGGTACTTTCTTGATTTGGGA | SEQ ID NO:27 |
| 17 | CGAGCGTGGGGGGTGGGTTTCGGGGTTTCCGGAGCTCCGGAGCACTTTG | SEQ ID NO:28 |
| 18 | CACTGGATTCGTTGGGGTTCTTTTGGGGATATTCCGGGGTGG | SEQ ID NO:29 |
| 19 | GCACCGTGGGCGGCTATACTTCTTTTTCATTTGGGTGGGAGGTGCA | SEQ ID NO:30 |
| 20 | GGTCCAATCGTTGGGGATTTGGGAGGATGCAGGTAGGTTGTCC | SEQ ID NO:31 |
| 21 | CTGTGGGTGGGGGGATTTGGGAGGATGCAGGTAGGTTGTCC | SEQ ID NO:32 |
| 22 | CAGGGGAGGTGGGTTTTTTGGGTAGTTTTGGATCAATGGCCCG | SEQ ID NO:33 |

FIG. 51 (Contd.)

APTAMER SEQUENCES

| sequence ID# | | |
|---|---|---|
| 2 | GCATGTTTGGGTGGGATATTGGCGTGTTTGGGTTGGGACTGCT | SEQ ID NO:34 |
| 3 | GCATGTTTGGGTGGGATATTGGCGTGTTTGGGTTGGGACTGCT | SEQ ID NO:35 |
| 5 | CGCATTTGGGTGGGATTGTTATTTGGGTCGGGATTGGCAGTT | SEQ ID NO:36 |
| 8 | CGCATTTGGGTGGGATTGTTATTTGGGTCGGGATTGGCAGTT | SEQ ID NO:37 |
| 4 | GTGGGCGGGTTTATATTCGGTGTGGTGGGGGTGGTTCTGT | SEQ ID NO:38 |
| 7 | CGTGGGTGGGTTTATATTCGGTGGTGGTGGGGTGGTACTGTT | SEQ ID NO:39 |
| 23 | CGTGGGCGGGTTTATATTGGGTGGTGGTGGGGTACTGTT | SEQ ID NO:40 |
| 28 | CGTGGGTGGGTTTATATTCGGTGGTGGTGGGGGTACTGTT | SEQ ID NO:41 |
| 1 | CCCACCAACTCGACCAAGTCGCTGCTCCTCTCCGCCCACCCC | SEQ ID NO:42 |
| 6 | CAACGGACCCTGGGATGTATTCGTTCCTACTCTGCCCTACAGAACCG | SEQ ID NO:43 |
| 9 | CCGTCCCCCCGTTGTGTTCCCTATGCCCTGTTTTCGGTATGTGTGTG | SEQ ID NO:44 |
| 10 | CCGTTCTCGTCGTTGTTTTTCTGTTTCGGTTATGTTGTGTG | SEQ ID NO:45 |
| 11 | GACGGGGCGGTTCTTGCTTGTTCTCGCCCTTGATCGTCCCTGGCCCGTT | SEQ ID NO:46 |
| 13 | CCTCCTCATTGCTTGTTCTCGCCCTTGATCGTCCCTGGCCCGTT | SEQ ID NO:47 |
| 14 | CCCTCACTGTAGTCCCTGACTGTCGTATTCCCGGTTTTCTGT | SEQ ID NO:48 |
| 15 | CCCTGGCCCCCCCTCACTGGTCCCGTCATTTCTTCTATGCCCGCCC | SEQ ID NO:49 |
| 16 | CCCGGCTGTCCCCATTGGTCGTGCCTGTTTCCTCGTTCGCCC | SEQ ID NO:50 |
| 17 | CCCCCGGCCTCTCGAGCATTACCACCCGGCGCTTCAGTTTG | SEQ ID NO:51 |
| 18 | CCCGTTTGGTATATCCCCATTTTGGTCGTGTTGTGAAGTGGGGTGT | SEQ ID NO:52 |
| 19 | CAGGGAGGTGGGTTCTTGGGTATTTTGTCTAATCTAGTCTCTTTGTCT | SEQ ID NO:53 |
| 20 | CCCGACCCCATCCGACGCTGTATTTTCCCTCTTCCGACCACCCCT | SEQ ID NO:54 |
| 21 | CCCGACCGGCGCGCTTTTCCCTCTTCCGTCACCTCCTTTCGAT | SEQ ID NO:55 |
| 22 | CCCGACCCGGCCGCTTTTCCCCTCTTCCGTCACCTCCTTTCGAT | SEQ ID NO:56 |
| 24 | GCGTCGGATTGGTGTGCCGGGCTTTTCGTTGGTTTGTTGTGTGT | SEQ ID NO:57 |
| 26 | CCAGGGGAGCATGCGCGGGGTCTTTGGTGGTGGTAATATTGCTCGCT | SEQ ID NO:58 |
| 27 | GCGGTTCTGTGTGCATCTCGGTTGGTGGTGGGTAATATTGCTCGCT | SEQ ID NO:59 |
| 29 | TCCCTCTTTTGCATCTCCGGTCGGTATACCCCGCCCTTTAACCGTGTG | SEQ ID NO:60 |
| 30 | TGGGGTTGGGTTGGGTTGGGTCGATTGCGTCTCTCTTTG | SEQ ID NO:61 |
| 31 | CAGGGAGGAGGTTGGCAGAGAGGTGTTTAGTGTGTCCGGGTTT | SEQ ID NO:62 |

FIG. 51 (Contd.)

APTAMER SEQUENCES

| | | |
|---|---|---|
| 32 | CCACCGGCGCTGATCTTGCTCCCTTCCGTCCGTCGTTCCTCCC | SEQ ID NO: 63 |
| 33 | CCCTCGACAGCCTTCTCGTCCTCTGTATTGGGCCATCCTCCC | SEQ ID NO: 64 |
| 34 | CCTAGTACATTTCATCCGCCTCGTTGTCGCCCTTCCCGCCGT | SEQ ID NO: 65 |
| 35 | CGGTTTGGTGTGGTTCGCGAGTACGTTTCCTTCTCGACTTG | SEQ ID NO: 66 |
| 36 | CGGGTGCTTTGTTGTATGTTGTGTGTGGGCTTTTTTGGTGTGG | SEQ ID NO: 67 |

FIG. 51 (Contd.)

APTAMERS FOR TARGETED ACTIVATION OF T CELL-MEDIATED IMMUNITY

CLAIM OF PRIORITY

This application is the national stage entry of International Application No. PCT/IB2019/052641, filed on Mar. 30, 2019, which claims the benefit of U.S. Provisional Patent Application Ser. No. 62/650,522, filed on Mar. 30, 2018. The entire contents of the foregoing are hereby incorporated by reference.

SEQUENCE LISTING SUBMITTED VIA EFS-WEB

The entire content of the following electronic submission of the sequence listing via the USPTO EFS-WEB server, as authorized and set forth in MPEP § 1730 II.B.2(a), is incorporated herein by reference in its entirety for all purposes. The sequence listing is within the electronically filed text file that
is identified as follows:
File Name: Seq_Listing.txt
Date of Creation: Sep. 29, 2020
Size (bytes): 39,195 bytes.

TECHNICAL FIELD OF THE INVENTION

The invention relates generally to compositions comprising aptamers, and methods of use thereof as carrier molecules in cell-mediated immunotherapies. In particular, the invention relates to efficient antigen presentation and processing of aptamer conjugated antigenic peptides by antigen presenting cells to elicit antigen-specific activation of a T cell response.

BACKGROUND OF THE INVENTION

It is of great interest for therapeutics to use cells of the innate immune system (e.g., dendritic cells) to activate effector cells of the acquired immune system (e.g., T cells). This approach requires carrier molecules to deliver antigens to antigen presenting cells. Exemplary carrier molecules include antibodies, nanoparticles and viruses. However, these molecules proved to be unsuitable in some cases because they either have intrinsic immunostimulatory activity, cause undesired side effects, act unspecifically, or have low stability.

Aptamers, short single-stranded oligonucleic acids, are an alternative carrier molecule that bind to their target molecules with high specificity and affinity. In a selection process, SELEX (Systematic Evolution of Ligands by EXponential enrichment), aptamers can be identified to a variety of target molecules, such as small molecules, proteins or cells.

While aptamers have been used as a carrier molecule, e.g., for siRNA or chemotherapeutic agents, the use of aptamers in cellular immunotherapy has been limited. Wengerter et al. published the selection of aptamers that bind DEC-205, a receptor expressed by dendritic cells. After conjugation to ovalbumin protein, activation of ovalbumin-specific CD8+ T cells was induced. However, the study continues to raise questions. First, there is disagreement in the literature on whether the DEC-205 receptor is for activation of the CD4+ or CD8+ T cell subpopulation. Second, it has already been described that the complete ovalbumin protein is taken up without conjugation by a carrier molecule, processed and leading to T cell activation. It is therefore unknown whether the conjugation to the aptamer enhanced the T cell activation by ovalbumin. Third, the ovalbumin protein was processed differently dependent on the entryway into the dendritic cell and caused activation of both the CD8+ and also CD4+ T cells. The CD4+ T cell activation was noted in Wengerter et al. but not studied.

As discussed herein, aspects of the present invention address the aforementioned challenges and unmet needs by providing, inter alia, aptamers that bind specifically to antigen presenting cells (e.g., dendritic cells (DCs)), which are internalized and localized within adequate antigen processing compartments, yet have low inherent immunogenicity. In particular, the present invention provides aptamers which are useful as DC-targeting carriers to mediate targeted activation of specific T cells, and for development of aptamer-based DC vaccines for in vivo applications.

BRIEF SUMMARY OF THE INVENTION

The present invention provides compositions comprising at least one antigenic peptide conjugated to an aptamer, wherein the aptamer specifically binds a target on an antigen presenting cell and upon contact with the cell, is internalized and wherein the aptamer is not immunostimulatory. In certain embodiments, the antigen presenting cell comprises a professional antigen presenting cell. In certain embodiments, the professional antigen presenting cell is selected from the group consisting of a monocyte, macrophage, a B cell, and a dendritic cell. In particular embodiments, the professional antigen presenting cell comprises a dendritic cell. In certain embodiments, the dendritic cell is a bone marrow-derived dendritic cell. In particular embodiments, the target comprises a mannose receptor. In certain embodiments, the antigenic peptide comprises an MHC-I restricted antigenic peptide, MHC-II restricted antigenic peptide, or a combination thereof. In certain embodiments, the antigenic peptide comprises an MHC-I and MHC-II restricted antigenic peptide. In certain embodiments, the antigenic peptide is derived from a pathogen-associated antigen, a human self protein, a tumor antigen, or a vaccine antigen. In certain embodiments, the aptamer comprises a nucleic acid sequence as set forth in any of the aptamer sequences disclosed herein. In certain embodiments, the aptamer comprises a nucleic acid sequence as set forth in any one of SEQ ID NOS: 1-67, or a nucleic acid sequence having at least 80%, at least 85%, at least 90%, at least 95%, at least 96%, at least 97%, at least 98%, or at least 99% sequence identity therewith over the entire length of said any one of SEQ ID NOS: 1-67. In particular embodiments, the aptamer comprises the nucleic acid sequence as set forth in any one of SEQ ID NOS: 19 (CTL #5), 36 (D #5) or 39 (D #7) or a nucleic acid sequence having at least 80%, at least 85%, at least 90%, at least 95%, at least 96%, at least 97%, at least 98%, or at least 99% sequence identity therewith over the entire length of said any one of SEQ ID NOS: 19 (CTL #5), 36 (D #5) or 39 (D #7). In certain embodiments, the aptamer comprises an oligoribonucleotide or oligodeoxyribonucleotide. In certain embodiments, the aptamer comprises a modification selected from the group consisting of: a 2'-O-methyl (2'-OMe) modification, a 2'-F modification, a 2'-NH$_2$ modification, a locked nucleic acid (LNA) modification, polyethylene glycol (PEG)-conjugation, fluorescent tagging, monothiophosphate (e.g., a thioaptamer), or any combination thereof. In certain embodiments, the composition further comprises an immunological adjuvant.

In certain embodiments, the present invention provides a method of loading an MHC molecule with a peptide, comprising contacting any of the aforementioned embodiments of the composition provided by the present invention, with an antigen presenting cell. In particular embodiments the method further comprises internalization of the composition into a cellular compartment of the antigen presenting cell. In certain embodiments of the method, the cellular compartment comprises an endosome or a lysosome. In certain embodiments of the method, the antigen presenting cell comprises a professional antigen presenting cell selected from the group consisting of a monocyte, macrophage, a B cell, and a dendritic cell. In certain embodiments of the method, the professional antigen presenting cell comprises a dendritic cell. In particular embodiments of the method, the dendritic cell is an autologous dendritic cell. In certain embodiments of the method, the MHC molecule is an MHC-I molecule or an MHC-II molecule. In particular embodiments of the method, the contacting elicits an immune response. In certain embodiments of the method, the immune response comprises an activation of CD8$^+$ T cells, CD4$^+$ T cells, or a combination thereof. In particular embodiments of the method, the immune response comprises an activation of CD8$^+$ T cells and CD4$^+$ T cells. In certain embodiments of the method, the immune response comprises a prophylactic or a therapeutic immune response.

In certain embodiments, the present invention provides a method of delivering one or more antigenic peptides to an antigen presenting cell comprising contacting the antigen presenting cell with any of the aforementioned embodiments of the composition provided by the present invention. In particular embodiments the method further comprises internalization of the composition into a cellular compartment of the antigen presenting cell. In certain embodiments of the method, the cellular compartment comprises an endosome or a lysosome. In certain embodiments of the method, the antigen presenting cell comprises a professional antigen presenting cell selected from the group consisting of a monocyte, macrophage, a B cell, and a dendritic cell. In certain embodiments of the method, the professional antigen presenting cell is bone marrow-derived. In certain embodiments of the method, the professional antigen presenting cell is a bone marrow-derived dendritic cell. In particular embodiments of the method, the dendritic cell is an autologous dendritic cell. In certain embodiments of the method, the antigenic peptide comprises an MHC-I restricted peptide, an MHC-II restricted antigenic peptide, or a combination thereof. In certain embodiments of the method, the antigenic peptide comprises an MHC-I and MHC-II restricted antigenic peptide. In particular embodiments of the method, the contacting elicits an immune response. In certain embodiments of the method, the immune response comprises an activation of CD8$^+$ T cells, CD4$^+$ T cells, or a combination thereof. In particular embodiments of the method, the immune response comprises an activation of CD8$^+$ T cells and CD4$^+$ T cells. In certain embodiments of the method, the immune response comprises a prophylactic or a therapeutic immune response.

In certain embodiments, the present invention provides a method of eliciting an immune response in a subject in need thereof comprising administering to the subject a composition comprising an aptamer conjugated to at least one antigenic peptide, wherein the aptamer comprises a nucleic acid sequence as set forth in any one of SEQ ID NOS: 1-67, or a nucleic acid sequence having at least 80%, at least 85%, at least 90%, at least 95%, at least 96%, at least 97%, at least 98%, or at least 99% sequence identity therewith over the entire length of said any one of SEQ ID NOS: 1-67. In particular embodiments of the method, the aptamer comprises the nucleic acid sequence as set forth in any one of SEQ ID NOS: 19 (CTL #5), 36 (D #5) or 39 (D #7) or a nucleic acid sequence having at least 80%, at least 85%, at least 90%, at least 95%, at least 96%, at least 97%, at least 98%, or at least 99% sequence identity therewith over the entire length of said any one of SEQ ID NOS: 19 (CTL #5), 36 (D #5) or 39 (D #7). In certain embodiments of the method, the aptamer comprises an oligoribonucleotide or oligodeoxyribonucleotide. In certain embodiments of the method, the aptamer comprises a modification selected from the group consisting of: a 2'-O-methyl (2'-OMe) modification, a 2'-F modification, a 2'-O-methyl (2'-OMe) modification, a 2'-F modification, a 2'-NH$_2$ modification, a locked nucleic acid (LNA) modification, polyethylene glycol (PEG)-conjugation, fluorescent tagging, monothiophosphate (e.g., a thioaptamer), or any combination thereof. In certain embodiments of the method, wherein the at least one antigenic peptide comprises an MHC-I restricted antigenic peptide, MHC-II restricted antigenic peptide, or a combination thereof. In certain embodiments of the method, the antigenic peptide comprises an MHC-I and MHC-II restricted antigenic peptide. In certain embodiments of the method, the antigenic peptide is derived from a pathogen-associated antigen, a human self protein, a tumor antigen, or a vaccine antigen. In certain embodiments of the method, the antigen presenting cell comprises a professional antigen presenting cell selected from the group consisting of a monocyte, macrophage, a B cell, and a dendritic cell. In certain embodiments of the method, the professional antigen presenting cell comprises a dendritic cell. In certain embodiments of the method, the dendritic cell is an autologous dendritic cell. In certain embodiments of the method, the autologous dendritic cell is loaded ex vivo with the composition prior to administration to the subject. In certain embodiments of the method, the immune response comprises an activation of CD8$^+$ T cells, CD4$^+$ T cells, or a combination thereof. In certain embodiments of the method, the immune response comprises an activation of CD8$^+$ T cells and CD4$^+$ T cells. In certain embodiments of the method, the immune response comprises a prophylactic or a therapeutic immune response.

In certain embodiments, the present invention provides a method for identifying a dendritic cell (DC)-binding aptamer, the method comprising: (a) performing a SELEX protocol comprising contacting a DNA library with a recombinant mannose receptor protein or a dendritic cell, and; (b) selecting a DC-binding aptamer which is capable of delivering at least one antigenic peptide to the dendritic cell and eliciting an immune response comprising activation of CD4$^+$ T cells and CD8$^+$ T cells. In certain embodiments of the method, the SELEX protocol is a protein-SELEX protocol and the recombinant mannose receptor protein comprises a recombinant Fc-CTL protein or a recombinant Fc-FN protein. In certain embodiments of the method, the SELEX protocol is a cell-SELEX protocol and the dendritic cell is a bone-marrow derived dendritic cell. In certain embodiments of the method, the at least one antigenic peptide comprises an MHC-I and MHCII restricted antigen. In certain embodiments of the method, the at least one antigenic peptide is derived from a pathogen-associated antigen, a human self protein, a tumor antigen, or a vaccine antigen. In certain embodiments of the method, the DC-binding aptamer is capable of internalization and localization within cellular compartments of the dendritic cell. In certain embodiments of the method, the cellular compartment comprises an endosome or a lysosome. In certain embodiments of the method, the DC-binding aptamer comprises a nucleic acid sequence as set forth in any one of SEQ ID NOS: 1-67, or a nucleic acid sequence having at least 80%, at least 85%, at least 90%, at least 95%, at least 96%, at least 97%, at least 98%, or at least 99% sequence identity therewith over the entire length of said any one of SEQ ID NOS: 1-67. In particular embodiments of the method, the DC-binding aptamer comprises the nucleic acid sequence as set forth in any one of SEQ ID NOS: 19 (CTL #5), 36 (D #5) or 39 (D #7) or a nucleic acid sequence having at least 80%, at least 85%, at least 90%, at least 95%, at least 96%, at least 97%, at least 98%, or at least 99% sequence identity therewith over the entire length of said any one of SEQ ID NOS: 19 (CTL #5), 36 (D #5) or 39 (D #7). In certain embodiments of the method, the DC-binding aptamer comprises an oligoribonucleotide or oligodeoxyribonucleotide. In certain embodiments of the method, the DC-binding aptamer comprises a modification selected from the group consisting of: a 2'-O-methyl (2'-OMe) modification, a 2'-F modification, a 2'-NH$_2$ modification, a locked nucleic acid (LNA) modification, polyethylene glycol (PEG)-conjugation, fluorescent tagging, monothiophosphate (e.g., a thioaptamer), or any combination thereof.

The comparison of sequences and determination of percent identity between two sequences can be accomplished using a mathematical algorithm. For example, the percent identity between two sequences can determined using the Needleman and Wunsch ((1970) J. Mol. Biol. 48:444-453) algorithm which has been incorporated into the GAP program in the GCG software package (available on the world wide web at gcg.com), using the default parameters for the length of sequence, or using Huang and Miller algorithm (published in Adv. Appl. Math. (1991) 12:337-357), which has been incorporated into the LALIGN program, which is part of the FASTA package of sequence analysis program.

Also provided herein are compositions as described herein, e.g., comprising an aptamer as described herein, and a pharmaceutically acceptable carrier.

Further, provided herein are methods of treating a cancer in a subject, comprising administering to the subject a therapeutically effective amount of a composition as described herein. In addition, the compositions described herein a provided for use in medical therapy, e.g., in a method of treating a cancer (e.g., a solid tumor, or other cancer as described herein or known in the art) in a subject, or in a method of manufacturing a medicament.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF SUMMARY OF THE SEVERAL VIEWS OF THE DRAWINGS

FIG. 11A-B: Schematic representation of the targets used in SELEX approaches to identify BM-DC-binding aptamers. Recombinant mannose receptor (MR) proteins or murine bone marrow-derived DCs (BM-DCs) were used to identify aptamers. The recombinant proteins Fc-CTL (2) or Fc-FN (3) consist of the human IgG1 Fc portion and protein domains of the murine MR (1) (A). The murine MR (1) consists of a cysteine-rich (CR), a fibronectin type II (FNII), eight C-type lectin-like domains (CTLD 1-8) and a transmembrane domain (modified after Martinez-Pomares et al). BM-DCs were isolated from the C57/BL6J mouse strain and cell progenitors derived from bone marrow of hind limbs were differentiated for 7 d with GM-CSF (B). CR=cysteinrich, FNII=fibronectin type II, CTLD=C-type lectin-like domain; MR=mannose receptor, GM-CSF=granulocyte macrophage colony-stimulating factor.

FIG. 12A-D: Aptamer selection targeting Fc-CTL or Fc-FN results in enrichment of DNA. 1 pmol of $^{32}$P-DNA was incubated with increasing concentrations of Fc-CTL (A+B) or Fc-FN proteins (C+D) and the mixtures were passed through a nitrocellulose membrane. The amount of $^{32}$P-DNA retained on Fc-CTL or Fc-FN was determined by autoradiography (n=2, mean±. SD). Representative dot blots are shown in (B) and (D). Radioactivity appears as black spots. On the left, $^{32}$P-DNA retained on the proteins is shown and on the right, 0.8 pl of $^{32}$P-DNA is spotted to allow the quantification of the percentage of bound DNA.

FIG. 13A-B: DNA libraries targeting Fc-CTL or Fc-FN discriminate between recombinant proteins. DNA libraries of the 1$^{st}$ and 6th selection cycle of Fc-CTL (A) and Fc-FN (B) targeting SELEX were incubated with 1000 nM of proteins and analyzed by radioactive filter retention assay. The protein-$^{32}$P-DNA mixture was therefore passed through a nitrocellulose membrane and the retained DNA was measured by autoradiography (n=2, mean±SD).

FIG. 14A-B: DNA sequences share motifs. DNA sequences obtained by cloning and sequencing of DNA library targeting Fc-CTL were grouped according to their sequence similarities. (SEQ ID NOs: 19, 21, 22, 23, 25, 20, 27, and 32, in order of appearance).

FIG. 17A-B: SELEX targeting BM-DCs results only in enrichment of DNA. $^{32}$P-DNA (A) or $^{32}$P-2'F-RNA (B) were incubated with 0.5×10$^5$ BM-DCs and the retained radioactivity on the cells was determined by liquid scintillation (n=6 (A)/n=2 (B), mean±SD).

FIG. 18A-B: DNA sequences share sequence similarities. According to their composition, some DNA sequences obtained from cell-SELEX were grouped into sequence family 1 and 2. (SEQ ID NOs: 38, 39, 40, 41, 34, 35, 36, 37, in order of appearance).

FIG. 35A-C: Aptamer-targeted delivery of OT-I peptide activates CD8 T cells. 1×10$^5$ OVA-specific CD8 T cells were stained with CFSE and added to 5×104 BM-DCs treated with 1 nM MHC I peptide, different concentrations of OT-I peptide (A), 100 nM DNA (B) or increasing concentrations of aptamer-OT-I conjugates (C). CFSE profiles were measured by flow cytometry. Non-proliferated population is shown in grey. Mean division index of triplicates is given in numbers (mean±SD). Representative results out of n=4 are shown (refer to FIG. 45A-C-FIG. 47). The assays were done with blinded samples.

FIG. 36A-C: Aptamer-peptide conjugates induce CD8 cytotoxicity. 2×10$^5$ BM-DCs were treated with 50 nM MHC I peptide or 100 nM CTL #5-OT-I (A), D #5-OT-I (B) or D

7-OT-I (C) conjugates. 4×105 OVA-specific CD8 T cells were added. After 72 h, T cells were isolated and incubated with CFSE-labeled target and control cells for another 24 hours. On day 5, cells were stained with Hoechst 33258 and analyzed by flow cytometry. The percentages of T cell cytotoxicity were determined (n=2, mean±SD). The assays were performed with blinded samples.

FIG. 37A-C: Structure and sequence similarities of the CTLDs of murine MR and rat mannose-binding protein-A. The ribbon diagrams of the CTLD 4 of murine MR (A) and the CTLD of rat mannose-binding protein-A (MBP-A) (B) illustrate the typical CTLD fold consisting of two a helices, two antiparallel 13 sheets (13 strands 1-5) and four loops (L1-4). The CTLD of MBP-A is composed of two Ca2+ ions binding sites, whereas the CTLD 4 of MR has only one binding site. Highly conserved disulfide bonds are shown in purple and the regions connecting the external loop of CTLD 4 to the core is depicted in yellow (modified from Feinberg et al. 139). The alignment of the eight CTLDs (CRD 1-8) and the CTLD of MBP-A reveals conserved amino acids (C), shaded amino acids are conserved in five or more CTLDs. The predicted secondary structures, a helix, 13 strand or loop (L), are given in the boxes below the sequences. Highly conserved cysteine residues are highlighted in purple boxes (modified from Harris et al.). CRD=carbohydrate-recognition domain. (SEQ ID NOs: 71-78, in order of appearance)

FIG. 38: DNA sequences obtained from Fc-FN SELEX. (SEQ ID NOs: 1-14, in order of appearance)

FIG. 39: DNA sequences derived from Fc-CTL SELEX. CTL unique sequences are shown. (SEQ ID NOs: 15-18, 24, 26, 28, 29, 30, 31, 33, in order of appearance)

Figure 40:
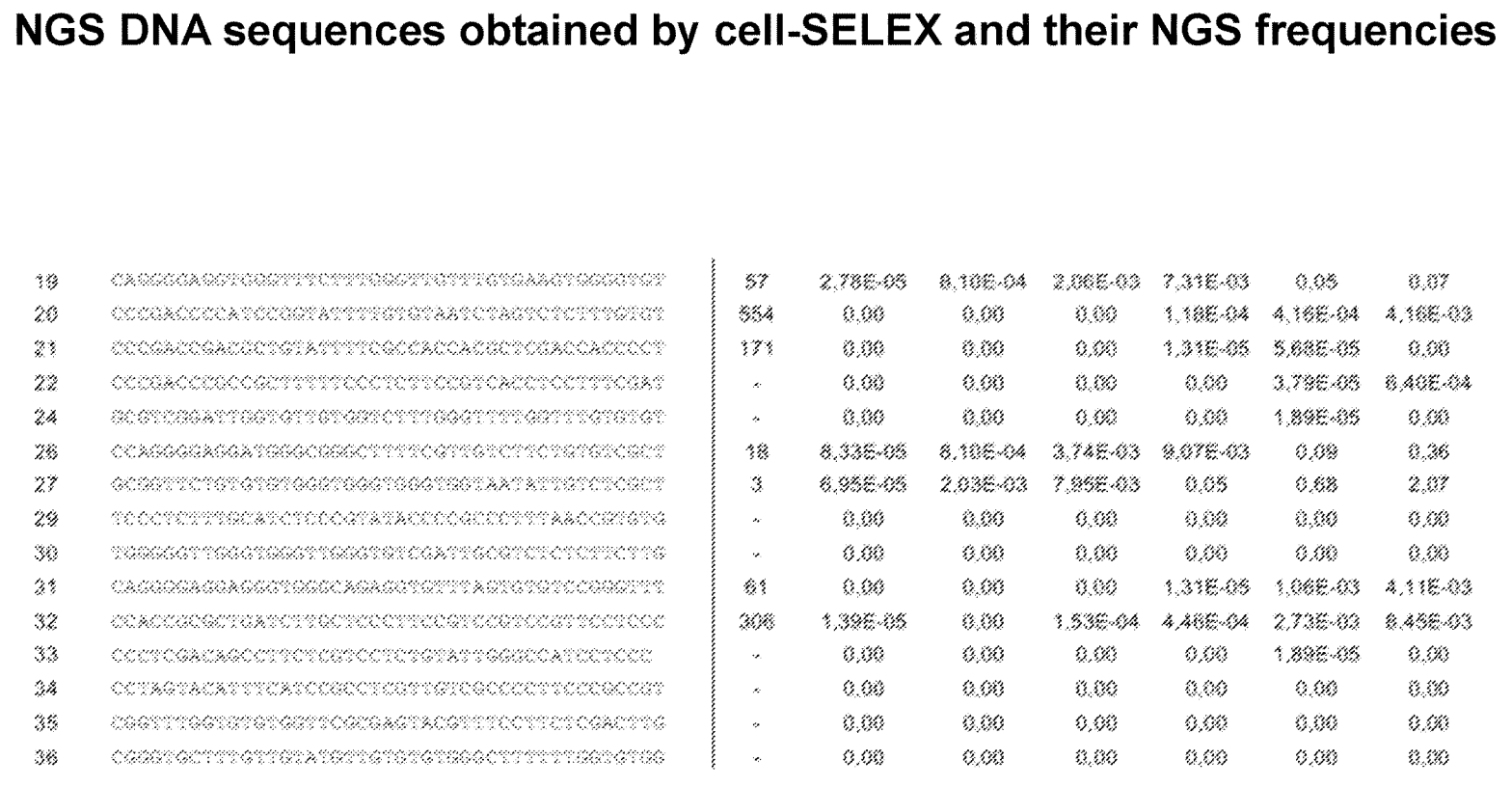

FIG. 40: NGS analysis of DNA sequences obtained by cell-SELEX. Sequences obtained by cell-SELEX and their NGS frequencies Classical cloning and sequencing. (SEQ ID NOs: 34-67, in order of appearance).

FIG. 41: Consensus sequences and number of sequences of the 15 most abundant NGS patterns. (SEQ ID NOs: 79-93, in order of appearance)

Figure 42:
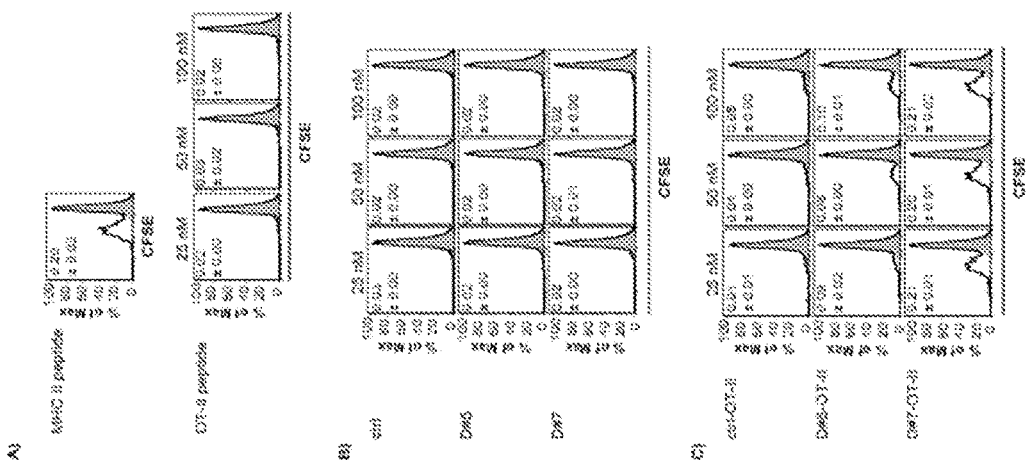

FIG. 42A-C: Activation of CD4 T cells. BM-DCs were treated with different concentrations of MHC II peptide or 100 nM OT-II peptide (A), 100 nM of oligonucleotides (B) or increasing concentrations of aptamer-peptide conjugates (C). Subsequently, BM-DCs were co-cultured for 72 h with CFSE-labeled OVA-dependent CD4 T cells and the proliferation profile indicated by changes of CFSE signals was measured by flow cytometry. FACS histograms with one representative profile out of triplicate measurement are depicted. Numbers gives the division index (mean±SD). The non-proliferated population is shown in grey.

Figure 43:
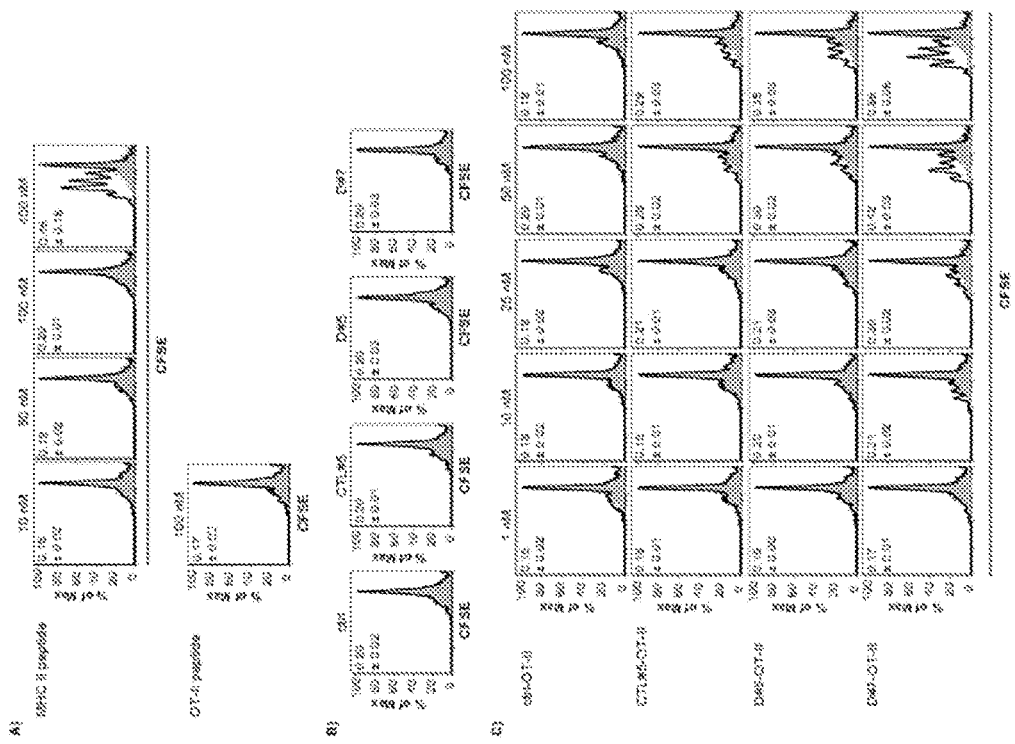

FIG. 43A-C: Activation of CD4 T cells. BM-DCs were treated with different concentrations of MHC II peptide or 100 nM OT-II peptide (A), 100 nM of oligonucleotides (B) or increasing concentrations of aptamer-peptide conjugates (C). Afterwards, BM-DCs were co-cultured for 72 h with CFSE-labeled OVA-dependent CD4 T cells and the CFSE profile was measured by flow cytometry. FACS histograms with one representative profile out of triplicate measurement are depicted. Division index (mean±SD) is depicted within the FACS histograms. The non-proliferated population is shown in grey.

Figure 44:
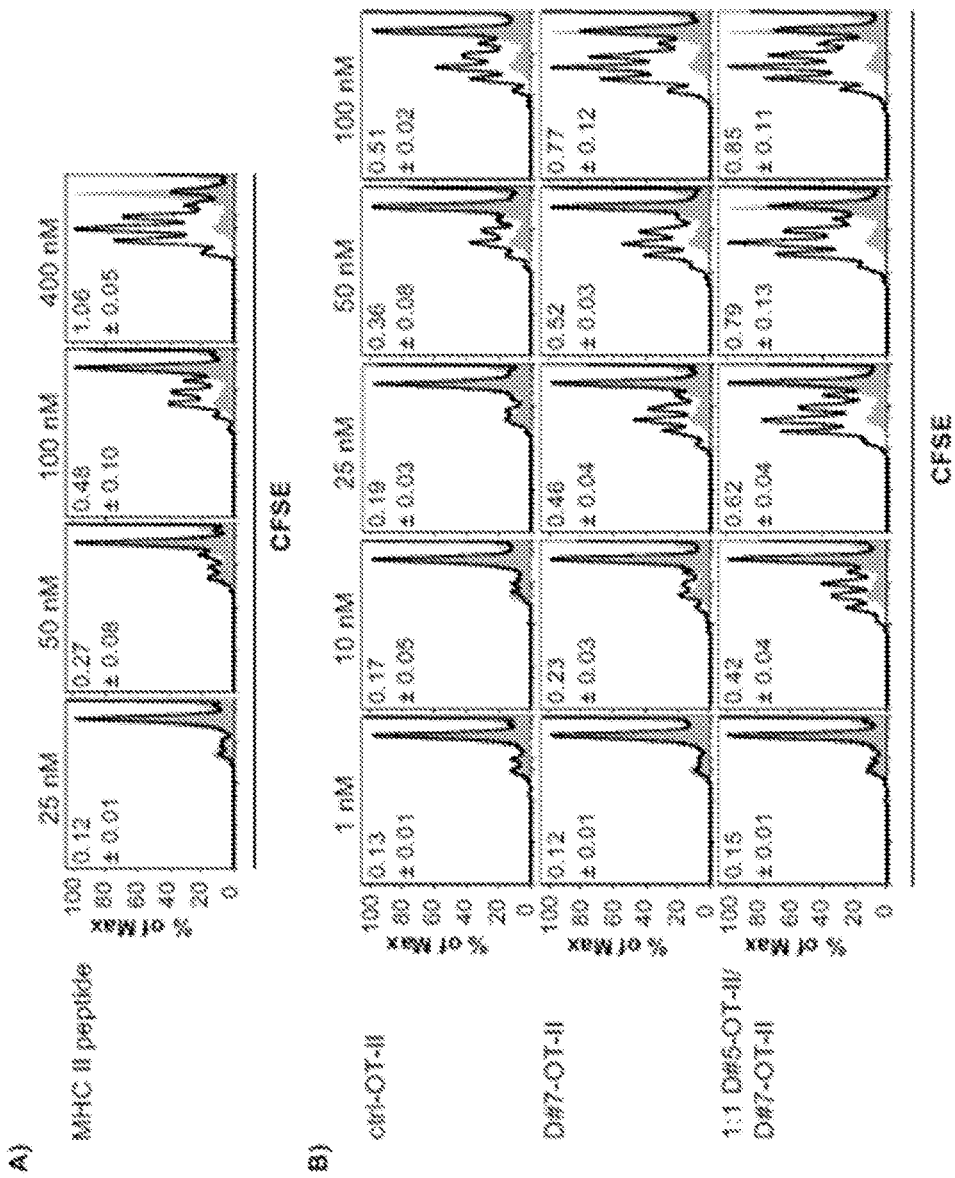

FIG. 44A-B: Activation of CD4 T cells. BM-DCs were treated with different concentrations of MHC II peptide or 100 nM OT-II peptide (A), 100 nM of oligonucleotides (B) or increasing concentrations of aptamer-peptide conjugates (C). Next, BM-DCs were co-cultured for 72 h with CFSE-labeled OVA-dependent CD4 T cells and the proliferation profile was measured by flow cytometry. FACS histograms with one representative profile out of triplicate measurement are depicted. Numbers gives the division index (mean±SD). The non-proliferated population is shown in grey.

Figure 45:
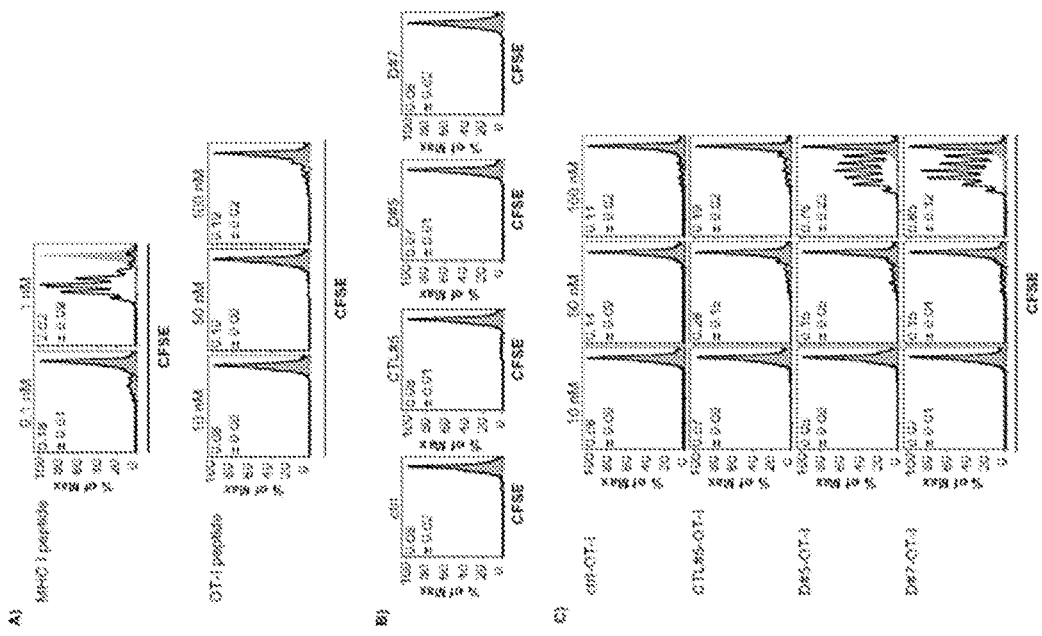

FIG. 45A-C: Activation of CD8 T cells. BM-DCs were treated with different concentrations of MHC I or OT-I peptide (A), 100 nM of oligonucleotides (B) or increasing concentrations of aptamer-peptide conjugates (C). Afterwards, BM-DCs were co-cultured for 72 h with CFSE-labeled OVA-dependent CD8 T cells and the proliferation profile indicated by changes of CFSE signals was measured by flow cytometry. FACS histograms with one representative profile out of triplicate measurement are depicted. Numbers gives the division index (mean±SD). The non-proliferated population is shown in grey.

Figure 46:
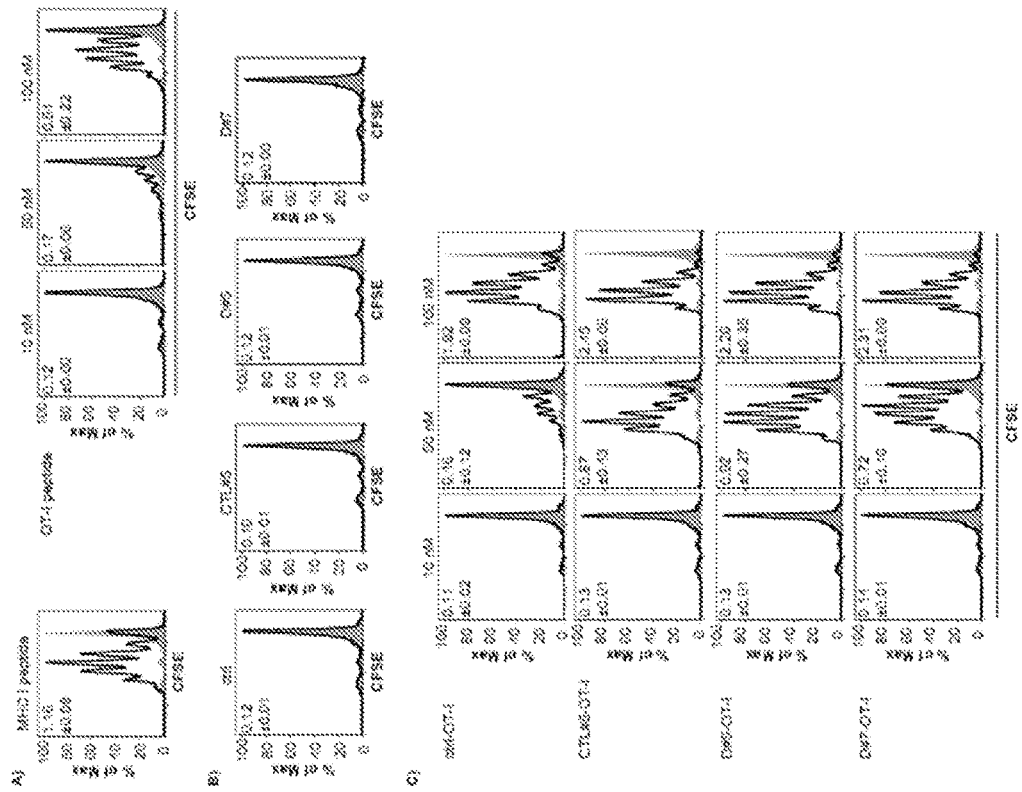

FIG. 46A-C: Activation of CD8 T cells. BM-DCs were treated with 1 nM MHC I peptide or different concentrations of OT-I peptide (A), 100 nM of oligonucleotides (B) or increasing concentrations of aptamer-peptide conjugates (C). Subsequently, BM-DCs were co-cultured for 72 h with CFSE-labeled OVA-dependent CD8 T cells and the CFSE profile was measured by flow cytometry. FACS histograms with one representative profile out of triplicate measurement are depicted. Division index (mean±SD) is depicted within the FACS histograms. The non-proliferated population is shown in grey.

Figure 47:
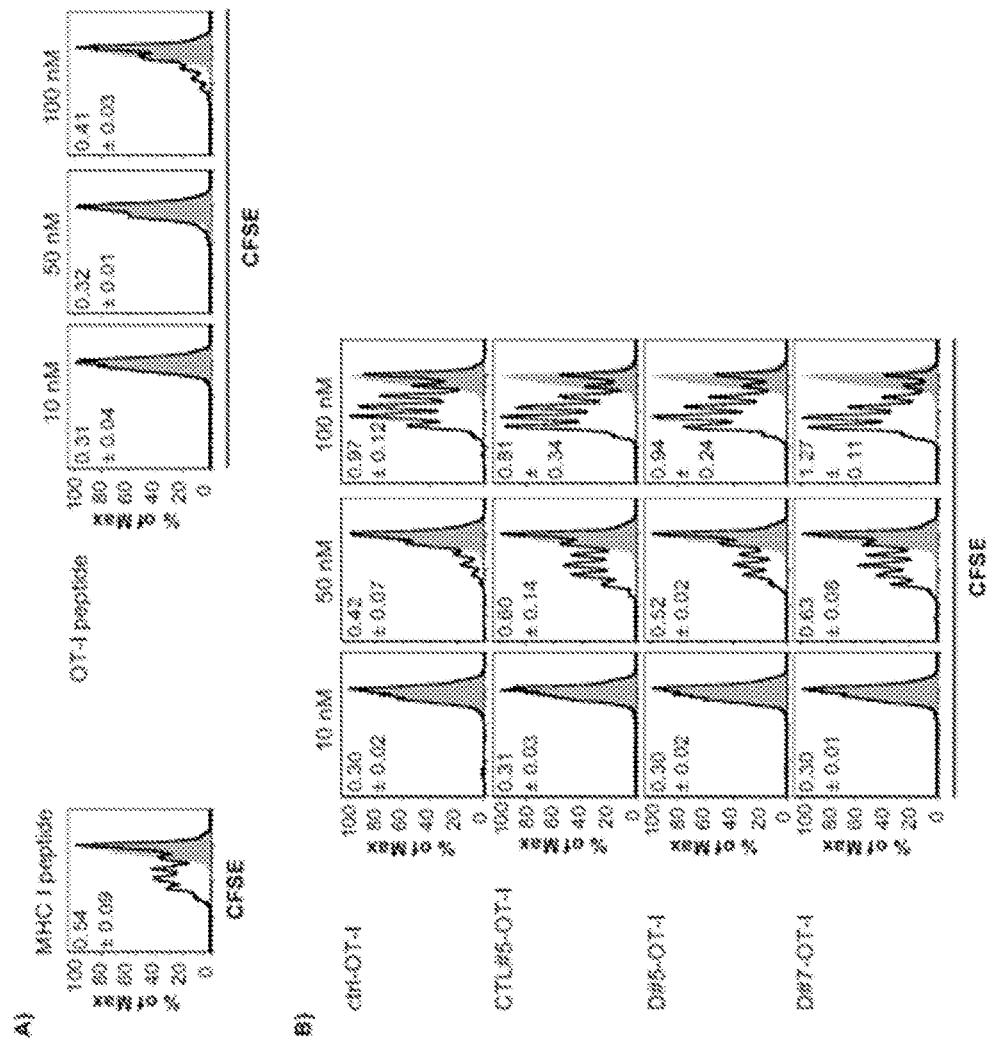

FIG. 47A-B: Activation of CD8 T cells. BM-DCs were treated with 1 nM MHC I peptide, different concentrations of OT-I peptide (A) or increasing concentrations of aptamer-peptide conjugates (B). Next, BM-DCs were co-cultured for 72 h with CFSE-labeled OVA-dependent CD8 T cells and the proliferation profile was measured by flow cytometry. FACS histograms with one representative profile out of triplicate measurement are depicted. Numbers gives the division index (mean±SD). The non-proliferated population is shown in grey.

Figure 48:
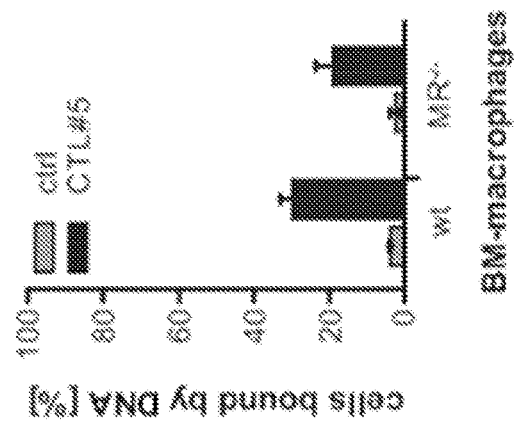

FIG. 48: CTL #5 binds to wildtype and MR knockout murine bone marrow-derived macrophages. Murine bone marrow-derived macrophages were treated with 400 nM ATTO 647N-labeled CTL #5 and the amount of cells bound by CTL #5 was measured by flow cytometry and normalized to the control (ctrl) sequence. The experiment was done once in duplicates (mean±SD).

FIG. 49A-B: Binding analysis of NGS patterns to DCs. NGS analysis of cell-SELEX revealed sequence patterns with increasing sequence frequencies from selection cycle 1 to 10. The consensus sequences of pattern 9-12 were chosen for flow cytometry binding analysis. BM-DCs were treated with 50 and 500 nM of ATTO 647N-labeled control sequence (ctrl), aptamers (A) or NGS pattern sequences (B) and analyzed by flow cytometry. Data were given as ratio of binding in comparison to the ctrl sequence (n=2, mean±SD).

FIG. 50A-F: Binding analysis of human cells. The binding ability of BM-DC-targeting aptamers to human peripheral blood cells was analyzed by flow cytometry (mean±SD). CD14+ blood monocytes of at least two different blood donors (exception E: n=1) were either used directly in FACS binding assay or further differentiated according to Xue et al. and Nino-Castro et al. Cells were incubated with ATTO 647N-labeled aptamers and co-stained with cell surface marker CD14 (A+B), CD86 (C), CD23 (D), CD25 (E), CD209 (F+G).

FIG. 51: Aptamer sequences provided by the instant invention. (SEQ ID NOs: 1-67, in order of appearance)

DETAILED DESCRIPTION OF THE INVENTION

An attractive way of preventing or curing infections and diseases is to mobilize a patient's own defense mechanism, the immune system. Treatments following this approach are commonly known as immunotherapies. The development of protective long-term immunity requires activation of the effectors of the adaptive immune system, in particular T cells, by cells involved in innate immunity.

Dendritic cells (DCs) represent the interface between the non-specific innate immunity and the highly specific adaptive immunity. Upon recognition of antigenic structures, DCs deliver all signals necessary for adequate T cell priming. Hence, immunization with DC-based vaccines is of great interest in immunotherapy. One such approach is to conjugate antigens to carrier molecules that specifically target DCs.

In the present study, it was investigated if aptamers represent a promising novel class of DC-targeting carriers for immunotherapeutic applications. Aptamers are nucleic acids ligands that may adopt a defined three dimensional structure and bind with high affinity and specificity to their particular targets.

Herein, DC-binding aptamers were selected by two different strategies. First, aptamer CTL #5 was identified by addressing recombinant proteins originated from the murine mannose receptor (MR) in a protein-SELEX approach. The MR is an endocytic receptor crucial in recognizing, uptake and processing of antigens by DCs. Second, aptamers D #5 and D #7 were selected by directly using murine bone marrow-derived DCs as complex targets in a cell-SELEX process.

It was demonstrated that the selected aptamers exhibit all properties to function as suitable carriers. They bind specifically to DCs, are internalized and localized within adequate antigen processing compartments and have low immunogenicity.

Most importantly, the present study revealed that the selected aptamers are potent mediators of targeted activation of specific T cells. By using an ovalbumin (OVA) model system it was demonstrated that aptamer-based delivery of antigenic OVA peptides to DCs resulted in strong activation of OVA-specific CD4 or CD8 T cells.

In summary, the present invention demonstrates the applicability of aptamers as DC-targeting carriers for use as aptamer-based DC vaccines.

The Immune System:

The mammalian immune system is a complex network of organs, cells and proteins. It protects the host from invading pathogens like microorganisms and pollutants.

In general, the mammalian immune system is divided into innate and adaptive immunity. Initial defense mechanisms are mediated by the innate immunity. Various components like physical barriers, innate immune cells, antimicrobial proteins, complement and cytokines are involved in the rapid and relatively non-specific response towards broad classes of pathogenic structures.

A key feature of the innate immunity is the discrimination between self and non-self molecules. Monocytes, granulocytes, macrophages, dendritic cells (DCs) and natural killer cells, for example, recognize highly conserved pathogen-associated molecular patterns (PAMPs) by a range of pattern recognition receptors (PRRs). As a consequence, these cells degrade ingested pathogens and secrete cytokines and chemokines to promote inflammation. In turn, inflammation triggers the recruitment of more immune cells and antimicrobial molecules such as complement to the site of infection. Innate immune responses occur within the first 96 hours of infections and lead to the elimination of pathogens. The establishment of infection is thereby hampered or retarded.

If the innate immunity is evaded or overwhelmed, an adaptive immune response is required. Adaptive immune responses take days rather than hours to develop and result in protective immunological memory formation. Consequently, upon exposure to the same antigen, an amplified immune response is induced.

Specialized lymphocytes, namely B and T cells, are the effector cells of adaptive immunity. They are activated by cells involved in innate immunity and realize highly antigen-specific immunity. One discriminates between humoral and T cell-mediated immunity. Activated B cells differentiate into antibody-producing plasma cells and execute humoral immunity, whereby T cell-mediated immunity is initiated by activated T cells. Activation of T cells is the critical event of most adaptive immune responses.

T Cell-Mediated Immunity:

The transition between innate and adaptive immune responses is mediated by specialized immune cells. These cells, including dendritic cells, macrophages and B cells, are termed professional antigen-presenting cells (APCs). The interaction of APCs with T cells in peripheral lymphoid tissues, i.e. lymph nodes, spleen and mucosal-associated lymphoid tissues, initiates T cell-mediated immunity.

During cell development, every T cell is equipped with a specific T cell receptor (TCR) that recognizes a single antigenic structure bound to major histocompatibility complex (MHC) molecules present on the surface of an activated APC. Remarkably, every mammalian organism expresses millions of different TCR gene variants. On the plasma membrane TCR pairs with CD4 or CD8 co-receptors.

Figure 1:
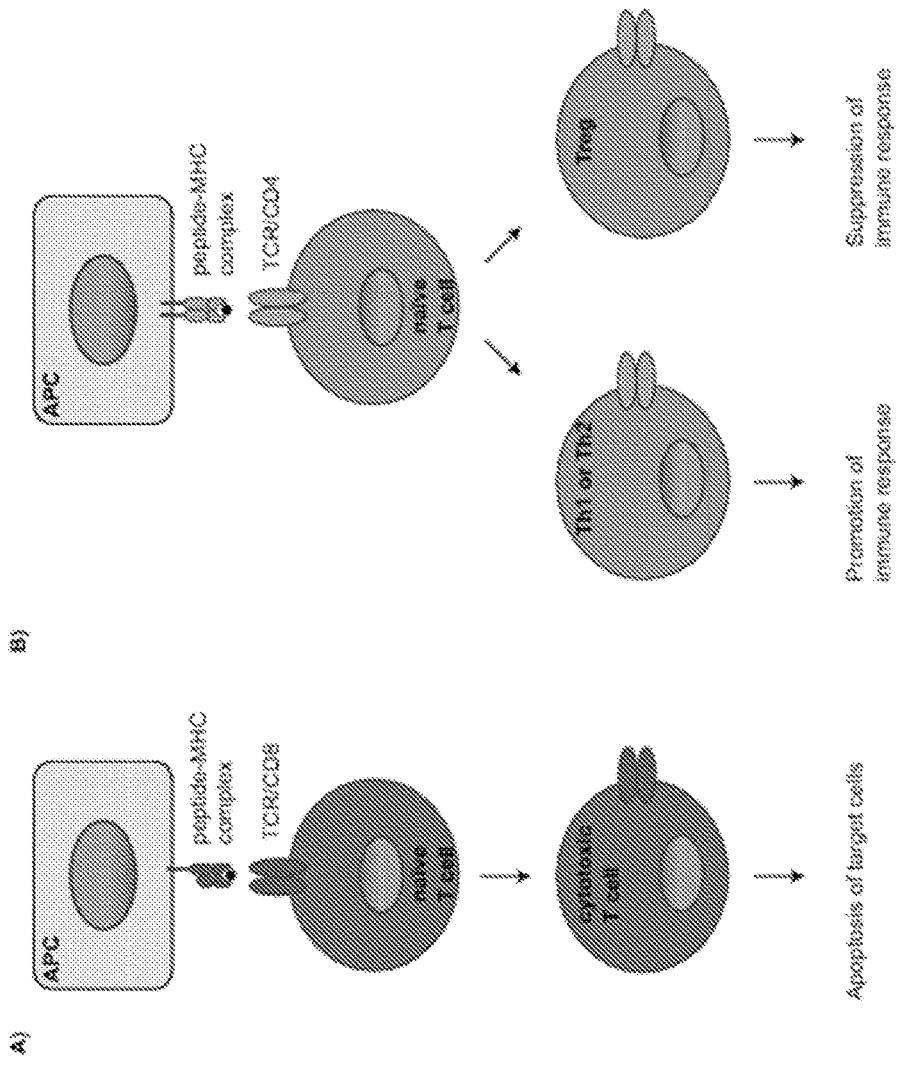
FIGS. 1A-B: Schematic representation of the differentiation of T cells. Upon recognition of the respective peptide-MHC complex on an activated APC, naïve CD8 (A) or CD4 (B) T cells undergo differentiation. CD8 T cells acquire cytotoxic capacity and induce apoptosis of target cells, whereas CD4 T cells differentiate into either activating T helper 1 (Th1) or Th2 or suppressing regulatory T cells (Treg).

Naïve T cells continuously circulate through peripheral lymphoid tissues to encounter their appropriate peptide-MHC complex presented on an activated APC. Consequently, T cells undergo clonal expansion and differentiation into highly antigen-specific CD4 or CD8 effector T cells. Activated CD8 T cells acquire cytotoxic capability, whereas CD4 T cells polarize into either activator or suppressor cells5 (FIG. 1A-B).

Cytotoxic CD8 T cells mediate apoptosis of target cells expressing the respective antigen-MHC complex; in doing so, they either interact with death receptors such as Fas or directly release cytotoxic granules like perform and granzymes.

Activating CD4 T helper 1 (Th1) or Th2 cells promote the differentiation of B cells into antibody-producing plasma cells or enhance the development of cytotoxic CD8 T cells, while suppressing regulatory CD4 T cells negatively regulate the activation of T cells.

T Cell Priming:

Three signals are necessary for adequate T cell priming. First, the convenient peptide-MHC complex is recognized by TCR/CD4 or TCR/CD8 molecules. Second, interaction of co-stimulatory molecules, e.g. CD28:CD80/CD86 or 4-1BB:4-1BBL, initiate signaling cascades which trigger activation, differentiation and survival of T cells. Third, inflammatory cytokines like IL-12 and IFN-α/β polarize the differentiation of T cells into effector cells8. Furthermore, activated T cells upregulate the expression of IL-2 receptors (IL-2R) and IL-2, which in turn promote their proliferation and differentiation. Long-term effector function of T cells requires prolonged signaling of all three activation signals.

Incomplete activated T cells become tolerant. Consequently, T cells undergo clonal anergy or deletion. T cell anergy describes the induced unresponsive state of T cells; in other words, these cells fail to develop effector functions and additionally become refractory to activation by the respective antigen even if adequate activation signals are present. Apart from that, some incomplete activated T cells undergo clonal deletion through activation-induced cell death initiated by e.g. Fas/Fas ligand-mediated apoptosis. After a brief period of activation and cell division, these T cells experience apoptosis. Both mechanisms, anergy and deletion, are thought to maintain the peripheral self-tolerance of mammals.

After an infection is effectively repelled, some effector T cells undergo apoptosis and are rapidly cleared by cells of the innate immunity. However, a small population of effector cells persists as so-called memory T cells. These cells mediate long-lasting immunological protection for a certain antigen. Upon re-infection, memory T cells induce immediate and amplified immune responses.

Figure 2:
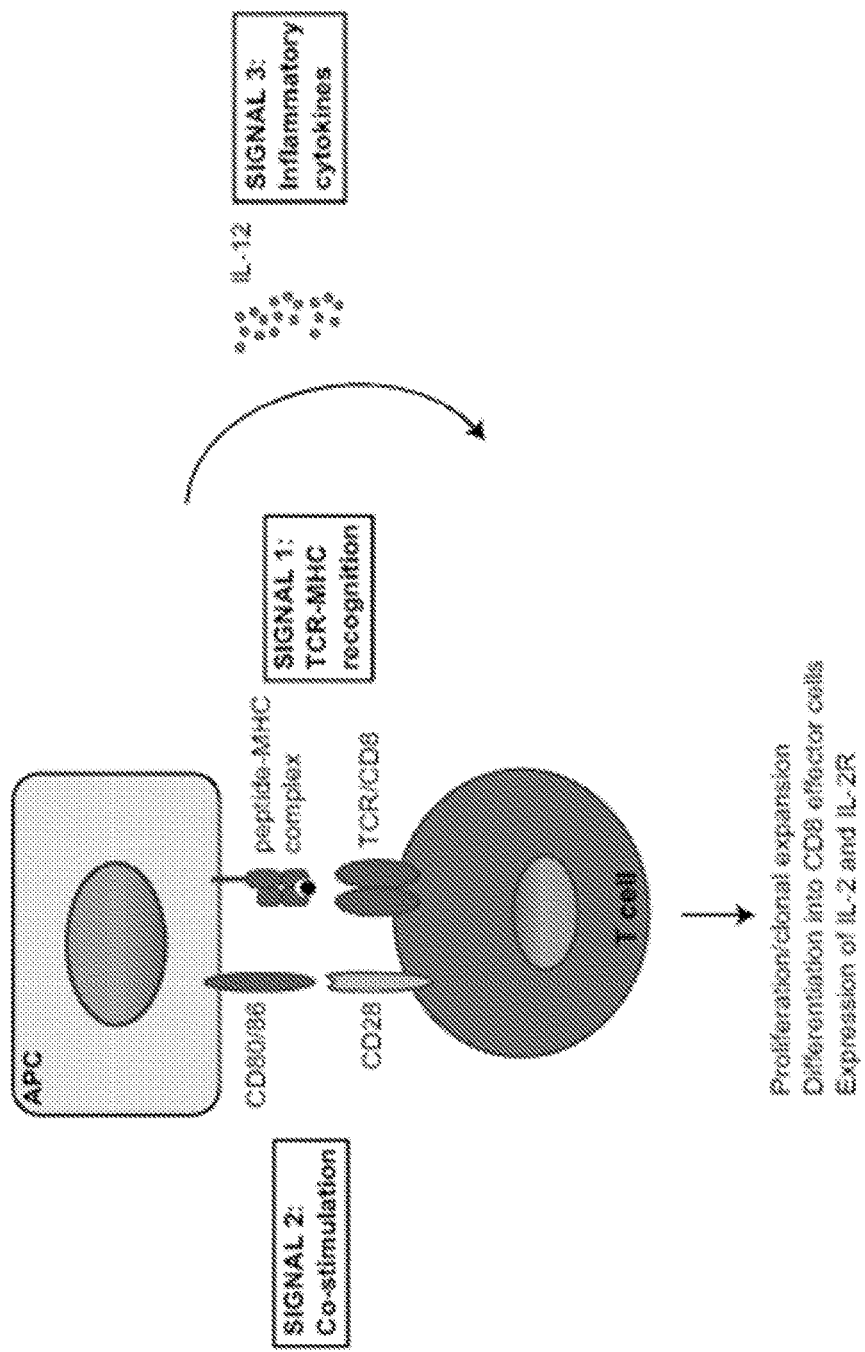
FIG. 2: Schematic representation of the priming of T cells. Efficient T cell priming requires three signals delivered by an APC. First, the respective antigen bound to MHC molecules is presented by the APC and recognized by the TCR and, in this example, a CD8 co-receptor. Second, co-stimulatory molecules like CD80/CD86 and CD28 are expressed and interact. Third, the APC secretes inflammatory cytokines such as IL-12. The priming of T cells results in proliferation and clonal expansion, differentiation into effector cells and expression of IL-2 and IL-2R.

As previously stated, T cell-mediated immunity is initiated by the interaction of APCs with T cells. The underlying reason is that the three signals necessary for adequate T cell priming are only provided by activated APCs (FIG. 2). APCs are distributed all over the body and are thereby able to recognize pathogens invading through different routes. Antigens are captured, processed into T cell epitopes and subsequently loaded on MHC molecules to facilitate antigen presentation to T cells. The cells migrate to peripheral lymphoid tissues to enable the recognition of the peptide-MHC complex by rare T cell clones expressing the TCR specific for that particular peptide (signal 1). High levels of co-stimulatory molecules such as CD80/CD86 are only expressed on the surface of activated APCs and interact with a binding molecule, e.g. CD28, on the T cell side (signal 2). Signal 3 is delivered through secretion of inflammatory cytokines, e.g. IL-12, by the APC8. After the T cell received all three signals, it migrates to the side of infection and executes its effector function.

Dendritic Cells:

It is generally accepted that dendritic cells (DCs) are the most potent T cell activators among the APCs. DCs link the unspecific innate immunity to the antigen-specific adaptive immunity by priming T cells.

DCs originate from both myeloid and lymphoid progenitors within the bone marrow. Under non-inflammatory steady-state conditions immature DCs reside in most tissues and continuously sample a wide array of pathogens. Consequent to inflammatory stimuli, DCs mature into professional APCs and thus acquire capability to initiate T cell-mediated immunity.

Figure 3:
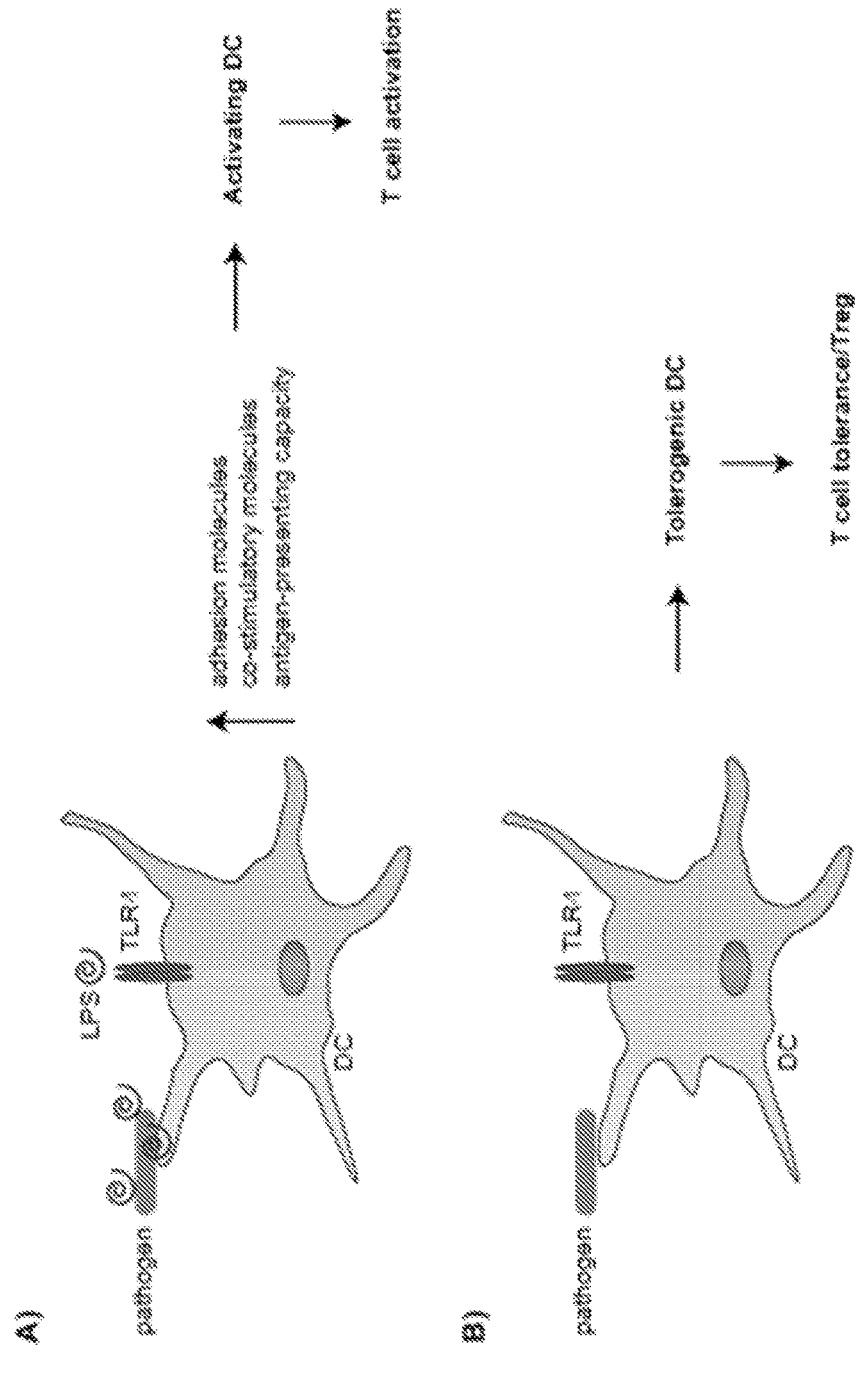
FIG. 3A-B: Schematic representation of the maturation of DCs. Immature DCs recognize a wide array of pathogens. Dependent on the presence (A) or absence (B) of inflammatory stimuli such as lipopolysaccharides (LPS), DCs polarize into activating or tolerogenic DCs. The TLR4 ligand LPS triggers the expression of adhesion and co-stimulatory molecules and enhance the antigen-presenting capacity. Activating DCs activate T cells, whereas tolerogenic DCs induce T cell tolerance or the differentiation of T cells into regulatory T cells (Treg).

Maturation of DCs is induced by activation of PRRs such as Toll-like receptors (TLRs) or tumor necrosis factor (TNF) receptors like CD40. For instance, microbial agents like lipopolysaccharides (LPS) are recognized by TLR4, which in turn triggers downstream signaling for DC maturation. As a result, DCs undergo radical functional and morphological changes; they up-regulate adhesion and co-stimulatory molecules and increase their antigen-presenting capacity 16. Mature DCs migrate subsequently to peripheral lymphoid tissues to present peptide-MHC complexes to T cells (FIG. 3A).

In the absence of inflammatory stimuli, DCs become tolerogenic upon pathogen recognition. Tolerogenic DCs are deficient in adequate signaling for T cell activation or they only deliver co-inhibitory signals. Consequently, T cells become tolerant or polarize into regulatory T cells (FIG. 3B).

Figure 4:
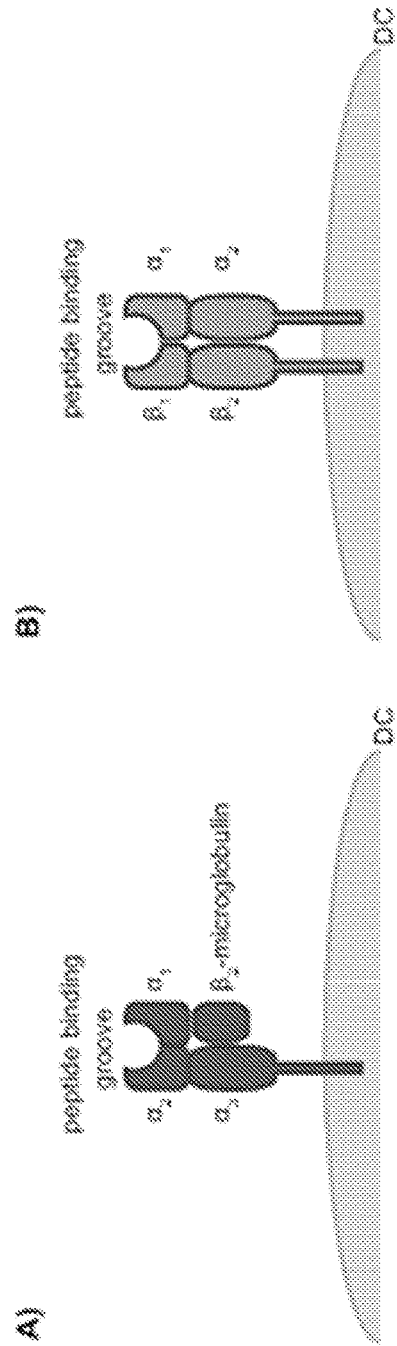
FIG. 4A-B: Schematic representation of the MHC molecules. MHC class I (A) or class II (B) molecules are composed of two non-covalently associated polypeptide chains. The MHC I molecule consists of an α chain and a β2-microglobulin and its peptide binding groove is formed by the α1 and α2 domains of the α chain. The α3 domain spans the membrane. The MHC II molecule is composed of an α and a β chain. The α1 and β1 domains fold into the peptide binding groove, whereas α2 and β2 are connected to the cell membrane.

Antigen Presentation:

Depending on the entry route of pathogens into DCs, they are degraded into antigenic peptides in distinct cellular compartments and are loaded on either MHC class I (MHC I) or class II (MHC II) molecules. MHC molecules are glycoproteins encoded by genes known to be the most polymorphic in higher mammals. Every individual possesses multiple MHC molecules with highly variable peptide binding properties. Basically, MHC molecules consist of two different polypeptide chains. An MHC I molecule is composed of a membrane-spanning $\alpha$ chain which is non-covalently associated with a polypeptide termed $\beta 2$-microglobulin (FIG. 4A). The $\alpha$ chain is further subdivided into the $\alpha_1$, $\alpha_2$ and $\alpha_3$ domains and two of them, $\alpha_1$ and $\alpha_2$, form the peptide binding groove, whereas $\alpha_3$ is connected to the cell membrane.

MHC II molecules consist of two non-covalently associated transmembrane polypeptides, namely $\alpha$ and $\beta$ chains (FIG. 4B). Each chain has two domains and one domain of every chain, $\alpha_1$ and $\beta_1$, are part of the peptide binding groove. The $\alpha_2$ and $\beta_2$ domains span the membrane. The $\alpha$ chains of the MHC molecules are different polypeptides.

Peptide-MHC complexes are presented on the surface of maturated DCs to activate either CD8 or CD4 T cells.

Figure 5:
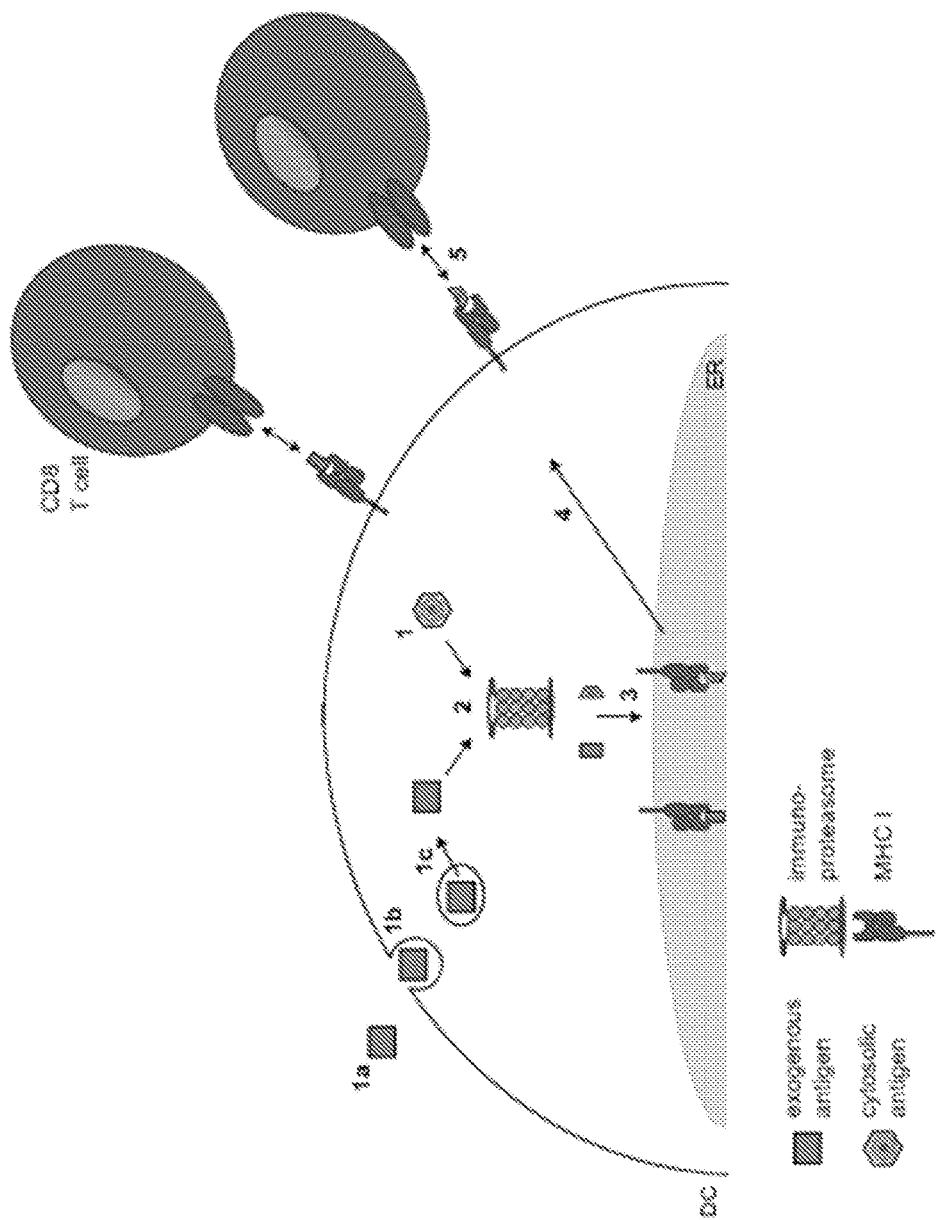
FIG. 5: Schematic representation of the MHC I pathway. In the classical MHC I pathway a cytosolic antigen (1) is degraded by the immunoproteasome (2) and loaded on MHC I molecules in the endoplasmic reticulum (ER) (3). Peptide-MHC I complexes are transported to the cell membrane (4) for the presentation to a CD8 T cell expressing the appropriate TCR (5). The alternative MHC I pathway is cross-presentation. An exogenous antigen (1a) is endocytosed (1b) and translocated out of the early endosome (1c) to encounter the immunoproteasome.

MHC I-Mediated Antigen Presentation to CD8 T Cells:

Processing of intracellular antigens originating from viruses or parasites, for example, starts within the cytosol. Here, a multi-catalytic protease complex, the immunoproteasome, degrades antigens in an ubiquitin-dependent manner. The peptides are subsequently shuttled into the endoplasmic reticulum (ER) and finally trimmed by endoplasmic reticulum aminopeptidase associated with antigen processing (ERAAP). The folding and complete assembly of the two chains of MHC I molecules and the antigenic peptides occurs within the ER. MHC I molecules preferentially bind peptides being 8-9 amino acids in length and having hydrophobic or basic residues at the C-terminus. Finally, the peptide-MHC I complex is transported to the cell membrane (FIG. 5).

In addition to the classical MHC I pathway, DCs are able to load exogenous antigens on MHC I molecules by a mechanism termed cross-presentation. During cross-presentation, extracellular antigens are recognized by endocytic receptors like the mannose receptor (MR) and internalized via clathrin-mediated endocytosis. The antigens are entrapped in slowly maturing early endosomes and are subsequently translocated into the cytosol for degradation by the immunoproteasome (FIG. 5).

MHC II-Mediated Antigen Presentation to CD4 T Cells:

The classical MHC II pathway facilitates the presentation of exogenous antigens to CD4 T cells. MHC class II expression is restricted to professional APCs.

Figure 6:
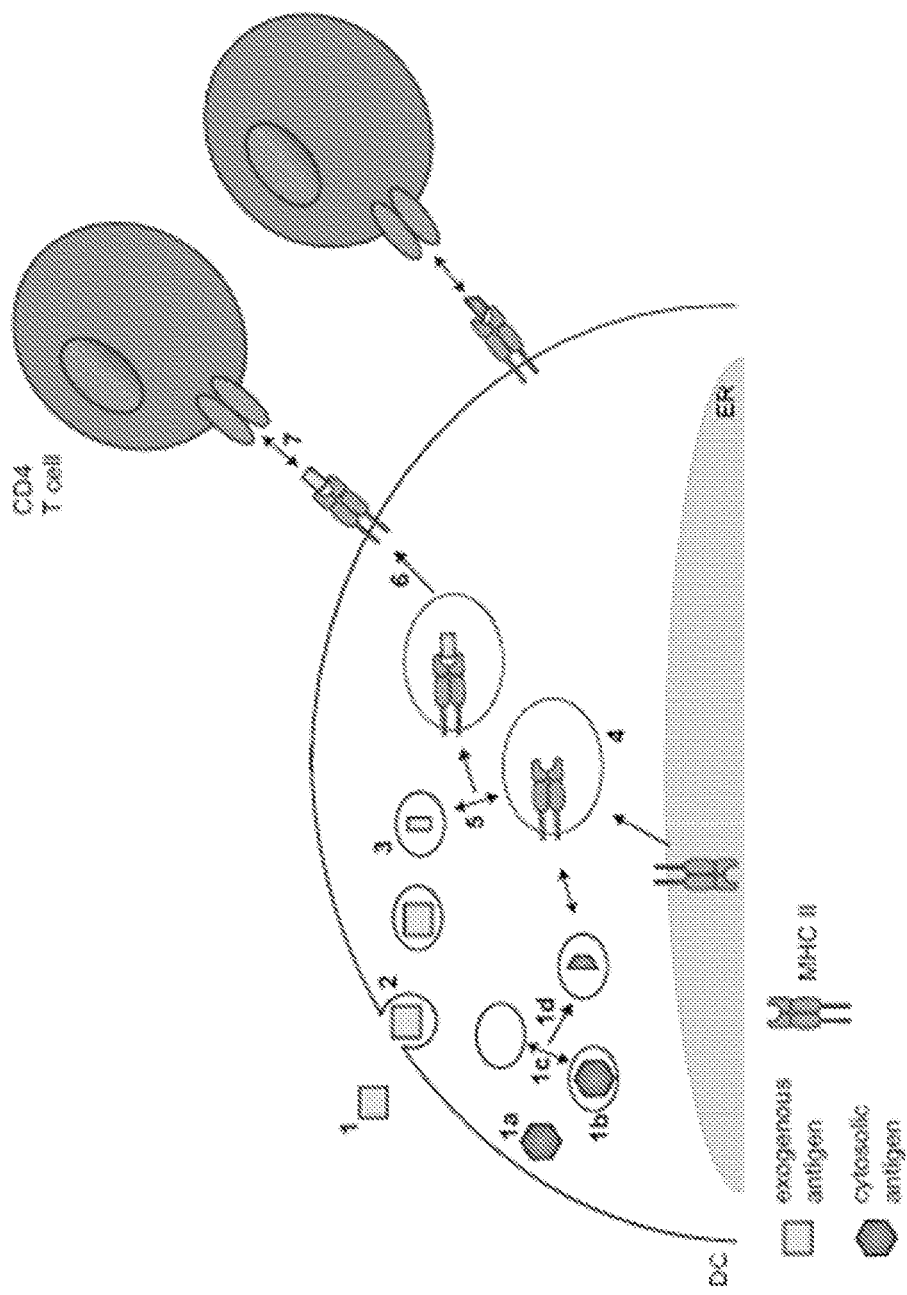
FIG. 6: Schematic representation of the MHC II pathway. In the classical MHC II pathway an exogenous antigen (1) is internalized (2) and processed into peptides inside late endosomes or lysosomes (3). MHC II molecules are formed in the endoplasmic reticulum (ER) and released within multivesicular bodies (MVBs) (4). MVBs subsequently fuse with the peptide-containing vesicle, where the peptide is loaded on the MHC II molecule (5). The peptide-MHC complex is translocated to the membrane (6) and presented to CD4 T cells (7). The alternative MHC II pathway is autophagy. A cytosolic antigen (1a) is entrapped by an autophagosome (1b) which fuses with late endosomes or lysosomes (1c). In accordance with the classical pathway, the antigen is degraded (1d) and the peptide-containing vesicle fuse with MVBs.

MHC II-restricted antigens are endocytosed by macropinocytosis, phagocytic or endocytic receptors, and are degraded in late endosomes or lysosomes. These late endolysosomal antigen-processing compartments are enriched in acid proteases like cathepsin S and L, and disulfide reductases. The two chains of MHC II molecules are assembled in the ER, the peptide binding groove is thereby blocked by a protein so-called the invariant chain, and the whole complex is enclosed and released within multivesicular bodies (MVBs). Subsequently, MVBs fuse with peptide-containing vesicles, the invariant chain is degraded and supplemented by the antigenic peptide. MHC II molecules bind peptides being at least 18 amino acids in length. In the end, the peptide-MHC II complex is inserted into the plasma membrane (FIG. 6).

The classical MHC II pathway can be bypassed by a process named autophagy. Cytosolic macromolecules and organelles that are entrapped within autophagosomes are delivered to late endolysosomal antigen-processing compartments for degradation (FIG. 6).

Internalization Mechanisms:

DCs feature various mechanisms to internalize pathogens; they practice phagocytosis, macropinocytosis and receptor-mediated clathrin-dependent endocytosis.

Macropinoctytosis or phagocytosis mediate the non-specific uptake of large quantities of extracellular fluids or macromolecules; solutes or large particles are thereby engulfed by plasma membrane protrusions and subsequently transported into endolysosomal compartments. However, phagocytosis can also be mediated by phagocytic receptors such as Fc receptors or scavenger receptor A.

Figure 7:
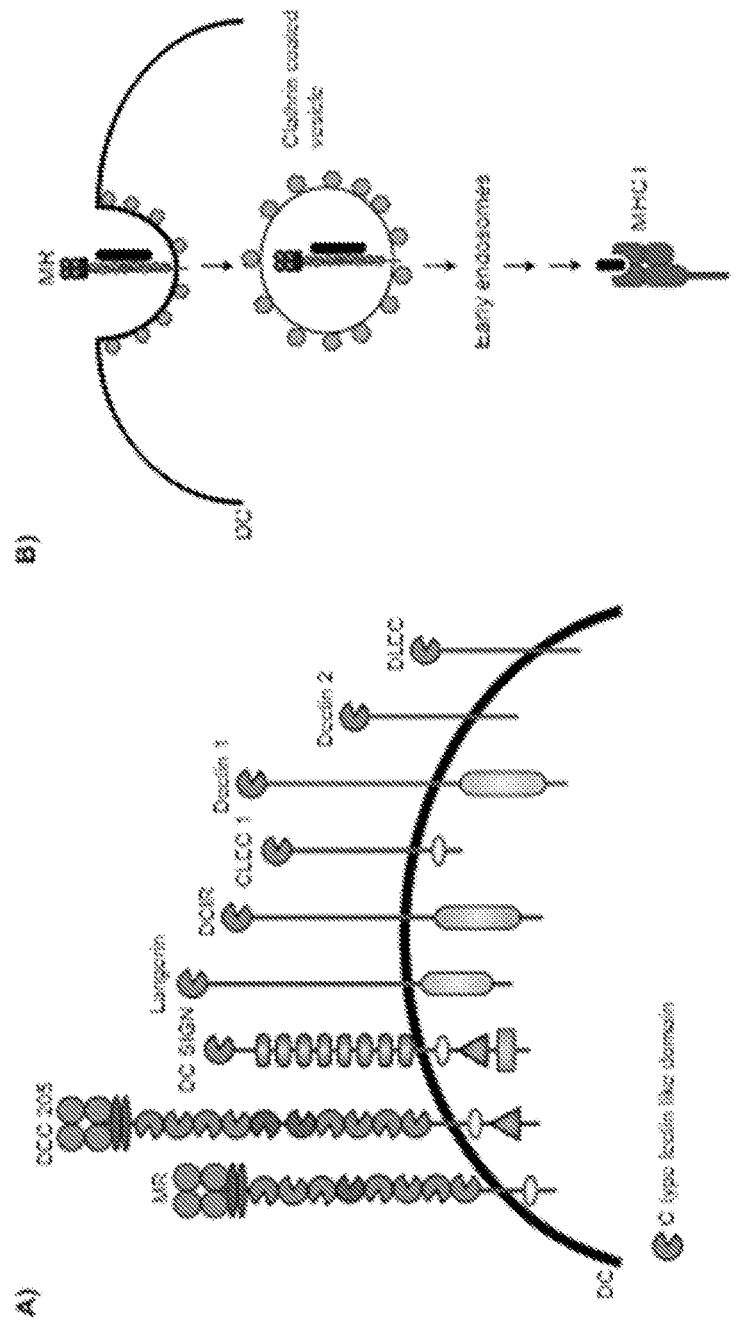
FIG. 7A-B: Schematic representation of C-type lectin receptors expressed on DCs and the MR-mediated clathrin-dependent endocytosis of pathogens. Several receptors composed of at least one C-type lectin-like domain are expressed on DCs (A) (modified from Figdor et al.). Upon ligand (black bar) binding to endocytic receptors, in this example the C-type lectin receptor mannose receptor (MR), the receptor-ligand complex is internalized by clathrin-dependent endocytosis into DCs (B). A clathrin-coated vesicle is formed and fuse subsequently with early endosomes for enabling cross-presentation on MHC I molecules. MR=mannose receptor; DEC-205=dendritic and epithelial cells, 205 kDa; DC-SIGN=DC specific ICAM-3 grabbing non-integrin; DLEC=DC lectin; DCIR=DC immunoreceptor; CLEC-1=C-type lectin receptor-1; Dectin=DC-associated C-type lectins

Moreover, DCs express a variety of endocytic receptors to facilitate specific clathrin-dependent endocytosis of pathogens. Prominent examples are receptors of the C-type lectin family like the mannose receptor (MR) or dendritic and epithelial cells 205 kDa (DEC-205) (FIG. 7A-B). C-type lectin receptors are non-canonical PRR that capture specific ligand structures, but fail to induce adequate signaling for DC maturation33. Basically, C-type lectins were identified to bind carbohydrates in a Ca2+-dependent manner using highly conserved C-type lectin like domains (CTLDs). For example, the MR is described to recognize glycan residues of various microorganisms such as *Candida albicans* and *Mycobacterium tuberculosis*. However, other C-type lectin receptors such as DEC-205 were reported to express non-classical CTLDs lacking the ability to bind carbohydrates31. The natural ligand for DEC-205 has not been defined yet.

Interestingly, the recognition and uptake of pathogens by C-type lectin receptors determine the subsequent processing and antigen presentation. For example, ligands internalized by the MR are entrapped in slowly maturing early endosomes for cross-presentation on MHC I molecules, whereas ligands taken up by DEC-205 are transported towards late endolysosomal antigen-processing compartments for presentation on MHC II molecules.

DCs as Targets for Immunotherapy:

The superior capacity of DCs in modifying downstream T cell responses has made them suitable targets in the development of vaccines for immunotherapeutic applications. DC-based vaccines are currently under investigation for the prevention and treatment of infections, cancer, allograft rejections or autoimmune diseases. To this end, DCs are either stimulated to become activating or tolerogenic (FIG. 3A-B). Immunologists follow different strategies to generate these immunocompetent DCs. DCs are either pulsed ex vivo with antigens or targeted in situ by different carriers coupled to antigens.

Autologous DCs are loaded ex vivo with antigens and reinfused into the patient. Depending on the kind of co-delivered stimuli, DCs develop an activating or tolerogenic phenotype.

To date, one DC-based vaccine, which is based on pulsed DCs, has been approved by the United States Food and Drug Administration (FDA). Sipuleucel-T, sold under the trade name Provenge®, is used in prostate cancer therapy. For this purpose, autologous APCs are isolated and activated ex vivo with the recombinant protein PA2024 consisting of prostatic acid phosphatase (PAP) fused to granulocyte macrophage colony-stimulating factor (GM-CSF). GM-CSF is a hematopoietic growth factor that initiates activation and maturation of DCs. Consequently, DCs up-regulate adhesion and co-stimulatory molecules and increase their antigen-presenting capacity. PAP is a prostate-derived enzyme which is often up-regulated in prostate cancers. Although the precise mechanism of action of sipuleucel-T is not defined yet, it was demonstrated that the PA2024 fusion protein is internalized, processed and presented by DCs. Upon re-infusion, a T cell-mediated anti-tumor immune response is initiated. Because of the high treatment costs of $104,534 (around € 93,000) for the three prescribed infusions, the marketing authorization of sipuleucel-T in the European Union was withdrawn by the European Commission in 2015.

Ex vivo generation of tolerant DCs has also been tested for the treatment of several autoimmune diseases. For example, DCs isolated from patients suffering multiple sclerosis were incubated with a tolerogenicity-inducing vitamin D 3 metabolite in addition to myelin peptides as specific self-antigen. As a result, DCs developed a tolerogenic phenotype and mediated anergy of myelin-reactive T cells.

Much work on the potential of ex vivo pulsed DCs has been carried out, however there are still some critical issues. For example, it is proven to be difficult to sufficiently recapitulate DC maturation ex vivo and ex vivo induced tolerogenicity of DCs was observed to be rapidly inverted into an activating phenotype after reinfusion into the patient. Moreover, treatments with ex vivo pulsed DCs can result in the development of severe autoimmune diseases.

Therefore, enabling DC-based vaccination in their natural environment in vivo is a major goal in the field of DC-based immunotherapy. For this purpose, carrier molecules were applied to deliver antigens specifically to DCs. Often, monoclonal antibodies targeting DC surface molecules such as C-type lectin receptors, are used and two are currently investigated in clinical trials (Table 3-1). For example, vaccination with the mannose receptor antibody CDX-1307 is currently tested in phase II clinical trial for the treatment of muscle-invasive bladder cancer. CDX-1307 consists of a human anti-MR monoclonal antibody fused to the human chorionic gonadotropin beta-chain, a tumor antigen frequently expressed by epithelial tumors. When co-administered with the hematopoietic growth factor GM-CSF and TLR agonists, CDX-1307 induces activation of APCs and subsequent activation of a T cell-mediated anti-tumor immune response.

Other molecules used for antigen delivery are nanoparticles, synthetic long peptides, receptor ligands, viruses, toxins and liposomes.

Even though more than 100 DC-targeting studies were published at the time of filing, efficient and specific delivery of antigens remains a challenge. The reasons are multifarious. Carriers like antibodies, viruses or toxins, for example, exhibit intrinsic immunostimulatory potential and, thus, increase the risk of adverse side effects. Furthermore, the design and development of some carrier molecules are pricey, time-consuming and associated with technical challenges. For example, the generation and screening of monoclonal antibodies is time-consuming and expensive and liposomal vesicles have critical stability issues. Moreover, the shelf-life of antibodies or proteins is limited and cell-based products like antibodies are difficult to process into clinical grade reagents with invariable quality. Last, liposomes and nanoparticles lack specificity for DCs and they are internalized by highly phagocytically active macrophages rather than by DCs. Accordingly, there is a need for eligible carriers and a promising alternative are nucleic acid ligands, known as aptamers.

TABLE 3-1

DC-targeting with C-type lectin receptor-binding antibodies

| Phase | Targeting strategy | Indication | Reference |
|---|---|---|---|
| I/II | MR Ab CDX-1307 fused with recombinant human chorionic gonadotropin beta-chain tumor antigen with/without GM-CSF and TLR 3 or 7/8 agonists | Advanced epithelial malignancies/Muscle-invasive bladder cancer | Morse et al. 2011, Morse et al. 2011 |
| I/II | DEC-205 Ab CDX-1401 fused with NY-ESO-1 tumor antigen with TLR3 or 7/8 agonists | Advanced malignancies/Ovarian, Fallopian Tube, Primary peritoneal cancer | Riedmann 2012, Dhodapkar et al. 2014 |
| Examples of antibodies used in pre-clinical studies: | | | |
| — | DEC-205 Ab fused with HIV gap 24 | HIV | Cheong et al. 2010, Idoyaga et al. 2011, Flynn et al. 2011 |
| — | DEC-205 Ab fused with mycobacterial ESX antigen | Tuberculosis | Dong et al. 2013 |
| — | DC-SIGN Ab fused to gp100/pmel17 tumor antigen | Melanoma | Tacken et al. 2008 |
| — | MR Ab fused with gp100/pmel17 tumor antigen | Melanoma | Ramakrishna et al. 2004 |
| — | Dectin-1 Ab fused to MART-1 tumor antigen | Melanoma | Ni et al. 2010 |

Ab = antibody

Figure 8:
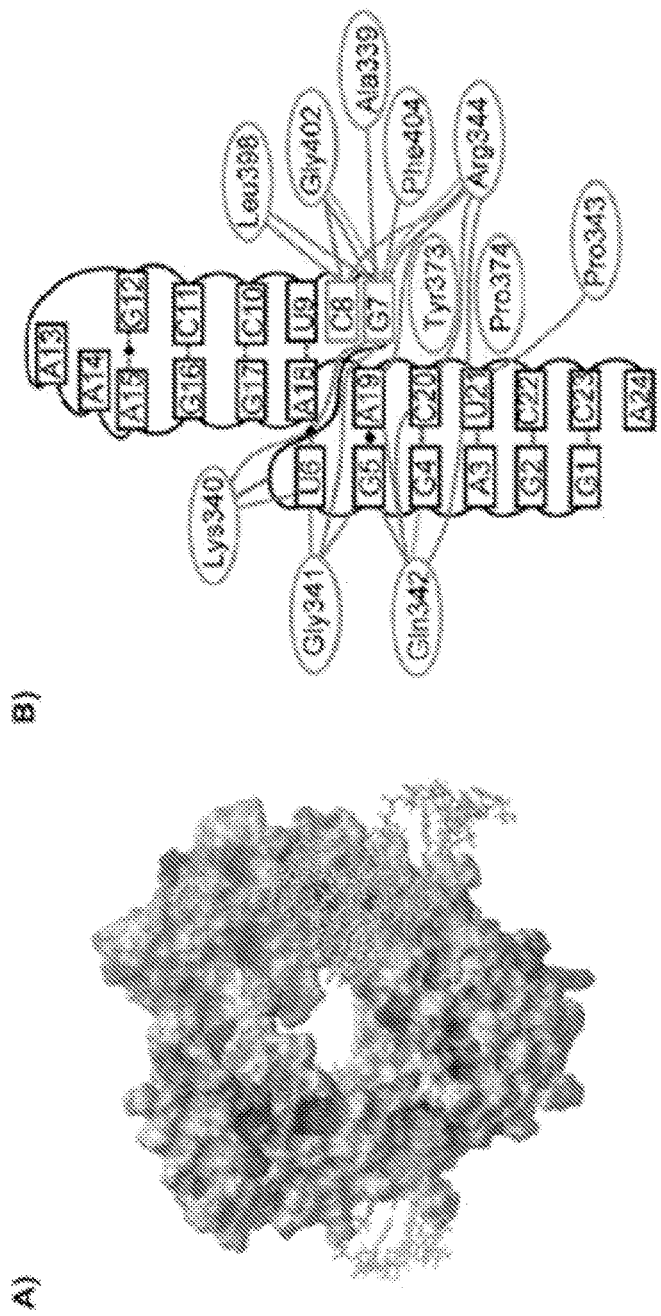
FIG. 8A-B: Interactions between aptamers and their targets. Aptamers bind to their target molecules via different intermolecular interactions. In this example, the structure of an aptamer bound to the Fc fragment of human IgGi (hIgGi Fc) is shown (A). The interactions between the nucleotides of the aptamer and the amino acids of hIgGi Fc are ion pairing, hydrogen bond formation, van der Waals forces and pi-stacking (B) (modified from Nomura et al.). (SEQ ID NO:68)

Aptamers:

In general, aptamers are nucleic acids, which bind target molecules with high specificity and affinity. They adopt unique conformations like stems, loops, hairpins or quadruplexes that enable the specific interaction with their targets. Aptamer-target interactions are mediated through pi-stacking of aromatic rings, electrostatic and van der Waals forces, or by hydrogen bond formation (FIG. 8A-B).

Figure 9:
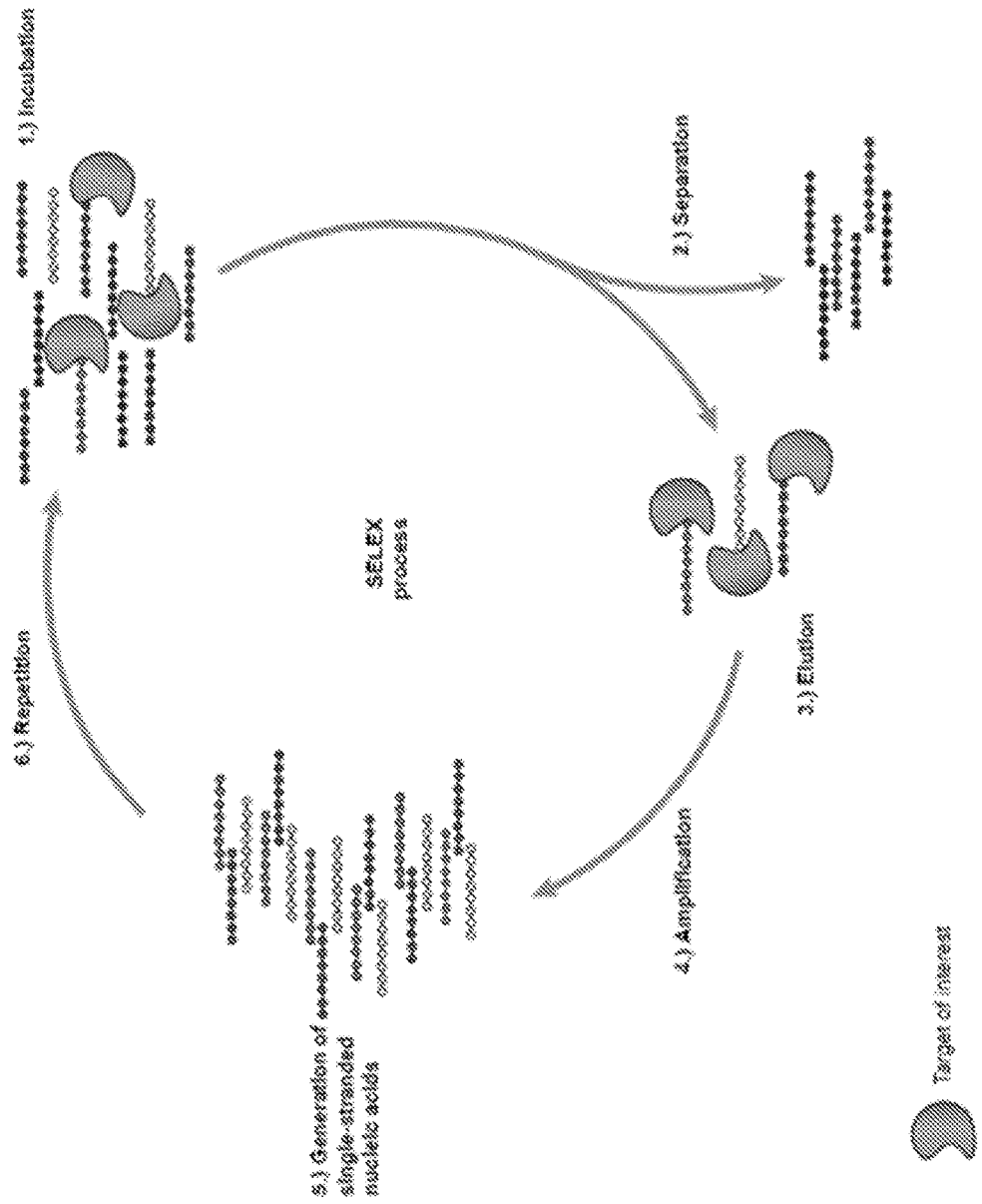
FIG. 9: Schematic representation of the SELEX process. Systematic evolution of ligands by exponential enrichment (SELEX) is carried out to identify high affinity aptamers. The SELEX process is initiated by incubating the target of interest with the naïve oligonucleotide library (1). The bound sequences are separated from the unbound (2), eluted from the target (3), amplified (4) and implemented as single-stranded oligonucleotides (5) in the next selection cycle (6).

Identification of Aptamers:

In 2015, the first identified aptamers celebrated their 25th anniversary. Tuerk & Gold and Ellington & Szostak both published the identification of the first nucleic acids-based ligands by a technique termed systematic evolution of ligands by exponential enrichment (SELEX). Briefly, target-binding nucleic acid sequences are enriched in an oligonucleotide library by iterative cycles of incubation, separation and amplification (FIG. 9). The starting point of a SELEX process is the incubation of the target of interest with the naïve oligonucleotide library. This oligonucleotide library is composed of a random region embedded between fixed primer binding sites. Next, background or target non-binding sequences are removed and the binders eluted from the target. To achieve that, the respective target is either immobilized on a matrix or the non-binders are removed by centrifugation, electrophoresis or flow cytometry. Elution is carried out either by denaturing conditions or, for instance, by using competitive molecules. The eluted sequences are amplified by polymerase chain reaction (PCR) and subsequently single-stranded nucleic acids are generated. Single chained RNA is easily obtained by in vitro transcription methods, whereas multiple methods are employed to separate double-stranded DNA. For example, biotin or phosphate moieties are introduced during PCR and used to separate the strands by biotin-streptavidin interaction or enzymatic cleavage, respectively. Finally, the resulting library of nucleic acid sequences is used in the next selection cycle.

To identify individual aptamers, the enriched nucleic acid libraries are inserted into bacterial vectors, transformed into bacteria and sequenced or they are analyzed by next-generation sequencing. For further analysis, selected aptamers are obtained by solid phase synthesis.

Cell-Binding Aptamers:

Aptamers have been developed for a plethora of target structures, ranging from small molecules to complex organisms. Nowadays, aptamers represent essential tools for fundamental research and bioanalytical diagnostics, and a growing number of aptamers are extensively investigated in pre-clinical studies. Moreover, a few aptamers are currently in clinical trials. In 2004 the first, and up to now only, aptamer-based drug was approved by the FDA. Aptamer NX1838, sold under the trade name Macugen®, is used for the therapy of age-related macular degeneration.

Overview on Aptamers that are Currently Tested in Clinical Trials:

Aptamers successfully tested in pre-clinical trials are now investigated in clinical trials for the treatments of different cancer types or diseases (see Sun et al.)

In recent years, there has been considerable interest in using aptamers recognizing mammalian cells. Cell-specific aptamers are identified by using purified cell surface proteins in a protein-SELEX approach or living cells in a cell-SELEX process. Mammalian cells express several accessible target structures on their surface. In cell-SELEX, membrane proteins maintain their native conformation and the consistent accessibility of the epitopes is warranted. Target molecules which are difficult to isolate from the cell surface can be addressed by this selection strategy. In addition, aptamers can be identified by a sole in vivo selection process. For example, aptamers targeting colon cancer cells were identified by injecting a modified RNA library into tumor-bearing mice for several selection cycles.

Cell-specific aptamers have several advantageous properties. Because of their nucleic acid composition, they can be easily modified to increase their chemical diversity and biological properties. Some modifications like unnatural base pairs or modified nucleobases are applied during aptamer selection, whereas others like disulfide or amino groups can be incorporated post-selectively.

Figure 10:
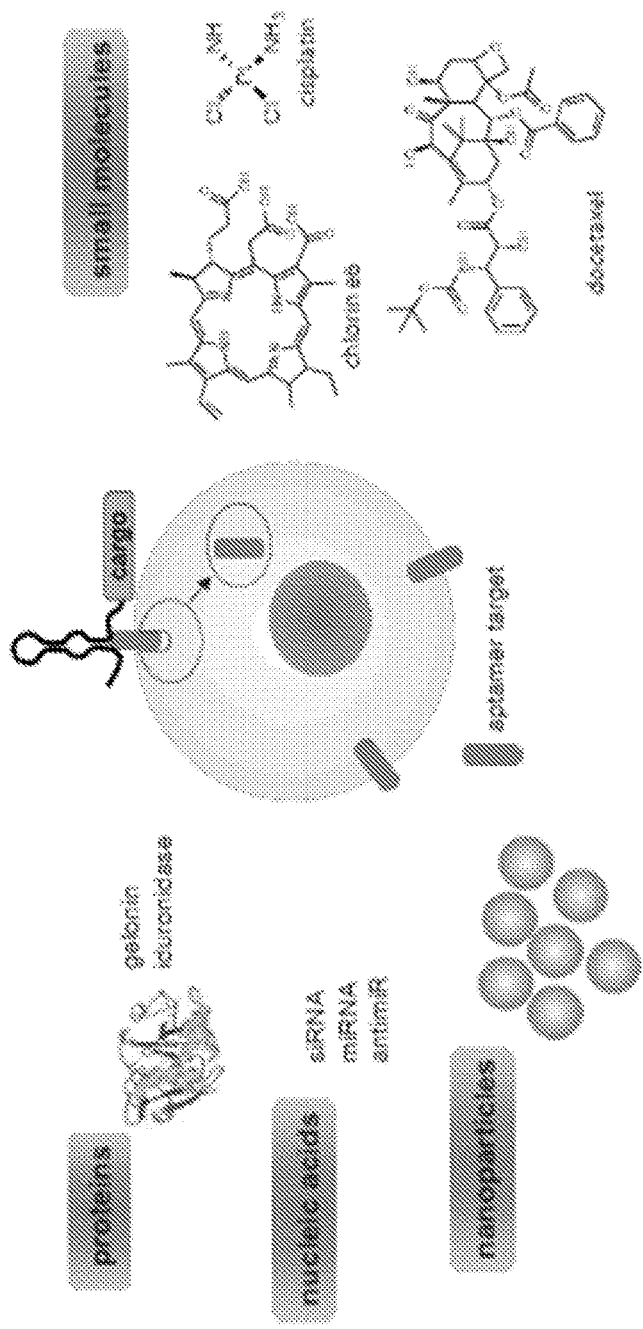
FIG. 10: Overview on cargo molecules delivered by cell-specific aptamers. Cell-specific aptamers can be conjugated to multiple cargo molecules for selective delivery approaches (modified from Mayer et al.).

A second property is that they represent promising delivery vehicles. They are often internalized by the respective cell and a variety of cargo molecules can be attached covalently or by hybridization. Indeed, several cargo molecules such as proteins or small molecules conjugated to cell-specific aptamers were effectively delivered and endocytosed (FIG. 10). The ribosomal toxin gelonin, for example, was selectively delivered to pancreas carcinoma cells upon conjugation to an aptamer.

Overview on Cargo Molecules Delivered by Cell-Specific Aptamers:

Cell-specific aptamers can be conjugated to multiple cargo molecules for selective delivery approaches (modified from Mayer et al.).

Moreover, studies in mammals elucidated low to no immunogenicity and toxicity of aptamers in vivo. The main reason for this is that the identified aptamers are obtained by cell-free solid phase synthesis, therefore they are free of contaminations derived from other species. The chemical synthesis warrants reproducibility, thus, leading to a reduced batch to batch variability.

However, chemical modifications are often required to increase the stability of aptamers for in vivo applications. Because of their small size and composition, aptamers are prone to be degraded by nucleases or rapidly removed by renal clearance. Addition of high-molecular weight compounds, for example, could slow down the clearance of aptamers. For instance, attached polyethylene glycol moieties increased the in vivo circulation half-life of a breast cancer targeting aptamer from 16 to 22 hours.

Considering the characteristics and possible applications, cell-specific aptamers are a promising alternative class of cell-targeting molecules that might overcome the limitations of other molecules used for immunotherapy so far.

Aptamers for Immunotherapeutic Applications:

In recent years there has been a considerable interest in identifying aptamer-based immunomodulatory ligands. Aptamers have been proven to function as inhibitors, agonists, opsonizing agents or antigen delivery tools for vaccination strategies.

One strategy of immunomodulation is to block immunosuppressive pathways and thereby circumvent tumor evasion mechanisms. Programmed cell death (PD-1) and cytotoxic T-lymphocyte-associated protein 4 (CTLA-4) are examples of receptors which negatively regulate T cell effector functions. Blocking aptamers have been identified to both receptors. These aptamers potentiated anti-cancer immunity in murine tumor models.

Another strategy of immunotherapy is to enhance T cell activation by applying receptor agonists. Besides recognition of antigen-MHC complex by TCR and triggering of cell differentiation by inflammatory cytokines, co-stimulatory signals are necessary for adequate priming of naïve T cells. 4-1BB is the major co-stimulatory receptor expressed on activated CD8 T cells. In 2008, McNamara et al. selected aptamers which function as natural ligands of 4-1BB and thereby boost T cell activation and survival.

A further attempt of immunomodulation is to opsonize cancer cells, in other words, to recruit T cells directly to the tumor site. On that account, 4-1BB aptamers were conjugated with prostate cancer-binding prostate-specific membrane antigen (PSMA) aptamers and thereby T cell co-stimulation at the tumor site was facilitated.

Although cell-specific aptamers are proven to be suitable carriers (FIG. 10), few researchers have addressed their ability to bind or to deliver antigens to DCs for vaccination strategies. Berezovski and co-workers enriched DNA libraries targeting either immature or mature murine bone marrow-derived DCs (BM-DCs) for the identification of cell state-specific biomarkers, but binding or functionality of individual aptamers was not examined. Hui et al. identified BM-DC-binding aptamers by using a recombinant protein of the C-type lectin receptor DC-SIGN in a SELEX approach. However, the inhibitory function of the aptamers on the adhesion of DCs to endothelial cells was investigated rather than their capability as delivery tools.

In 2014, aptamer-based antigen delivery was reported by Wengerter et al. Here, DC-targeting aptamers were selected against the C-type lectin receptor DEC-205 using a combinatorial approach of protein- and cell-SELEX. These aptamers were subsequently conjugated with ovalbumin (OVA) and reported to facilitate cross-presentation by DCs following CD8 T cell activation. In addition, multivalent aptamer-OVA conjugates were observed to induce CD8 cytotoxicity against OVA-expressing melanoma cells in vivo. Still, open questions remain. First and foremost, no investigations concerning CD4 T cell activation were done, although the used antigen OVA exhibits both MHC I- and MHC II-restricted epitopes. Second, there is no general agreement on DEC-205 mediated MHC I-restricted CD8 T cell activation. In other studies, it was demonstrated that targeting of DEC-205 boost MHC II-restricted CD4 T cell activation rather than CD8 T cell stimulation. Third, OVA was demonstrated to be internalized, processed and cross-presented by DCs in its natural unconjugated form. It is then questionable if the aptamers improve the effect of OVA on DCs and T cells.

One approach of DC-based immunotherapy is to deliver antigens specifically to DCs for efficient T cell activation. Several molecules like antibodies, viruses or nanoparticles are currently under investigation; however, antigen delivery to DCs remains a challenge.

The instant invention addresses the potential applicability of aptamers as a novel class of DC-targeting carriers for immunotherapeutic applications.

Two strategies were followed to identify DC-binding aptamers. First, purified membrane proteins were implemented in a protein-SELEX approach. In addition, DCs were directly used in a cell-SELEX process.

In protein-SELEX, specific membrane proteins can be chosen, because of their ability to facilitate presentation on MHC I or MHC II molecules. For example, the C-type lectin receptor MR is described to direct its ligands towards cross-presentation. Thus, aptamers specific for MR may be internalized into cellular compartments adequate for presentation on MHC I molecules. In cell-SELEX, the specific target structure is unknown. Nevertheless, aptamers could be identified for targets that enable presentation to T cells and that are not easy to isolate from the membrane.

Potential DC-based antigen delivery tools can be optimized to meet several criteria. For example, specific binding to DCs, internalization within adequate antigen processing compartments, and low to no immunogenicity. In addition, the aptamers should retain sufficient binding ability upon conjugation for delivery of desired antigens to DCs. Effective targeting of antigens to DCs should also result in activation of T cell-mediated immunity. To demonstrate the invention, an OVA model system was chosen and both targeted CD4 and CD8 T cell activation were analyzed.

Therapeutic Applications

As used herein "therapeutically effective amount" refers to an amount of a composition that relieves (to some extent, as judged by a skilled medical practitioner) one or more symptoms of a medical condition such as a disease or disorder in a subject. Additionally, by "therapeutically effective amount" of a composition is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered, such as intravenously, subcutaneously, intraperitoneally, orally, or through inhalation. The precise amount of the composition required to be therapeutically effective will depend upon numerous factors, e.g., such as the specific activity of the active agent, the delivery device employed, physical characteristics of the agent, purpose for the administration, in addition to many patient specific considerations. But a determination of a therapeutically effective amount is within the skill of an ordinarily skilled clinician upon the appreciation of the disclosure set forth herein.

The terms "treating," "treatment," "therapy," and "therapeutic treatment" as used herein refer to curative therapy, prophylactic therapy, or preventative therapy. An example of "preventative therapy" is the prevention or lessening the chance of a targeted disease (e.g., cancer or other proliferative disease) or related condition thereto. Those in need of treatment include those already with the disease or condition as well as those prone to have the disease or condition to be prevented. The terms "treating," "treatment," "therapy," and "therapeutic treatment" as used herein also describe the management and care of a mammal for the purpose of combating a disease, or related condition, and includes the administration of a composition to alleviate the symptoms, side effects, or other complications of the disease, condition. Therapeutic treatment for cancer includes, but is not limited to, surgery, chemotherapy, radiation therapy, gene therapy, and immunotherapy.

As used herein, the term "agent" or "drug" or "therapeutic agent" refers to a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug can be purified, substantially purified or partially purified. An "agent" as used herein also includes a radiation therapy agent or a "chemotherapuetic agent."

As used herein, the term "diagnostic agent" refers to any chemical used in the imaging of diseased tissue, such as, e.g., a tumor.

As used herein, the term "chemotherapuetic agent" refers to an agent with activity against cancer, neoplastic, and/or proliferative diseases, or that has ability to kill cancerous cells directly.

As used herein, "pharmaceutical formulations" include formulations for human and veterinary use with no significant adverse toxicological effect. "Pharmaceutically acceptable formulation" as used herein refers to a composition or formulation that allows for the effective distribution of the nucleic acid molecules described herein in the physical location most suitable for their desired activity.

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated.

Aptamer Conjugates as a Cancer Therapeutics

Previous work has developed the concept of antibody-toxin conjugates ("immunoconjugates") as potential therapies for a range of indications, mostly directed at the treatment of cancer with a primary focus on hematological tumors. A variety of different payloads for targeted delivery have been tested in pre-clinical and clinical studies, including protein toxins, high potency small molecule cytotoxics, radioisotopes, and liposome-encapsulated drugs. While these efforts have successfully yielded several FDA-approved therapies for hematological tumors, immunoconjugates as a class (especially for solid tumors) face challenges that have been attributable to multiple different properties of antibodies, including tendencies to develop neutralizing antibody responses to non-humanized antibodies, limited penetration in solid tumors, loss of target binding affinity as a result of toxin conjugation, and imbalances between antibody half-life and toxin conjugate half-life that limit the overall therapeutic index (reviewed by Reff and Heard, Critical Reviews in Oncology/Hematology, 40 (2001):25-35).

Aptamers are functionally similar to antibodies in target recognition, although their absorption, distribution, metabolism, and excretion ("ADME") properties are intrinsically different and they generally lack many of the immune effector functions generally associated with antibodies (e.g., antibody-dependent cellular cytotoxicity, complement-dependent cytotoxicity). In comparing many of the properties of aptamers and antibodies previously described, several factors suggest that toxin-delivery via aptamers offers several concrete advantages over delivery with antibodies, ultimately affording them better potential as therapeutics. Several examples of the advantages of toxin-delivery via aptamers over antibodies are as follows:

1) Aptamer-toxin conjugates are entirely chemically synthesized. Chemical synthesis provides more control over the nature of the conjugate. For example, the stoichiometry (ratio of toxins per aptamer) and site of attachment can be precisely defined. Different linker chemistries can be readily tested. The reversibility of aptamer folding means that loss of activity during conjugation is unlikely and provides more flexibility in adjusting conjugation conditions to maximize yields.

2) Smaller size allows better tumor penetration. Poor penetration of antibodies into solid tumors is often cited as a factor limiting the efficacy of conjugate approaches. See Colcher, D., Goel, A., Pavlinkova, G., Beresford, G., Booth, B., Batra, S. K. (1999) "Effects of genetic engineering on the pharmacokinetics of antibodies," Q. J. Nucl. Med., 43: 132-139. Studies comparing the properties of unPEGylated anti-tenascin C aptamers with corresponding antibodies demonstrate efficient uptake into tumors (as defined by the tumor:blood ratio) and evidence that aptamer localized to the tumor is unexpectedly long-lived ($t_{1/2}$>12 hours) (Hicke, B. J., Stephens, A. W., "Escort aptamers: a delivery service for diagnosis and therapy", J. Clin. Invest., 106:923-928 (2000)).

3) Tunable PK. Aptamer half-life/metabolism can be more easily tuned to match properties of payload, optimizing the ability to deliver toxin to the tumor while minimizing systemic exposure. Appropriate modifications to the aptamer backbone and addition of high molecular weight PEGs should make it possible to match the half-life of the aptamer to the intrinsic half-life of the conjugated toxin/linker, minimizing systemic exposure to non-functional toxin-bearing metabolites (expected if $t_{1/2}$(aptamer)<<$t_{1/2}$(toxin)) and reducing the likelihood that persisting unconjugated aptamer will functionally block uptake of conjugated aptamer (expected if $t_{1/2}$(aptamer)>>$t_{1/2}$ (toxin)).

4) Relatively low material requirements. It is likely that dosing levels will be limited by toxicity intrinsic to the cytotoxic payload. As such, a single course of treatment will likely entail relatively small (<100 mg) quantities of aptamer, reducing the likelihood that the cost of oligonucleotide synthesis will be a barrier for aptamer-based therapies.

5) Parenteral administration is preferred for this indication. There will be no special need to develop alternative formulations to drive patient/physician acceptance.

The invention provides a pharmaceutical composition comprising a therapeutically effective amount of an aptamer provided herein or a salt thereof, and a pharmaceutically acceptable carrier or diluent. The invention also provides a pharmaceutical composition comprising a therapeutically effective amount of the aptamer or a salt thereof, and a pharmaceutically acceptable carrier or diluent. Relatedly, the invention provides a method of treating or ameliorating a disease or disorder, comprising administering the pharmaceutical composition to a subject in need thereof. As non-limiting examples, administering a therapeutically effective amount of the composition to the subject may result in: (a) an enhancement of the delivery of the active agent to a disease site relative to delivery of the active agent alone; (b) an enhancement of target clearance resulting in a decrease of at least 10%, 20%, 30%, 40%, 50%, 60%, 70%, 80%, or 90% in a blood level of target targeted by the aptamer; (c) a decrease in size of at least 10%, 20%, 30%, 40%, 50%, 60%, 70%, 80%, or 90% of a tumor targeted by the aptamer; or (d) an decrease in biological activity of targets of the aptamer of at least 10%, 20%, 30%, 40%, 50%, 60%, 70%, 80%, or 90%. In an embodiment, the biological activity of microvesicles comprises immune suppression or transfer of genetic information. The disease or disorder can include without limitation those disclosed herein. For example, the disease or disorder may comprise a neoplastic, proliferative, or inflammatory, metabolic, cardiovascular, or neurological disease or disorder.

In some embodiments, an aptamer described herein is modified to comprise at least one chemical modification. The modification may include without limitation a chemical substitution at a sugar position; a chemical substitution at a phosphate position; and a chemical substitution at a base position of the nucleic acid. In some embodiments, the modification is selected from the group consisting of: biotinylation, incorporation of a fluorescent label, incorporation of a modified nucleotide, a 2'-modified pyrimidine, 3' capping, conjugation to an amine linker, conjugation to a high molecular weight, non-immunogenic compound, conjugation to a lipophilic compound, conjugation to a drug, conjugation to a cytotoxic moiety, and labeling with a radioisotope, or other modification as disclosed herein. The position of the modification can be varied as desired. For example, the biotinylation, fluorescent label, or cytotoxic moiety can be conjugated to the 5' end of the aptamer. The biotinylation, fluorescent label, or cytotoxic moiety can also be conjugated to the 3' end of the aptamer.

In some embodiments, the cytotoxic moiety is encapsulated in a nanoparticle. The nanoparticle can be without limitation at least one of liposomes, dendrimers, and comb polymers. In other embodiments, the cytotoxic moiety comprises a small molecule cytotoxic moiety. The small molecule cytotoxic moiety can include without limtation vinblastine hydrazide, calicheamicin, vinca alkaloid, a cryptophycin, a tubulysin, dolastatin-10, dolastatin-15, auristatin E, rhizoxin, epothilone B, epithilone D, taxoids, maytansinoids and any variants and derivatives thereof. In still other embodiments, the cytotoxic moiety comprises a protein toxin. For example, the protein toxin can be selected from the group consisting of diphtheria toxin, ricin, abrin, gelonin, and *Pseudomonas* exotoxin A. Non-immunogenic, high molecular weight compounds for use with the compositions described herein include polyalkylene glycols, e.g., polyethylene glycol. Appropriate radioisotopes include yttrium-90, indium-111, iodine-131, lutetium-177, copper-67, rhenium-186, rhenium-188, bismuth-212, bismuth-213, astatine-211, and actinium-225. The aptamer may be labeled with a gamma-emitting radioisotope.

In some embodiments described herein, an active agent is conjugated to the aptamer. For example, the active agent may be a therapeutic agent or a diagnostic agent. The therapeutic agent may be selected from the group consisting of tyrosine kinase inhibitors, kinase inhibitors, biologically active agents, biological molecules, radionuclides, adriamycin, ansamycin antibiotics, asparaginase, bleomycin, busulphan, cisplatin, carboplatin, carmustine, capecotabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, melphalan, methotrexate, rapamycin (sirolimus), mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, transplatinum, anti-vascular endothelial growth factor compounds ("anti-VEGFs"), anti-epidermal growth factor receptor compounds ("anti-EGFRs"), 5-fluorouracil and derivatives, radionuclides, polypeptide toxins, apoptosis inducers, therapy sensitizers, enzyme or active fragment thereof, and combinations thereof.

to the active agent conjugated to the aptamer may be chosen to illicit a complement mediated immune response that can induce apoptosis. For example, the active agent region may comprise an oligonucleotide sequence including without limitation Toll-Like Receptor (TLR) agonists like CpG sequences which are immunostimulatory and/or polyG sequences which can be anti-proliferative or pro-apoptotic. The moiety can be vaccine like moiety or antigen that stimulates an immune response. In an embodiment, the immune stimulating moiety comprises a superantigen. In some embodiments, the superantigen can be selected from the group consisting of staphylococcal enterotoxins (SEs), a *Streptococcus pyogenes* exotoxin (SPE), a *Staphylococcus aureus* toxic shock-syndrome toxin (TSST-1), a streptococcal mitogenic exotoxin (SME), a streptococcal superantigen (SSA), a hepatitis surface antigen, or a combination thereof. Other bacterial antigens that can be used with the compositions and method described herein comprise bacterial antigens such as Freund's complete adjuvant, Freund's incomplete adjuvant, monophosphoryl-lipid A/trehalose dicorynomycolate (Ribi's adjuvant), BCG (Calmette-Guerin *Bacillus; Mycobacterium bovis*), and *Corynebacterium parvum*. The immune stimulating moiety can also be a non-specific immunostimulant, such as an adjuvant or other non-specific immunostimulator. Useful adjuvants comprise without limitation aluminium salts, alum, aluminium phosphate, aluminium hydroxide, squalene, oils, MF59, and AS03 ("Adjuvant System 03"). The adjuvant can be selected from the group consisting of Cationic liposome-DNA complex JVRS-100, aluminum hydroxide vaccine adjuvant, aluminum phosphate vaccine adjuvant, aluminum potassium sulfate adjuvant, Alhydrogel, ISCOM(s)™, Freund's Complete Adjuvant, Freund's Incomplete Adjuvant, CpG DNA Vaccine Adjuvant, Cholera toxin, Cholera toxin B subunit, Liposomes, Saponin Vaccine Adjuvant, DDA Adjuvant, Squalene-based Adjuvants, Etx B subunit Adjuvant, IL-12 Vaccine Adjuvant, LTK63 Vaccine Mutant Adjuvant, TiterMax Gold Adjuvant, Ribi Vaccine Adjuvant, Montanide ISA 720 Adjuvant, *Corynebacterium*-derived P40 Vaccine Adjuvant, MPL™ Adjuvant, ASO4, AS02, Lipopolysaccharide Vaccine Adjuvant, Muramyl Dipeptide Adjuvant, CRL1005, Killed *Corynebacterium parvum* Vaccine Adjuvant, Montanide ISA 51, *Bordetella pertussis* component Vaccine Adjuvant, Cationic Liposomal Vaccine Adjuvant, Adamantylamide Dipeptide Vaccine Adjuvant, Arlacel A, VSA-3 Adjuvant, Aluminum vaccine adjuvant, Polygen Vaccine Adjuvant, Adjumer™, Algal Glucan, Bay R1005, Theramide®, Stearyl Tyrosine, Specol, Algammulin, Avridine®, Calcium Phosphate Gel, CTA1-DD gene fusion protein, DOC/Alum Complex, Gamma Inulin, Gerbu Adjuvant, GM-CSF, GMDP, Recombinant hIFN-gamma/Interferon-g, Interleukin-1β, Interleukin-2, Interleukin-7, Sclavo peptide, Rehydragel LV, Rehydragel HPA, Loxoribine, MF59, MTP-PE Liposomes, Muramethide, Murapalmitine, D-Murapalmitine, NAGO, Non-Ionic Surfactant Vesicles, PMMA, Protein Cochleates, QS-21, SPT (Antigen Formulation), nanoemulsion vaccine adjuvant, AS03, Quil-A vaccine adjuvant, RC529 vaccine adjuvant, LTR192G Vaccine Adjuvant, *E. coli* heat-labile toxin, LT, amorphous aluminum hydroxyphosphate sulfate adjuvant, Calcium phosphate vaccine adjuvant, Montanide Incomplete Seppic Adjuvant, Imiquimod, Resiquimod, AF03, Flagellin, Poly(I:C), ISCOMATRIX®, Abisco-100 vaccine adjuvant, Albumin-heparin microparticles vaccine adjuvant, AS-2 vaccine adjuvant, B7-2 vaccine adjuvant, DHEA vaccine adjuvant, Immunoliposomes Containing Antibodies to Costimulatory Molecules, SAF-1, Sendai Proteoliposomes, Sendai-containing Lipid Matrices, Threonyl muramyl dipeptide (TMDP), Ty Particles vaccine adjuvant, Bupivacaine vaccine adjuvant, DL-PGL (Polyester poly (DL-lactide-co-glycolide)) vaccine adjuvant, IL-15 vaccine adjuvant, LTK72 vaccine adjuvant, MPL-SE vaccine adjuvant, non-toxic mutant E112K of Cholera Toxin mCT-E112K, and Matrix-S. Additional adjuvants that can be used with the aptamers described herein can be identified using the Vaxjo database. See Sayers S, Ulysse G, Xiang Z, and He Y. Vaxjo: a web-based vaccine adjuvant database and its application for analysis of vaccine adjuvants and their uses in vaccine development. Journal of Biomedicine and Biotechnology. 2012; 2012:831486. Epub 2012 Mar. 13. PMID: 22505817; violinet.org/vaxjo/. Other useful non-specific immunostimulators comprise histamine, interferon, transfer factor, tuftsin, interleukin-1, female sex hormones, prolactin, growth hormone vitamin D, deoxycholic acid (DCA), tetrachlorodecaoxide (TCDO), and imiquimod or resiquimod, which are drugs that activate immune cells through the toll-like receptor 7. An aptamer provided herein can be part of a construct that comprises more than one immunomodulating moiety, e.g., using segments that span CpG sequences which are immunostimulatory with complement directed segments that can stimulate apoptosis.

In various embodiments, the active agent conjugated to the aptamer comprises an antigenic moiety, such as an antigenic peptide. As non-limited examples, the antigenic peptide can be derived from a pathogen-associated antigen, a human self protein, a tumor antigen, or a vaccine antigen. As desired, the at least one antigenic peptide comprises an MHC-I and MHC-II restricted antigen. The aptamer can be conjugated to more than one antigenic peptide as desired.

In some embodiments, the immune stimulating moiety is formulated in a pharmaceutical composition with the aptamer provided herein. The aptamer may be conjugated with immunomodulating active agents and also formulated in a composition comprising immunomodulating adjuvants as desired.

Modifications

Modifications to the aptamer provided herein can be made to alter desired characteristics, including without limitation in vivo stability, specificity, affinity, avidity or nuclease susceptibility. Alterations to the half life may improve stability in vivo or may reduce stability to limit in vivo toxicity. Such alterations can include mutations, truncations or extensions. The 5' and/or 3' ends of the aptamer constructs can be protected or deprotected to modulate stability as well. Modifications to improve in vivo stability, specificity, affinity, avidity or nuclease susceptibility or alter the half life to influence in vivo toxicity may be at the 5' or 3' end and include but are not limited to the following: locked nucleic acid (LNA) incorporation, unlocked nucleic acid (UNA) incorporation, phosphorothioate backbone instead of phosphodiester backbone, amino modifiers (i.e. C6-dT), dye conjugates (Cy dues, Fluorophores, etc), Biotinylation, PEG linkers, Click chemistry linkers, dideoxynucleotide end blockers, inverted end bases, cholesterol TEG or other lipid based labels.

Linkage options for segments of the aptamer described herein can be on the 5' or 3' end of an oligonucleotide or to a primary amine, sulfhydryl or carboxyl group of an antibody and include but are not limited to the following: Biotin-target oligonucleotide/Ab, streptavidin-complement oligonucleotide or vice versa, amino modified-target Ab/oligonucleotide, thiol/carboxy-complement oligonucleotide or vice versa, Click chemistry-target Ab/oligonucleotide, corresponding Click chemistry partner-complement oligonucleotide or vice versa. The linkages may be covalent or non-covalent and may include but are not limited to monovalent, multivalent (i.e. bi, tri or tetra-valent) assembly, to a DNA scaffold (i.e. DNA origami structure), drug/chemotherapeutic agent, nanoparticle, microparticle or a micelle or liposome.

A linker region can comprise a spacer with homo- or multifunctional reactive groups that can vary in length and type. These include but are not limited to the following: spacer C18, PEG4, PEG6, PEG8, and PEG12.

The aptamer provided herein can further comprise additional elements to add desired biological effects. For example, the aptamer described herein may comprise a membrane disruptive moiety. The aptamer described herein may also be conjugated to one or more chemical moiety that provides such effects. For example, the aptamer may be conjugated to a detergent-like moiety to disrupt the membrane of a target cell or microvesicle. Useful ionic detergents include sodium dodecyl sulfate (SDS, sodium lauryl sulfate (SLS)), sodium laureth sulfate (SLS, sodium lauryl ether sulfate (SLES)), ammonium lauryl sulfate (ALS), cetrimonium bromide, cetrimonium chloride, cetrimonium stearate, and the like. Useful non-ionic (zwitterionic) detergents include polyoxyethylene glycols, polysorbate 20 (also known as Tween 20), other polysorbates (e.g., 40, 60, 65, 80, etc), Triton-X (e.g., X100, X114), 3-[(3-cholamidopropyl) dimethylammonio]-1-propanesulfonate (CHAPS), CHAPSO, deoxycholic acid, sodium deoxycholate, NP-40, glycosides, octyl-thio-glucosides, maltosides, and the like. One of skill will appreciate that functional fragments, such as membrance disruptive moieties, can be covalently or non-covalently attached to the aptamer as desired.

Oligonucleotide segments, including those of aaptamer construct, can include any desirable base modification known in the art. In certain embodiments, oligonucleotide segments are 10 to 50 nucleotides in length. One having ordinary skill in the art will appreciate that this embodies oligonucleotides of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range derivable there within.

In certain embodiments, the aptamer provided herein comprises a chimeric oligonucleotide that contains two or more chemically distinct regions, each made up of at least one nucleotide. Such chimeras can be referred to using terms such as multipartite, multivalent, or the like. The oligonucleotides portions may contain at least one region of modified nucleotides that confers one or more beneficial properties, e.g., increased nuclease resistance, bioavailability, increased binding affinity for the target. Chimeric nucleic acids provided herein may be formed as composite structures of two or more oligonucleotides, two or more types of oligonucleotides (e.g., both DNA and RNA segments), modified oligonucleotides, oligonucleosides and/or oligonucleotide mimetics. Such compounds have also been referred to in the art as hybrids. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

In certain embodiments, an aptamer described herein comprises at least one nucleotide modified at the 2' position of the sugar, including without limitation a 2'-O-alkyl, 2'-O-alkyl-O-alkyl or 2'-fluoro-modified nucleotide. In other embodiments, RNA modifications include 2'-fluoro, 2'-amino and 2' O-methyl modifications on the ribose of pyrimidines, a basic residue or an inverted base at the 3' end of the RNA. Such modifications are routinely incorporated into oligonucleotides and these oligonucleotides have been shown to have higher target binding affinity in some cases than 2'-deoxyoligonucleotides against a given target.

A number of nucleotide and nucleoside modifications have been shown to make an oligonucleotide more resistant to nuclease digestion, thereby prolonging in vivo half-life. Specific examples of modified oligonucleotides include those comprising backbones comprising, for example, phosphorothioates, phosphotriesters, methyl phosphonates, short chain alkyl or cycloalkyl intersugar linkages or short chain heteroatomic or heterocyclic intersugar linkages. The aptamerprovided herein can comprise oligonucleotides with phosphorothioate backbones and/or heteroatom backbones, e.g., CH2-NH—0-CH2, CH, ~N(CH3)~0~CH2 (known as a methylene(methylimino) or MMI backbone], CH2-O—N (CH3)-CH2, CH2-N(CH3)-N(CH3)-CH2 and O—N(CH3)-CH2-CH2 backbones, wherein the native phosphodiester backbone is represented as O—P—O—CH,); amide backbones (De Mesmaeker et ah, 1995); morpholino backbone structures (Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone (Nielsen, et al., 1991), each of which is herein incorporated by reference in its entirety. Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3*-5* to 5*-3* or 2*-5* to 5*-2*; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety. Morpholino-based oligomeric compounds are known in the art described in Braasch & Corey, Biochemistry vol. 41, no. 14, 2002, pages 4503-4510; Genesis vol. 30, 2001, page 3; Heasman, J. Dev. Biol. vol. 243, 2002, pages 209-214; Nasevicius et al. Nat. Genet. vol. 26, 2000, pages 216-220; Lacerra et al. Proc. Natl. Acad. Sci. vol. 97, 2000, pages 9591-9596 and U.S. Pat. No. 5,034,506, issued Jul. 23, 1991, each of which is herein incorporated by reference in its entirety. Cyclohexenyl nucleic acid oligonucleotide mimetics are described in Wang et al., J. Am. Chem. Soc. Vol. 122, 2000, pages 8595-8602, the contents of which is incorporated herein in its entirety. An aptamer described herein can comprise at least such modification as desired.

Modified oligonucleotide backbones that do not include a phosphorus atom therein have backbones that can be formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety. An aptamer described herein can comprise at least such modification as desired.

In certain embodiments, an oligonucleotide aptamer described herein comprises one or more substituted sugar moieties, e.g., one of the following at the 2' position: OH, SH, $SCH_3$, F, OCN, $OCH_3$ $OCH_3$, $OCH_3$ $O(CH2)n$ $CH_3$, $O(CH_2)n$ $NH_2$ or $O(CH_2)n$ $CH_3$ where n is from 1 to about 10; Ci to CIO lower alkyl, alkoxyalkoxy, substituted lower alkyl, alkaryl or aralkyl; CI; Br; CN; $CF_3$; $OCF_3$; O-, S-, or N-alkyl; O-, S-, or N-alkenyl; $SOCH_3$; $SO_2$ $CH_3$; $ONO_2$; N O$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacokinetic/pharmacodynamic properties of an oligonucleotide and other substituents having similar properties. A useful modification includes 2'-methoxyethoxy [2'-0-CH2CH2OCH3, also known as 2'-0-(2-methoxyethyl)]. Other preferred modifications include 2*-methoxy (2*-0-CH3), 2*-propoxy (2*-OCH2 CH2CH3) and 2*-fiuoro (2*-F). Similar modifications may also be made at other positions on the oligonucleotide, e.g., the 3' position of the sugar on the 3' terminal nucleotide and the 5' position of 5' terminal nucleotide. Oligonucleotides may also have sugar mimetics such as cyclobutyls in place of the pentofuranosyl group.

In certain embodiments, an oligonucleotide aptamer described herein comprises one or more base modifications and/or substitutions. As used herein, "unmodified" or "natural" bases include adenine (A), guanine (G), thymine (T), cytosine (C) and uracil (U). Modified bases include, without limitation, bases found only infrequently or transiently in natural nucleic acids, e.g., hypoxanthine, 6-methyladenine, 5-Me pyrimidines, particularly 5-methylcytosine (also referred to as 5-methyl-2' deoxy cytosine and often referred to in the art as 5-Me-C), 5-hydroxymethylcytosine (HMC), glycosyl HMC and gentobiosyl HMC, as well as synthetic bases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine (Kornberg, 1980; Gebeyehu, et ah, 1987). A "universal" base known in the art, e.g., inosine, can also be included. 5-Me-C substitutions can also be included. These have been shown to increase nucleic acid duplex stability by 0.6-1.20C. See, e.g., Sanghvi et al., 'Antisense Research & Applications', 1993, CRC PRESS pages 276-278. Further suitable modified bases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

It is not necessary for all positions in a given oligonucleotide to be uniformly modified, and in fact more than one of the aforementioned modifications may be incorporated in a single oligonucleotide or even at within a single nucleoside within an oligonucleotide.

In certain embodiments, both a sugar and an internucleoside linkage, i.e., the backbone, of one or more nucleotide units within an oligonucleotide described herein are replaced with novel groups. The base can be maintained for hybridization with an appropriate nucleic acid target compound. One such oligomeric compound, an oligonucleotide mimetic that has been shown to retain hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al. Science vol. 254, 1991, page 1497, which is herein incorporated by reference.

In certain embodiments, the oligonucleotide aptamer described herein is linked (covalently or non-covalently) to one or more moieties or conjugates that enhance activity, cellular distribution, or localization. Such moieties include, without limitation, lipid moieties such as a cholesterol moiety (Letsinger et al. Proc. Natl. Acad. Sci. Usa. vol. 86, 1989, pages 6553-6556), cholic acid (Manoharan et al. Bioorg. Med. Chem. Let. vol. 4, 1994, pages 1053-1060), a thioether, e.g., hexyl-S-tritylthiol (Manoharan et al. Ann. N. Y. Acad. Sci. Vol. 660, 1992, pages 306-309; Manoharan et al. Bioorg. Med. Chem. Let. vol. 3, 1993, pages 2765-2770), a thiocholesterol (Oberhauser et al. Nucl. Acids Res. vol. 20, 1992, pages 533-538), an aliphatic chain, e.g., dodecandiol or undecyl residues (Kabanov et al. Febs Lett. vol. 259, 1990, pages 327-330; Svinarchuk et al. Biochimie. vol. 75, 1993, pages 49-54), a phospholipid, e.g., di-hexadecyl-rac-glycerol or triethylammonium 1,2-di-O-hexadecyl-rac-glycero-3-H-phosphonate (Manoharan et al. Tetrahedron Lett. vol. 36, 1995, pages 3651-3654; Shea et al. Nucl. Acids Res. vol. 18, 1990, pages 3777-3783), a polyamine or a polyethylene glycol chain (Mancharan et al. Nucleosides & Nucleotides vol. 14, 1995, pages 969-973), or adamantane acetic acid (Manoharan et al. Tetrahedron Lett. vol. 36, 1995, pages 3651-3654), a palmityl moiety (Mishra et al. Biochim. Biophys. Acta vol. 1264, 1995, pages 229-237), or an octadecylamine or hexylamino-carbonyl-t oxycholesterol moiety (Crooke et al. J. Pharmacol. Exp. Ther. vol. 277, 1996, pages 923-937), each of which is herein incorporated by reference in its entirety. See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety.

The oligonucleotide aptamer described herein can be modified to incorporate a wide variety of modified nucleotides as desired. For example, the construct may be synthesized entirely of modified nucleotides or with a subset of modified nucleotides. The modifications can be the same or different. Some or all nucleotides may be modified, and those that are modified may contain the same modification. For example, all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). Thus, the construct may comprise any combination of desired modifications, including for example, ribonucleotides (2'-OH), deoxyribonucleotides (2'-deoxy), 2'-amino nucleotides (2'-NH2), 2'-fluoro nucleotides (2'-F) and 2'-0-methyl (2'-OMe) nucleotides.

In some embodiments, the oligonucleotide aptamer described herein is synthesized using a transcription mixture containing modified nucleotides in order to generate a modified construct. For example, a transcription mixture may contain only 2'-OMe A, G, C and U and/or T triphosphates (2'-OMe ATP, 2'-OMe UTP and/or 2*-OMe TTP, 2*-OMe CTP and 2*-OMe GTP), referred to as an MNA or mRmY mixture. Oligonucleotides generated therefrom are referred to as MNA oligonucleotides or mRmY oligonucleotides and contain only 2'-0-methyl nucleotides. A transcription mixture containing all 2'-OH nucleotides is referred to as an "rN" mixture, and oligonucleotides generated therefrom are referred to as "rN", "rRrY" or RNA oligonucleotides. A transcription mixture containing all deoxy nucleotides is referred to as a "dN" mixture, and oligonucleotides generated therefrom are referred to as "dN", "dRdY" or DNA oligonucleotides. Aternatively, a subset of nucleotides (e.g., C, U and/or T) may comprise a first modified nucleotides (e.g, 2'-OMe) nucleotides and the remainder (e.g., A and G) comprise a second modified nucleotide (e.g., 2'-OH or 2'-F). For example, a transcription mixture containing 2'-F U and 2'-OMe A, G and C is referred to as a "fUmV" mixture, and oligonucleotides generated therefrom are referred to as "fUmV" oligonucleotides. A transcription mixture containing 2'-F A and G, and 2'-OMe C and U and/or T is referred to as an "fRmY" mixture, and oligonucleotides generated therefrom are referred to as "fRmY" oligonucleotides. A transcription mixture containing 2'-F A and 2'-OMe C, G and U and/or T is referred to as "fAmB" mixture, and oligonucleotides generated therefrom are referred to as "fAmB" oligonucleotides.

One of skill in the art can improve various characteristics of pre-identified aptamer segments (e.g., variable/binding regions or immunomodulatory regions that comprise an aptamer to a biomarker target or other entity) using various process modifications. Examples of such process modifications include, but are not limited to, truncation, deletion, substitution, or modification of a sugar or base or internucleotide linkage, capping, and PEGylation. In addition, the sequence requirements of an aptamer may be explored through doped reselections or aptamer medicinal chemistry. Doped reselections are carried out using a synthetic, degenerate pool that has been designed based on the aptamer of interest. The level of degeneracy usually varies from about 70-85% from the aptamer of interest. In general, sequences with neutral mutations are identified through the doped reselection process. Aptamer medicinal chemistry is an aptamer improvement technique in which sets of variant aptamers are chemically synthesized. These variants are then compared to each other and to the parent aptamer. Aptamer medicinal chemistry is used to explore the local, rather than global, introduction of substituents. For example, the following modifications may be introduced: modifications at a sugar, base, and/or internucleotide linkage, such as 2'-deoxy, 2'-ribo, or 2'-0-methyl purines or pyrimidines, phosphorothioate linkages may be introduced between nucleotides, a cap may be introduced at the 5' or 3' end of the aptamer (such as 3' inverted dT cap) to block degradation by exonucleases, or a polyethylene glycol (PEG) element may be added to the aptamer to increase the half-life of the aptamer in the subject.

Compositions comprising an aptamer described herein and uses thereof are further described below.

Pharmaceutical Compositions

In an aspect, the pharmaceutical compositions described herein comprise one or more aptamer described herein, e.g., as a standalone drug, as a drug delivery agent, or any combination thereof. Provided herein are methods of administering such compositions.

The term "condition," as used herein means an interruption, cessation, or disorder of a bodily function, system, or organ. Representative conditions include, but are not limited to, diseases such as cancer, inflammation, diabetes, and organ failure.

The phrase "treating," "treatment of," and the like include the amelioration or cessation of a specified condition.

The phrase "preventing," "prevention of," and the like include the avoidance of the onset of a condition.

The term "salt," as used herein, means two compounds that are not covalently bound but are chemically bound by ionic interactions.

The term "pharmaceutically acceptable," as used herein, when referring to a component of a pharmaceutical composition means that the component, when administered to an animal, does not have undue adverse effects such as excessive toxicity, irritation, or allergic response commensurate with a reasonable benefit/risk ratio. Accordingly, the term "pharmaceutically acceptable organic solvent," as used herein, means an organic solvent that when administered to an animal does not have undue adverse effects such as excessive toxicity, irritation, or allergic response commensurate with a reasonable benefit/risk ratio. Preferably, the pharmaceutically acceptable organic solvent is a solvent that is generally recognized as safe ("GRAS") by the United States Food and Drug Administration ("FDA"). Similarly, the term "pharmaceutically acceptable organic base," as used herein, means an organic base that when administered to an animal does not have undue adverse effects such as excessive toxicity, irritation, or allergic response commensurate with a reasonable benefit/risk ratio.

The phrase "injectable" or "injectable composition," as used herein, means a composition that can be drawn into a syringe and injected subcutaneously, intraperitoneally, or intramuscularly into an animal without causing adverse effects due to the presence of solid material in the composition. Solid materials include, but are not limited to, crystals, gummy masses, and gels. Typically, a formulation or composition is considered to be injectable when no more than about 15%, preferably no more than about 10%, more preferably no more than about 5%, even more preferably no more than about 2%, and most preferably no more than about 1% of the formulation is retained on a 0.22 μm filter when the formulation is filtered through the filter at 98° F. There are, however, some compositions described herein, which are gels, that can be easily dispensed from a syringe but will be retained on a 0.22 μm filter. In some embodiments, the term "injectable," as used herein, includes these gel compositions. In some embodiments, the term "injectable," as used herein, further includes compositions that when warmed to a temperature of up to about 40° C. and then filtered through a 0.22 μm filter, no more than about 15%, preferably no more than about 10%, more preferably no more than about 5%, even more preferably no more than about 2%, and most preferably no more than about 1% of the formulation is retained on the filter. In some embodiments, an example of an injectable pharmaceutical composition is a solution of a pharmaceutically active compound (for example, one or more oligonucleotide described herein, e.g., a multipartite construct, an anti-C1Q oligonucleotide, a 10.36 oligonucleotide, as described above, or any combination thereof) in a pharmaceutically acceptable solvent. One of skill will appreciate that injectable solutions have inherent properties, e.g., sterility, pharmaceutically acceptable excipients and free of harmful measures of pyrogens or similar contaminants.

The term "solution," as used herein, means a uniformly dispersed mixture at the molecular or ionic level of one or more substances (solute), in one or more other substances (solvent), typically a liquid.

The term "suspension," as used herein, means solid particles that are evenly dispersed in a solvent, which can be aqueous or non-aqueous.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human. In some embodiments, the animal is a mammal. In some embodiments, the animal is a human. In some embodiments, the animal is a non-human. In some embodiments, the animal is a canine, a feline, an equine, a bovine, an ovine, or a porcine.

The phrase "drug depot," as used herein means a precipitate, which includes one or more oligonucleotide described herein, e.g., a multipartite construct, an anti-C1Q oligonucleotide, a 10.36 oligonucleotide, as described above, or any combination thereof, formed within the body of a treated animal that releases the oligonucleotide over time to provide a pharmaceutically effective amount of the oligonucleotide.

The phrase "substantially free of," as used herein, means less than about 2 percent by weight. For example, the phrase "a pharmaceutical composition substantially free of water" means that the amount of water in the pharmaceutical composition is less than about 2 percent by weight of the pharmaceutical composition.

The term "effective amount," as used herein, means an amount sufficient to treat or prevent a condition in an animal.

The nucleotides that make up the oligonucleotide aptamers described herein can be modified to, for example, improve their stability, i.e., improve their in vivo half-life, and/or to reduce their rate of excretion when administered to an animal. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Modified nucleotides may also include 2' substituted sugars such as 2'-O-methyl-; 2'-O-alkyl; 2'-O-allyl; 2'-S-alkyl; 2'-S-allyl; 2'-fluoro-; 2'-halo or 2'-azido-ribose; carbocyclic sugar analogues; α-anomeric sugars; and epimeric sugars such as arabinose, xyloses or lyxoses, pyranose sugars, furanose sugars, and sedoheptulose.

Modified nucleotides are known in the art and include, but are not limited to, alkylated purines and/or pyrimidines; acylated purines and/or pyrimidines; or other heterocycles. These classes of pyrimidines and purines are known in the art and include, pseudoisocytosine; N4,N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyladenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; and 1-methylcytosine.

An oligonucleotide aptamer described herein can also be modified by replacing one or more phosphodiester linkages with alternative linking groups. Alternative linking groups include, but are not limited to embodiments wherein P(O)O is replaced by P(O)S, P(S)S, P(O)NR2, P(O)R, P(O)OR', CO, or CH2, wherein each R or R' is independently H or a substituted or unsubstituted C1-C20 alkyl. A preferred set of R substitutions for the P(O)NR2 group are hydrogen and methoxyethyl. Linking groups are typically attached to each adjacent nucleotide through an —O— bond, but may be modified to include —N— or —S— bonds. Not all linkages in an oligomer need to be identical.

The oligonucleotide aptamer described herein can also be modified by conjugation to a polymer, for example, to reduce the rate of excretion when administered to an animal. For example, the oligonucleotide can be "PEGylated," i.e., conjugated to polyethylene glycol ("PEG"). In some embodiments, the PEG has an average molecular weight ranging from about 20 kD to 80 kD. Methods to conjugate an oligonucleotide with a polymer, such PEG, are known to those skilled in the art (See, e.g., Greg T. Hermanson, Bioconjugate Techniques, Academic Press, 1966).

The oligonucleotide described herein can be used in the pharmaceutical compositions disclosed herein or known in the art.

In some embodiments, the pharmaceutical composition further comprises a solvent.

In some embodiments, the solvent comprises water.

In some embodiments, the solvent comprises a pharmaceutically acceptable organic solvent. Any useful and pharmaceutically acceptable organic solvents can be used in the compositions described herein.

In some embodiments, the pharmaceutical composition is a solution of the salt in the pharmaceutically acceptable organic solvent.

In some embodiments, the pharmaceutical composition comprises a pharmaceutically acceptable organic solvent and further comprises a phospholipid, a sphingomyelin, or phosphatidyl choline. Without wishing to be bound by theory, it is believed that the phospholipid, sphingomyelin, or phosphatidyl choline facilitates formation of a precipitate when the pharmaceutical composition is injected into water and can also facilitate controlled release of the oligonucleotide from the resulting precipitate. Typically, the phospholipid, sphingomyelin, or phosphatidyl choline is present in an amount ranging from greater than 0 to 10 percent by weight of the pharmaceutical composition. In some embodiments, the phospholipid, sphingomyelin, or phosphatidyl choline is present in an amount ranging from about 0.1 to 10 percent by weight of the pharmaceutical composition. In some embodiments, the phospholipid, sphingomyelin, or phosphatidyl choline is present in an amount ranging from about 1 to 7.5 percent by weight of the pharmaceutical composition. In some embodiments, the phospholipid, sphingomyelin, or phosphatidyl choline is present in an amount ranging from about 1.5 to 5 percent by weight of the pharmaceutical composition. In some embodiments, the phospholipid, sphingomyelin, or phosphatidyl choline is present in an amount ranging from about 2 to 4 percent by weight of the pharmaceutical composition.

The pharmaceutical compositions provided herein can optionally comprise one or more additional excipients or additives to provide a dosage form suitable for administration to an animal. When administered to an animal, the oligonucleotide containing pharmaceutical compositions are typically administered as a component of a composition that comprises a pharmaceutically acceptable carrier or excipient so as to provide the form for proper administration to the animal. Suitable pharmaceutical excipients are described in Remington's Pharmaceutical Sciences 1447-1676 (Alfonso R. Gennaro ed., 19th ed. 1995), incorporated herein by reference. The pharmaceutical compositions can take the form of solutions, suspensions, emulsion, tablets, pills, pellets, capsules, capsules containing liquids, powders, suppositories, emulsions, aerosols, sprays, suspensions, or any other form suitable for use.

In some embodiments, the pharmaceutical compositions are formulated for intravenous or parenteral administration. Typically, compositions for intravenous or parenteral administration comprise a suitable sterile solvent, which may be an isotonic aqueous buffer or pharmaceutically acceptable organic solvent. Where necessary, the compositions can also include a solubilizing agent. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where oligonucleotide-containing pharmaceutical compositions are to be administered by infusion, they can be dispensed, for example, with an infusion bottle containing, for example, sterile pharmaceutical grade water or saline. Where the pharmaceutical compositions are administered by injection, an ampoule of sterile water for injection, saline, or other solvent such as a pharmaceutically acceptable organic solvent can be provided so that the ingredients can be mixed prior to administration.

In another embodiment, the pharmaceutical compositions are formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Oral compositions can include standard excipients such as mannitol, lactose, starch, magnesium stearate, sodium saccharin, cellulose, and magnesium carbonate. Typically, the excipients are of pharmaceutical grade. Orally administered compositions can also contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. A time-delay material such as glycerol monostearate or glycerol stearate can also be used.

The pharmaceutical compositions further comprising a solvent can optionally comprise a suitable amount of a pharmaceutically acceptable preservative, if desired, so as to provide additional protection against microbial growth. Examples of preservatives useful in the pharmaceutical compositions described herein include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chlorides (e.g., benzethonium chloride).

In some embodiments, the pharmaceutical compositions described herein optionally contain a suitable amount of a pharmaceutically acceptable polymer. The polymer can increase the viscosity of the pharmaceutical composition. Suitable polymers for use in the compositions and methods described herein include, but are not limited to, hydroxypropylcellulose, hydroxypropylmethylcellulose (HPMC), chitosan, polyacrylic acid, and polymethacrylic acid.

Typically, the polymer is present in an amount ranging from greater than 0 to 10 percent by weight of the pharmaceutical composition. In some embodiments, the polymer is present in an amount ranging from about 0.1 to 10 percent by weight of the pharmaceutical composition. In some embodiments, the polymer is present in an amount ranging from about 1 to 7.5 percent by weight of the pharmaceutical composition. In some embodiments, the polymer is present in an amount ranging from about 1.5 to 5 percent by weight of the pharmaceutical composition. In some embodiments, the polymer is present in an amount ranging from about 2 to 4 percent by weight of the pharmaceutical composition. In some embodiments, the pharmaceutical compositions described herein are substantially free of polymers.

In some embodiments, any additional components added to the pharmaceutical compositions described herein are designated as GRAS by the FDA for use or consumption by animals. In some embodiments, any additional components added to the pharmaceutical compositions described herein are designated as GRAS by the FDA for use or consumption by humans.

The components of the pharmaceutical composition (the solvents and any other optional components) are preferably biocompatible and non-toxic and, over time, are simply absorbed and/or metabolized by the body.

As described above, the pharmaceutical compositions described herein can further comprise a solvent.

In some embodiments, the solvent comprises water.

In some embodiments, the solvent comprises a pharmaceutically acceptable organic solvent.

In an embodiment, the oligonucleotide aptamer provided herein are available as the salt of a metal cation, for example, as the potassium or sodium salt. These salts, however, may have low solubility in aqueous solvents and/or organic solvents, typically, less than about 25 mg/mL. The pharmaceutical compositions described herein comprising (i) an amino acid ester or amino acid amide and (ii) a protonated oligonucleotide, however, may be significantly more soluble in aqueous solvents and/or organic solvents. Without wishing to be bound by theory, it is believed that the amino acid ester or amino acid amide and the protonated oligonucleotide form a salt, such as illustrated above, and the salt is soluble in aqueous and/or organic solvents.

The pharmaceutical compositions provided herein may comprise (i) an oligonucleotide described herein; (ii) a divalent metal cation; and (iii) optionally a carboxylate, a phospholipid, a phosphatidyl choline, or a sphingomyelin form a salt, such as illustrated above, and the salt is soluble in aqueous and/or organic solvents.

In some embodiments, the concentration of the oligonucleotide aptamer described herein in the solvent is greater than about 2 percent by weight of the pharmaceutical composition. In some embodiments, the concentration of the aptamer in the solvent is greater than about 5 percent by weight of the pharmaceutical composition. In some embodiments, the concentration of the aptamer in the solvent is greater than about 7.5 percent by weight of the pharmaceutical composition. In some embodiments, the concentration of the aptamer in the solvent is greater than about 10 percent by weight of the pharmaceutical composition. In some embodiments, the concentration of the aptamer in the solvent is greater than about 12 percent by weight of the pharmaceutical composition. In some embodiments, the concentration of the aptamer in the solvent is greater than about 15 percent by weight of the pharmaceutical composition. In some embodiments, the concentration of the aptamer in the solvent is ranges from about 2 percent to 5 percent by weight of the pharmaceutical composition. In some embodiments, the concentration of the aptamer in the solvent is ranges from about 2 percent to 7.5 percent by weight of the pharmaceutical composition. In some embodiments, the concentration of the aptamer in the solvent ranges from about 2 percent to 10 percent by weight of the pharmaceutical composition. In some embodiments, the concentration of the aptamer in the solvent is ranges from about 2 percent to 12 percent by weight of the pharmaceutical composition. In some embodiments, the concentration of the aptamer in the solvent is ranges from about 2 percent to 15 percent by weight of the pharmaceutical composition. In some embodiments, the concentration of the aptamer in the solvent is ranges from about 2 percent to 20 percent by weight of the pharmaceutical composition.

Any pharmaceutically acceptable organic solvent can be used in the pharmaceutical compositions described herein. Representative, pharmaceutically acceptable organic solvents include, but are not limited to, pyrrolidone, N-methyl-2-pyrrolidone, polyethylene glycol, propylene glycol (i.e., 1,3-propylene glycol), glycerol formal, isosorbid dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide, and combinations thereof.

In some embodiments, the pharmaceutically acceptable organic solvent is a water soluble solvent. A representative pharmaceutically acceptable water soluble organic solvent is triacetin.

In some embodiments, the pharmaceutically acceptable organic solvent is a water miscible solvent. Representative pharmaceutically acceptable water miscible organic solvents include, but are not limited to, glycerol formal, polyethylene glycol, and propylene glycol.

In some embodiments, the pharmaceutically acceptable organic solvent comprises pyrrolidone. In some embodiments, the pharmaceutically acceptable organic solvent is pyrrolidone substantially free of another organic solvent.

In some embodiments, the pharmaceutically acceptable organic solvent comprises N-methyl-2-pyrrolidone. In some embodiments, the pharmaceutically acceptable organic solvent is N-methyl-2-pyrrolidone substantially free of another organic solvent.

In some embodiments, the pharmaceutically acceptable organic solvent comprises polyethylene glycol. In some embodiments, the pharmaceutically acceptable organic solvent is polyethylene glycol substantially free of another organic solvent.

In some embodiments, the pharmaceutically acceptable organic solvent comprises propylene glycol. In some embodiments, the pharmaceutically acceptable organic solvent is propylene glycol substantially free of another organic solvent.

In some embodiments, the pharmaceutically acceptable organic solvent comprises glycerol formal. In some embodiments, the pharmaceutically acceptable organic solvent is glycerol formal substantially free of another organic solvent.

In some embodiments, the pharmaceutically acceptable organic solvent comprises isosorbid dimethyl ether. In some embodiments, the pharmaceutically acceptable organic solvent is isosorbid dimethyl ether substantially free of another organic solvent.

In some embodiments, the pharmaceutically acceptable organic solvent comprises ethanol. In some embodiments, the pharmaceutically acceptable organic solvent is ethanol substantially free of another organic solvent.

In some embodiments, the pharmaceutically acceptable organic solvent comprises dimethyl sulfoxide. In some embodiments, the pharmaceutically acceptable organic solvent is dimethyl sulfoxide substantially free of another organic solvent.

In some embodiments, the pharmaceutically acceptable organic solvent comprises tetraglycol. In some embodiments, the pharmaceutically acceptable organic solvent is tetraglycol substantially free of another organic solvent.

In some embodiments, the pharmaceutically acceptable organic solvent comprises tetrahydrofurfuryl alcohol. In some embodiments, the pharmaceutically acceptable organic solvent is tetrahydrofurfuryl alcohol substantially free of another organic solvent.

In some embodiments, the pharmaceutically acceptable organic solvent comprises triacetin. In some embodiments, the pharmaceutically acceptable organic solvent is triacetin substantially free of another organic solvent.

In some embodiments, the pharmaceutically acceptable organic solvent comprises propylene carbonate. In some embodiments, the pharmaceutically acceptable organic solvent is propylene carbonate substantially free of another organic solvent.

In some embodiments, the pharmaceutically acceptable organic solvent comprises dimethyl acetamide. In some embodiments, the pharmaceutically acceptable organic solvent is dimethyl acetamide substantially free of another organic solvent.

In some embodiments, the pharmaceutically acceptable organic solvent comprises dimethyl formamide. In some embodiments, the pharmaceutically acceptable organic solvent is dimethyl formamide substantially free of another organic solvent.

In some embodiments, the pharmaceutically acceptable organic solvent comprises at least two pharmaceutically acceptable organic solvents.

In some embodiments, the pharmaceutically acceptable organic solvent comprises N-methyl-2-pyrrolidone and glycerol formal. In some embodiments, the pharmaceutically acceptable organic solvent is N-methyl-2-pyrrolidone and glycerol formal. In some embodiments, the ratio of N-methyl-2-pyrrolidone to glycerol formal ranges from about 90:10 to 10:90.

In some embodiments, the pharmaceutically acceptable organic solvent comprises propylene glycol and glycerol formal. In some embodiments, the pharmaceutically acceptable organic solvent is propylene glycol and glycerol formal. In some embodiments, the ratio of propylene glycol to glycerol formal ranges from about 90:10 to 10:90.

In some embodiments, the pharmaceutically acceptable organic solvent is a solvent that is recognized as GRAS by the FDA for administration or consumption by animals. In some embodiments, the pharmaceutically acceptable organic solvent is a solvent that is recognized as GRAS by the FDA for administration or consumption by humans.

In some embodiments, the pharmaceutically acceptable organic solvent is substantially free of water. In some embodiments, the pharmaceutically acceptable organic solvent contains less than about 1 percent by weight of water. In some embodiments, the pharmaceutically acceptable organic solvent contains less about 0.5 percent by weight of water. In some embodiments, the pharmaceutically acceptable organic solvent contains less about 0.2 percent by weight of water. Pharmaceutically acceptable organic solvents that are substantially free of water are advantageous since they are not conducive to bacterial growth. Accordingly, it is typically not necessary to include a preservative in pharmaceutical compositions that are substantially free of water. Another advantage of pharmaceutical compositions that use a pharmaceutically acceptable organic solvent, preferably substantially free of water, as the solvent is that hydrolysis of the oligonucleotide is minimized. Typically, the more water present in the solvent the more readily the oligonucleotide can be hydrolyzed. Accordingly, oligonucleotide containing pharmaceutical compositions that use a pharmaceutically acceptable organic solvent as the solvent can be more stable than oligonucleotide containing pharmaceutical compositions that use water as the solvent.

In some embodiments, comprising a pharmaceutically acceptable organic solvent, the pharmaceutical composition is injectable.

In some embodiments, the injectable pharmaceutical compositions are of sufficiently low viscosity that they can be easily drawn into a 20 gauge and needle and then easily expelled from the 20 gauge needle. Typically, the viscosity of the injectable pharmaceutical compositions are less than about 1,200 cps. In some embodiments, the viscosity of the injectable pharmaceutical compositions are less than about 1,000 cps. In some embodiments, the viscosity of the injectable pharmaceutical compositions are less than about 800 cps. In some embodiments, the viscosity of the injectable pharmaceutical compositions are less than about 500 cps. Injectable pharmaceutical compositions having a viscosity greater than about 1,200 cps and even greater than about 2,000 cps (for example gels) are also within the scope described herein provided that the compositions can be expelled through an 18 to 24 gauge needle.

In some embodiments, comprising a pharmaceutically acceptable organic solvent, the pharmaceutical composition is injectable and does not form a precipitate when injected into water.

In some embodiments, comprising a pharmaceutically acceptable organic solvent, the pharmaceutical composition is injectable and forms a precipitate when injected into water. Without wishing to be bound by theory, it is believed, for pharmaceutical compositions that comprise a protonated oligonucleotide and an amino acid ester or amide, that the α-amino group of the amino acid ester or amino acid amide is protonated by the oligonucleotide to form a salt, such as illustrated above, which is soluble in the pharmaceutically acceptable organic solvent but insoluble in water. Similarly, when the pharmaceutical composition comprises (i) an oligonucleotide; (ii) a divalent metal cation; and (iii) optionally a carboxylate, a phospholipid, a phosphatidyl choline, or a sphingomyelin, it is believed that the components of the composition form a salt, such as illustrated above, which is soluble in the pharmaceutically acceptable organic solvent but insoluble in water. Accordingly, when the pharmaceutical compositions are injected into an animal, at least a portion of the pharmaceutical composition precipitates at the injection site to provide a drug depot. Without wishing to be bound by theory, it is believed that when the pharmaceutically compositions are injected into an animal, the pharmaceutically acceptable organic solvent diffuses away from the injection site and aqueous bodily fluids diffuse towards the injection site, resulting in an increase in concentration of water at the injection site, that causes at least a portion of the composition to precipitate and form a drug depot. The precipitate can take the form of a solid, a crystal, a gummy mass, or a gel. The precipitate, however, provides a depot of the oligonucleotide at the injection site that releases the oligonucleotide over time. The components of the pharmaceutical composition, i.e., the amino acid ester or amino acid amide, the pharmaceutically acceptable organic solvent, and any other components are biocompatible and non-toxic and, over time, are simply absorbed and/or metabolized by the body.

In some embodiments, comprising a pharmaceutically acceptable organic solvent, the pharmaceutical composition is injectable and forms liposomal or micellar structures when injected into water (typically about 500 μL are injected into about 4 mL of water). The formation of liposomal or micellar structures are most often formed when the pharmaceutical composition includes a phospholipid. Without wishing to be bound by theory, it is believed that the oligonucleotide in the form of a salt, which can be a salt formed with an amino acid ester or amide or can be a salt with a divalent metal cation and optionally a carboxylate, a phospholipid, a phosphatidyl choline, or a sphingomyelin, that is trapped within the liposomal or micellar structure. Without wishing to be bound by theory, it is believed that when these pharmaceutically compositions are injected into an animal, the liposomal or micellar structures release the oligonucleotide over time.

In some embodiments, the pharmaceutical composition further comprising a pharmaceutically acceptable organic solvent is a suspension of solid particles in the pharmaceutically acceptable organic solvent. Without wishing to be bound by theory, it is believed that the solid particles comprise a salt formed between the amino acid ester or amino acid amide and the protonated oligonucleotide wherein the acidic phosphate groups of the oligonucleotide protonates the amino group of the amino acid ester or amino acid amide, such as illustrated above, or comprises a salt formed between the oligonucleotide; divalent metal cation; and optional carboxylate, phospholipid, phosphatidyl choline, or sphingomyelin, as illustrated above. Pharmaceutical compositions that are suspensions can also form drug depots when injected into an animal.

By varying the lipophilicity and/or molecular weight of the amino acid ester or amino acid amide it is possible to vary the properties of pharmaceutical compositions that include these components and further comprise an organic solvent. The lipophilicity and/or molecular weight of the amino acid ester or amino acid amide can be varied by varying the amino acid and/or the alcohol (or amine) used to form the amino acid ester (or amino acid amide). For example, the lipophilicity and/or molecular weight of the amino acid ester can be varied by varying the R1 hydrocarbon group of the amino acid ester. Typically, increasing the molecular weight of R1 increase the lipophilicity of the amino acid ester. Similarly, the lipophilicity and/or molecular weight of the amino acid amide can be varied by varying the R3 or R4 groups of the amino acid amide.

For example, by varying the lipophilicity and/or molecular weight of the amino acid ester or amino acid amide it is possible to vary the solubility of the oligonucleotide aptamer described herein in water, to vary the solubility of the oligonucleotide in the organic solvent, vary the viscosity of the pharmaceutical composition comprising a solvent, and vary the ease at which the pharmaceutical composition can be drawn into a 20 gauge needle and then expelled from the 20 gauge needle.

Furthermore, by varying the lipophilicity and/or molecular weight of the amino acid ester or amino acid amide (i.e., by varying R1 of the amino acid ester or R3 and R4 of the amino acid amide) it is possible to control whether the pharmaceutical composition that further comprises an organic solvent will form a precipitate when injected into water. Although different oligonucleotides exhibit different solubility and behavior, generally the higher the molecular weight of the amino acid ester or amino acid amide, the more likely it is that the salt of the protonated oligonucleotide and the amino acid ester of the amide will form a precipitate when injected into water. Typically, when R1 of the amino acid ester is a hydrocarbon of about C16 or higher the pharmaceutical composition will form a precipitate when injected into water and when R1 of the amino acid ester is a hydrocarbon of about C12 or less the pharmaceutical composition will not form a precipitate when injected into water. Indeed, with amino acid esters wherein R1 is a hydrocarbon of about C12 or less, the salt of the protonated oligonucleotide and the amino acid ester is, in many cases, soluble in water. Similarly, with amino acid amides, if the combined number of carbons in R3 and R4 is 16 or more the pharmaceutical composition will typically form a precipitate when injected into water and if the combined number of carbons in R3 and R4 is 12 or less the pharmaceutical composition will not form a precipitate when injected into water. Whether or not a pharmaceutical composition that further comprises a pharmaceutically acceptable organic solvent will form a precipitate when injected into water can readily be determined by injecting about 0.05 mL of the pharmaceutical composition into about 4 mL of water at about 98° F. and determining how much material is retained on a 0.22 μm filter after the composition is mixed with water and filtered. Typically, a formulation or composition is considered to be injectable when no more than 10% of the formulation is retained on the filter. In some embodiments, no more than 5% of the formulation is retained on the filter. In some embodiments, no more than 2% of the formulation is retained on the filter. In some embodiments, no more than 1% of the formulation is retained on the filter.

Similarly, in pharmaceutical compositions that comprise a protonated oligonucleotide and a diester or diamide of aspartic or glutamic acid, it is possible to vary the properties of pharmaceutical compositions by varying the amount and/or lipophilicity and/or molecular weight of the diester or diamide of aspartic or glutamic acid. Similarly, in pharmaceutical compositions that comprise an oligonucleotide; a divalent metal cation; and a carboxylate, a phospholipid, a phosphatidyl choline, or a sphingomyelin, it is possible to vary the properties of pharmaceutical compositions by varying the amount and/or lipophilicity and/or molecular weight of the carboxylate, phospholipid, phosphatidyl choline, or sphingomyelin.

Further, when the pharmaceutical compositions that further comprises an organic solvent form a depot when administered to an animal, it is also possible to vary the rate at which the oligonucleotide is released from the drug depot by varying the lipophilicity and/or molecular weight of the amino acid ester or amino acid amide. Generally, the more lipophilic the amino acid ester or amino acid amide, the more slowly the oligonucleotide is released from the depot. Similarly, when the pharmaceutical compositions that further comprises an organic solvent and also further comprise a carboxylate, phospholipid, phosphatidyl choline, sphingomyelin, or a diester or diamide of aspartic or glutamic acid and form a depot when administered to an animal, it is possible to vary the rate at which the oligonucleotide is released from the drug depot by varying the amount and/or lipophilicity and/or molecular weight of the carboxylate, phospholipid, phosphatidyl choline, sphingomyelin, or the diester or diamide of aspartic or glutamic acid.

Release rates from a precipitate can be measured injecting about 50 μL of the pharmaceutical composition into about 4 mL of deionized water in a centrifuge tube. The time that the pharmaceutical composition is injected into the water is recorded as T=0. After a specified amount of time, T, the sample is cooled to about −9° C. and spun on a centrifuge at about 13,000 rpm for about 20 min. The resulting supernatant is then analyzed by HPLC to determine the amount of oligonucleotide present in the aqueous solution. The amount of oligonucleotide in the pellet resulting from the centrifugation can also be determined by collecting the pellet, dissolving the pellet in about 10 μL of methanol, and analyzing the methanol solution by HPLC to determine the amount of oligonucleotide in the precipitate. The amount of oligonucleotide in the aqueous solution and the amount of oligonucleotide in the precipitate are determined by comparing the peak area for the HPLC peak corresponding to the oligonucleotide against a standard curve of oligonucleotide peak area against concentration of oligonucleotide. Suitable HPLC conditions can be readily determined by one of ordinary skill in the art.

Methods of Treatment

The pharmaceutical compositions described herein are useful in human medicine and veterinary medicine. Accordingly, the present disclosure further relates to a method of treating or preventing a condition in an animal comprising administering to the animal an effective amount of the pharmaceutical composition described herein. In some embodiments, the subject is identified, e.g., identified as likely to benefit from the treatment, using a method described herein.

In some embodiments, the present disclosurerelates to methods of treating a condition in an animal comprising administering to an animal in need thereof an effective amount of a pharmaceutical composition described herein.

In some embodiments, the present disclosurerelates to methods of preventing a condition in an animal comprising administering to an animal in need thereof an effective amount of a pharmaceutical composition described herein.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical. The mode of administration is left to the discretion of the practitioner. In some embodiments, administration will result in the release of the aptamer described herein into the bloodstream.

In some embodiments, the method of treating or preventing a condition in an animal comprises administering to the animal in need thereof an effective amount of an oligonucleotide by parenterally administering the pharmaceutical composition described herein. In some embodiments, the pharmaceutical compositions are administered by infusion or bolus injection. In some embodiments, the pharmaceutical composition is administered subcutaneously.

In some embodiments, the method of treating or preventing a condition in an animal comprises administering to the animal in need thereof an effective amount of an oligonucleotide by orally administering the pharmaceutical composition described herein. In some embodiments, the composition is in the form of a capsule or tablet.

The pharmaceutical compositions can also be administered by any other convenient route, for example, topically, by absorption through epithelial or mucocutaneous linings (e.g., oral, rectal, and intestinal mucosa, etc.).

The pharmaceutical compositions can be administered systemically or locally.

The pharmaceutical compositions can be administered together with another biologically active agent.

In some embodiments, the animal is a mammal.

In some embodiments, the animal is a human.

In some embodiments, the animal is a non-human animal.

In some embodiments, the animal is a canine, a feline, an equine, a bovine, an ovine, or a porcine.

The effective amount administered to the animal depends on a variety of factors including, but not limited to the type of animal being treated, the condition being treated, the severity of the condition, and the specific aptamer being administered. A treating physician can determine an effective amount of the pharmaceutical composition to treat a condition in an animal.

The aptamer provided herein can be an aptamer that inhibits a neoplastic growth or a cancer. In embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. The compositions and methods described herein can be used to treat these and other cancers.

EXAMPLES

The invention is now described with reference to the following Examples. These Examples are provided for the purpose of illustration only, and the invention is not limited to these Examples, but rather encompasses all variations which are evident as a result of the teachings provided herein.

Example 1: Identification of BM-DC Targeting Aptamers

DC-binding aptamers can be identified by using purified cell surface proteins or living cells as target structures in SELEX approaches. DCs express a variety of endocytic receptors and prominent examples among them are the C-type lectin receptors. The C-type lectin receptor MR is described to direct antigens towards cross-presentation for CD8 T cell activation. Thus, the MR was chosen as an attractive target to identify aptamers that are internalized and localized in DCs in a similar way as MR ligands. To identify aptamers recognizing the MR, the recombinant proteins Fc-CTL and Fc-FN were deployed in a protein-SELEX approach. These proteins were designed and described by Linehan et al. and Martinez-Pomares et al., and were used to analyze the ligand binding specificity of the MR protein domains. Fc-CTL consists of the C-type lectin-like domains 4-7 (CTLD 4-7) of the MR fused to the human IgG1 Fc portion, whereas Fc-FN is composed of the MR domains cysteine-rich domain, fibronectin type II domain and CTLD 1-3, fused to the Fc part (FIG. 11A).

Murine bone marrow-derived dendritic cells (BM-DCs) are a widely used cellular model. In general, DCs develop from bone marrow-derived progenitors and are distributed as a rare cell population in most of mammalian tissues. By treating murine bone marrow-derived progenitors with the hematopoietic growth factor GM-CSF for 7 days, a high yield (up to 1-3×10⁸) of BM-DCs can be generated. BM-DCs were often used to investigate the capacity of DCs to modify downstream T cell responses and are therefore a suitable target in cell-SELEX for the identification of DC-binding aptamers (FIG. 11B).

Enrichment of DNA Libraries Targeting Fc-CTL and Fc-FN:

The recombinant Fc-CTL and Fc-FN proteins were kindly provided by Prof. Sven Burgdorf from the LIMES Institute, University of Bonn. Briefly, the proteins were expressed in HEK293 cells and purified by immobilization on protein G columns.

Prior to the SELEX process, the proteins were immobilized on protein G-coated magnetic beads. The SELEX processes were initiated by incubation of the immobilized Fc-CTL or Fc-FN with a naïve DNA library in selection buffer (PBS, 1 mM $MgCl_2$, 1 mM $CaCl_2$, 0.01 mg/ml BSA) for 30 minutes at 37° C. From the second selection cycle, counter selection steps were introduced, i.e. DNA was pre-incubated with Fc-FN in SELEX targeting Fc-CTL and vice versa. After 11 selection cycles, the DNA libraries were analyzed by radioactive filter retention assay. To this end, the obtained DNA was labeled with $^{32}P$ at the 5'-end, incubated with increasing concentrations of the proteins in selection buffer, the mixture was then passed through a nitrocellulose membrane, washed and the retained $^{32}P$-DNA on the proteins was quantified by autoradiography.

The percentage of $^{32}P$-labeled DNA bound to Fc-CTL strongly increased from the 1st to the 6th and 11th selection cycle (FIG. 12A). Additionally, the quantity of bound DNA increased in a concentration-dependent manner.

In contrast, the increase of the percentage of Fc-FN-bound $^{32}P$-DNA was observed to be much weaker (FIG. 12B). The amount of bound DNA of the 6th and 11th selection cycle increased only around 2-2.5-fold in comparison to the first selection cycle.

Even though SELEX is a notionally simple method, it does not always result in the enrichment of aptamers with desired properties. There is a risk of an accumulation of non-selective background binders. Therefore, the enriched libraries of the sixth selection cycle were taken for the analysis of target selectivity. (see FIG. 12A-D).

Selectivity of Fc-CTL and Fc-FN Binding DNA Libraries:

The selectivity of the enriched DNA libraries for recombinant Fc-CTL or Fc-FN protein was tested by radioactive filter retention assay. To this end, the obtained DNA libraries of the 1$^{st}$ and 6$^{th}$ cycle of both selections were 5'-labeled with $^{32}P$ and incubated with Fc-CTL, Fc-FN, hIgG1 Fc, protein G, activated protein C (aPC), thrombin, extracellular signal-regulated kinase 2 (Erk2) or the Sec7 domain of cytohesin-1 (Cyt1 Sec7) in selection buffer for 30 minutes at 37° C.

During SELEX, Fc-CTL and Fc-FN were immobilized on protein G magnetic beads through their hIgG1 Fc tag. To exclude the binding of the enriched libraries to the protein tag or the immobilization matrix, hIgG1 Fc and protein G were included in the radioactive filter retention assays. In addition, the binding to the proteins thrombin, aPC, Erk2 and Cyt1 Sec7 which differ in their protein structures and were successfully addressed in previous aptamer selections, were also examined.

The DNA libraries derived from the 6$^{th}$ selection cycle targeting Fc-CTL (FIG. 13A) or Fc-FN (FIG. 13B) bound to both Fc-CTL and Fc-FN proteins. This result was not expected, because Fc-FN was used in the counter selection step in Fc-CTL-SELEX and vice versa. However, binding to both proteins is partly mediated by addressing the hIgG1 Fc tag (FIG. 13A-B). Plus, Fc-CTL as well as Fc-FN contains C-type lectin-like domains (FIG. 11A). Although the eight CTLDs of MR differ in their function and ligand specificity, they share conserved amino acid residues to form the typical CTLD fold.

Apart from that, no or a low amount of $^{32}P$-DNA retained on aPC, thrombin, Erk2 or Cyt1 Sec7 was observed. Plus, no binding to the immobilization matrix protein G was detected, indicating that the enriched DNA specifically bound to the protein domains used in SELEX. (see FIG. 13A-B)

To investigate whether the enriched DNA libraries consisted of specific aptamers, further experiments based on single sequence level were performed.

Identification of Aptamer Sequences Obtained from Protein-SELEX:

To identify individual aptamer sequences, DNA libraries from the 6th selection cycle were amplified by PCR, ligated into pCR2.1-TOPO vectors, transformed in the chemically competent TOP10 *E. coli* strain and subsequently sequenced. For Fc-CTL, 19 DNA sequences were obtained (FIG. 14A-B and FIG. 39) and 14 DNA sequences were found within the Fc-FN selected DNA library (FIG. 38).

At this point, the selection against Fc-FN was not further investigated. First of all, the libraries of the 6$^{th}$ and 11$^{th}$ selection cycles bound weakly to Fc-FN (FIG. 12B). Second, on the single sequence level no similarities within the DNA sequences were found (FIG. 38). Taking all this into account, no enrichment of high-affinity and specific DNA aptamers against Fc-FN was achieved.

On contrary, Fc-CTL-targeting DNA libraries bound strongly to Fc-CTL (FIG. 12A and FIG. 13A). Furthermore, two families sharing DNA motifs were identified among the 19 found DNA sequences. DNA sequences named CTL #5, 7, 9, 10 and 13 formed family 1, whereas CTL #6, 16 and 21 were grouped as family 2 (FIG. 14A-B). The remaining DNA sequences were unique (FIG. 39).

DNA sequences obtained by cloning and sequencing of DNA library targeting Fc-CTL were grouped according to their sequence similarities. (see FIG. 14A-B).

Next, the binding properties of individual sequences were investigated by radioactive filter retention assay.

Figure 15:
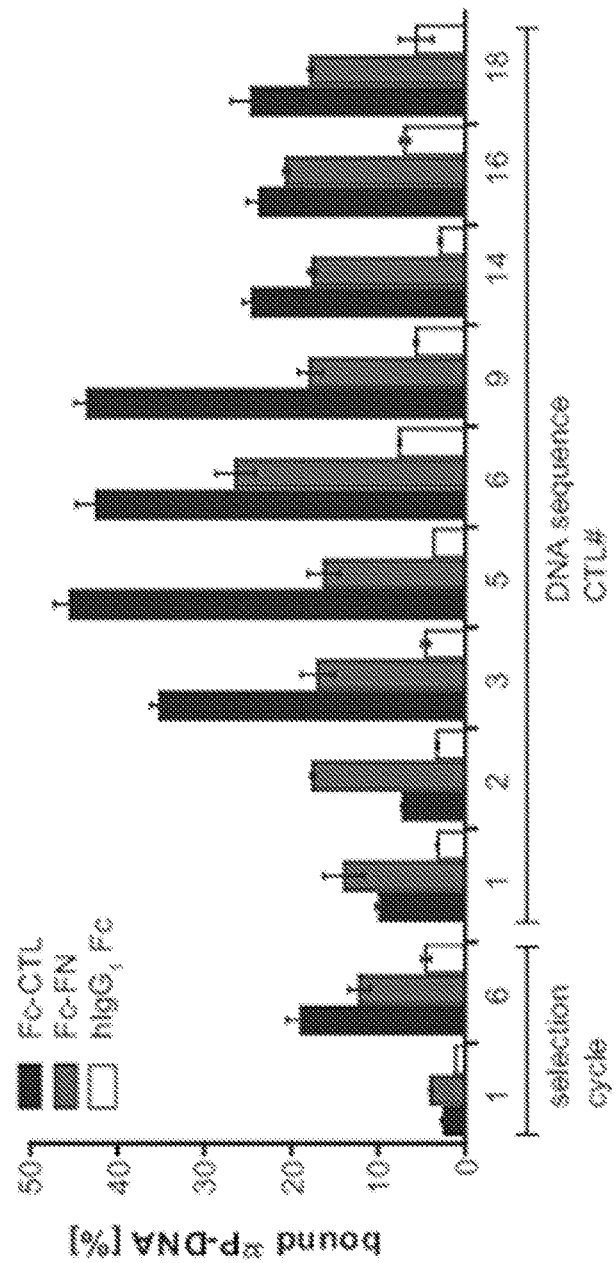
FIG. 15: Binding behavior of DNA sequences to Fc-CTL, Fc-FN and hIgGi Fc 1 pmol of $^{32}$P-DNA was incubated with 500 nM of proteins, the mixture was passed through a nitrocellulose membrane and the retained $^{32}$P-DNA was measured by autoradiography (n=2, mean±SD).

Binding of Fc-CTL Selected DNA Sequences:

Representative DNA sequences of each motif family (FIG. 14A-B), namely CTL #5, CTL #9, CTL #6 and CTL #16, and unique sequences CTL #1, #2, #3, #14 and #18 (FIG. 39) were chosen for further analysis. Therefore, their binding ability to Fc-CTL, Fc-FN and the IgG1 Fc protein tag was monitored by radioactive filter retention assay (FIG. 15). DNA was end labeled with $^{32}P$ and mixed with the corresponding proteins at a concentration of 500 nM. The mixtures were incubated in selection buffer for 30 minutes at 37° C. and applied on a nitrocellulose membrane. Finally, the amount of bound DNA was detected by autoradiography.

Equally to the 6$^{th}$ selection cycle library (FIG. 13A), some sequences targeted both proteins, Fc-CTL and Fc-FN (FIG. 15). Exceptions were CTL #5 and CTL #9 which showed more than two-fold higher binding to Fc-CTL in comparison to Fc-FN, and a low binding to the protein tag.

CTL #5 and CTL #9 belong to sequence family 1 whereby the shared motif is located differently within these sequences (FIG. 14A-B). As CTL #5 showed a higher degree of discrimination between Fc-CTL and Fc-FN, it is most likely that its sequence composition favors tertiary structure formation critical for specific Fc-CTL binding. For that reason, CTL #5 was picked for further analysis.

Figure 16:
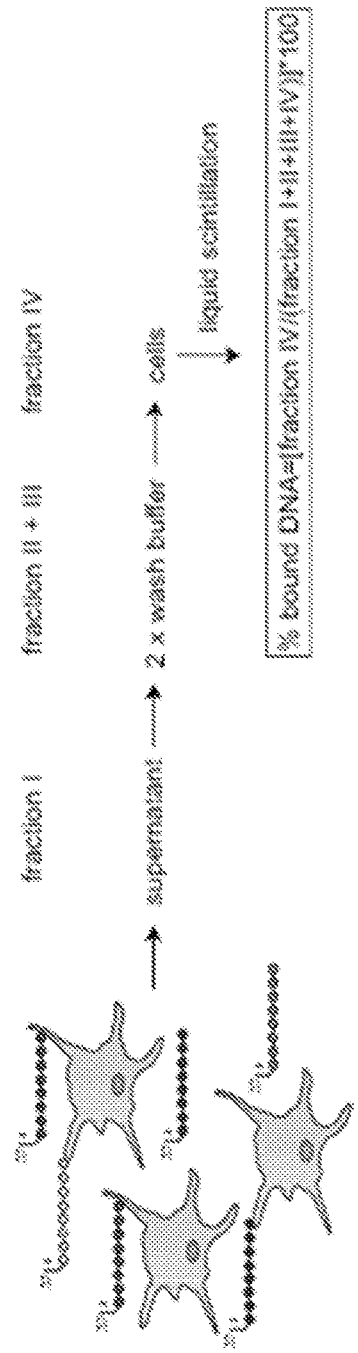
FIG. 16: Schematic representation of the radioactive binding assay. 0.5×10$^5$ BM-DCs were incubated with 1 pmol of $^{32}$P-DNA or $^{32}$P-2'F-RNA for 10 minutes at 37° C. Afterwards, the cell supernatant was collected as fraction I. The cells were washed twice and both wash fractions were transferred into new tubes (fraction II+III). The cells were detached and collected as fraction IV. Finally, the radioactivity of the fractions was measured by liquid scintillation and the percentage of bound DNA calculated by using the depicted formula.

Enrichment of DNA Libraries in Cell-SELEX:

The second approach to identify DC-binding aptamers was the use of living murine BM-DCs as targets in a cell-SELEX process (FIG. 11B). BM-DCs express a variety of molecules on their surface that are involved in modulating downstream T cell responses. These molecules represent accessible targets for aptamer selection. Previously to every selection cycle, murine bone marrow-derived progenitor cells were isolated from the hind limbs and differentiated for 7 days into BM-DCs with the hematopoietic factor GM-CSF. The cell-SELEX process was initiated by incubating living BM-DCs with a naïve DNA or 2'F-RNA library in cell-SELEX selection buffer (DPBS, 1 mM $MgCl_2$, 0.01 mg/ml BSA) at 37° C. for 30 minutes. To increase the selection pressure during SELEX, the incubation time was decreased to 10 minutes in the 9th selection cycle. After 10 and 12 selection cycles, $^{32}$P-labeled DNA or 2'F-RNA libraries were examined by radioactive binding assay. For this purpose, $^{32}$P-DNA or $^{32}$P-2'F-RNA was incubated with BM-DCs in cell-SELEX selection buffer and the amount of bound 32P-labeled nucleic acids was measured by liquid scintillation (FIG. 16). A 2'-deoxy-2'-fluoro-ribonucleic acid (2'F-RNA)-based library was used because 2'F-RNA is described to be less immunogenic in comparison to unmodified RNA. In addition, by substituting the 2'-hydroxyl group by a fluoro group, the stability of RNA to chemical or enzymatic hydrolysis is enhanced.

As a result, around 4-fold higher binding of the DNA library of the 10th selection cycle in comparison to the $1^{st}$ cycle was determined (FIG. 17A), indicating enrichment of DNA binders targeting BM-DCs. In contrast, no enrichment of 2'F-RNA was observed (FIG. 17B). Therefore, the obtained 2'F-RNA library was not further investigated.

To find high-affinity and specific DNA aptamers, further experiments were done on single sequence base.

Identification of Aptamer Sequences Obtained from Cell-SELEX:

Cloning and sequencing of the 10th selection cycle of cell-SELEX resulted in 31 DNA sequences. Eight sequences were grouped into two motif-sharing sequence families (FIG. 18A-B). The remaining sequences were unique (FIG. 40). Next, the cloned sequences were analyzed by radioactive binding assay.

Binding of Selected DNA Sequences to BM-DCs:

The binding ability of the individual sequences was analyzed by radioactive binding assay (FIG. 16). For that purpose, $^{32}$P-DNA was incubated with BM-DCs in cell-SELEX selection buffer for 10 minutes at 37° C. The amount of $^{32}$P-DNA retained on BM-DCs was determined and the ratio of binding calculated as the amount of bound DNA of the sample divided by the $1^{st}$ selection cycle. A ratio of binding higher than 1 indicates binding to BM-DCs.

Figure 19:
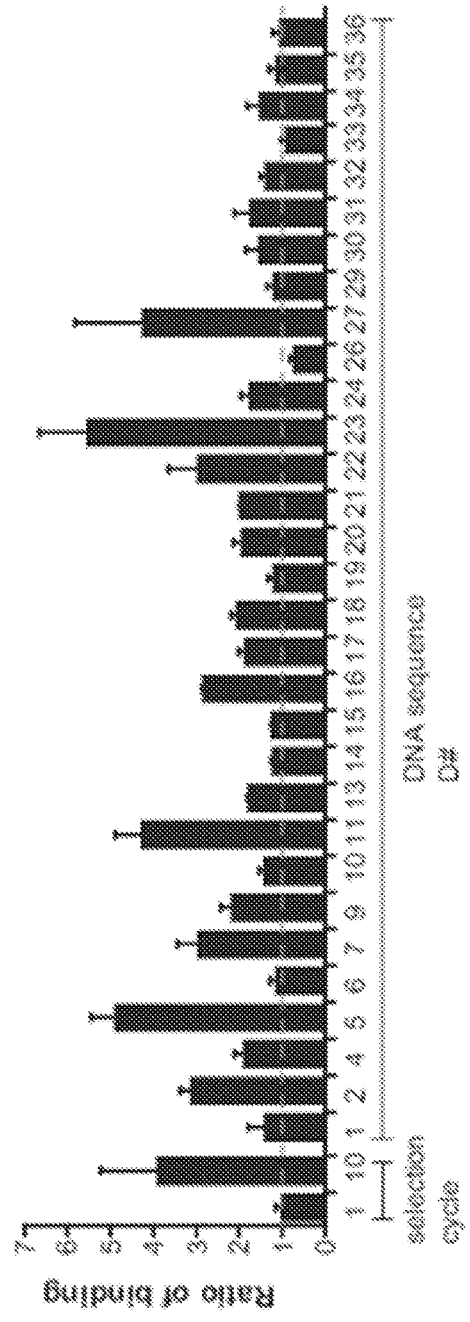
FIG. 19: DNA sequences derived from cell-SELEX show different binding capabilities. 0.5×10$^5$ BM-DCs were incubated with 1 pmol of $^{32}$P-labeled DNA. Subsequently, the amount of cell-bound DNA was determined by liquid scintillation. The percentages of bound $^{32}$P-DNA of samples were divided by the 1$^{st}$ selection cycle to give the ratio of binding. The experiments were performed at least twice (mean±SD).

As a result, the binding ability of DNA sequences D #2, #5, #7, #11, #16, #22, #23 and #27 was comparable to the $10^{th}$ selection cycle library, thus, they were categorized as BM-DC binding sequences (FIG. 19). Notably, sequences from both motif-sharing sequence families (FIG. 18A-B) are classified as BM-DC binders. The outcome of cell-SELEX was additionally verified by next-generation sequencing (NGS).

Analysis of Cell-SELEX by NGS:

To further investigate the enrichment of BM-DC-binders, the naïve DNA library and the libraries of the $1^{st}$, $2^{nd}$, $3^{rd}$, $4^{th}$, $7^{th}$ and $10^{th}$ selection cycles of cell-SELEX were introduced in NGS analysis. This high-throughput sequencing technology enables the identification of millions of DNA sequences. The raw data was analyzed by algorithms developed by AptaIT GmbH (Munchen).

Figure 20:
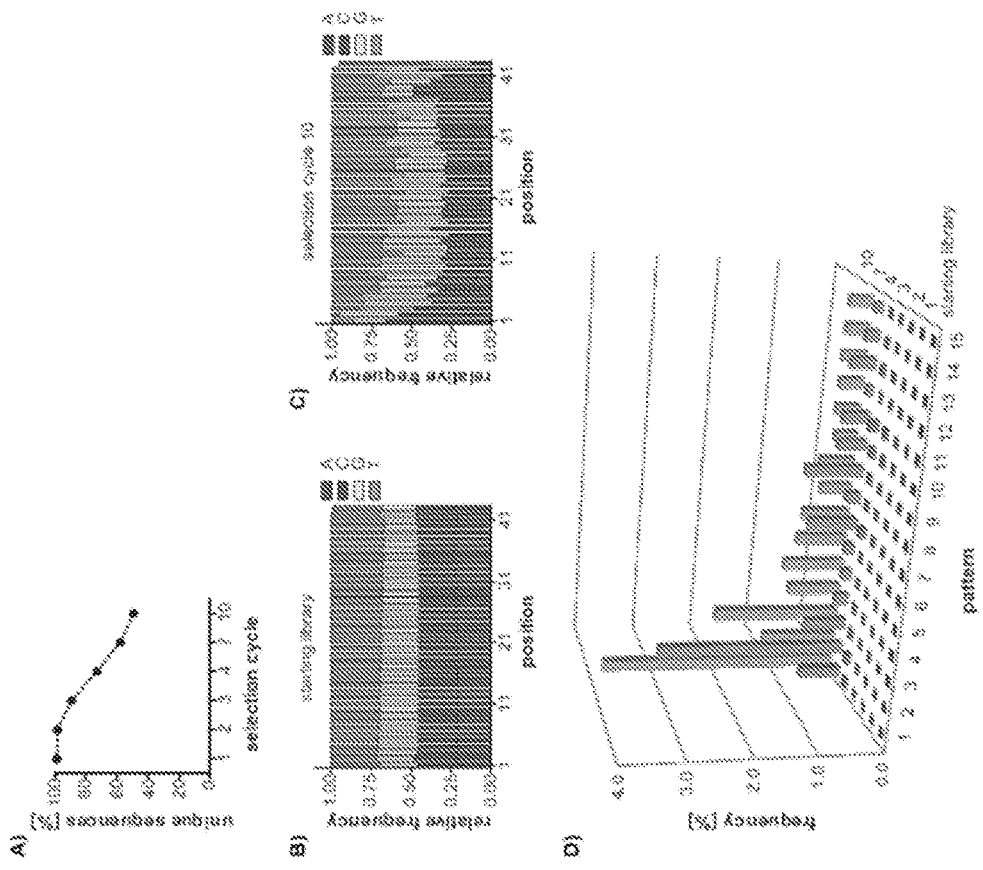
FIG. 20A-D: NGS analysis verified enrichment of DNA sequences in cell-SELEX. DNA of the naïve starting library and different selection cycles obtained from SELEX targeting BM-DCs were introduced in high throughput NGS analysis. The alterations of unique sequence numbers (A) and nucleotide distributions (B+C) were investigated by algorithms developed by AptaIT GmbH (Munchen). Plus, dependent on the degree of similarities, DNA sequences were grouped into patterns (D). The patterns were numbered according to their frequencies. Here, the 15 most abundant patterns are shown (refer to FIG. 41).

Around 100% of sequences in selection cycle 1 were unique. Starting from the $3^{rd}$ round, the number of unique sequences decreased to around 50% in the $10^{th}$ selection cycle (FIG. 20A). Certain DNA sequences become more frequent, indicating that the complexity of the libraries decreased with increasing selection cycle.

Moreover, a change of nucleotide distribution in the random region was observed. The naïve SELEX starting DNA library contained equal amounts of nucleotides, around 25% each of adenine, cytosine, guanine and thymine (FIG. 20B). In contrast, the composition of the library of the 10th selection cycle was changed; adenine strongly decreased whereby the amount of thymine at certain sequence positions increased (FIG. 20C). These results suggest that certain sequence arrangements were favorably accumulated within cell-SELEX.

Correlated to the nucleic acid sequences composition, the sequence reads were grouped in patterns (FIG. 20D and FIG. 41). These patterns were numbered according to their read frequencies, where pattern 1 had the highest frequency of around 4% in the 10th selection cycle.

Next, DNA sequences obtained by classical cloning and sequencing procedure were traced within the NGS reads (FIG. 40). Remarkably, sequences grouped to motif-sharing families (FIG. 18A-B) were present in pattern 1 and 2. Taking that into account in addition to the results of the radioactive binding assay (FIG. 19), D #5 (family 1) and D #7 (family 2) were chosen for further investigations.

Example 2: Characterization of BM-DC Targeting Aptamers

Figure 21:
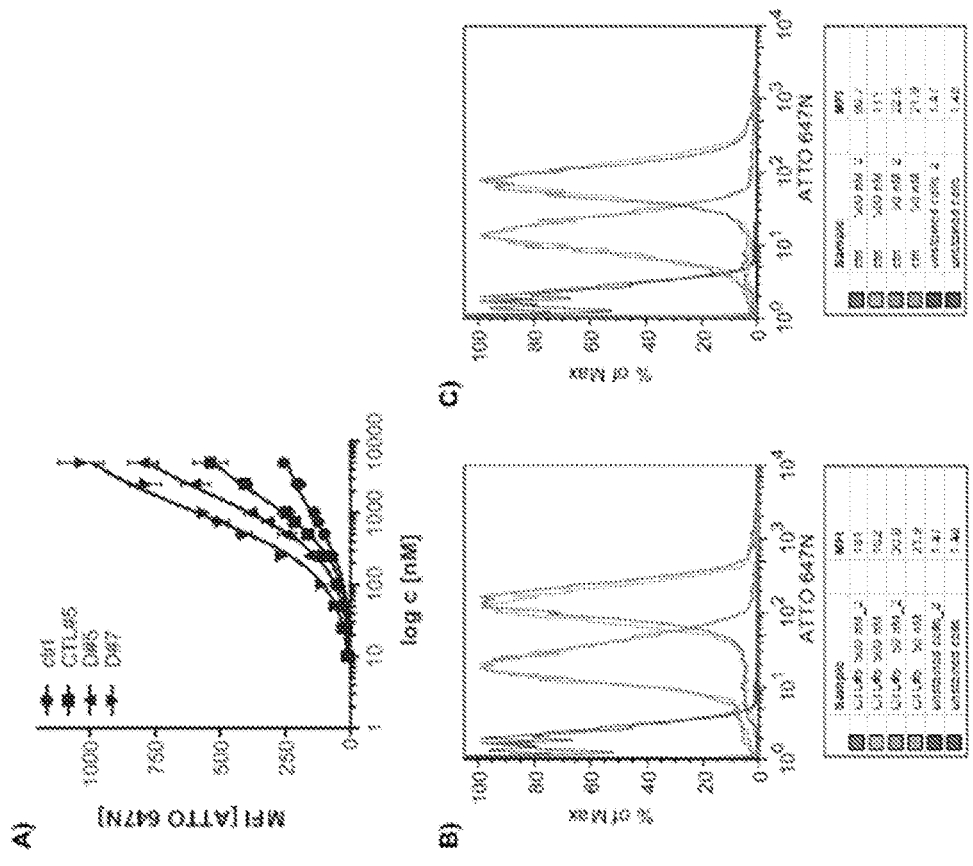
FIG. 21A-C: Aptamers bind in a concentration-dependent manner to BM-DCs. 4×10$^5$ BM-DCs were incubated with increasing concentrations of ATTO 647N-labeled aptamers and analyzed by flow cytometry (A). The mean fluorescence intensities (MFI) of ATTO 647N were determined (n=2, mean±SD). Representative flow cytometry histograms of 50 and 500 nM CTL #5 and ctrl and the corresponding MFI are depicted in (B) and (C). ctrl=control sequence.

Binding and Specificity of BM-DC-Binding Aptamers:

Binding of Aptamers to BM-DCs:

The binding of aptamers was analyzed by flow cytometry binding assay. Increasing concentrations of 5'-ATTO 647N-labeled aptamers CTL #5, D #5 and D #7 were incubated with 4×105 BM-DCs, the amount of bound DNA was detected by flow cytometry and the mean fluorescence intensities (MFI) were determined (FIG. 21B-C). A scrambled sequence based on CTL #5 was used as non-specific control sequence (ctrl). Here, the binding capacities of the aptamers were analyzed in DC cell medium for 10 minutes at 37° C.

All aptamers showed an increased binding capacity to murine BM-DCs compared to the control sequence, which is also concentration-dependent (FIG. 21A-C). Mean fluorescence intensities (MFI) increased with increasing concentrations of aptamers. Remarkably, CTL #5 derived from Fc-CTL protein-SELEX was also able to bind BM-DCs.

D #7, obtained from cell-SELEX, was shown to have the highest MFI, followed by D #5 and CTL #5. Surprisingly, the MFI of the labeled control sequence also rose with increasing concentration, albeit to a lesser extent (FIG. 21A). This fact is probably caused by the ability of BM-DCs to continuously internalize surrounding fluids by macropinocytosis.

As observed in FIG. 21A-C, binding curves fail to access saturation even at high concentrations. One reason could be the continuous endocytosis of aptamers.

Specificity of Aptamers to BM-DCs:

As the aptamers were intended to be used to mediate the activation of adaptive immunity, binding of effector cells, B and T cells, was investigated.

For that purpose, murine splenocytes were isolated and stained for T and B cell surface marker CD8, CD4 and B220, respectively. CD8 is mainly expressed by MHC I-restricted T cells, CD4 is primarily expressed by MHC II-restricted T cell subsets and B220 can be found in general on cells of the B cell lineage. $2\times10^5$ BM-DCs or splenocytes were incubated with 500 nM of 5'-ATTO 647N-labeled aptamers for 30 minutes at 37° C., the amount of cell-bound ATTO 647N-labeled aptamers was measured by flow cytometry and normalized to the control sequence.

Figure 22:
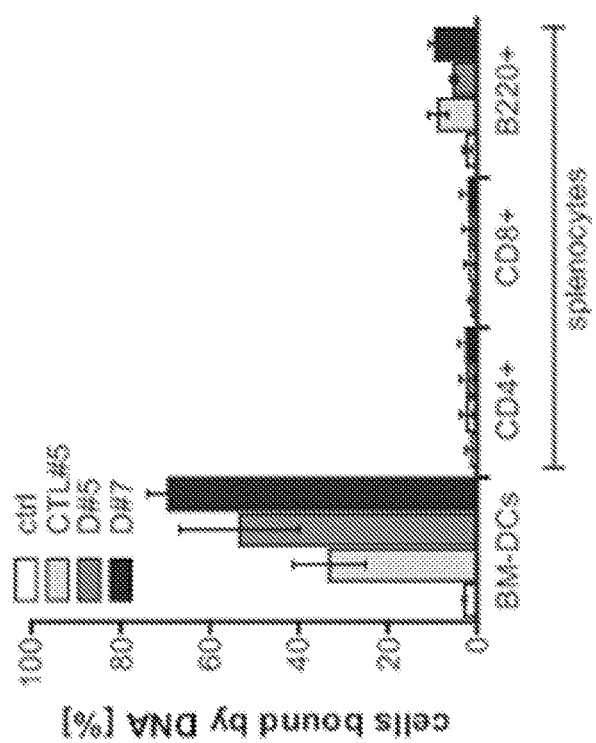
FIG. 22: Aptamers bind specifically to BM-DCs. 500 nM ATTO 647N-labeled aptamers were incubated with 2×105 BM-DCs or splenocytes and analyzed by flow cytometry. Cells bound by DNA were normalized to the control DNA (ctrl), the experiments were performed at least twice (mean±SD). Splenocytes were co-stained with CD4, CD8 or B220 (CD45RA) antibodies.

Results are given in FIG. 22. Aptamers bound specifically to BM-DCs whereas no binding to T cells was observed and less than 10% of B cells were recognized by aptamers.

B cells are grouped together with DCs and macrophages as professional APCs according to their ability to activate T cell responses. Additionally, professional APCs share some common cell surface structures for antigen recognition, e.g. Fc receptors for IgG27. This may mean that the aptamer target structures are expressed by B cells as well. However, the results suggest that the target expression is less prominent on B cells in contrast to BM-DCs.

Figure 23:
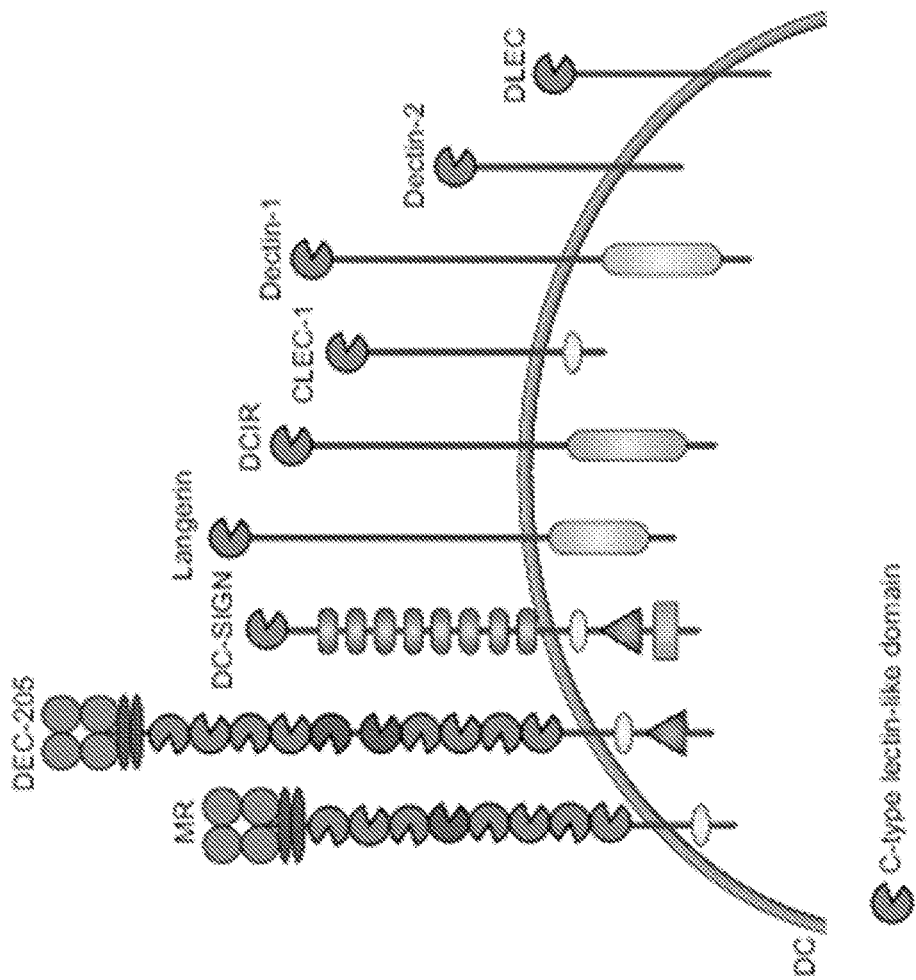
FIG. 23: Schematic representation of CTLD-containing receptors expressed on DCs. Several receptors composed of at least one C-type lectin-like domain are expressed on DCs (modified from Figdor et al.). MR=mannose receptor; DEC-205=dendritic and epithelial cells, 205 kDa; DC-SIGN=DC specific ICAM-3 grabbing non-integrin; DLEC=DC lectin; DCIR=DC immunoreceptor; CLEC-1=C-type lectin receptor-1; Dectin=DC-associated C-type lectins.

CTL #5 Specificity Towards MR:

The recombinant protein Fc-CTL was used to select CTL #5. As shown in FIG. 11A, Fc-CTL is composed of CTLD 4-7 derived from murine MR and human IgG1 Fc region. In 2002, Figdor et al. reviewed several receptors of the C-type lectin family expressed on DCs (FIG. 23). Even though the receptors differ in their ligand specificity, their C-type lectin-like domains share conserved residues responsible for the typical formation of a hydrophobic fold. To evaluate if only the CTLDs of MR were bound by CTL #5, confocal microscopy and flow cytometry binding assay were used.

First, co-localization of CTL #5 with MR was investigated. In 2006, Burgdorf et al. elucidated that the uptake of OVA by BM-DCs is dependent on MR expression. Hence, co-localization studies of CTL #5 with MR were carried out in comparison with the co-localization of OVA with MR.

$2\times10^5$ BM-DCs were double stained with MR antibody-Alexa Fluor 488 conjugate and 250 ng/ml OVA-Alexa Fluor 647 or 250 nM CTL #5-ATTO 647N in DC cell medium for 30 minutes at 37° C. The co-localization was analyzed by confocal microscopy and quantified with Pearson's correlation coefficient (PCC). PCC correlates fluorescence intensities; 1 means perfect relation, while 0 means no relation of the fluorescence intensities. High values of PCC indicate that the stained molecules are in close proximity. According to Zinchuk et al. PCC values were translated in weak to strong correlation.

Figure 24:
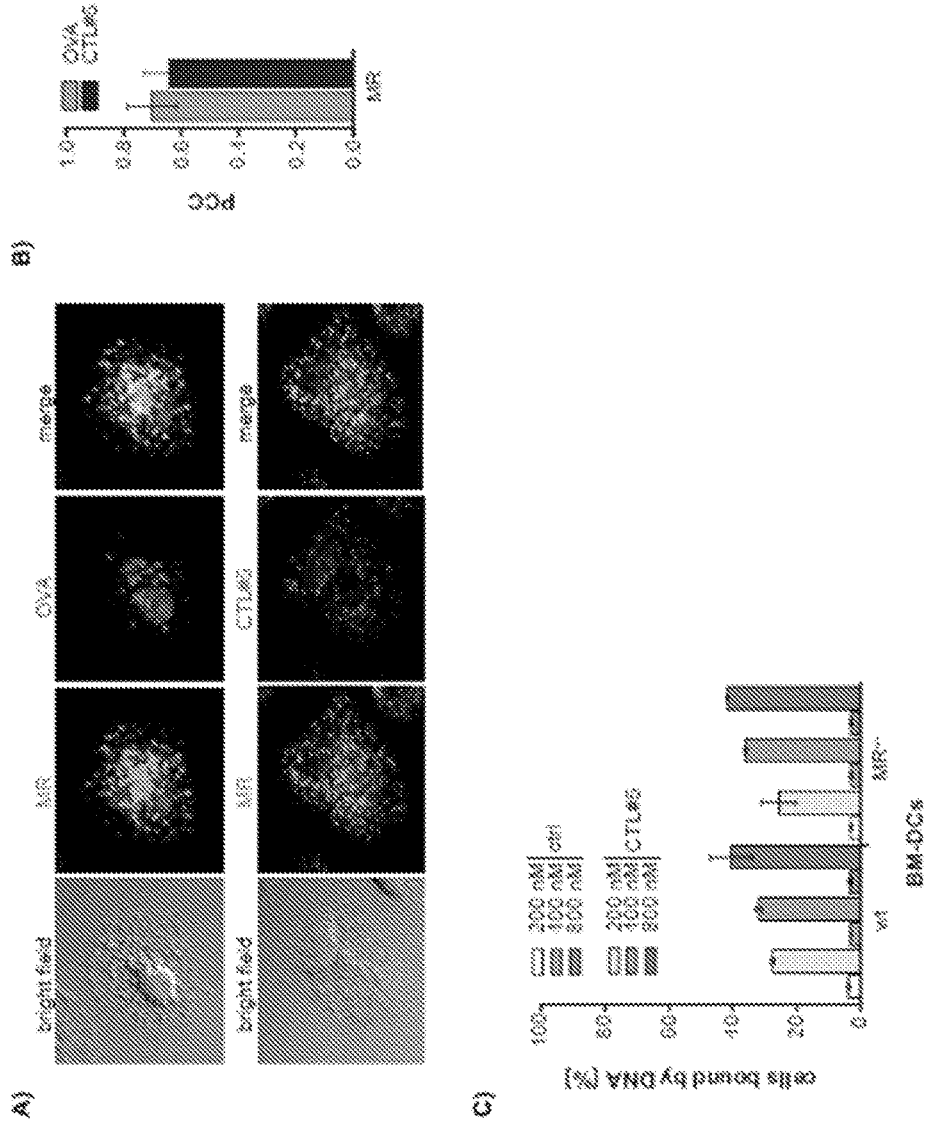
FIG. 24A-C: CTL #5 binding is not only mediated by the MR. Targeting of the MR by CTL #5 was analyzed in confocal microscopy and flow cytometry. For co-localization study, 2×105 BM-DCs were co-stained with OVA-Alexa Fluor 647 or CTL #5-ATTO 647N and MR antibody-Alexa Fluor 488 conjugates. Representative pictures out of at least twice performed experiments are shown (A). Fluorescence intensities were quantified as Pearson's correlation coefficient (PCC) (mean±SD) (B). 4×105 wildtype or MR−/− BM-DCs were incubated with increasing concentrations of ATTO 647N-labeled CTL #5 and the amount of cells bound by CTL #5 was measured by flow cytometry and normalized to the control (ctrl) sequence (n=2, mean±SD) (C).

In line with Burgdorf et al. and Rauen et al., co-localization of OVA and MR was observed. In accordance to Zinchuk et al., the correlation of both CTL #5 and OVA with MR is classified as strong (FIG. 24A-B). These results support the idea that similar to OVA, CTL #5 targets MR.

To attest that CTL #5 only binds to MR, binding to wildtype and MR knockout (MR−/−) BM-DCs was compared in flow cytometry (FIG. 24C). To this end, $4\times10^5$ BM-DCs were incubated with increasing concentrations of CTL #5 or the control sequence (ctrl) for 30 minutes at 37° C. in DC cell medium. We found that binding behavior of CTL #5 was similar for both cell types, as the knockout of MR did not change the amount of cells bound by the aptamer. Without being bound by theory, it may be that CTL #5 targeting is not MR-specific.

Internalization and Cellular Localization of BM-DC-Binding Aptamers:

Internalization of Aptamers by BM-DCs:

Cell-specific aptamers were often reported to be internalized into cells. To investigate if aptamers CTL #5, D #5 and D #7 were taken up by BM-DCs, confocal microscopy was used. $2\times10^5$ BM-DCs were incubated with 250 nM ATTO 647N-conjugated aptamers in DC cell medium at 37° C. for 30 minutes (CTL #5) or 10 minutes (D #5 and D #7), then, the cells were fixed in paraformaldehyde and co-stained with the membrane marker wheat germ agglutinin (WGA)-Alexa Fluor 488 and the nuclear stain DAPI. In confocal microscopy, pictures of cells at various depths within the Z-axis were taken (Z-stacks). The incubation times were chosen in accordance to the incubation times used in the SELEX approaches.

Figure 25:
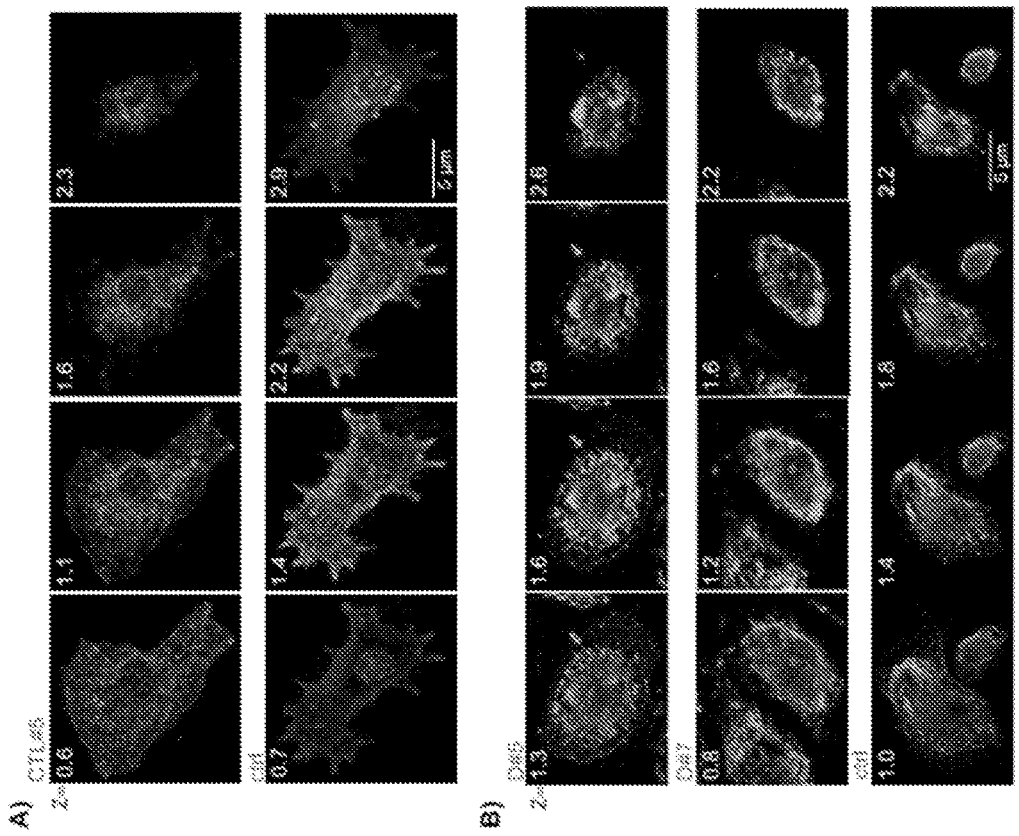
FIG. 25A-B: Aptamers internalize into BM-DCs. 2×10$^5$ BM-DCs were incubated with 250 nM aptamers-ATTO 647N conjugates, fixed and co-stained with membrane marker wheat germ agglutinin-Alexa Fluor 488 and nuclear marker DAPI. In confocal microscopy, pictures along the Z-axis were taken (Z numbers are given in μm). CTL #5 (A), D #5 and D #7 (B) were present as punctuate structures in the cytoplasm of BM-DCs. Representative pictures out of at least twice performed experiments are shown. ctrl=control sequence.

All aptamers were localized within almost every BM-DC whereby only % of cells contained the control sequence (FIG. 25A-B).

In previous studies, it was reported that the mechanism of uptake and cellular trafficking influences antigen processing and presentation by BM-DCs. For example, ligands internalized by the MR were entrapped in slowly maturing early endosomes for cross-presentation on MHC I molecules, whereas ligands taken up by DEC-205 are transported towards late endosomes or lysosomes for presentation on MHC II molecules. Thus, the cellular localization of CTL #5, D #5 and D #7 can influence the processing and presentation of a conjugated antigen. To investigate the cellular localization of the aptamers, confocal microscopy was applied.

Cellular Localization of Aptamers:

Ingested antigens route through endolysosomal compartments within DCs and are finally loaded on MHC I or MHC II molecules for presentation. To assess the cellular localization of CTL #5, D #5 and D #7, co-localization studies in confocal microscopy were done. $2\times10^5$ BM-DCs were treated with 250 nM ATTO 647N-labeled aptamers in DC cell medium at 37° C. for 30 minutes (CTL #5) or 10 minutes (D #5 and D #7) and co-stained with either early endosome antigen 1 (EEA1) or lysosome-associated membrane glycoprotein-1 (LAMP-1) antibody-Alexa Fluor 488 conjugates. Co-localization was quantified by using the PCC. The incubation times were chosen in accordance to the incubation times used in the SELEX approaches.

Figure 26:
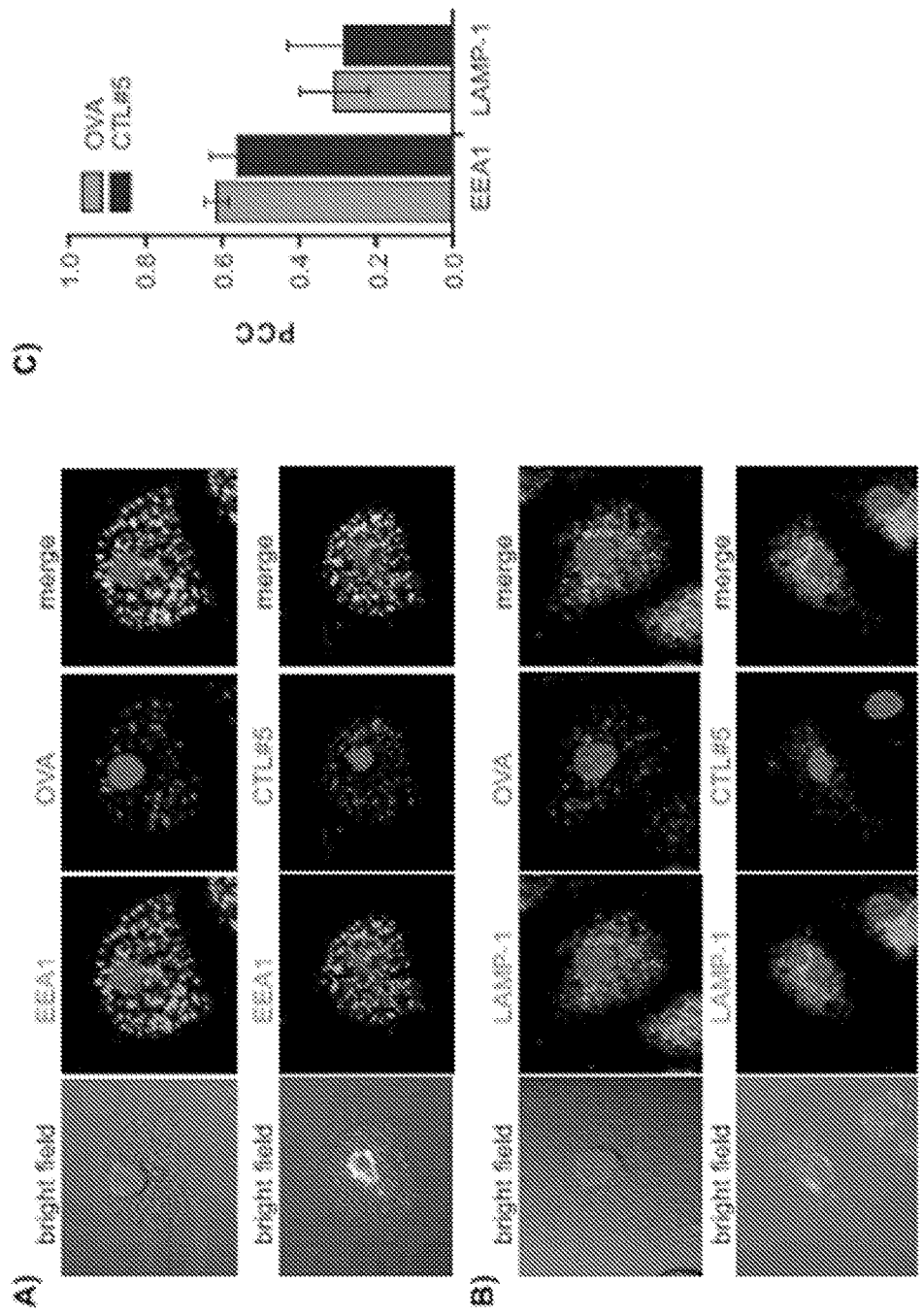
FIG. 26A-C: CTL #5 and OVA co-localize with EEA1 and LAMP-1. The cellular localization of CTL #5 and OVA was analyzed by co-localization studies in confocal microscopy. 2×10$^5$ BM-DCs were incubated with 250 nM aptamer-ATTO 647N or 250 ng/ml OVA-Alexa Fluor 647 conjugates, fixed and co-stained with early endosome marker EEA1 (A) or lysosome marker LAMP-1 (B), both labeled with Alexa Fluor 488. Representative pictures out of at least twice performed experiments are shown. The fluorescence signals were quantified as Pearson's correlation coefficient (PCC) (mean±SD) (C).

First, co-localization studies of CTL #5 were done in comparison with the model antigen OVA. Co-localization, as indicated by shades of yellow, was observed in some punctate structures. OVA as well as CTL #5 co-localized strongly with EEA1 (FIG. 26A-C). This finding is consistent with previous studies about co-localization of OVA and EEA1 done by Burgdorf et al. and Rauen et al. Additionally, weak correlation between OVA or CTL #5 and LAMP-1 was observed (FIG. 26B-C).

Figure 27:
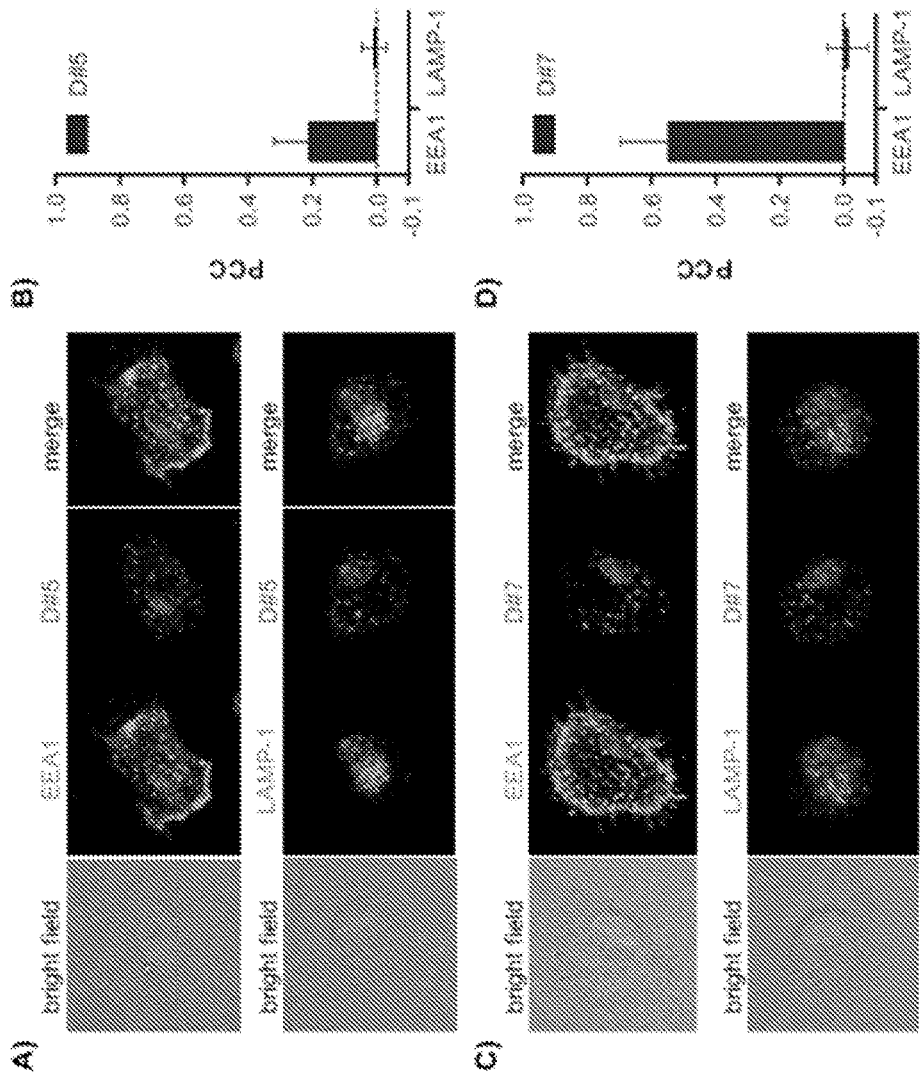
FIGS. 27A-D: D #5 and D #7 co-localize with EEA1. The cellular localization of aptamers was analyzed by co-localization studies in confocal microscopy. 2×10$^5$ BM-DCs were incubated with 250 nM D #5-(A+B) or D #7-ATTO 647N (C+D) conjugates, fixed and co-stained with early endosome marker EEA1 or lysosome marker LAMP-1, both labeled with Alexa Fluor 488. Representative pictures out of at least twice performed experiments are shown. The fluorescence signals were quantified as Pearson's correlation coefficient (PCC) (mean±SD) (B+D).

In a similar way, cellular localization of D #5 and D #7 was analyzed. It was shown that neither D #5 nor D #7 were located in organelles containing LAMP-1 (FIG. 27A-D). D #5-ATTO 647N correlated weak with EEA1-Alexa Fluor 488 (FIG. 27A-B) while D #7 co-localized strongly with EEA1 (FIG. 27C-D).

The results of the co-localization studies indicated internalization of aptamers into BM-DCs and localization within endolysosomal compartments. These results underline the potency of the selected aptamers to deliver antigens into cellular compartments important for adequate processing and presentation.

Figure 28:
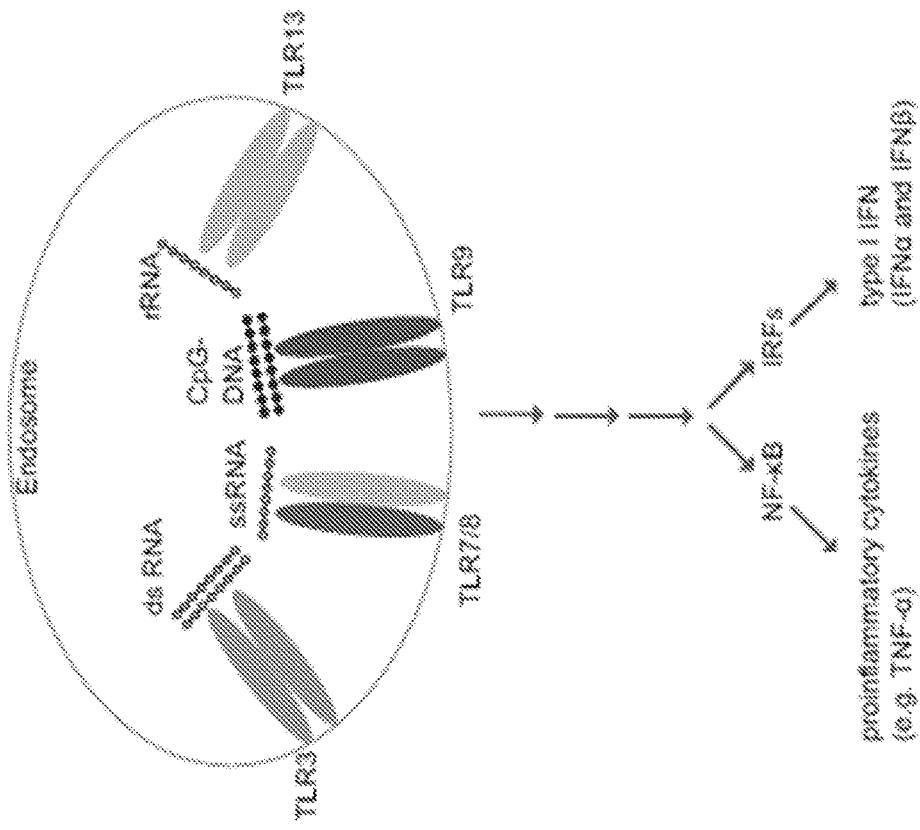
FIG. 28: Schematic representation of TLR signaling TLR 3, 7/8, 9 and 13 are localized in endosomal compartments. Upon recognition of their nucleic acid ligands, transcription factors such as nuclear factor-KB (NF-KB) and interferon-regulatory factors (IRFs) get activated. Consequence of TLR signaling is the induction of proinflammatory cytokines, e.g. tumor necrosis factor-α (TNF-α) and type I interferons (IFNs). ds=double-stranded, ss=single-stranded, r=ribosomal.

Immunogenicity of BM-DC-Binding Aptamers:

Cells involved in innate immunity evolved several sensors for foreign nucleic acids, termed pattern recognition receptors (PRRs). Most prominent among them are the Toll-like receptors (TLRs) 3, 7/8, 9 and 13, which are localized within endosomes. Upon recognition of nucleic acid ligands, signaling cascades are activated resulting in secretion of proinflammatory cytokines like tumor necrosis factor-α (TNF-α) or type I interferons (IFNs) (FIG. 28).

To investigate if BM-DC targeting aptamers were sensed by TLRs, secretion of TNF-α was measured by homogeneous time-resolved fluorescence (HTRF) assay. HTRF is based on fluorescence resonance energy transfer (FRET). Here, FRET donor and acceptor molecules were attached to anti-TNF-α antibodies and in close proximity to the molecules the fluorescence emission spectrum changes. This change is proportional to the TNF-α concentration in the sample.

Figure 29:
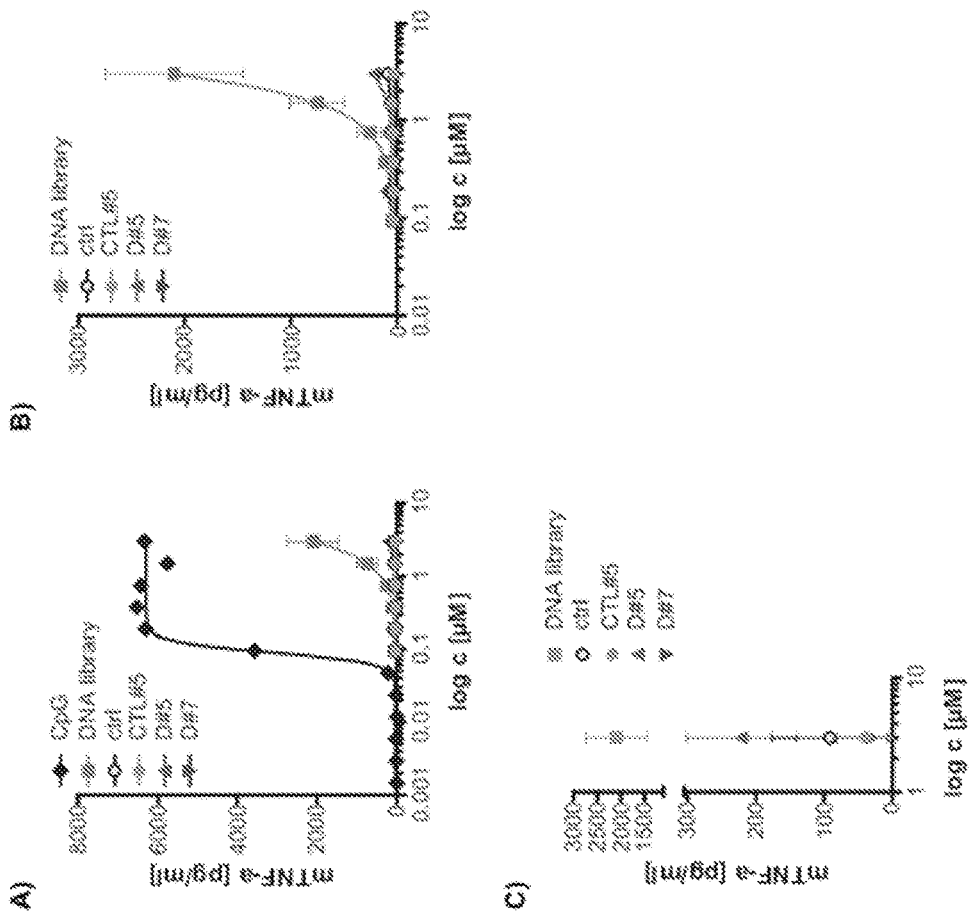
FIG. 29A-C: Aptamers induce low TNF-α secretion. Immortalized murine embryonic stem cell-derived macrophages were incubated with increasing concentrations of CpG ODN 1826 type B, naïve DNA library or aptamers (A) for 24 h and the concentration of TNF-α in the supernatant was determined by HTRF assay (n=4, mean±SD). For a better comparison, the results without CpG ODN are depicted in (B). The amount of TNF-α after treatment with 3 μM of DNA is shown in (C). The assays were performed as blinded analyses by James Stunden, member of Prof. Latz group, University Hospitals Bonn. ctrl=control sequence.

Immortalized murine embryonic stem cell-derived macrophages were used to investigate TLR activation. CpG ODN 1826 is described to activate TLR9148 and was used as positive control. In general, CpG ODNs are composed of unmethylated CpG motif (cytosine-phosphodiester or phosphorothioate-guanosine) flanked by 5' purines and 3' pyrimidines149. Here, to increase stability, CpG ODN 1826 has a phosphorothioate backbone. As expected, CpG ODN 1826 activated TNF-α secretion at concentrations in the nanomolar range (FIG. 29A). The DNA library used for aptamer selection induced TNF-α production at concentrations higher than 0.5 µM (FIG. 29A-B). In comparison, all aptamers demonstrated low TLR activation only at the highest concentration of 3 µM. D #5 mediated secretion of around 220 pg/ml TNF-α whereas CTL #5 and D #7 treatment induced less than 50 pg/ml TNF-α (FIG. 29C). The control sequence caused secretion of approximately 100 pg/ml TNF-α. Thus, in comparison to the DNA library which induced secretion of around 2100 pg/ml TNF-α, the aptamers are 10-40 times less potent in activation of TNF-α response.

Example 3: Aptamer-Targeted Activation of T Cell-Mediated Immunity

In the previous parts of this chapter, it was demonstrated that the selected aptamers exhibit all requirements to function as suitable delivery tools in an immunological context. They were shown to bind specifically to BM-DCs, get internalized, be transported into appropriate antigen processing compartments and be non-immunogenic.

To investigate if BM-DC aptamers indeed deliver antigens to mediate targeted activation of T cells, an OVA model system was applied. This system was chosen because it is one of the most feasible ways to investigate T cell-mediated immunity. OVA possess MHC I and MHC II binding sites $OVA_{257-264}$ (MHC I peptide) and $OVA_{323-339}$ (MHC II peptide), respectively. Accordingly, Hogquist et al. and Barnden and co-workers established transgenic mouse models producing OVA-specific CD8 or CD4 T cells. These mice develop either CD8 T cells recognizing MHC I bound $OVA_{257-264}$ or CD4 T cells specific for MHC II bound $OVA_{323-339}$ recognition.

Figure 30:
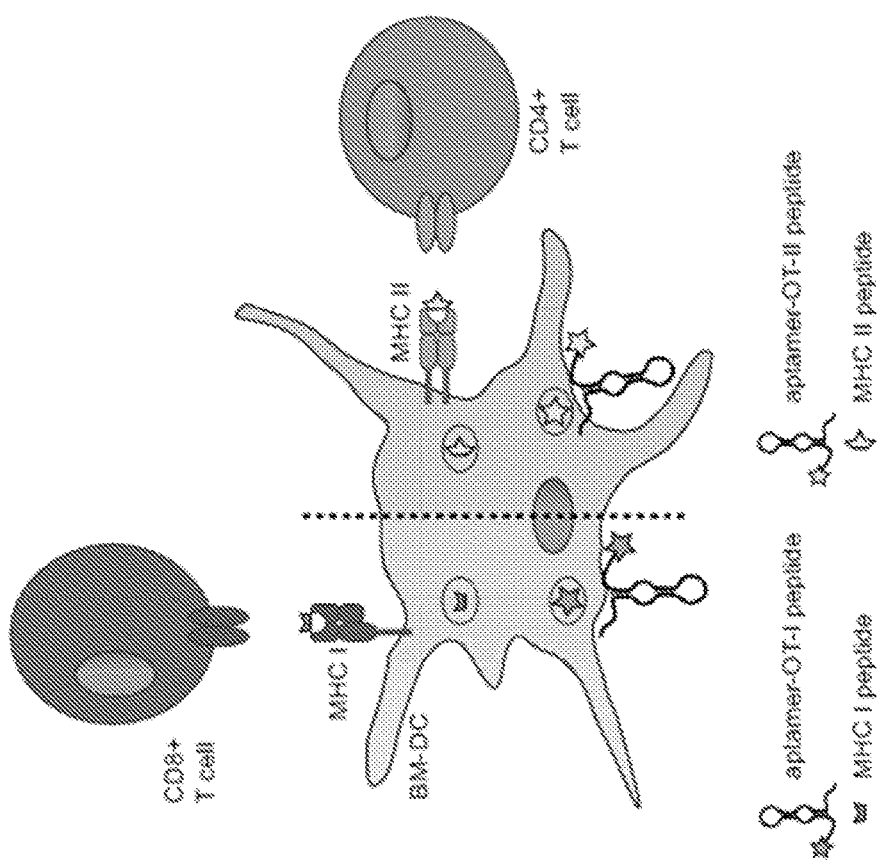
FIG. 30: Schematic representation of aptamer-targeted delivery of OVA peptides to induce specific T cell-mediated immune responses. In theory, the OT-I (green star) or OT-II (yellow star) peptides that are coupled to BM-DC binding aptamers will be taken up by the BM-DCs and then digested into smaller MHC I (cutted green star) or MHC II (cutted yellow star) peptides, respectively. Finally, MHC I or MHC II peptides will be loaded on MHC I or MHC II molecules and presented to CD8 or CD4 T cells for activation of T cell-mediated immunity. MHC I peptide=OVA$_{257-264}$, MHC II peptide=OVA$_{323-339}$, OT-I peptide=OVA$_{249-272}$, OT-II peptide=OVA$_{317-345}$.

Isolated MHC I or MHC II peptides can directly bind to MHC molecules expressed on the cell surface. Therefore, prolonged OVA peptides, namely OT-I ($OVA_{249-272}$) and OT-II ($OVA_{317-345}$), expanding either MHC I or MHC II recognition sequences were attached to the aptamers. In theory, upon binding and internalization of aptamer-OT-I or -OT-II conjugates by BM-DCs, activation of either CD8 or CD4 T cells is expected (FIG. 30).

Thiol-maleimide chemistry was used to conjugate aptamers with OT-I or OT-II peptides. Targeted activation of T cell immunity was tested by in vitro proliferation and cytotoxicity assays.

Figure 31:
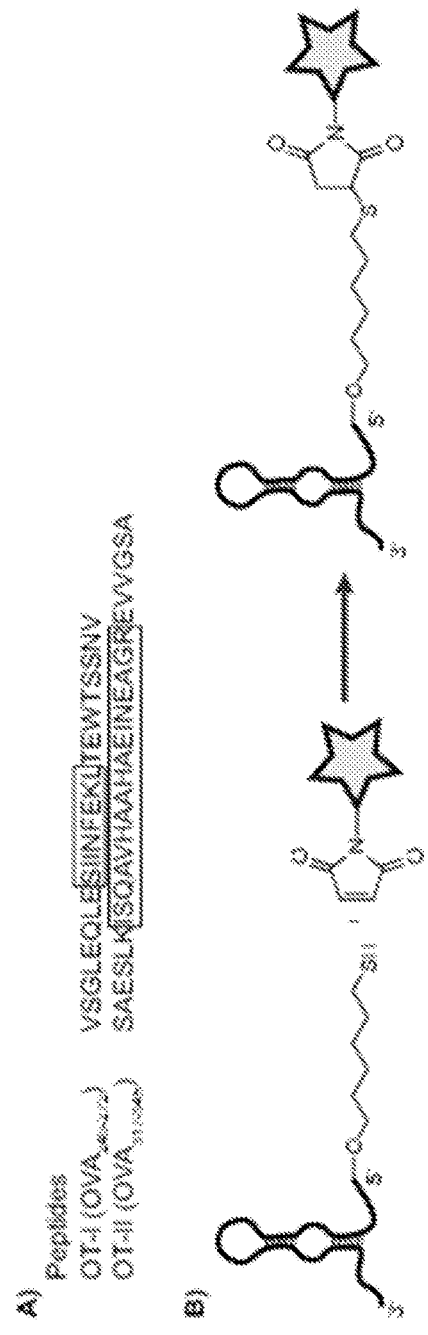
FIG. 31A-B: OVA peptides and thiol-maleimide chemistry were used to synthesize aptamer-peptide conjugates. OVA peptides expanding MHC I- or MHC II recognition sequences were used for coupling to BM-DC targeting aptamers (A). MHC I peptide OVA$_{257-264}$ and MHC II peptide OVA$_{323-339}$ are highlighted in boxes. Coupling was performed by thiol-maleimide chemistry (B). 5' thiol-modified DNA was conjugated to N-terminal maleimide functionalized peptides (star). (SEQ ID NOs: 69-70, in order of appearance)

Synthesis and Binding Ability of Aptamer-Peptide Conjugates:

Coupling of Aptamers and OVA Peptides:

MHC I-restricted OT-I or MHC II-binding OT-II OVA peptides were crosslinked via thiol-maleimide chemistry to aptamers CTL #5, D #5 or D #7, or the control sequence (ctrl) (FIG. 31A-B). To this end, 5'-disulfide modified aptamers were reduced to corresponding thiol derivatives and added to N-terminal maleimide functionalized OVA peptides. Maleimide reacts specifically with sulfhydryl groups, resulting in a stable thioether linkage.

After purification by reversed-phase high-performance liquid chromatography (RP-HPLC), the mass of the conjugates was determined by liquid chromatography-mass spectrometry (LC-MS). The quantities of thiol-modified DNA used for coupling, the yields and the calculated and measured monoisotopic masses are given in the Table below.

TABLE

Obtained yields and masses of aptamer-peptide conjugates:

| DNA-peptide chimera | used SH-ODN [pmol] | yield [pmol] | yield [%] | monoisotopic mass | |
|---|---|---|---|---|---|
| | | | | theoretical | experimental |
| ctrl-OT-I | 8000 | 3320 | 42 | 27639.3 | 27643.4 |
| ctrl-OT-II | 8000 | 3720 | 47 | 27847.5 | 27850.3 |
| CTL#5-OT-I | 4000 | 2240 | 56 | 27639.3 | 27645.2 |
| CTL#5-OT-II | 4000 | 2000 | 50 | 27847.5 | 27853.2 |
| D#5-OT-I | 4000 | 2080 | 52 | 27544.2 | 27552.4 |
| D#5-OT-II | 4000 | 1920 | 48 | 27752.4 | 27756.5 |
| D#7-OT-I | 4000 | 1640 | 41 | 27945.3 | 27951.3 |
| D#7-OT-II | 4000 | 1360 | 34 | 28153.5 | 28162.3 |

All chimeras were shown to have the expected monoisotopic mass and were further characterized with regard to binding capability to BM-DCs.

Binding Capability of Aptamer-Peptide Conjugates:

After the synthesis of aptamer-peptide conjugates, it was investigated if the binding ability of aptamers to BM-DCs was maintained. This was done by using a competition assay. $2 \times 10^5$ of 7 days differentiated BM-DCs were simultaneously incubated with 250 nM ATTO 647N-labeled aptamers and a two-fold molar excess of unlabeled competitors in DC cell medium for 10 minutes at 37° C. Fluorescence intensities were measured by flow cytometry and normalized to the control sequence (ctrl).

Figure 32:
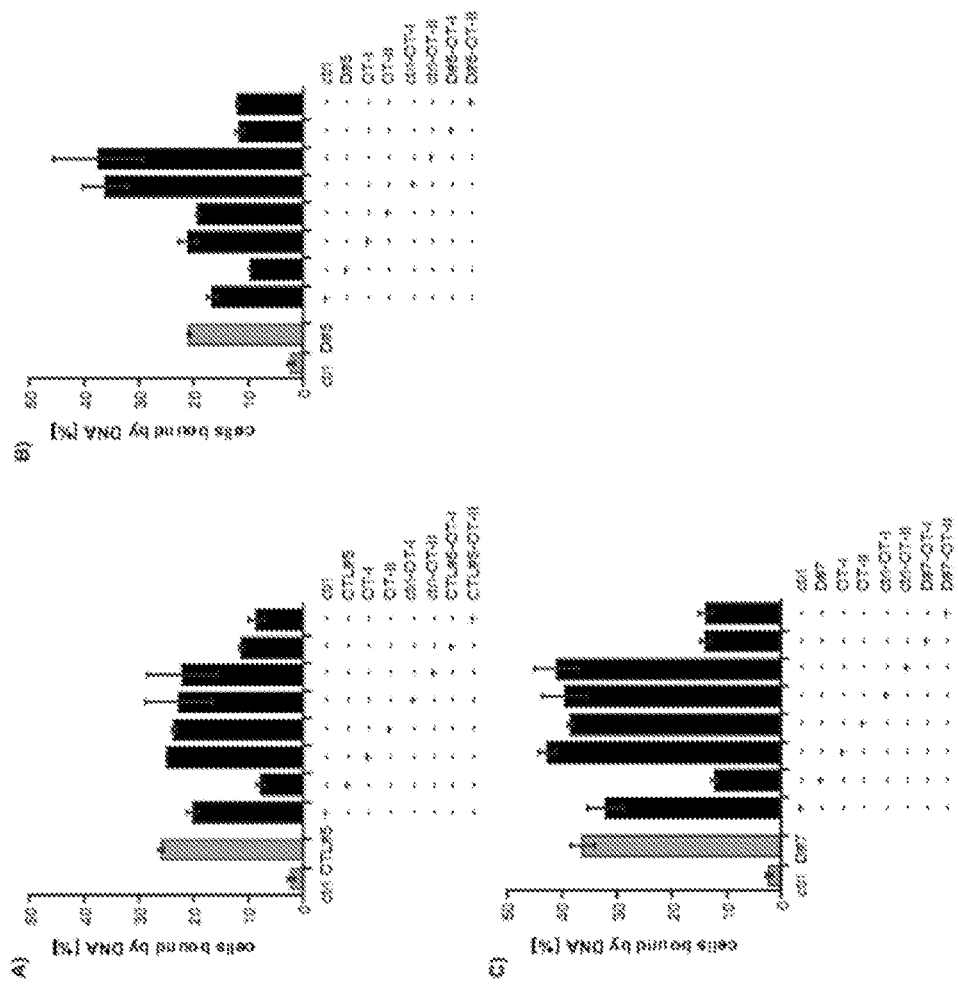
FIG. 32A-C: Binding capability of aptamers coupled to peptides is maintained. 2×10$^5$ BM-DCs were incubated with 250 nM ATTO 647N-labeled CTL #5 (A), D #5 (B) and D #7 (C) without (grey bars) or in presence of 500 nM competitors (black bars) and analyzed by flow cytometry (n=2, mean±SD).

The amount of cells bound by CTL #5 (FIG. 32A), D #5 (FIG. 32B) or D #7 (FIG. 32C) was strongly decreased when adding the particular aptamer or aptamer-peptide conjugates as competitors. No or low competition was induced by the control sequence, unconjugated OT-I and OT-II peptides or control-peptide conjugates.

To conclude, all aptamers were shown to preserve their binding capability to BM-DCs within crosslinked molecules. Finally, the functionality of conjugates was investigated.

Activation of T Cell-Mediated Immunity:

Aptamer-Targeted Activation of CD4 T Cells:

OVA-specific CD4 T cells derived from transgenic mice are activated by MHC II peptide presented on MHC II molecules by BM-DCs. To investigate if OT-II peptides delivered by aptamers mediate CD4 T cell activation, an in vitro proliferation assay was used. $5 \times 10^4$ of murine BM-DCs were either treated with MHC II or OT-II peptides, non-conjugated aptamers or aptamer-OT-II conjugates in DC cell medium for 10 minutes at 37° C. $1 \times 10^5$ OVA-specific CD4 T cells were isolated from the spleen, CFSE-labeled and subsequently incubated for 72 h with the BM-DCs.

Carboxyfluorescein succinimidyl ester (CFSE) is a staining dye used to track cell division frequencies. The non-fluorescent form of CFSE enters the cell and is hydrolyzed by cellular esterases into the fluorescent form. Finally, the dye is retained within the cell through interactions of the succinimidyl mioety with primary amines and is equally distributed among daughter cells upon divisions. CFSE proliferation profile of T cells was measured by flow cytometry and quantified as division index.

Figure 33:
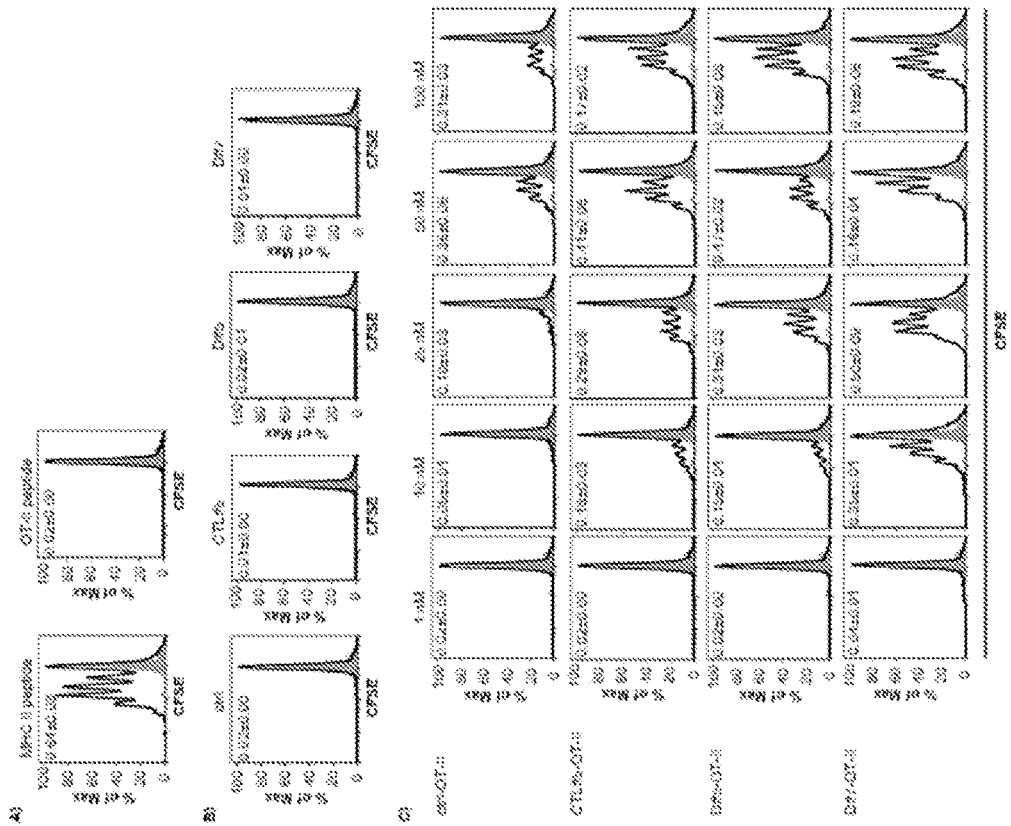
FIG. 33A-C: Aptamer-targeted delivery of OT-II peptide induces CD4 T cell activation. 5×10$^4$ BM-DCs were either treated with 400 nM MHC II peptide, 100 nM OT-II peptide (A), 100 nM DNA (B) or increasing concentrations of aptamer-peptide conjugates (C). 1×10$^5$ OVA-specific CD4 T cells were labeled with CFSE and added for 72 h. The CFSE profiles were measured by flow cytometry. One FACS histogram profile of one representative experiment out of n=4 is shown, where non-proliferative population is given in grey. Numbers show division index of triplicates (mean±SD). For more information see FIG. 42A-C-FIG. 44. The assays were done with blinded samples.

The results are shown in FIG. 33A-C and FIG. 42A-C-FIG. 44A-B. The non-proliferative population (grey peak) was obtained by adding T cells to non-treated BM-DCs. MHC II peptide compromised of only the OVA MHC II recognition amino acid sequence (FIG. 31A), is bound directly by MHC II molecules on the surface of BM-DCs. As anticipated, 400 nM MHC II peptide strongly activated CD4 T cells (FIG. 33A). In comparison, OT-II peptides need to be taken up by BM-DCs, processed and degraded into MHC II peptides. Without carrier, OT-II peptide was not observed to induce CD4 T cell proliferation (FIG. 33A). In addition, no CD4 T cell activation occurred after treatment with aptamers alone (FIG. 33B).

All aptamer-OT-II conjugates mediated CD4 T cell activation in a concentration-dependent manner (FIG. 33C). D #7-OT-II was the most potent activator, followed by D #5-OT-II and CTL #5-OT-II. In contrast, less T cell divisions were detectable after treatment with 25-100 nM of ctrl-OT-II, where no activation of CD4 T cells was observed at 1 nM concentration.

Over the past three decades, many human and mouse studies revealed that CD4 T cells were able to acquire cytotoxic function similar to CD8 T cells. Thus, activation of OVA-specific CD4 T cells was further analyzed by an in vitro cytotoxicity assay.

Cytotoxic Capacity of Activated CD4 T Cells:

In theory, cytotoxic CD4 T cells recognize their respective antigens on MHC II molecules and induce apoptosis of the carrier cell.

To investigate if the potent CD4 T cell activator D #7-OT-II (FIG. 33C) induces CD4-mediated cytotoxicity, an in vitro cytotoxicity assay was performed. $2 \times 10^5$ BM-DCs were incubated with MHC II peptide, D #7-OT-II or ctrl-OT-II in DC cell medium for 10 minutes at 37° C. $4 \times 10^5$ CD4 T cells were primed for 72 h by the differently treated BM-DCs, isolated and added to a mixture of differently CFSE-labeled target cells loaded with MHC II peptide and non-loaded control cells. On day 5, the target and control cells were stained with the viability marker Hoechst and analyzed by flow cytometry.

Figure 34:
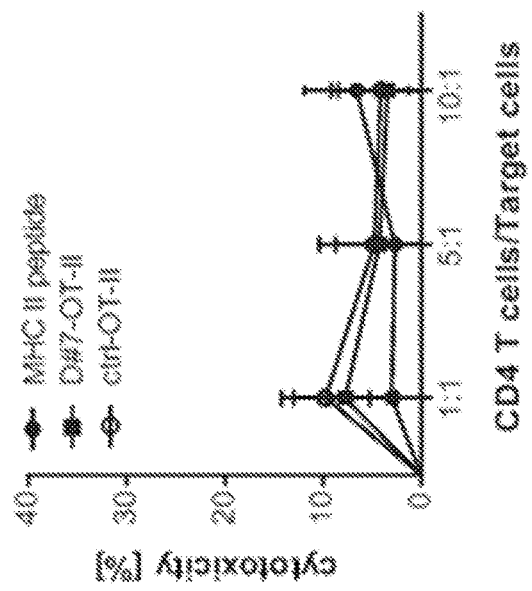
FIG. 34: CD4 cytotoxicity is not induced by aptamer-peptide conjugates. 2×10$^5$ BM-DCs were treated with 400 nM MHC II peptide, 100 nM D #7-OT-II or ctrl-OT-II conjugates. Next, 4×10$^5$ OVA-specific CD4 T cells were added. After 72 h, T cells were isolated by density gradient separation and incubated for another 24 h with CFSE-labeled target and control cells. Alive and dead target and control cells were distinguished by flow cytometry according to CFSE and Hoechst 33258 signals. The percentages of T cell cytotoxicity were determined (n=3, mean±SD).

As a result, no cytotoxic capacity of CD4 T cells was detectable upon priming with MHC II peptide, ctrl-OT-II or D #7-OT-II treated BM-DCs (FIG. 34).

In summary, the results of the in vitro proliferation assay (FIG. 33A-C) show that aptamers CTL #5, D #5 and D #7 are potent mediators of specific CD4 T cell activation. However, activation of T cells by D #7-OT-II did not result in cytotoxic capability.

Next, we investigated if aptamer based delivery of MHC I-restricted OVA peptides induce CD8 T cell activation.

Aptamer-Targeted Activation of CD8 T Cells:

Murine OVA-specific CD8 T cells were genetically modified to recognize $OVA_{257-264}$ (MHC I peptide; FIG. 31A) immobilized onto MHC I molecules on the surface of BM-DCs. To evaluate if aptamer-OT-I conjugates mediate targeted activation of OVA-specific CD8 T cell, an in vitro proliferation assay was utilized. Similarly as for CD4 T cells, $5 \times 10^4$ murine BM-DCs were either treated with MHC I or OT-I peptides, non-conjugated aptamers or aptamer-OT-I conjugates in DC cell medium for 10 minutes at 37° C. $1 \times 10^5$ OVA-specific CD8 T cells were isolated from spleen of transgenic mice, labeled with CFSE and subsequently added for 72 h to the treated BM-DCs. CFSE proliferation profile of T cells was monitored by flow cytometry and quantified as division index.

Results are shown in FIG. 35A-C and FIG. 45A-C-FIG. 47A-B. Profiles of non-proliferative T cells population (grey peaks) were acquired by measuring T cells incubated with non-treated BM-DCs. MHC I peptide is directly bound by MHC I molecules on the surface of BM-DCs. As expected, this peptide mediated strong CD8 proliferation at 1 nM concentration (FIG. 35A-C).

In contrast, the prolonged OVA peptide, OT-I peptide, was not anticipated to have intrinsic capacity to activate CD8 T cells (FIG. 35A), nevertheless, it was observed that at concentrations of 25-100 nM OT-I peptide induced CD8 proliferation.

As observed above for CD4 T cell activation (FIG. 33B), CD8 T cells were not activated by BM-DCs treated with non-conjugated aptamers (FIG. 35B).

All aptamer-OT-I chimeras activated CD8 T cells at different concentrations (FIG. 35C). In comparison to ctrl-OT-I, proliferation profiles of 25-50 nM aptamer-OT-I revealed that almost all cells of starting population (grey peak) shifted to the left, indicating cell divisions. No CD8 T cell proliferation was detectable at 10 nM.

In conclusion, all aptamers mediated CD8 T cell proliferation upon delivery of OT-I peptide.

Cytotoxic Capacity of Activated CD8 T Cells:

Activation of CD8 T cells results not only in proliferation, but also in gain of cytotoxic function. To verify that aptamer-mediated OT-I delivery results in CD8 T cell activation, an in vitro cytotoxicity assay was done. To this end, $4 \times 10^5$ OVA-specific CD8 T cells were incubated with $2 \times 10^5$ of differently treated BM-DCs and subsequently added to a mixture of differently CFSE-labeled target cells loaded with MHC I peptide and non-loaded control cells. Finally, the amount of alive and dead target and control cells was measured in flow cytometry by using Hoechst as viability marker and quantified as percentage of cytotoxicity.

As forecasted, 50 nM MHC I peptide induced rising CD8 T cell cytotoxicity with increasing T cell to target cell ratio (FIG. 36A-C). In addition, aptamer-OT-I conjugates functionalized CD8 T cells become cytotoxic effector cells. In comparison to ctrl-OT-I, cytotoxicity of aptamer-OT-I was elevated to an extent similar to MHC I peptide. These data highlight that aptamer-targeted delivery of OT-I peptide indeed activates CD8 T cells.

Discussion of Results in Examples:

Protective immunity requires activation of T cells. DCs mediate the transition between innate immunity and adaptive T cell-mediated immunity allowing for such activation to occur. Hence, DC-based vaccination is an emerging field in immunotherapy. Our approach for developing a DC vaccine is to conjugate antigens to carrier molecules that specifically target DCs.

Carrier molecules used thus far exhibit several limitations such as cost-intensive manufacturing, chemical stability, variations in production charges or intrinsic immunostimulatory potential. Aptamer-based carrier molecules may overcome these limitations.

We investigated if aptamers are capable to mediate T cell activation through targeted delivery of antigens to DCs. Aptamers targeting DCs were selected by two different strategies. First, aptamer CTL #5 was identified by addressing recombinant proteins originated from the cell surface receptor MR in a SELEX approach. Second, aptamers D #5 and D #7 were selected without knowledge of the respective target structure by directly using BM-DCs in a cell-SELEX process.

Next, the properties of the selected aptamers were elucidated. All identified candidate aptamers were found to bind BM-DCs, were internalized and localized within appropriate antigen processing compartments and had low immunogenicity.

Finally, functionality of aptamers as DC-targeting carrier molecules was analyzed in an OVA model system. We showed that our aptamers conjugated to antigenic OVA peptides were potent mediators of targeted activation of OVA-specific T cells.

Selection of DC-Targeting Aptamers:

Protein-SELEX:

DCs express a variety of endocytic receptors that are crucial for recognizing and processing antigenic structures for efficient T cell activation. Prominent examples are C-type lectin receptors, e.g. the MR. It is described that the recognition and uptake of pathogens by C-type lectin receptors determine the subsequent processing and antigen presentation. The C-type lectin receptor MR is known to direct antigens towards cross-presentation for CD8 T cell activation. Thus, the MR was chosen as an attractive target to identify aptamers that are internalized and localized in DCs in a similar way as MR ligands. In this work, the recombinant proteins Fc-CTL and Fc-FN, composed of domains of murine MR, were used in a protein-SELEX approach to select BM-DC-specific aptamers. As a result, a repertoire of aptamers that bind to both Fc-CTL and Fc-FN was selected.

Even though SELEX is a notionally simple method, it does not always result in aptamers with desired properties. Several factors influence the outcome of SELEX, including structural characteristics of targets, size and complexity of the starting library, choice of partitioning and elution methods and concentrations of targets and competitors.

Indeed, we did not identify sufficient Fc-FN binding sequences. Nevertheless, SELEX targeting Fc-CTL resulted in the identification of aptamer CTL #5. CTL #5 showed more than two-fold higher binding to Fc-CTL in comparison to Fc-FN (FIG. 15) and was additionally proven to bind BM-DCs (FIG. 21A-C).

Cell-SELEX:

As outlined in the introduction, in-depth knowledge of the respective target is not necessary for cell-aptamer selection. BM-DCs express a variety of molecules on their surface that are involved in modulating downstream T cell responses. These molecules represent accessible targets for aptamer selection. In the present work, aptamers D #5 and D #7 that are functional in targeted activation of T cells through antigen delivery to DCs, were identified without knowledge of the respective target structures on BM-DCs. This result extends previous findings in the literature. Since 1998, a growing number of aptamers recognizing mammalian cell types were identified by cell-SELEX. In several studies, cancer cell lines are the target of interest. For example, Tang and co-workers reported the generation of a series of aptamers as molecular probes for Burkitt lymphoma cells. Moreover, one aptamer, namely TD05, was observed to be functional in targeting of lymphoma cells in vivo.

The use of somatic cells in cell-SELEX has been also reported. Berezovski and co-workers enriched DNA libraries targeting either immature or mature murine BM-DCs for identification of cell state-specific biomarkers. In fact, biomarkers such as protein CXorf17 homologue and serine β-lactamase-like protein were until then unknown. However, binding or functionality of individual DNA sequences was not investigated.

Properties of DC-Aptamers:

Aptamers CTL #5, D #5 and D #7 were found to discriminate between BM-DCs and splenic T and B cells (FIG. 22). This highlights the specificity of the selected aptamers for targets mainly expressed by BM-DCs.

However, a small amount of B cells were bound by the aptamers. Without being bound by theory, B cells and DCs are classified as professional APCs with common functions and shared expression of surface receptors, which may explain these findings. Moreover, preliminary data revealed binding of CTL #5 to murine bone marrow-derived macrophages that represent the third type of professional APC (FIG. 48).

This result is comparable with previous studies, which utilize the mannose receptor targeting vaccine CDX-1307, and indicate binding to DCs as well as macrophages. Interestingly, binding to both cell types does not necessarily negatively influence the therapeutic efficacy; CDX-1307 is currently tested in phase II clinical trials for treatment of muscle-invasive bladder cancer (Table 3-1).

Immunogenicity of Aptamers:

Repeated administration of immunogenic molecules can cause severe adverse immunological reactions ranging from dizziness, flushing and headache, to inducing the secretion of autoantibodies.

In comparison to other carrier molecules like antibodies or viruses, aptamers are described to be low or non-immunogenic. This was confirmed for the selected aptamers in this work by the obtained results.

Here, the immunogenicity of the selected aptamers was investigated by measuring the TNF-α concentration in the supernatant of treated cells. Upon recognition of nucleic acids ligands by TLR3, 7/8, 9 or 13, signaling cascades are activated which triggers the secretion of the proinflammatory cytokine TNF-α (FIG. 28). As a result, only the naïve DNA library induced strong cytokine secretion (FIG. 29A-C). In theory, the library is composed of up to $10^{15}$-$10^{17}$ unique DNA sequences. Thus, it is very likely that some sequences resemble TLR ligands such as CpG rich motifs (Table below, which provides SEQ ID NOs:94-97)).

| ODN type | Representative sequence | Structural characteristics |
| --- | --- | --- |
| D- also referred to as A-class | GGTGCATCGATGCAGGGGGG | Mixed phosphodiester/phosphorothioate backbone<br>Single CpG motif<br>CpG flanking region forms a palindrome<br>Poly G tail at 3' end |
| K- also referred to as B-class | TCCATGGACGTTCCTGAGCGTT | Phosphorothioate backbone<br>Multiple CpG motifs<br>5' motif most stimulatory |
| C | TCGTCGTTCGAACGACGTTGAT | Phosphorothioate backbone<br>Multiple CpG motifs<br>TCG dimer at 5' end<br>CpG motif imbedded in a central palindrome |
| P | TCGTCGACGATCGGCGCGCGCCG | Phosphorothioate backbone<br>Two palindromes<br>Multiple CpG motifs |

Similar results were obtained in previous studies done by Avci-Adali et al. They observed upregulation of TLR pathway-related transcripts after treating human blood cells with a DNA starting library.

In general, CpG motifs are composed of a central unmethylated CG dinucleotide flanked by 5' purines and 3' pyrimidines. Four classes of CpG-rich oligonucleotides (ODN) are described so far and are used as TLR 9 ligands in pre-clinical and clinical studies (modified after Bode et al.). The phosphorothioate backbone increases the stability of the ODN.

Nevertheless, the conformation of aptamers might influence the immunogenicity. Other aptamers that were identified in our group to target breast cancer cells elicit elevated secretion of TNF-α (unpublished data). Consequently, immunogenicity of aptamers may be tested for individual sequences of interest.

Differentiation of murine bone marrow progenitors with GM-CSF results in a mixture of immature and mature DCs. Consequently, BM-DCs express moderate levels of co-stimulatory molecules like CD80, CD86 and CD40 which function as secondary signal for adequate T cell priming.

However, the situation in vivo may be different. Under non-inflammatory steady-state conditions DCs reside as immature cells in different tissues, i.e. they lack co-stimulatory molecules. Only after receiving inflammatory stimuli, DCs mature into professional APCs and acquire the capability to activate T cells. In turn, delivery of antigens to immature DCs in absence of inflammatory stimuli results in tolerogenicity. For instance, Bonifaz et al. observed that T cell proliferation and subsequent deletion occurred upon antibody-mediated OVA delivery to DEC-205 on DCs in absence of inflammatory stimuli.

Consequently, the use of the described aptamers for aptamer-based antigen delivery treatments in vivo may offer several therapeutic possibilities.

CTL #5 Specificity Towards MR:

C-type lectin receptors are non-canonical PRRs that enable the discrimination of self from non-self by cells involved in innate immunity. The C-type lectin receptor MR is mainly expressed by DCs and macrophages and described to direct antigens towards cross-presentation for CD8 T cell activation. Thus, the MR is an attractive target for DC-based vaccine strategies to recruit cytotoxic CD8 T cells.

We used recombinant Fc-CTL, composed of CTLD 4-7 from the MR (FIG. 11A), to identify aptamer CTL #5.

Although CTL #5 was observed to co-localize strongly with MR (FIG. 24A-B), MR−/− DCs were bound to the same extent as wild-type DCs (FIG. 24C). Thus, DC-targeting by CTL #5 may not only mediated by MR.

Without being bound by theory, a reasonable explanation could be that other C-type lectin receptors expressed on BM-DCs like DEC-205 or dectin-1 are recognized by CTL #5 (FIG. 23). A common structure of these receptors are CTLDs. Although CTLDs exhibit different ligand specificity among the receptors, they share conserved residues responsible for the typical formation of a hydrophobic fold (FIG. 37A-B).

Previous studies demonstrated that antigens endocytosed by the MR are entrapped within slowly maturing early endosomes for cross-presentation. Thus, co-localization of MR ligands with EEA1 is anticipated rather than lysosomal marker LAMP-1. Within this Example, both OVA and CTL #5 were observed to co-localize weakly with LAMP-1 besides the co-localization with EEA1 (FIG. 26A-C). Without being bound by theory, this suggests that upon endocytosis, both OVA and CTL #5 are shuttled into slowly as well as rapid maturing early endosome populations. Plus, OVA and CTL #5 may be internalized by other endocytic receptors apart from the MR or by distinct mechanisms like phagocytosis. For example, targeting of other receptors of the C-type lectin family like DEC-205 are described to potentiate internalization into early endosomes that rapidly mature into late endosomes and lysosomes. Subsequently, cargoes are immobilized onto MHC II molecules and presented to CD4 T cells.

Hence, antigens coupled to CTL #5 can be directed towards cellular compartments adequate for both MHC I and MHC II-epitope generation.

Aptamer-Targeted Activation of T Cell-Mediated Immunity:

Aptamer-Targeted Activation of CD4 T Cells:

This Example demonstrates aptamer-mediated CD4 T cell activation through targeting of DCs with a MHC II-restricted antigen.

CD4 T cells recognize antigenic peptides immobilized on MHC II. Basically, exogenous antigens are degraded within late endosomes or lysosomes and subsequently loaded onto MHC II in multivesicular bodies (MVBs). In the present study, all aptamers conjugated to the MHC II-restricted OT-II peptide mediated CD4 T cell activation in a concentration-dependent manner, as measured by in vitro proliferation assays (FIG. 33C).

However, only CTL #5 was observed to co-localize with the lysosomal marker LAMP-1 (FIG. 26B-C). A possible explanation may be that recycling of MHC II from the cell surface might enable the loading or exchange of antigens within early endosomes MHC II molecules are thought to be continuously recycled from the plasma membrane to early endosomes and back to the membrane. Some antigenic MHC II-epitopes were demonstrated to simply require unfolding and mild proteolysis that is enabled by proteases present in early endosomes. These epitopes can bind to recycled MHC II and are transported to the plasma membrane for presentation.

Another possible explanation is that aptamer-OT-II conjugates are internalized by phagocytic receptors. Antigens taken up by these receptors are entrapped within phagosomes. Phagosomes are composed of elements derived from early endosomes and the ER, thus they are detectable by staining of EEA1.

A third possible explanation may be that the attached OT-II peptide influenced the trafficking and processing within DCs.

Apart from that, ctrl-OT-II conjugates were observed to induce CD4 T cell division (FIG. 33C). This result was unexpected because neither the control sequence nor unconjugated OT-II peptide elicited T cell proliferation in their singular, unconjugated form (FIG. 33A-B). Furthermore, the control sequence was not internalized by BM-DCs (FIG. 25A-B). Without being bound by theory, it may be that the coupling of both molecules affects the internalization and processing by BM-DCs. Wengerter et al. observed minimal CD8 T cell division after treatment of splenic DCs with control sequence—as well as antibody isotype-OVA conjugates.

In general, activated CD4 T cells polarize into activator or suppressor cells that regulate other effectors of the adaptive immunity. However, a growing body of literature has analyzed the ability of CD4 T cells to acquire cytotoxic activity upon activation. Here, no CD4 T cell cytotoxicity was detectable in in vitro cytotoxicity assays (FIG. 34). There is no general agreement on the nature and role of cytotoxic CD4 T cells. Some studies revealed the development of cytotoxic CD4 T cells upon chronic viral infections, whereas others proposed their occurrence in anti-cancer immunity. Moreover, there are discrepancies if cytotoxic CD4 T cells represent a specialized subset of T cells or if they are associated with the Th1 phenotype Aptamer-Targeted Activation of CD8 T Cells.

CD8 T cells recognize antigens immobilized on MHC I molecules expressed by DCs. In the classical MHC I pathway, endogenous antigens are loaded onto MHC I molecules. However, this pathway can be bypassed by a process named cross-presentation. Exogenous antigens are thereby endocytosed by DCs and actively translocated out of slowly maturing early endosomes into the cytosol for generation of MHC I epitopes.

In the present study, aptamer-targeted delivery of OT-I peptide elicited strong CD8 T cell activation. This indicates that in accordance with the observed co-localization of all aptamers with early endosomes marker EEA1 (FIG. 26A-C and FIG. 27A-D), aptamer-based delivery of OT-I peptide mediated cross-presentation on MHC I molecules for efficient CD8 T cell activation (FIG. 35C).

These results are in agreement with Wengerter et al., where they targeted full-length OVA attached to DEC-205 specific aptamers to splenic DCs and observed proliferation of CD8 T cells. However, in other studies, OVA was demonstrated to be internalized, processed and cross-presented by DCs in its natural unconjugated form. It is questionable if the DEC-205 aptamers improved the effect of OVA on DCs and T cells.

Furthermore, activation of CD8 T cells was verified with in vitro cytotoxicity assays. In comparison to ctrl-OT-I conjugates, CD8 T cell cytotoxicity induced by aptamer-OT-I was elevated to an extent similar to MHC I peptide (FIG. 36A-C). This highlights the potential of aptamers to mediate efficient cytotoxic activity of CD8 T cells.

Unlike the OT-II peptide (FIG. 33A), the OT-I peptide was observed to have an intrinsic capacity to activate CD8 T cell divisions (FIG. 35A). Moreover, although ctrl-OT-I mediated low cytotoxic activity (FIG. 36A-C), it was observed to induce cell division (FIG. 35C). Similar results were obtained with ctrl-OT-II conjugates (FIG. 33C).

Herein we demonstrated the use of aptamers as delivery tools in an immunological context. The investigated DC-aptamers were selected with and without knowledge of the target structures. Both selections yielded aptamers that are potent DC-based vaccines in vitro. All aptamers direct antigens into eligible processing compartments for efficient antigen presentation and T cell activation.

Materials:

TABLE

| Equipment: | |
|---|---|
| Equipment | Manufacturer |
| FACS Canto II | BD |
| FACS LSR II | BD |
| FluoView FV1000 confocal laser scanning microscope | Olympus |
| Genoplex UV transilluminator | VWR |
| HPLC 1260 series, C18 Eclipse column | Agilent |
| LC-MS: HPLC 1100 series/ Easy-nLC esquire HCT | Agilent/Bruker |
| Liquid scintillation counter WinSpectral 1414 | Perkin Elmer |
| LSM 710 confocal laser scanning microscope | Zeiss |
| Nanodrop 2000c Spectrophotometer | Thermo Scientific |
| NanoQuant Infinite M200 Spectrophotometer | Tecan |
| PCR Mastercycler personal | Eppendorf |
| Phosphorimager FLA-3000 | Fujifilm |
| Pipets | Eppendorf |
| SpeedVac | Thermo Scientific |
| Water purification system | TKA/Thermo Scientific |

TABLE

| Consumables | |
|---|---|
| Consumable | Supplier |
| Amicon Ultra-0.5 Centrifugal Filter Devices 10K | Millipore |
| Cell culture plates | Sarstedt; TPP; Greiner Bio One |
| FACS tubes, 5 ml, 12 mm | Sarstedt |
| Falcon cell strainer 40 μm | Sarstedt |
| G25 columns | GE Healthcare |
| Nitrocellulose membrane (Protran 0.45 μm) | Schleicher and Schuell |
| Pipet tips | Sarstedt |
| Reaction tubes | Sarstedt; Eppendorf |

TABLE

Chemicals and reagents

| Reagent | Supplier |
| --- | --- |
| 1,1,1,3,3,3-hexafluoro-2-propanol (HFIP) | Sigma Aldrich |
| 1,4-Dithiothreitol (DTT) | Roth |
| 4',6-diamidino-2-phenylindole (DAPI) | Sigma Aldrich |
| Acetic acid | Merck |
| Acetonitril | Fluka |
| Agar | Sigma Aldrich |
| Agarose | Merck; Genaxxon |
| Ammoniumacetate | Gruessing |
| Ammoniumperoxodisulfate (APS) | Roth |
| Ampicillin sodium salt | AppliChem |
| Bis-Acrylamid, Rotiphorese | Roth |
| Bovine serum albumin (BSA, nuclease and protease free) | Calbiochem |
| Bromophenol blue | Merck |
| β-mercaptoethanol | Roth |
| Carboxyfluorescein succinimidyl ester (CFSE) | BD |
| Cell culture media | PAA |
| Chloroform | AppliChem |
| Calf intestinal alkaline phosphatase (CIAP) | Promega |
| Coomassie Brilliant Blue G250 | Biorad |
| Di-sodiumhydrogenphosphate-dihydrate | Merck |
| DNA ladders | Fermentas; Thermo Scientific |
| dNTPs/NTPs | Larova |
| DPBS | Gibco |
| Dynabeads Protein G | Invitrogen |
| Ethanol abs. | Sigma Aldrich |
| Ethdiumbromide | Roth |
| Ethylendiamintetraacetic acid (EDTA) | AppliChem |
| FCS Clone | PAA |
| Ficoll-Paque Premium 1.084 | GE Healthcare |
| Fluorogel mounting medium | EMS |
| Formaldehyde | Fluka |
| γ-$^{32}$P-ATP | Perkin Elmer |
| Glycine | Roth |
| Hoechst 33258 | Invitrogen |
| Inorganic pyrophosphatase (IPP) | Roche |
| Isopropanol | Merck |
| Lambda Exonuclease | Fermentas |
| Low fat dry milk powder | Roth |
| Magnesiumchloride-hexahydrate | AppliChem |
| Mouse serum | PAA |
| N,N,N',N'-tetramethylethylendiamide (TEMED) | Roth |
| Ovalbumin (OVA)-Alexa Fluor 647 | Life Technologies |
| Penicillin [10000 U/ml]/Streptomycin [10 mg/ml] | PAA |
| Phenol | Roth |
| Potassium chloride (KCl) | Gruessing |
| RNasin ribonuclease inhibitor | Promega |
| Rotiphorese sequencing gel concentrate | Roth |
| Prolong diamond antifade mountant | Life technologies |
| Protein ladders | Sigma Aldrich; Fermentas |
| Pwo polymerase | Genaxxon |
| Sodium chloride (NaCl) | AppliChem |
| Sodium dodecylsulfate (SDS) | Roth |
| Sodiumacetate | Gruessing |
| Superscript II reverse transcriptase | Thermo Scientific |
| T4 polynucleotide kinase (PNK) | NEB |
| T7 Y639F RNA-polymerase | Inhouse production |
| Taq polymerase | In house production; Promega |
| Tricine | Roth |
| Triethylamine (TEA) | Sigma Aldrich |
| Triethylammonium acetat (TEAA) | Sigma Aldrich |
| Tris | Roth |
| Triton-X 100 | Merck |
| Trypsin [0.05%]/EDTA [0.5M] | Thermo Scientific |
| Urea | AppliChem |
| Wheat germ agglutinin-Alexa Fluor 488 | Invitrogen |

TABLE

Kits

| Kit | Supplier |
| --- | --- |
| NucleoSpin Extract II Gel and PCR Clean-up | Macherey and Nagel |
| NucleoSpin plasmid | Macherey and Nagel |
| TOPO TA Cloning | Invitrogen |
| TruSeq DNA PCR-Free LT | Illumina |

Buffers and Solutions
1× Phosphate buffered saline (PBS)
137 mM NaCl, 2.7 mM KCl, 6.5 mM $Na_2HPO_4$, 1.47 mM $NaH_2OP_4$, pH 7.4
Gel Electrophoresis
1×TBE
90 mM Tris pH 8.0, 90 mM Borat, 2 mM EDTA
1×DNA loading buffer
25 mM Tris pH 8.0, 25% glycerol, 25 mM EDTA, bromphenol blue
1×RNA loading buffer
50% formamide, 0.013% SDS, 0.25 mM EDTA, bromophenol blue
10×PAA loading buffer
60% formamide, 5% SDS, 0.25 mM EDTA, bromphenol blue
3× Tricine SDS gel buffer
3 M Tris, 0.3% SDS, pH 8.45
1× Tricine SDS cathode buffer
0.1 M Tris, 0.1 M tricine, 0.1% SDS, pH 8.25
1× Tricine SDS anode buffer
0.2 M Tris, dissolved in $ddH_2O$, pH 8.9
4× non-reducing sample buffer
150 mM Tris pH 6.8, 30% glycerol, 12% SDS, bromophenol blue
4× Laemmli buffer
150 mM Tris pH 6.8, 30% glycerol, 12% SDS, 15% β-mercaptoethanol, bromophenol blue
10×SDS running buffer
250 mM Tris, 2 M glycine, 1% SDS
Coomassie staining solution
10% acetic acid, Coomassie Brilliant Blue G250
Coomassie destaining solution
10% acetic acid
Bacteria Culture
Agarose plates w/ ampicillin
3.8 g agarose, 5 g LB broth, 250 ml $ddH_2O$, 250 μl 100 mg/ml ampicillin
LB Medium w/ Ampicillin
10 g LB broth, 500 ml $ddH_2O$, 500 μl 100 mg/ml ampicillin
Flow Cytometry
FACS buffer
0.1% BSA, 0.005% $NaN_3$ in PBS
SELEX
Selection buffer protein-SELEX
PBS, 1 mM $MgCl_2$, 1 mM $CaCl_2$, 0.01 mg/ml BSA
Selection buffer cell-SELEX
DPBS (Gibco pH 7.0-7.2), 1 mM $MgCl_2$, 0.01 mg/ml BSA
Wash buffer
Selection buffer w/o BSA
Cell Culture
DC culture medium (DC-medium)
IMDM, 10% heat inactivated FCS, 50 μM β-mercaptoethanol, 100 U/ml penicillin, 0.1 mg/ml streptomycin, 2.5% R1/J558 supernatant w/ GM-CSF Macrophage Culture Medium (Macrophage-Medium)
IMDM, 10% heat inactivated FCS, 50 µM β-mercaptoethanol, 100 U/ml penicillin, 0.1 mg/ml streptomycin, 2.5% R1/J558 supernatant w/ M-CSF T Cell Medium
RPMI 1640, 10% heat inactivated FCS, 50 µM β-mercaptoethanol, 100 U/ml penicillin, 0.1 mg/ml streptomycin, 2 mM L-glutamine Oligonucleotides
All oligonucleotides, including 5'-thiol-C6 and 5'-ATTO 647N modified aptamers and control sequences (ctrl), were purchased from Ella Biotech GmbH (Martinsried). The DNA was supplied HPLC-purified and lyophilized.

TABLE

Oligonucleotides

| Name | Sequence 5'-3' | SEQ ID NO: |
|---|---|---|
| D3 DNA library | GCTGTGTGACTCCTGCAA-N43-GCAGCTGTATCTTGTCTCC | 98 |
| D3 fwd Primer | GCTGTGTGACTCCTGCAA | 99 |
| D3 rev Primer, 5'-phosphorylated | GGAGACAAGATACAGCTGC | 100 |
| CTL#5 | GCTGTGTGACTCCTGCAATGCAATCTAGCTGACAATGGGGGGAAGAATGTGGGTGGGTGGCAGCTGTATCTTGTCTCC | 101 |
| D#5 | GCTGTGTGACTCCTGCAACGCATTTGGGTGGGATTGTTATTTGGGTCGGGATTGGCAGTTGCAGCTGTATCTTGTCTCC | 102 |
| D#7 | GCTGTGTGACTCCTGCAACGTGGGTGGGTTTATATTCGGTGGTGGTGGGGGTGGTACTGTTGCAGCTGTATCTTGTCTCC | 103 |
| ctrl (CTL#5sc) | GCTGTGTGACTCCTGCAAGTGGTGTTAAGAGGTGAGGTATAACGCGGAATGGTGCGAGGCGCAGCTGTATCTTGTCTCC | 104 |

D3 NGS primer

| Name | Sequence 5'-3' | SEQ ID NO: |
|---|---|---|
| F1 | ATCACGGCTGTGTGACTCCTGCAA | 105 |
| R1 | ATCACGGGAGACAAGATACAGCTGC | 106 |
| F2 | CGATGTGCTGTGTGACTCCTGCAA | 107 |
| R2 | CGATGTGGAGACAAGATACAGCTGC | 108 |
| F3 | TTAGGCGCTGTGTGACTCCTGCAA | 109 |
| R3 | TTAGGCGGAGACAAGATACAGCTGC | 110 |
| F4 | TGACCAGCTGTGTGACTCCTGCAA | 111 |
| R4 | TGACCAGGAGACAAGATACAGCTGC | 112 |
| F5 | ACAGTGGCTGTGTGACTCCTGCAA | 113 |
| R5 | ACAGTGGGAGACAAGATACAGCTGC | 114 |
| F6 | GCCAATGCTGTGTGACTCCTGCAA | 115 |
| R6 | GCCAATGGAGACAAGATACAGCTGC | 116 |
| F7 | CAGATCGCTGTGTGACTCCTGCAA | 117 |
| R7 | CAGATCGGAGACAAGATACAGCTGC | 118 |
| F8 | ACTTGAGCTGTGTGACTCCTGCAA | 119 |
| R8 | ACTTGAGGAGACAAGATACAGCTGC | 120 |
| F9 | GATCAGGCTGTGTGACTCCTGCAA | 121 |
| R9 | GATCAGGGAGACAAGATACAGCTGC | 122 |
| F10 | TAGCTTGCTGTGTGACTCCTGCAA | 123 |
| R10 | TAGCTTGGAGACAAGATACAGCTGC | 124 |
| F11 | GGCTACGCTGTGTGACTCCTGCAA | 125 |
| R11 | GGCTACGGAGACAAGATACAGCTGC | 126 |
| F12 | CTTGTAGCTGTGTGACTCCTGCAA | 127 |
| R12 | CTTGTAGGAGACAAGATACAGCTGC | 128 |
| A50 library (DNA/RNA) | ATAGCTAATACGACTCACTATAGGGAGAGGAGGGAAGTCTACATCTT-N50-TTTCTGGAGTTGACGAAGCTT / GGGAGAGGAGGGAAGUCUACAUCUU-N50-UUUCUGGAGUUGACGAAGCUU | 129 |
| A50 fwd Primer | ATAGCTAATACGACTCACTATAGGGAGAGGAGGGAAGTCTACATCTT | 130 |
| A50 rev Primer | AAGCTTCGTCAACTCCAGAAA | 131 |

TABLE

Mouse strains

| Mouse strain | Description |
|---|---|
| C57/BL6J | Wildtype strain, Haplotype H-2K$^b$ |
| MR$^{-/-}$ | C57/BL6 background, stop codon inserted at the MR start codon of Exon 1, preventing its expression[192] |
| OTI Rag2$^{-/-}$ | C57/BL6 background, CD8 T cells express TCR specific for OVA$_{257-264}$ on MHC I, no endogenous TCR expression because of recombinant activating gene 2 (Rag2) deficiency[155] |
| OTII | C57/BL6 background, CD4 T cells express TCR specific for OVA$_{323-339}$ on MHC II[150] |

TABLE

Ovalbumin (OVA) peptides

| Protein | Sequence (N-C) | SEQ ID NO: | Supplier |
|---|---|---|---|
| MHC I peptide (OVA$_{257-264}$) | SIINFEKL | 132 | Tebu-Bio |
| MHC II peptide (OVA$_{323-339}$) | ISQAVHAAHAEINEAGR | 133 | Tebu-Bio |

TABLE-continued

Ovalbumin (OVA) peptides

| Protein | Sequence (N-C) | SEQ ID NO: | Supplier |
|---|---|---|---|
| OT-I peptide | VSGLEQLESIINFEKLTEWTSSNV | 69 | Panatecs |
| OT-II peptide | SAESLKISQAVHAAHAEINEAGRE VVGSA | 70 | Panatecs |

N-terminal functionalized maleimide OT-I and OT-II peptides were also purchased from Panatecs. OT-I and OT-II peptides were supplied HPLC-purified and lyophilized.

TABLE

Proteins

| Protein | Supplier |
|---|---|
| Activated Protein C (aPC), Xigris | Lilly |
| Humanes Alpha Thrombin | Cellsystems |
| Humanes Cytohesin 1 Sec 7 (Cyt1 Sec7) | In house production |
| Humanes Erk2 | In house production |
| Protein G | Invitrogen |

TABLE

Antibodies

| Antibody | Supplier |
|---|---|
| B220 (CD45RA)-eFluor450, Clone RA3-6B2 | eBioscience |
| B220 (CD45RA)-FITC, Clone T6D11 | Miltenyi |
| CD4-PerCP-Cy5.5, Clone Gk 1.5 | Biolegend |
| CD8α-eFluor450, Clone 53-6.7 | eBioscience |
| CD8α-PE, Clone 53-6.7 | eBioscience |
| EEA1, Clone H-300 | Santa Cruz |
| LAMP-1, Clone 1D4B | BD |
| MR-Alexa Fluor 488, Clone MR5D3 | AbD Serotec |
| Rabbit-Alexa Fluor 488 | Life Technologies |
| Rat-Alexa Fluor 488 | Life Technologies |

Methods:

If not noted otherwise, all experimental steps were done at room temperature.

Handling of Nucleic Acids

General Handling and Storage

Purchased lyophilized nucleic acids were dissolved in ddH$_2$0 according to the manufacturer manuals. The concentration was determined by UV spectrometry at 260 and 280 nm and the quality checked by agarose gel electrophoresis. For long-term storage, nucleic acids were kept at −20° C.

To determine the labeling efficiency, ATTO 647 N-labeled DNA was separated by gel electrophoresis and the fluorescence was monitored by Phosphorimager FLA-3000 (Fujifilm).

Agarose Gel Electrophoresis

4% agarose gels were used to monitor purchased nucleic acids, PCR products, generated single-stranded DNA or transcribed 2'F-RNA. To this end, 4 g agarose was dissolved in 100 ml TBE buffer and boiled for several minutes in the microwave. 40 ml was poured into the gel cast and stained with ethidiumbromide at a 1:10000 dilution.

Samples were diluted in DNA or RNA loading buffer, where RNA loading buffer was used for single-stranded DNA or 2'F-RNA to enable optimal separation. Gels were run in TBE buffer at 130 V for 25 minutes and bands were visualized by UV transilluminator (VWR) and evaluated by comparison with the standard DNA ladder.

Polyacrylamide Gel Electrophoresis (PAGE)

Polyacrylamide gel electrophoresis was used to separate nucleic acids for monitoring labeling efficiency of $^{32}$P-labeling. A 10% gel was prepared as described below (in "Table-Pipetting scheme for one 10% polyacrylamide gel") and poured into the gel cast. After polymerization for at least 1 hour, the gel was placed into a running chamber filled with 1×TBE buffer. The gel was pre-run for 30 minutes at 370 V and 15 W. Before loading the samples, the pockets were cleared with 1×TBE. Samples were diluted in PAA loading buffer and boiled for 3 minutes at 95° C. The gel was run for 45 minutes at 370 V and 15 W.

TABLE

Pipetting scheme for one 10% polyacrylamide gel

| Solution | Volume |
|---|---|
| Rotiphorese sequencing gel concentrate | 28 ml |
| 8.3M Urea | 35 ml |
| 8.3M Urea in 10 x TBE | 7 ml |
| 10% APS | 560 μl |
| TEMED | 28 μl |

Radioactivity was monitored by Phosphorimager FLA-3000 (Fujifilm).

Polymerase Chain Reaction (PCR)

The following pipetting scheme and PCR program were used to amplify DNA.

TABLE

Pipetting scheme for one PCR reaction

| Reagent | Stock concentration | Volume [μl] | Final concentration |
|---|---|---|---|
| Taq reaction buffer | 10× | 10 | 1× |
| MgCl$_2$ | 100 mM | 2 | 2 mM |
| dNTPs | 25 mM each | 0.8 | 0.2 mM |
| D3 fwd primer | 100 μM | 1 | 1 μM |
| D3 rev primer | 100 μM | 1 | 1 μM |
| Taq polymerase | 2.5 U/μl | 2 | 5 U |
| DNA template | | | 1-10 nM |
| ddH$_2$0 | | ad 100 μl | |

5'-phosphorylated reverse primers were used to enable single strand displacement by lambda exonuclease digestion.

TABLE

PCR program

| Step | Time [min] | Temperature [° C.] |
|---|---|---|
| Activation of Taq (first cycle) | 5 | 95 |
| Denaturation | 1 | 95 |
| Annealing | 1 | 64 |
| Elongation | 1.5 | 72 |
| Final elongation (last cycle) | 3 | 72 |
| Storage | ∞ | 4 |

PCR products were purified with the commercially available NucleoSpin clean-up kit from Machery and Nagel. In brief, 3 PCR reactions were pooled for 1 silica column and eluted with 2×25 μl ddH$_2$O.

Reverse Transcription-PCR (RT-PCR)

The following pipetting scheme and PCR program were used to reverse transcribe 2'F-RNA and amplify the obtained DNA.

TABLE

Pipetting scheme for one RT-PCR reaction

| Reagent | Stock concentration | Volume [µl] | Final concentration |
|---|---|---|---|
| Taq reaction buffer | 10× | 10 | 1× |
| First strand buffer | 5× | 4 | 0.2× |
| MgCl$_2$ | 100 mM | 1.5 | 1.5 mM |
| DTT | 100 mM | 2 | 2 mM |
| dNTPs | 25 mM each | 1.2 | 0.3 mM |
| A50 fwd primer | 100 µM | 1 | 1 µM |
| A50 rev primer | 100 µM | 1 | 1 µM |
| Taq polymerase | 2.5 U/µl | 2 | 5 U |
| Reverse Transcriptase | 200 U/µl | 1 | 2 U |
| DNA template | | | 1-10 nM |
| ddH$_2$O | | ad 100 µl | |

TABLE

RT-PCR program

| Step | Time [min] | Temperature [° C.] |
|---|---|---|
| Reverse transcription | 10 | 54 |
| Denaturation | 1 | 95 |
| Annealing | 1 | 60 |
| Elongation | 1.5 | 72 |
| Final elongation (last cycle) | 3 | 72 |
| Storage | ∞ | 4 |

Single Strand Displacement by Lambda Exonuclease Digestion

Lambda exonuclease selectively digests the 5'-phosphorylated strand of double-stranded DNA and thereby generates single-stranded DNA. The following reaction mixture was incubated for 45 minutes at 37° C. and the reaction was stopped by heating the samples for 15 minutes at 80° C.

TABLE

Pipetting scheme for one digestion reaction

| Reagent | Stock concentration | Volume [µl] | Final concentration |
|---|---|---|---|
| Lambda exonuclease reaction buffer | 10× | 5 | 1× |
| Purified PCR product | | 45 | |
| Lambda exonuclease | 10 U/µl | 1 | 10 U |

Single-stranded DNA was purified with the commercially available NucleoSpin clean-up kit from Machery and Nagel. In brief, 2 digestion reactions were pooled for 1 silica column and eluted with 2×20 µl ddH$_2$O. The concentration was determined by UV-spectrometry at 260 and 280 nm.

In Vitro Transcription:

The following pipetting scheme was used to transcribe DNA into 2'F-RNA. The T7 RNA-polymerase mutant Y639F was used to enable the introduction of 2'F-pyrimidines. The reaction mixture was incubated for 4 hours at 37° C. and purified by phenol/chloroform extraction and ethanol precipitation.

TABLE

Pipetting scheme for one in vitro transcription reaction:

| Reagent | Stock concentration | Volume [µl] | Final concentration |
|---|---|---|---|
| Tris pH 7.9 | 200 mM | 20 | 40 mM |
| MgCl$_2$ | 100 mM | 15 | 15 mM |
| DTT | 100 mM | 5 | 5 mM |
| ATP | 100 mM | 0.5 | 0.5 mM |
| GTP | 100 mM | 0.5 | 0.5 mM |
| 2'F-dUTP | 100 mM | 2 | 2 mM |
| 2'F-dCTP | 100 mM | 2 | 2 mM |
| RNasin | 40 U/µl | 1 | 40 U |
| T7 Y639F RNA-polymerase | 10 U/µl | 5 | 50 U |
| IPP | 2 U/µl | 0.2 | 0.4 U |
| DNA template | | | 1-10 nM |
| ddH$_2$O | | ad 100 µl | |

Phenol/Chloroform Extraction and Ethanol Precipitation

Phenol/Chloroform extraction and ethanol precipitation was used to isolate DNA or 2'F-RNA sequences from BM-DCs during cell-SELEX. One volume of phenol was mixed with one volume of nucleic acid solution by extensive vortexing. After spinning the samples at maximum speed for 3 minutes, the upper phase was transferred into a new tube. Two volumes of chloroform were added and the samples mixed and centrifuged. Again, the upper phase was transferred into a new tube for ethanol precipitation. DNA was precipitated with 1/10 volume 3 M NaOAc pH 5.4 and 3 volumes of cold ethanol absolute for at least 10 minutes at −80° C. Afterwards the samples were centrifuged at maximum speed for 20 minutes and the pellets washed with 70% cold ethanol. After spinning at maximum speed for 5 minutes, the pellets were air-dried and resuspended in 50 µl ddH$_2$O.

Quantification: Concentrations of nucleic acids were determined by using the NanoQuant infinite 200 (Tecan) or Nanodrop 2000c (Thermo Scientific) devices. In principle, absorption of nucleic acids at 260 nm was measured and correlated to the respective concentration by using the Lambert-Beer law. Ratio of absorbance at 260 nm and 280 nm determined the purity of nucleic acid solutions.

$^{32}$P-labeling of nucleic acids: For radioactive filter retention assay or binding assay, single-stranded DNA or dephosphorylated 2'F-RNA (Table) was labeled with $^{32}$P at the 5'-end by using the T4 polynucleotide kinase (PNK). The following reaction mixture (Table) was incubated for 1 hour at 37° C. and subsequently desalted by passing through a G25 column.

TABLE

Pipetting scheme of one dephosphorylation reaction:

| Reagent | Stock concentration | Volume [µl] | Final concentration |
|---|---|---|---|
| CIAP reaction buffer | 10× | 5 | 1× |
| BSA | 10 mg/ml | 5 | 1 mg/ml |
| 2'F-RNA | | | 1.5 µM |
| RNasin | 40 U/µl | 0.5 | 20 U |
| CIAP | 20 U/µl | 0.85 | 17 U |
| ddH$_2$O | | ad 50 µl | |
| Incubate for 15 minutes at 37° C. | | | |
| CIAP | 20 U/µl | 0.425 | 8.5 U |
| Incubate for 15 minutes at 55° C. | | | |
| EDTA | 0.5M | 0.5 µl | 5 mM |

TABLE-continued

Pipetting scheme of one dephosphorylation reaction:

| Reagent | Stock concentration | Volume [µl] | Final concentration |
|---|---|---|---|
| Incubate for 10 minutes at 75° C. | | | |
| ddH$_2$0 | | ad 100 µl | |

TABLE

Pipetting scheme for one $^{32}$P-labeling reaction:

| Reagent | Stock concentration | Volume [µl] | Final concentration |
|---|---|---|---|
| T4 PNK reaction buffer | 10× | 2 | 1× |
| γ-$^{32}$P-ATP | 10 µCi/µl | 1 | 10 µCi |
| DNA or 2'F-RNA | 1 µM | 10 | 10 pmol |
| T4 PNK | 10 U/µl | 2 | 20 U |
| ddH$_2$0 | | 5 | |

Labeling efficiency was monitored by polyacrylamide gel electrophoresis.

Cloning and sequencing: Cloning reaction was done in accordance with the manufacturer's protocol (TOPO-TA cloning kit, Invitrogen). In brief, freshly prepared PCR product was ligated into pCR2.1-TOPO vectors and cloned into OneShot Mach1-T1 chemical competent E. coli. Bacteria were plated on 10 cm agarose plates supplemented with 100 µg/ml ampicillin. After overnight incubation at 37° C., single bacteria colonies were picked and cultivated in 5 ml LB-medium supplemented with 100 µg/ml ampicillin overnight under vigorous shaking (150 rpm). Plasmids were prepared by using the commercially available Nucleospin plasmid kit from Machery and Nagel. In brief, 5 ml overnight culture solution was centrifuged and the plasmids isolated from the pellet by alkaline lysis reaction. Finally, the plasmids were purified by using a silica column. For sequencing, 30 ng of single sequences in a final volume of 20 µl was sent to GATC biotech AG (Koln). The appropriate M13-RP primer for sequencing was provided by GATC.

Next-Generation Sequencing (NGS)

PCR amplified DNA libraries obtained by SELEX were used for preparation of NGS samples. In four steps DNA is generated which contains index and adaptor sequences. Differently indexed DNA can be sequenced in one run and be assigned in later data analysis. Added adaptors enable the immobilization and processing of the sample by the Sequencing instrument.

TABLE

NGS Indices:

| Index | Sequence 5'-3' |
|---|---|
| 1 | ATCACG |
| 2 | CGATGT |
| 3 | TTAGGC |
| 4 | TGACCA |
| 5 | ACAGTG |
| 6 | GCCAAT |
| 7 | CAGATC |
| 8 | ACTTGA |
| 9 | GATCAG |
| 10 | TAGCTT |
| 11 | GGCTAC |
| 12 | CTTGTA |

First, NGS indices were introduced by utilizing index-containing D 3 primers.

The following pipetting scheme was used for one PCR reaction.

TABLE

Pipetting scheme for one PCR reaction for NGS preparation:

| Reagent | Stock concentration | Volume [µl] | Final concentration |
|---|---|---|---|
| Pwo reaction buffer | 10× | 10 | 1× |
| dNTPs | 25 mM each | 0.8 | 0.2 mM |
| fwd primer D3 F | 100 µM | 1 | 1 µM |
| rev primer D3 R | 100 µM | 1 | 1 µM |
| Pwo polymerase | 2.5 U/µl | 1 | 2.5 U |
| DNA template | | | 1-10 nM |
| ddH$_2$0 | | ad 100 µl | |

Second, the PCR products were mixed and phosphorylated at the 5'-end using the T4 polynucleotide kinase (PNK). The following mixture was incubated for 1 hour at 37° C. and vigorous shaking at 650 rpm.

TABLE

Pipetting scheme for 5'-phosphorylating of NGS samples:

| Reagent | Stock concentration | Volume [µl] | Final concentration |
|---|---|---|---|
| T4 PNK reaction buffer | 10× | 6 | 1× |
| ATP | 100 mM | 0.6 | 1 mM |
| Mixed DNA | | | 1-1.2 µg |
| T4 PNK | 10 U/µl | 0.5 | 5 U |
| ddH$_2$0 | | ad 60 µl | |

The samples were purified with the commercially available NucleoSpin clean-up kit from Machery and Nagel and concentrated in SpeedVac (Thermo Scientific). Third, adapters were ligated by using the TruSeq DNA PCR-Free LT kit, commercially available from Illumina. The following steps according to the manufacture's protocol were applied: End Repair, Adenylation and (enzymatic) Adaptor Ligation. Here, adaptor no. 12 was used. Fourth, the desired DNA which contained indices and adapters on both ends, was isolated by using preparative agarose gel electrophoresis and the commercially available NucleoSpin clean-up kit from Machery and Nagel. Briefly, the samples were diluted in DNA loading buffer, loaded on 2-2.5% agarose gels and run for 1 hour at 100 V. The desired band was cut and purified by a silica column. The quantification of the samples and the final NGS run on the Illumina HiSeq 1500 instrument was performed by members of Prof. Schultze's group, LIMES institute Bonn. NGS data was analyzed by AptaIT GmbH (Munchen).

Working with Proteins and Peptides:

General handling and storage: All proteins and peptides were dissolved in DPBS (Gibco) or PBS and kept on ice or at 4° C. in use. Proteins were stored at −20° C. for long-term storage. OT-I and OT-II peptides were dissolved in degased DPBS at a final concentration of 1 mM and analyzed on Tricine-SDS gels. Proteins and peptides were quantified by UV spectrometry at 280 and 205 nm using NanoDrop 2000c, Thermo Scientific.

SDS Polyacrylamide Gel Electrophoresis (SDS PAGE):

Classical Glycine-SDS PAGE was used to analyze the coupling efficiency of Fc-CTL and Fc-FN to Protein G magnetic beads. 1-5 ug of proteins were eluted from the beads by adding 0.1 M glycine pH 2.5 for 2 minutes. Protein solution was neutralized with 1.5 M Tris pH 8.8 and diluted in Laemmli buffer. The samples were heated at 95° C. for 5 minutes and loaded on 12.5% Glycine-SDS-gel (Table 17). After running the gel for 45 minutes at 175 V, 300 mA and 25 W in SDS running buffer, the proteins were stained with Coomassie staining solution for 10 seconds at maximum power in the microwave. The gel was destained with Coomassie destaining solution for 30 seconds at maximum power in the microwave. This step was repeated until the protein bands became clearly visible. The gel was visualized by UV transilluminator (VWR). The bands were compared with the standard protein ladder.

TABLE

Pipetting scheme for one 12.5% Glycine-SDS gel:

| Reagent | Stock concentration | Volume [µl] | Final concentration |
|---|---|---|---|
| 12.5% Glycine-SDS gel | | | |
| Tris pH 8.8 | 1.5M | 1500 | 375 mM |
| ddH$_2$0 | | 1940 | |
| Bis-Acrylamide | 30% | 2500 | 12.5% |
| SDS | 10% | 60 | 0.1% |
| TEMED | | 6 | |
| APS | 10% | 60 | 0.1% |
| 4% stacking gel | | | |
| Tris pH 6.8 | 1M | 500 | 250 mM |
| ddH$_2$0 | | 1220 | |
| Bis-Acrylamide | 30% | 270 | 4% |
| SDS | 10% | 10 | 0.05% |
| TEMED | | 2.5 | |
| APS | 10% | 10 | 0.05% |

The purity of the purchased OT-I and OT-II peptides as well as the coupling to the aptamers were analyzed by Tricine-SDS PAGE. 1-5 µg of peptides were diluted in nonreducing sample buffer and heated for 5 minutes at 95° C. The samples were loaded on 16% Tricine-SDS gel and run for 1 hour 45 minutes at 175 V, 300 mA and 25 W in Tricine SDS Anode and Cathode buffer. Here, in the vertical electrophoresis apparatus (Biorad) the anode buffer was the lower electrode buffer and the cathode buffer was the upper one. The gel was stained with Coomassie blue as described before. DNA was visualized by staining the gel with 1:10000 ethidiumbromide in TBE buffer for 10 minutes.

TABLE

Pipetting scheme for one 16% Tricine-SDS gel:

| Reagent | Stock concentration | Volume [µl] | Final concentration |
|---|---|---|---|
| 16% Tricine-SDS gel | | | |
| Tricine SDS gel buffer | 3× | 2000 | 1 |
| ddH$_2$0 | | 200 | |
| Bis-Acrylamide | 30% | 3200 | 16% |
| Glycerole | 100% | 600 | 10% |
| TEMED | | 6 | |
| APS | 10% | 60 | 0.1% |
| 10% spacer gel | | | |
| Tricine SDS gel buffer | 3× | 800 | 1× |
| ddH$_2$0 | | 800 | |
| Bis-Acrylamide | 30% | 800 | 10% |
| TEMED | | 2.4 | |
| APS | 10% | 24 | 0.1% |
| 4% stacking gel | | | |
| Tricine SDS gel buffer | 3× | 800 | 1× |
| ddH$_2$0 | | 1280 | |
| Bis-Acrylamide | 30% | 320 | 4% |
| TEMED | | 2.4 | |
| APS | 10% | 24 | 0.1% |

Production of Fusion Proteins Fc-CTL and Fc-FN:

Fusion proteins Fc-CTL and Fc-FN, and IgGi Fc protein were kindly provided by Prof. Sven Burgdorf, LIMES institute Bonn. Briefly, HEK293T cells were transfected with the previously described plasmids pIgplus-CTLD4-7 or pIgplus-CR-FNII-CTLD1-3, or pFuse-hIgG1-Fc2 purchased from Invitrogen. After 5 days of cultivation the supernatant was collected and Fc-CTL, Fc-FN or IgGi Fc proteins were purified by immobilization on a protein G column. The proteins were stored in PBS at 4 or −20° C. for long-term storage. Functionality of the proteins was analyzed as previously described. In brief, ovalbumin and collagen R were coated onto wells of 96-well plates and incubated with either Fc-CTL or Fc-FN. Binding was assessed by adding anti-hIgGi antibody horseradish conjugate and peroxidase substrate. Absorbance was measured at 450 and 620 nm.

Handling of mice and cells: C57BL/6J, MR$^{-/-}$, OTI RAG2$^{-/-}$ and OTII mice were bred in the central animal facility of the LIMES institute under specific pathogen-free conditions. Mice between 8-16 weeks were used in accordance with local animal experimental guidelines.

Cell culture: Cells were cultured under standard conditions (37° C., 5% CO$_2$, 95% humidity). Cells were handled under sterile conditions according to Si lab regulations. BM-DCs were centrifuged for 5 min at 200× g, splenocytes for 10 min at 300× g.

Isolation and cultivation of bone marrow-derived dendritic cells (BM-DC) and macrophages (BM-macrophages): Wildtype or MR$^{-/-}$ mice were sacrificed and the femur and tibia extracted. The bone marrow was flushed out with PBS and filtered through a 40 µm nylon membrane. The cells of the bone marrow were cultivated in DC-medium or macrophage-medium for 7 days. After 3-4 days the medium was changed.

Isolation and cultivation of splenocytes: The mouse (C57/BL6J, OTI RAG2$^{-/-}$ or OTII) was sacrificed and the spleen extracted. The spleen was mashed with a syringe plunger into cold PBS and filtered through a 40 µm nylon membrane. The cells were centrifuged and resuspended in T-cell medium.

Human Peripheral Blood Mononuclear Cells (PBMCs):

Human PBMCs were kindly provided by Prof. Joachim Schultze, LIMES institute Bonn. Cells were isolated and cultured as previously described by the members of Prof. Schultze's group. In brief, human blood PBMCs were obtained from healthy donor at the Institute for Experimental Hematology and Transfusion Medicine of the University Hospitals Bonn (local ethics votes no. 288/13). $CD14^+$ blood monocytes were either differentiated with GM-CSF alone or GM-CSF supplemented with IL-4, IFN-γ or TPP stimuli (TNF-α/$PGE_2$/P3C) to generate baseline macrophages, M1 or M2 macrophages, DCs or TPP macrophages.

SELEX

Coupling of Fc-fusion proteins to Protein G magnetic beads: Fc-CTL and Fc-FN were coupled to magnetic beads Protein G conjugates. 10 mg beads were washed thrice with 50 mM NaOAc pH 5. 200 µg proteins were added for 30 minutes and vigorous shaking at 400 rpm. The mixture was thereby resuspended every 5 minutes. The samples were finally washed thrice with PBS and stored in 2 ml PBS supplemented with 0.01 mg/ml BSA at 4° C. until use. Coupling efficiency was analyzed by SDS polyacrylamide gel electrophoresis.

Protein SELEX: The SELEX procedure was started by incubation of 1 nmol D 3 DNA library with 400 µg Fc-CTL- or Fc-FN-beads in a total volume of 100 µl selection buffer for 30 min at 37° C. The beads were resuspended every 5 minutes. After washing with wash buffer the bound DNA was eluted in 65 µl ddH2O 3 min at 80° C. and amplified. After lambda exonuclease digestion the DNA was purified by silica column and eluted in a total volume of 30 µl $ddH_2O$. 18 µl eluate was introduced in the subsequent rounds of SELEX. From the second round counter selection was carried out, i.e. enriched DNA was pre-incubated with 400 µg of the other Fc-fusion protein-beads. To gradually enhance the stringency of the selection process, the two washing cycles from round 1 were increased by two per selection round, ending with 24 at round 11.

Cell-SELEX: Before every selection experiment the cultivated BM-DCs were detached by using PBS, containing 2 mM EDTA, and seeded in 6 cm petri dishes. After reattachment the cells were washed twice with wash buffer. The naïve D 3 DNA or A50 2'F-RNA library and enriched libraries were denatured by heating 5 min at 95° C. and immediately added to the selection buffer. The naïve D 3 DNA library was supplemented with the mixture of enriched libraries of the $3^{rd}$ round of protein-SELEX targeting Fc-CTL and Fc-FN. The SELEX procedure was started by incubation of 1 nmol naïve library with $5 \times 10^6$ BM-DCs in a total volume of 2 ml selection buffer for 30 min at 37° C. The cells were rotated gently every 5 minutes. After washing the cells with wash buffer, they were scraped and the bound oligonucleotides eluted in $ddH_2O$ 5 min at 95° C. The nucleic acids were isolated by phenol/chloroform extraction and ethanol precipitation and amplified. The DNA was digested by lambda exonuclease and purified by silica column. The 2'F-RNA was transcribed by using 2'F-pyrimidines and purified by phenol/chloroform extraction and ethanol precipitation. To gradually increase the selection pressure, the amount of cells were decreased, starting from $1 \times 10^6$ (round 4-5) to $7.5 \times 10^5$ (round 6-10). Additionally, the concentration of oligonucleotides and the incubation time were reduced from 500 pmol (round 2) to 250 pmol (round 3-10) and 20 min (round 7) to 10 min (round 9-10), respectively.

Characterization Assays:

Flow cytometry binding assay: $4 \times 10^5$ BM-DCs were seeded in 24-well plates and cultivated under standard conditions for at least one hour. The cells were washed once with wash buffer (DPBS, 1 mM $MgCl_2$) and subsequently incubated for 10 minutes at 37° C. with ATTO 647N-labeled aptamers diluted in 200 µl DC-medium in total. The cells were scraped and transferred into FACS tubes containing 2 ml wash buffer. The samples were centrifuged for 5 minutes at 200× g and the supernatant discarded. The cell pellets were washed again with 1 ml wash buffer. Mean fluorescence intensities (MFI) were acquired by BD FACS Canto II or LSR II and analyzed by FlowJo software (BD). Binding analysis of BM-macrophages was done as mentioned above. The binding specificity of the aptamers was determined as follows. $2 \times 10^5$ BM-DCs were seeded in 24-well plates and incubated with 500 nM ATTO 647N-labeled aptamers for 30 minutes at 37° C. Splenocytes were isolated from wildtype mice and $2 \times 10^5$ cells were transferred into FACS tubes for incubation with 500 nM ATTO 647N-labeled aptamers. BM-DCs were washed as mentioned above. Splenocytes were washed once with 1 ml wash buffer and subsequently stained with 1:200 antibodies-mixes (anti-CD8α/CD4/B220 (CD45RA)) in FACS buffer for 20 minutes at 4° C. In parallel, BM-DCs were kept at 4° C. Finally, splenocytes were washed with 1 ml FACS buffer. The competition of aptamers by aptamer-peptide conjugates was determined as follows. $2 \times 10^5$ BM-DCs were transferred into FACS tubes and incubated with 250 nM ATTO 647N-labeled aptamers in absence or presence of 500 nM competitors for 10 minutes at 37° C. BM-DCs were washed as mentioned above.

Radioactive Binding Assay:

Filter retention assay: The interaction of DNA with proteins was monitored by radioactive filter retention assay. $^{32}P$-DNA was incubated with increasing concentrations of proteins in 25 µl protein-SELEX selection buffer for 30 minutes at 37° C. In the meantime, the nitrocellulose membrane was soaked in 0.4 M KOH for 15-20 minutes and subsequently rinsed with PBS. The dot blot unit and the vacuum manifold were assembled. The membrane was equilibrated with 200 µl wash buffer (PBS, 1 mM $MgCl_2$, 1 mM $CaCl_2$) and 20 µl sample was loaded. Afterwards, the membrane was washed 4 times with 200 µl wash buffer. 0.8 µl $^{32}P$-DNA was spotted on a dry membrane to allow the quantification of the percentage of DNA bound to the proteins. Radioactivity was acquired on the Phosphorimager FLA-3000 (Fujifilm) and quantified by using AIDA image software (raytest).

Cell binding assay using Cherenkov protocol: 7.5.2.2 Cell binding assay using Cherenkov protocol: $0.5 \times 10^5$ BM-DCs were seeded in 24-well plates and cultivated under standard conditions for at least one hour. The cells were washed once with wash buffer (DPBS, 1 mM $MgCl_2$) and subsequently incubated for 10 minutes at 37° C. with 1 pmol $^{32}P$-DNA or $^{32}P$-2'F-RNA diluted in 500 µl cell-SELEX selection buffer in total. The incubation buffer was collected in 1.5 ml reaction tubes as fraction I. The cells were washed twice with 500 µl wash buffer and both fractions were collected (fraction II and III). The cells were detached by adding 500 µl Trypsin/EDTA for several minutes at 37° C. and collected as fraction IV. Radioactivity was measured on the Liquid scintillation counter WinSpectral (Perkin Elmer) using the Cherenkov protocol. The percentage of bound $^{32}P$-DNA or $^{32}P$-2'F-RNA was calculated with the following formula:

$$\% \text{ bound } DNA = \left[ \frac{\text{fraction } IV}{\text{fraction } I + \text{fraction } II + \text{fraction } III + \text{fraction } IV} \right] * 100$$

Confocal microscopy: 2×10⁵ BM-DCs were seeded onto cover slips in 12-well plates and cultivated under standard conditions for at least one hour. The cells were washed once with wash buffer (DPBS, 1 mM MgCl2) and subsequently incubated for 30 minutes at 37° C. with 250 nM ATTO 647N-labeled CTL #5 or for 10 minutes at 37° C. with 250 nM ATTO 647N-labeled D #5 or D #7 diluted in 300 μl DC-medium in total. The cells were washed thrice with wash buffer and once with 1 ml DPBS. After fixation in 4% paraformaldehyde diluted in DPBS for 20 minutes, cells were washed thrice with DPBS and permeabilized in 0.1% Triton X-100 in DPBS for 5 minutes. The cells were washed thrice with DPBS and blocked in 10% milk in DPBS for 1 hour. Primary antibodies were diluted in DPBS at a dilution of 1:100. The cells were stained for 45 minutes and subsequently washed thrice with DPBS. Secondary antibodies were diluted 1:400 in DPBS. The cells were stained for 45 minutes and subsequently washed thrice with DPBS. The nuclei were stained with 1:1000 1 mg/ml DAPI in DPBS for 5 minutes and washed once with DPBS and twice with 2 ml ddH$_2$O. Finally, cover slips were mounted onto slides with Fluorogel or Prolong Diamond mouting medium. The co-localization studies of CTL #5 was done in comparison with OVA. Here, the cells were stained for 30 minutes at 37° C. with 250 ng/ml OVA-Alexa Fluor 647. In internalization studies the membranes were stained after fixation with WGA-Alexa Fluor 488 (1.5 μl 1 mg/ml WGA-AF488 in 500 μl DPBS) for 10 minutes. Confocal microscopy data for CTL #5 were acquired by FluoView FV1000 confocal laser scanning microscope (Olympus), and for D #5 and D #7 by LSM 710 confocal laser scanning microscope (Zeiss). Co-localization was quantified by Olympus FluoView or Zeiss Zen software.

TNF-α HTRF assay: TNF-α homogeneous time-resolved fluorescence (HTRF) assay was performed In accordance with the manufacturer guidelines (Cisbio). In brief, immortalized murine embryonic stem cell-derived macrophages were treated with increasing concentrations of oligonucleotides for 24 hours. Subsequently, cell supernatants were stained with two different anti-TNF-α antibodies attached to either fluorescence energy transfer (FRET) donor or acceptor molecules. In close proximity of these molecules the fluorescence emission spectrum changes and this change is proportional to the TNF-α concentration in the sample.

Generation of Aptamer-Peptide Conjugates:

Thiol-maleimide coupling: 5'-thiol-C6 oligonucleotides were purchased from Ella Biotech, dissolved in degased ddH$_2$O at a final concentration of 100 μM and stored at −20° C. The oligonucleotides were reduced with a 2000-fold molar excess of freshly prepared DTT in 1 M TEAA pH 8.3-8.5, heated up for 3 min at 70° C. following 1 h incubation at room temperature. The reduced oligonucleotides were desalted using an Amicon 10 K column into degased ddH2O and subsequently incubated with a 55-fold molar excess of N-maleimide-peptides. The reaction mixture was incubated overnight at 4° C. and purified by reverse-phase HPLC on a C18 column using a linear gradient of 100 mM HFIP and 10 mM TEA. The collected fractions were analyzed by LC-MS and the concentration quantified with UV spectrometry.

Functional Assays:

In vitro proliferation assay: 5×10⁴ BM-DCs were seeded in 96-well plates and cultivated under standard conditions for at least one hour. OTI or OTII T cells (OVA-specific CD8 or CD4 T cells) were isolated from spleen and stained with 1 μM CFSE in PBS for 15 min at 37° C. The T cells were washed three times with 4° C. cold PBS and centrifuged. Meanwhile, MHC I or MHC II peptides, aptamers, aptamer-peptide conjugates and OT-I or OT-II peptides were diluted in DC-medium and added to the BM-DCs for 10 min at 37° C. Subsequently, the supernatants from BM-DCs were removed and 1×10⁵ OTI or OTII T cells in 100 μl T cell medium were added. After 24 hours, 200 μl T cell medium was given per well and the cells were incubated for another 48 hours. Finally, the T cells were stained with anti-CD4 or anti-CD8alpha antibodies-fluorophore conjugates and analyzed by flow cytometry. The antibodies were diluted 1:400 in FACS buffer supplemented with mouse serum at a 1:100 dilution.

In vitro cytotoxicity assay: 2×10⁵ BM-DCs were seeded in 24-well plates and cultivated under standard conditions for at least one hour. OTI or OTII T cells (OVA-specific CD8 or CD4 T cells) were isolated from spleen and centrifuged at 300×g for 10 min. Meanwhile, MHC I or MHC II peptides, aptamers, aptamer-peptide conjugates and OT-I or OT-II peptides were diluted in DC-medium and added to the BM-DCs for 10 min at 37° C. Subsequently, the supernatants from BM-DCs were removed and 4×10⁵ OTI or OTII T cells in 400 μl T cell medium were added. After 24 hours, 2 ml T cell medium was given per well and the cells were incubated for another 48 hours. On day 4, T cells were isolated using Ficoll density gradient centrifugation. Splenocytes derived from wildtype mice were stained with different concentrations of CFSE and used as target or control cells. Target cells stained with 0.1 μM CFSE and loaded with 2 μM MHC I or MHC II peptides, and control cells stained with 1 μM CFSE were mixed equally and added in different T cells:mixed cells ratios. After 24 hours, cells were labeled with Hoechst 33258 and analyzed by flow cytometry. The cytotoxic activity was calculated with the following formula:

% cytotoxicity=100−[100*(p target)/(p control)/(n target)/(n control)], where p and n indicates if target and control cells were incubated for 24 hours without T cells (no (n) T cells) or with primed (p) T cells.

Experimental Analysis:

Statistics: If not otherwise noted, data for statistical quantification were acquired from individual experiments repeated at least two times. Samples of individual experiments were prepared at least in duplicates. Mean and standard deviation values were calculated with Microsoft Office Excel 2007.

REFERENCES

1 Hoption et al. *Postgrad Med* J79, 672-680 (2003).
2 Murphy et al. *Janeway's Immunobiology.* 7th edn, 928 (Garland Science, 2007).
3 Kawai et al. *Nat Immunol* 11, 373-384, (2010).
4 Janeway et al. *Annu Rev Immunol* 20, 197-216, (2002).
5 Behrens, G. et al. *Immunol Cell Biol* 82, 84-90, (2004).
6 Chambers et al. *Curr Opin Cell Biol* 11, 203-210 (1999).
7 Cheuk et al. *Cancer Gene Ther* 11, 215-226, (2004).
8 Curtsinger et al. *Curr Opin Immunol* 22, 333-340, 2010).
9 Curtsinger et al. *J Immunol* 171, 5165-5171 (2003).
10 Xing et al. *Cold Spring Harb Perspect Biol* 4, (2012).

11 Green et al. *Immunol Rev* 193, 70-81 (2003).
12 Lanzavecchia et al. *Curr Opin Immunol* 17, 326-332, (2005).
13 Banchereau et al. *Nature* 392, 245-252, (1998).
14 Delamarre et al. *Science* 307, 1630-1634, (2005).
15 Liu et al. *Immunol Rev* 234, 45-54, (2010).
16 Mellman et al. *Cell* 106, 255-258 (2001).
17 Kaisho et al. *Acta Odontol Scand* 59, 124-130 (2001).
18 Steinman et al. *Annu Rev Immunol* 21, 685-711, (2003).
19 Burgdorf et al. *Science* 316, 612-616, (2007).
20 Platt et al. *Proc Natl Acad Sci USA* 107, 4287-4292, (2010).
21 Sommer et al. *Front Zool* 2, 16, (2005).
22 Bouvier et al. *Mol Immunol* 39, 697-706 (2003).
23 Fremont et al. *Science* 272, 1001-1004 (1996).
24 Schuette et al. *Curr Opin Immunol* 26, 63-68, (2014).
25 Blanchard et al. *J Immunol* 184, 3033-3042, (2010).
26 Lakadamyali et al. *Cell* 124, 997-1009, (2006).
27 Roche et al. *Nat Rev Immunol* 15, 203-216, (2015).
28 O'Brien et al. Immunome Res 4, 6, (2008).
29 Klein et al. *FEBS Lett* 584, 1405-1410, (2010).
30 Lim et al. *Immunol Cell Biol* 89, 836-843, (2011).
31 Figdor et al. *Nat Rev Immunol* 2, 77-84, (2002).
32 van Vliet et al. *Immunol Cell Biol* 86, 580-587, (2008).
33 Osorio et al. *Immunity* 34, 651-664, (2011).
34 East et al. *Biochim Biophys Acta* 1572, 364-386 (2002).
35 McGreal et al. *Mol Immunol* 41, 1109-1121, (2004).
36 Frenz et al. *Eur J Pharm Biopharm* 95, 13-17, (2015).
37 Chatterjee et al. *Blood* 120, 2011-2020, (2012).
38 Burgdorf et al. *J Immunol* 176, 6770-6776 (2006).
39 Mahnke et al. *J Cell Biol* 151, 673-684 (2000).
40 Bol et al. *Clin Cancer Res* 22, 1897-1906, (2016).
41 Kreutz et al. *Blood* 121, 2836-2844, (2013).
42 Banchereau et al. *Cell* 106, 271-274 (2001).
43 Figdor et al. *Nat Med* 10, 475-480, (2004).
44 Kastenmuller et al. *Nat Rev Immunol* 14, 705-711, (2014).
45 Kantoff et al. *N Engl J Med* 363, 411-422, (2010).
46 Makarov et al. *Annu Rev Med* 60, 139-151, (2009).
47 Anassi et al. P T 36, 197-202 (2011).
48 Hammerstrom et al. *Pharmacotherapy* 31, 813-828, (2011).
49 Bui et al. *J Manag Care Spec Pharm* 22, 163-170, (2016).
50 Commission, E. Pharmaceuticals—Community register, ec.europa.eu/health/documents/community-register/html/h867.htm (2015).
51 Raich-Regue et al. *Vaccine* 30, 378-387, (2012).
52 Gilboa et al. J Clin Invest 117, 1195-1203, (2007).
53 Morelli et al. *Nat Rev Immunol* 7, 610-621, (2007).
54 Amos et al. *Blood* 118, 499-509, (2011).
55 Ludewig et al. *J Exp Med* 191, 795-804 (2000).
56 Roskrow et al. *Leuk Res* 23, 549-557 (1999).
57 Leleux et al. *J Control Release* 219, 610-621, (2015).
58 Morse et al. *Expert Rev Vaccines* 10, 733-742, (2011).
59 Dangles et al. *Cancer Immunol Immunother* 50, 673-681, (2002).
60 Morse et al. *Clin Cancer Res* 17, 4844-4853, (2011).
61 Riedmann et al. *Hum Vaccin Immunother* 8, 1742 (2012).
62 Dhodapkar et al. *Sci Transl Med* 6, 232ra251, (2014).
63 Cheong et al. *Blood* 116, 3828-3838, (2010).
64 Idoyaga et al. *Proc Nall Acad Sci USA* 108, 2384-2389, (2011).
65 Flynn et al., *Proc Nati Acad Sci USA* 108, 7131-7136, (2011).
66 Dong et al. *Mucosal Immunol* 6, 522-534, (2013).
67 Tacken et al. *J Immunol* 180, 7687-7696 (2008).
68 Ramakrishna et al. *J Immunol* 172, 2845-2852 (2004).
69 Ni et al. *J Immunol* 185, 3504-3513, (2010).
70 Saluja et al. *Int J Nanomedicine* 9, 5231-5246, (2014).
71 Rauen et al. *PLoS One* 9, e103755, (2014).
72 Rosalia et al. *Eur J Immunol* 43, 2554-2565, (2013).
73 Hartung et al. *J Immunol* 194, 1069-1079, (2015).
74 Vingert et al. *Eur J Immunol* 36, 1124-1135, (2006).
75 Thomann et al. *Biomaterials* 32, 4574-4583, (2011).
76 Gangadhar et al. *Nat Rev Clin Oncol* 11, 91-99, (2014).
77 Gilboa et al. *Clin Cancer Res* 19, 1054-1062, (2013).
78 Nimjee et al. *Annu Rev Med* 56, 555-583, (2005).
79 Lehmann et al. *Vaccines* (Basel) 4, (2016).
80 Mayer. *Angew Chem Int Ed Engl* 48, 2672-2689, (2009).
81 Hermann & Patel. *Science* 287, 820-825 (2000).
82 Stoltenburg et al. *Biomol Eng* 24, 381-403, (2007).
83 Tuerk & Gold *Science* 249, 505-510 (1990).
84 Ellington & Szostak. *Nature* 346, 818-822, (1990).
85 Hamedani et al. *Chem Commun* (Camb) 51, 1135-1138, (2015).
86 Rhie et al. *J Biol Chem* 278, 39697-39705, (2003).
87 Hamedani et al. *Methods Mol Biol* 1380, 61-75, (2016).
88 Raddatz et al. *Angew Chem Int Ed Engl* 47, 5190-5193, (2008).
89 Stoltenburg et al *Anal Bioanal Chem* 383, 83-91, (2005).
90 Bridonneau et al. *Antisense Nucleic Acid Drug Dev* 9, 1-11 (1999).
91 Mayer et al., *Proc Natl Acad Sci USA* 98, 4961-4965, (2001).
92 Avci-Adali et al. *Molecules* 15, 1-11, (2010).
93 Schutze et al. *PLoS One* 6, e29604, (2011).
94 Muller et al. *Chem Biol* 16, 442-451, (2009).
95 Huizenga & Szostak. *Biochemistry* 34, 656-665 (1995).
96 Mayer et al. Vol. 29 261-283 (Springer Berlin Heidelberg, 2013).
97 Mann et al., *Biochem Biophys Res Commun* 338, 1928-1934, (2005).
98 Bock et al. *Nature* 355, 564-566, (1992).
99 Opazo et al. *Mol Ther Nucleic Acids* 4, e251, (2015).
100 Shamah et al. *Acc Chem Res* 41, 130-138, (2008).
101 Ku et al. Sensors (Basel) 15, 16281-16313, (2015).
102 Vance et al., *Sci Rep* 4, 5129, (2014).
103 Bruno et al. *J Fluoresc* 24, 267-277, (2014).
104 Sun et al. *Mol Ther Nucleic Acids* 3, e182, (2014).
105 Sundaram et al. *Eur J Pharm Sci* 48, 259-271, (2013).
106 Trujillo et al. *Clin Ophthalmol* 1, 393-402 (2007).
107 Meyer et al. *J Nucleic Acids* 2011, 904750, (2011).
108 Mi, J. et al. *Nat Chem Biol* 6, 22-24, (2010).
109 Cheng et al., *Mol Ther Nucleic Acids* 2, e67, (2013).
110 Sefah et al. *Proc Nall Acad Sci USA* 111, 1449-1454, (2014).
111 Tolle et al., *Angew Chem Int Ed Engl* 54, 10971-10974, (2015).
112 Chu et al. *Cancer Res* 66, 5989-5992, (2006).
113 Xiao et al., Chemistry 14, 1769-1775, (2008).
114 Yan & Levy, RNA Biol 6, 316-320 (2009).
115 Wengerter et al. *Mol Ther* 22, 1375-1387, (2014).
116 Farokhzad et al. *Cancer Res* 64, 7668-7672, (2004).
117 McNamara et al. *Nat Biotechnol* 24, 1005-1015, (2006).
118 Kim et al. *Biomaterials* 31, 4592-4599, (2010).
119 Drolet et al. *Pharm Res* 17, 1503-1510 (2000).
120 Da Pieve et al., *Bioconjug Chem* 23, 1377-1381, (2012).
121 Parry et al., *Mol Cell Biol* 25, 9543-9553, (2005).
122 Santulli-Marotto et al., *Cancer Res* 63, 7483-7489 (2003).
123 Prodeus, et al., *Mol Ther Nucleic Acids* 4, e237 (2015).
124 McNamara et al., *J Clin Invest* 118, 376-386, (2008).
125 Pastor et al., *Mol Ther* 19, 1878-1886, (2011).

126 Berezovski et al., *J Am Chem Soc* 130, 9137-9143, (2008).
127 Hui et al., *Mol Cell Biochem* 306, 71-77, (2007).
128 Rotzschke et al., *Eur J Immunol* 21, 2891-2894, (1991).
129 McFarland et al., *Biochemistry* 38, 16663-16670 (1999).
130 Linehan et al., *Eur J Immunol* 31, 1857-1866, (2001).
131 Martinez-Pomares et al., *Eur J Immunol* 36, 1074-1082, (2006).
132 Lutz et al., *Immunity* 44, 1-2, (2016).
133 Lutz et al., *J Immunol Methods* 223, 77-92 (1999).
134 Bonifaz et al., *J Exp Med* 196, 1627-1638 (2002).
135 Heckel & Mayer, *J Am Chem Soc* 127, 822-823, (2005).
136 Lennarz et al., *ACS Chem Biol* 10, 320-327, (2015).
137 Weis et al., *Immunol Rev* 163, 19-34 (1998).
138 Martinez-Pomares, *J Leukoc Biol* 92, 1177-1186, (2012).
139 Feinberg et al. *J Biol Chem* 275, 21539-21548, (2000).
140 Harris et al. *Blood* 80, 2363-2373 (1992).
141 Patra et al. *Angew Chem Int Ed Engl* 51, 11863-11866, (2012).
142 Manoharanv *Angew Chem Int Ed Engl* 50, 2284-2288, (2011).
143 Su, et al. *Expert Rev Mol Diagn* 11, 333-343, (2011).
144 Blank et al. *Methods Mol Biol* 1380, 85-95, (2016).
145 Zinchuk et al. *Sci Rep* 3, 1365, (2013).
146 O'Neill et al. *Nat Rev Immunol* 13, 453-460, (2013).
147 Paludan et al. *Immunity* 38, 870-880, (2013).
148 Ballasv et al. *J Immunol* 167, 4878-4886 (2001).
149 Bauer et al. *Immunobiology* 213, 315-328, (2008).
150 Barnden et al. *Immunol Cell Biol* 76, 34-40, (1998).
151 Quah et al. *Nat Protoc* 2, 2049-2056, (2007).
152 Appay et al. *Clin Exp Immunol* 138, 10-13, (2004).
153 Haabethv, *Front Immunol* 5, 174, (2014).
154 Penaloza-MacMaster et al. *Science* 347, 278-282, (2015).
155 Hogquist et al. *Cell* 76, 17-27 (1994).
156 Wang et al. *PLoS One* 7, e43940, (2012).
157 Gold et al. *PLoS One* 5, e15004, (2010).
158 Lupold et al. *Cancer Res* 62, 4029-4033 (2002).
159 Hicke et al. *J Biol Chem* 276, 48644-48654, (2001).
160 Dassie et al. *Nat Biotechnol* 27, 839-849, (2009).
161 Morris et al. *Proc Natl Acad Sci USA* 95, 2902-2907 (1998).
162 Zhang et al. *Bioanalysis* 2, 907-918, (2010).
163 Ohuchi, *Biores Open Access* 1, 265-272, (2012).
164 Tang et al. *Anal Chem* 79, 4900-4907, (2007).
165 Mallikaratchy et al. *Nucleic Acids Res* 39, 2458-2469, (2011).
166 Guo et al. *Mini Rev Med Chem* 7, 701-705 (2007).
167 Mitchell et al. *Cancer Immunol Res* 3, 320-325, (2015).
168 Avci-Adali et al. *PLoS One* 8, e68810, (2013).
169 Bode et al. *Expert Rev Vaccines* 10, 499-511, (2011).
170 Labeur et al. *J Immunol* 162, 168-175 (1999).
171 Walseng et al. *J Biol Chem* 283, 14717-14727, (2008).
172 Tewari et al. *Nat Immunol* 6, 287-294, (2005).
173 Gagnon et al. *Cell* 110, 119-131 (2002).
174 Vieira et al. *Mol Cell Biol* 23, 2501-2514 (2003).
175 Marshall et al. *J Biomed Biotechnol* 2011, 954602, (2011).
176 Hahn et al. *Eur J Immunol* 25, 2679-2685, (1995).
177 Bercovici et al. *Clin Diagn Lab Immunol* 7, 859-864 (2000).
178 Ohlfest et al. *J Immunol* 190, 613-620, (2013).
179 Bouchard et al. *Annu Rev Pharmacol Toxicol* 50, 237-257, (2010).
180 Romani et al. *Curr Top Microbiol Immunol* 351, 113-138, (2012).
181 Bonifaz et al. *J Exp Med* 199, 815-824, (2004).
182 Agrawal et al. *J Immunol* 171, 4984-4989 (2003).
183 Seliger et al. *Front Immunol* 4, 419, (2013).
184 Xue et al. *Immunity* 40, 274-288, (2014).
185 Min et al. *J Immunol* 190, 2437-2446, (2013).
186 Wherry. *Nat Immunol* 12, 492-499 (2011).
187 Leggatt et al. *Vaccines (Basel)* 2, 537-548, (2014).
188 Blankenstein et al. *Nat Rev Cancer* 12, 307-313, (2012).
189 Liu et al. *Eur J Cancer Care (Engl)*, (2016).
190 Roep et al. *Cold Spring Harb Perspect Med* 2, a007781, (2012).
191 Tsuji et al. *J Immunol* 186, 1218-1227, (2011).
192 Lee et al. *Science* 295, 1898-1901, (2002).
193 Schagger, H. *Nat Protoc* 1, 16-22, (2006).
194 Nino-Castro et al. *Innate Immun* 20, 401-411, (2014).

What is claimed is:

1. A composition comprising at least one antigenic peptide conjugated to an aptamer, wherein (i) the aptamer specifically binds a target on an antigen presenting cell (ii) the aptamer is internalized upon contact with the cell, (iii) the aptamer is not immunostimulatory, and (iv) wherein the aptamer comprises a nucleic acid sequence as set forth in any one of SEQ ID NOs: 1-67 or a nucleic acid sequence having at least 95% sequence identity therewith over the entire length of said any one of SEQ ID NOs: 1-67.

2. The composition of claim 1, wherein the antigen presenting cell comprises a professional antigen presenting cell, selected from the group consisting of a monocyte, macrophage, a B cell, and a dendritic cell.

3. The composition of claim 1, wherein the target comprises a mannose receptor.

4. The composition of claim 1, wherein the antigenic peptide comprises an MHC-I restricted antigenic peptide, MHC-II restricted antigenic peptide, or a combination thereof.

5. The composition of claim 1, wherein the antigenic peptide is derived from a pathogen-associated antigen, a human self protein, a tumor antigen, or a vaccine antigen.

6. The composition of claim 1, wherein the aptamer comprises the nucleic acid sequence as set forth in any one of SEQ ID NOs: 19 (CTL #5), 36 (D #5) or 39 (D #7) or a nucleic acid sequence having at least 95% sequence identity therewith over the entire length of said any one of SEQ ID NOS: 19, 36 or 39.

7. The composition of claim 1, wherein the aptamer comprises a modification selected from the group consisting of: a 2'-O-methyl (2'-OMe) modification, a 2'-F modification, a 2'-NH$_2$ modification, a locked nucleic acid (LNA)

modification, polyethylene glycol (PEG)-conjugation, fluorescent tagging, monothiophosphate, or any combination thereof.

8. A composition comprising the composition of claim 1, and a pharmaceutically acceptable carrier.

9. A method of loading an MHC molecule with a peptide, comprising contacting the composition of claim 1 with an antigen presenting cell.

10. The method of claim 9, wherein the contacting elicits an immune response comprising an activation of CD8+ T cells, CD4+ T cells, or a combination thereof.

11. The method of claim 10, wherein the immune response comprises a prophylactic or a therapeutic immune response.

12. A method of delivering one or more antigenic peptides to an antigen presenting cell comprising contacting the antigen presenting cell with the composition of claim 1.

13. The method of claim 12, further comprising internalization of the composition into a cellular compartment of the antigen presenting cell.

14. The method of claim 13, wherein the cellular compartment comprises an endosome or a lysosome.

15. A method of eliciting an immune response in a subject in need thereof comprising administering to the subject a composition comprising the composition of claim 1.

16. The method of claim 15, wherein the aptamer comprises the nucleic acid sequence as set forth in any one of SEQ ID NOS: 19 (CTL #5), 36 (D #5) or 39 (D #7) or a nucleic acid sequence having at least 95% sequence identity therewith over the entire length of said any one of SEQ ID NOS: 19, 36 or 39.

17. The method of claim 15, wherein the aptamer comprises a nucleic acid sequence as set forth in any one of SEQ ID NOS: 1-67, or a nucleic acid sequence having at least 95% sequence identity therewith over the entire length of said any one of SEQ ID NOS: 1-67, in an amount effective to elicit an immune response.

18. A method of treating a cancer in a subject, the method comprising administering to the subject a therapeutically effective amount of the composition of claim 1.

* * * * *

SEQUENCE LISTING

<160> NUMBER OF SEQ ID NOS: 133

<210> SEQ ID NO 1
<211> LENGTH: 43
<212> TYPE: DNA
<213> ORGANISM: Artificial
<220> FEATURE:
<223> OTHER INFORMATION: Aptamer

<400> SEQUENCE: 1
cgcgcggctt aggtggttgg ttcttttggt ggttcttgtg gtg                43

<210> SEQ ID NO 2
<211> LENGTH: 43
<212> TYPE: DNA
<213> ORGANISM: Artificial
<220> FEATURE:
<223> OTHER INFORMATION: Aptamer

<400> SEQUENCE: 2
ccccggaaat tgcgtacttg tatcggtcct ttatcttgtt gtg                43

```
<210> SEQ ID NO 3
<211> LENGTH: 46
<212> TYPE: DNA
<213> ORGANISM: Artificial
<220> FEATURE:
<223> OTHER INFORMATION: Aptamer

<400> SEQUENCE: 3
ccacgagtat ttgctgggtc ctggtggcgt gggttttttgt gatgca                    46

<210> SEQ ID NO 4
<211> LENGTH: 43
<212> TYPE: DNA
<213> ORGANISM: Artificial
<220> FEATURE:
<223> OTHER INFORMATION: Aptamer

<400> SEQUENCE: 4
cggcgcgggg atatggggta cgtgttctgg tcctcttaca ttg                       43

<210> SEQ ID NO 5
<211> LENGTH: 302
<212> TYPE: DNA
<213> ORGANISM: Artificial
<220> FEATURE:
<223> OTHER INFORMATION: Aptamer

<400> SEQUENCE: 5
cgggtttgct cttggttagt gcttgtggtg gtgtgcgact tgggggggatt ctgttttttt    60 tttgtaactc ggggttgggt atcgttgcct gttctgtgtt tatgtattgt tgttatagtt   120
gtgtttcctg cgtgggctgg gatttattgg ggtttgtgct tgtttgttag gctctggtgt   180
atgttctttg tgtggtttat tgatttattt ttccggcccc atgcgcttct tgctccgctc   240
ggtctccttg tccgccttgg gcgggaaggt ttgtgtattg cgtggtgaag gctccgtgat   300
gt                                                                  302

<210> SEQ ID NO 6
<211> LENGTH: 86
<212> TYPE: DNA
<213> ORGANISM: Artificial
<220> FEATURE:
<223> OTHER INFORMATION: Aptamer

<400> SEQUENCE: 6
cggtggccgt ggtttcttcg tgtggttgtg ttttcgtcc ttggcggggg cagtgttaag     60
tcgtttaggt ggtggtcgtg tggtgg                                         86

<210> SEQ ID NO 7
<211> LENGTH: 43
<212> TYPE: DNA
<213> ORGANISM: Artificial
<220> FEATURE:
<223> OTHER INFORMATION: Aptamer

<400> SEQUENCE: 7
cccgctgtgt ttccttctgt gatgtttcgt tcgtttgttt gcc                      43

<210> SEQ ID NO 8
<211> LENGTH: 42
<212> TYPE: DNA
<213> ORGANISM: Artificial
<220> FEATURE:
<223> OTHER INFORMATION: Aptamer
```

```
<400> SEQUENCE: 8
gccagtattt tgatttcttt gggcgggggg gaatttatgt gg                           42

<210> SEQ ID NO 9
<211> LENGTH: 214
<212> TYPE: DNA
<213> ORGANISM: Artificial
<220> FEATURE:
<223> OTHER INFORMATION: Aptamer

<400> SEQUENCE: 9
cagtccacga ggggaggtgg gaatttttt gggtggtttt gtcgccgggt gggagtgctc         60
tctgttgcat gtgggtgggt agcgtgggcg ccacgcttgt tgtgggcggg agtggtggga       120
aactacgtgt gcaatctagc tgacaatggg ggggaagaat gtgggtgggt gccgtgggtg       180
ggtgggaatt gggaggatgc ggaattaact cagg                                  214

<210> SEQ ID NO 10
<211> LENGTH: 42
<212> TYPE: DNA
<213> ORGANISM: Artificial
<220> FEATURE:
<223> OTHER INFORMATION: Aptamer

<400> SEQUENCE: 10
cgcaatctag ctgacaatgg ggggaagaa tgtgggtggg tg                            42

<210> SEQ ID NO 11
<211> LENGTH: 172
<212> TYPE: DNA
<213> ORGANISM: Artificial
<220> FEATURE:
<223> OTHER INFORMATION: Aptamer

<400> SEQUENCE: 11
cgagatgggg gggaaggatg tgggtgggtg atcttcgttg ggtcgttgtg gggggaagg         60 atgtgggtgg gtctgtttca ggagcacggt actgtggggg ggtgggtcgg gaagaacggc      120
gccaggcgtc gtggggggt tgatgagcat tgggtgggag ttcagggttt gg                172

<210> SEQ ID NO 12
<211> LENGTH: 43
<212> TYPE: DNA
<213> ORGANISM: Artificial
<220> FEATURE:
<223> OTHER INFORMATION: Aptamer

<400> SEQUENCE: 12
ccgtgcgtgg gagggtgtga ttttcctggg gtgggagcat ggg                          43

<210> SEQ ID NO 13
<211> LENGTH: 85
<212> TYPE: DNA
<213> ORGANISM: Artificial
<220> FEATURE:
<223> OTHER INFORMATION: Aptamer

<400> SEQUENCE: 13
cgtactgatg cgtgggtggg tgggtacttt cttgatttgg gacgagcgtg ggggggtggg        60
tttcgggagc tccgggagca ctttg                                             85

<210> SEQ ID NO 14
<211> LENGTH: 346
```

<212> TYPE: DNA
<213> ORGANISM: Artificial
<220> FEATURE:
<223> OTHER INFORMATION: Aptamer

<400> SEQUENCE: 14

```
cactggattc gttggggttc ttttggggga tattccgggg tgggcaccgt gggcgggcta    60
tacttctttt catttgggtg ggaggtgcag gtccaatcgt tggggtttgg ggcgttcact   120
tcatcggggc ggctgtgggt ggggggggatt tgggaggatg cagggtaggt tgtcccaggg   180
gaggtgggtt ttttgggtag ttttggatca atggcccggc atgtttgggt gggatattgg   240
cgtgtttggg ttgggactgc tgcatgtttg ggtgggatat tggcgtgttt gggttgggac   300
tgctcgcatt tgggtgggat tgttatttgg gtcgggattg gcagtt               346
```

<210> SEQ ID NO 15
<211> LENGTH: 84
<212> TYPE: DNA
<213> ORGANISM: Artificial
<220> FEATURE:
<223> OTHER INFORMATION: Aptamer

<400> SEQUENCE: 15

```
cgcatttggg tgggattgtt atttgggtcg ggattggcag ttgtgggcgg gtttatattc    60
ggtggtggtg ggggtggttc tgtt                                         84
```

<210> SEQ ID NO 16
<211> LENGTH: 129
<212> TYPE: DNA
<213> ORGANISM: Artificial
<220> FEATURE:
<223> OTHER INFORMATION: Aptamer

<400> SEQUENCE: 16

```
cgtgggtggg tttatattcg gtggtggtgg gggtggtact gttcgtgggc gggtttatat    60
ttggtggtgg tgggggtggt actgttcgtg gtgggtttta tattcggtgg tggtgggggt   120
ggtactgtt                                                           129
```

<210> SEQ ID NO 17
<211> LENGTH: 172
<212> TYPE: DNA
<213> ORGANISM: Artificial
<220> FEATURE:
<223> OTHER INFORMATION: Aptamer

<400> SEQUENCE: 17

```
ccccaccaac tcgaccaagt cgctgctcct cttccttgtg ttgcaacgga ccctgggatg    60
tattcgtctc tctcgccgcc caccccccgt cccccccgtt gtgttcctac tctcgcccta   120
cacgaaccgc cgttctcgtc gtcctgtatg cgcctgttcg tctcctgttc ct           172
```

<210> SEQ ID NO 18
<211> LENGTH: 43
<212> TYPE: DNA
<213> ORGANISM: Artificial
<220> FEATURE:
<223> OTHER INFORMATION: Aptamer

<400> SEQUENCE: 18

```
gacggggcgg ttgttttttc tggttttcgg tatgttgtgt gtg                     43
```

<210> SEQ ID NO 19

```
<211> LENGTH: 43
<212> TYPE: DNA
<213> ORGANISM: Artificial
<220> FEATURE:
<223> OTHER INFORMATION: Aptamer

<400> SEQUENCE: 19
cctcctcatt gcttgttctc gccttgatcg tccctggccc gtt          43

<210> SEQ ID NO 20
<211> LENGTH: 430
<212> TYPE: DNA
<213> ORGANISM: Artificial
<220> FEATURE:
<223> OTHER INFORMATION: Aptamer

<400> SEQUENCE: 20
ccctcactgt agtcctgact tgtcgtattc ccggtttttct tgtccctggc cccctcactc      60
cccgtcattt gttctatgcc cgcgccccg gctctcccca ttggtctgtg ctctttcctc      120
cgttcgcccc ccccgcctct cgagcattta ccacccgggc gcttcacgtt tgcccgtttg      180
gtatatcgcg cattttggtc ccgttccttg tttgtcaggg gaggtgggtt tctttgggtt      240
gtttgtgaag tggggtgtcc cgaccccatc cggtattttg tgtaatctag tctctttgtg      300
tcccgaccga cgctgtattt tcgccaccac gctcgaccac ccctcccgac ccgccgcttt      360
ttccctcttc cgtcacctcc tttcgatgcg tcggattggt gttgtggtct ttgggttttg      420
gtttgtgtgt                                                              430

<210> SEQ ID NO 21
<211> LENGTH: 258
<212> TYPE: DNA
<213> ORGANISM: Artificial
<220> FEATURE:
<223> OTHER INFORMATION: Aptamer

<400> SEQUENCE: 21
ccaggggagg atgggcgggc ttttcgttgt cttctgtgtc gctgcggttc tgtgtgtggg      60
tgggtgggtg gtaatattgt ctcgcttccc tctttgcatc tcccgtatac ccgcccttt      120 aaccgtgtgt gggggttggg tgggttgggt gtcgattgcg tctctcttct tgcaggggag      180
gagggtgggc agaggtgttt agtgtgtccg ggtttccacc gcgctgatct tgctcccttc      240
cgtccgtccg ttcctccc                                                    258

<210> SEQ ID NO 22
<211> LENGTH: 42
<212> TYPE: DNA
<213> ORGANISM: Artificial
<220> FEATURE:
<223> OTHER INFORMATION: Aptamer

<400> SEQUENCE: 22
ccctcgacag ccttctcgtc ctctgtattg ggccatcctc cc           42

<210> SEQ ID NO 23
<211> LENGTH: 43
<212> TYPE: DNA
<213> ORGANISM: Artificial
<220> FEATURE:
<223> OTHER INFORMATION: Aptamer

<400> SEQUENCE: 23
cctagtacat ttcatccgcc tcgttgtcgc cccttcccgc cgt          43
```

<210> SEQ ID NO 24
<211> LENGTH: 43
<212> TYPE: DNA
<213> ORGANISM: Artificial
<220> FEATURE:
<223> OTHER INFORMATION: Aptamer

<400> SEQUENCE: 24
cggtttggtg tgtggttcgc gagtacgttt ccttctcgac ttg    43

<210> SEQ ID NO 25
<211> LENGTH: 43
<212> TYPE: DNA
<213> ORGANISM: Artificial
<220> FEATURE:
<223> OTHER INFORMATION: Aptamer

<400> SEQUENCE: 25
cgggtgcttt gttgtatgtt gtgtgtgggc tttttggtg tgg    43

<210> SEQ ID NO 26
<211> LENGTH: 302
<212> TYPE: DNA
<213> ORGANISM: Artificial
<220> FEATURE:
<223> OTHER INFORMATION: Aptamer

<400> SEQUENCE: 26
cgggtttgct cttggttagt gcttgtggtg gtgtgcgact tgggggggatt ctgttttttt    60 tttgtaactc ggggttgggt atcgttgcct gttctgtgtt tatgtattgt tgttatagtt   120
gtgtttcctg cgtgggctgg gatttattgg ggtttgtgct tgtttgttag gctctggtgt   180
atgttctttg tgtggtttat tgatttattt ttccggcccc atgcgcttct tgctccgctc   240
ggtctccttg tccgccttgg gcgggaaggt ttgtgtattg cgtggtgaag gctccgtgat   300
gt                                                                  302

<210> SEQ ID NO 27
<211> LENGTH: 86
<212> TYPE: DNA
<213> ORGANISM: Artificial
<220> FEATURE:
<223> OTHER INFORMATION: Aptamer

<400> SEQUENCE: 27
cggtggccgt ggtttcttcg tgtggttgtg tttttcgtcc ttggcggggg cagtgttaag    60
tcgtttaggt ggtggtcgtg tggtgg                                         86

<210> SEQ ID NO 28
<211> LENGTH: 43
<212> TYPE: DNA
<213> ORGANISM: Artificial
<220> FEATURE:
<223> OTHER INFORMATION: Aptamer

<400> SEQUENCE: 28
cccgctgtgt ttccttctgt gatgtttcgt tcgtttgttt gcc    43

<210> SEQ ID NO 29
<211> LENGTH: 42
<212> TYPE: DNA
<213> ORGANISM: Artificial
<220> FEATURE:

```
<223> OTHER INFORMATION: Aptamer

<400> SEQUENCE: 29
gccagtattt tgatttcttt gggcgggggg gaatttatgt gg                    42

<210> SEQ ID NO 30
<211> LENGTH: 214
<212> TYPE: DNA
<213> ORGANISM: Artificial
<220> FEATURE:
<223> OTHER INFORMATION: Aptamer

<400> SEQUENCE: 30
cagtccacga ggggaggtgg gaattttttt gggtggtttt gtcgccgggt gggagtgctc    60
tctgttgcat gtgggtgggt agcgtgggcg ccacgcttgt tgtgggcggg agtggtggga   120
aactacgtgt gcaatctagc tgacaatggg ggggaagaat gtgggtgggt gccgtgggtg   180
ggtgggaatt gggaggatgc ggaattaact cagg                              214

<210> SEQ ID NO 31
<211> LENGTH: 42
<212> TYPE: DNA
<213> ORGANISM: Artificial
<220> FEATURE:
<223> OTHER INFORMATION: Aptamer

<400> SEQUENCE: 31
cgcaatctag ctgacaatgg gggggaagaa tgtgggtggg tg                     42

<210> SEQ ID NO 32
<211> LENGTH: 172
<212> TYPE: DNA
<213> ORGANISM: Artificial
<220> FEATURE:
<223> OTHER INFORMATION: Aptamer

<400> SEQUENCE: 32
cgagatgggg gggaaggatg tgggtgggtg atcttcgttg ggtcgttgtg gggggaagg     60 atgtgggtgg gtctgtttca ggagcacggt actgtggggg ggtgggtcgg gaagaacggc   120
gccaggcgtc gtggggggt tgatgagcat tgggtgggag ttcagggttt gg            172

<210> SEQ ID NO 33
<211> LENGTH: 43
<212> TYPE: DNA
<213> ORGANISM: Artificial
<220> FEATURE:
<223> OTHER INFORMATION: Aptamer

<400> SEQUENCE: 33
ccgtgcgtgg gagggtgtga ttttcctggg gtgggagcat ggg                    43

<210> SEQ ID NO 34
<211> LENGTH: 85
<212> TYPE: DNA
<213> ORGANISM: Artificial
<220> FEATURE:
<223> OTHER INFORMATION: Aptamer

<400> SEQUENCE: 34
cgtactgatg cgtgggtggg tgggtacttt cttgatttgg gacgagcgtg gggggtggg    60 tttcgggagc tccgggagca ctttg                                        85
```

```
<210> SEQ ID NO 35
<211> LENGTH: 346
<212> TYPE: DNA
<213> ORGANISM: Artificial
<220> FEATURE:
<223> OTHER INFORMATION: Aptamer

<400> SEQUENCE: 35
cactggattc gttggggttc ttttggggga tattccgggg tgggcaccgt gggcgggcta      60
tacttctttt catttgggtg ggaggtgcag gtccaatcgt tggggtttgg ggcgttcact     120
tcatcggggc ggctgtgggt gggggggatt tgggaggatg cagggtaggt tgtcccaggg     180
gaggtgggtt ttttgggtag ttttggatca atggcccggc atgtttgggt gggatattgg     240
cgtgtttggg ttgggactgc tgcatgtttg ggtgggatat tggcgtgttt gggttgggac     300
tgctcgcatt tgggtgggat tgttatttgg gtcgggattg gcagtt                    346

<210> SEQ ID NO 36
<211> LENGTH: 84
<212> TYPE: DNA
<213> ORGANISM: Artificial
<220> FEATURE:
<223> OTHER INFORMATION: Aptamer

<400> SEQUENCE: 36
cgcatttggg tgggattgtt atttgggtcg ggattggcag ttgtgggcgg gtttatattc      60
ggtggtggtg ggggtggttc tgtt                                             84

<210> SEQ ID NO 37
<211> LENGTH: 129
<212> TYPE: DNA
<213> ORGANISM: Artificial
<220> FEATURE:
<223> OTHER INFORMATION: Aptamer

<400> SEQUENCE: 37
cgtgggtggg tttatattcg gtggtggtgg gggtggtact gttcgtgggc gggtttatat      60
ttggtggtgg tggggtggt actgttcgtg ggtgggttta tattcggtgg tggtgggggt     120
ggtactgtt                                                            129

<210> SEQ ID NO 38
<211> LENGTH: 172
<212> TYPE: DNA
<213> ORGANISM: Artificial
<220> FEATURE:
<223> OTHER INFORMATION: Aptamer

<400> SEQUENCE: 38
ccccaccaac tcgaccaagt cgctgctcct cttccttgtg ttgcaacgga ccctgggatg      60
tattcgtctc tctcgccgcc caccccccgt cccccccgtt gtgttcctac tctcgcccta    120
cacgaaccgc cgttctcgtc gtcctgtatg cgcctgttcg tctcctgttc ct            172

<210> SEQ ID NO 39
<211> LENGTH: 43
<212> TYPE: DNA
<213> ORGANISM: Artificial
<220> FEATURE:
<223> OTHER INFORMATION: Aptamer

<400> SEQUENCE: 39
gacggggcgg ttgttttttc tggttttcgg tatgttgtgt gtg                       43
```

<210> SEQ ID NO 40
<211> LENGTH: 43
<212> TYPE: DNA
<213> ORGANISM: Artificial
<220> FEATURE:
<223> OTHER INFORMATION: Aptamer

<400> SEQUENCE: 40
cctcctcatt gcttgttctc gccttgatcg tccctggccc gtt         43

<210> SEQ ID NO 41
<211> LENGTH: 430
<212> TYPE: DNA
<213> ORGANISM: Artificial
<220> FEATURE:
<223> OTHER INFORMATION: Aptamer

<400> SEQUENCE: 41
ccctcactgt agtcctgact tgtcgtattc ccggttttct tgtccctggc cccctcactc     60
cccgtcattt gttctatgcc cgcgccccg gctctcccca ttggtctgtg ctctttcctc    120
cgttcgcccc cccgcctct cgagcattta ccacccgggc gcttcacgtt tgcccgtttg    180
gtatatcgcg cattttggtc ccgttccttg tttgtcaggg gaggtgggtt tctttgggtt    240
gtttgtgaag tggggtgtcc cgaccccatc cggtattttg tgtaatctag tctctttgtg    300
tcccgaccga cgctgtattt tcgccaccac gctcgaccac cctcccgac cgccgcttt    360 ttccctcttc cgtcacctcc tttcgatgcg tcggattggt gttgtggtct ttgggttttg    420
gtttgtgtgt                                                           430

<210> SEQ ID NO 42
<211> LENGTH: 258
<212> TYPE: DNA
<213> ORGANISM: Artificial
<220> FEATURE:
<223> OTHER INFORMATION: Aptamer

<400> SEQUENCE: 42
ccaggggagg atgggcgggc ttttcgttgt cttctgtgtc gctgcggttc tgtgtgtggg     60
tgggtgggtg gtaatattgt ctcgcttccc tctttgcatc tcccgtatac cccgcccttt    120
aaccgtgtgt gggggttggg tgggttgggt gtcgattgcg tctctcttct tgcaggggag    180
gagggtgggc agaggtgttt agtgtgtccg ggtttccacc gcgctgatct tgctcccttc    240
cgtccgtccg ttcctccc                                                  258

<210> SEQ ID NO 43
<211> LENGTH: 42
<212> TYPE: DNA
<213> ORGANISM: Artificial
<220> FEATURE:
<223> OTHER INFORMATION: Aptamer

<400> SEQUENCE: 43
ccctcgacag ccttctcgtc ctctgtattg ggccatcctc cc          42

<210> SEQ ID NO 44
<211> LENGTH: 43
<212> TYPE: DNA
<213> ORGANISM: Artificial
<220> FEATURE:
<223> OTHER INFORMATION: Aptamer

<400> SEQUENCE: 44
cctagtacat tcatccgcc tcgttgtcgc cccttcccgc cgt    43

<210> SEQ ID NO 45
<211> LENGTH: 43
<212> TYPE: DNA
<213> ORGANISM: Artificial
<220> FEATURE:
<223> OTHER INFORMATION: Aptamer

<400> SEQUENCE: 45
cggtttggtg tgtggttcgc gagtacgttt ccttctcgac ttg    43

<210> SEQ ID NO 46
<211> LENGTH: 43
<212> TYPE: DNA
<213> ORGANISM: Artificial
<220> FEATURE:
<223> OTHER INFORMATION: Aptamer

<400> SEQUENCE: 46
cgggtgcttt gttgtatgtt gtgtgtgggc tttttggtg tgg    43

<210> SEQ ID NO 47
<211> LENGTH: 302
<212> TYPE: DNA
<213> ORGANISM: Artificial
<220> FEATURE:
<223> OTHER INFORMATION: Aptamer

<400> SEQUENCE: 47
cgggtttgct cttggttagt gcttgtggtg gtgtgcgact tgggggattt ctgtttttt     60 tttgtaactc ggggttgggt atcgttgcct gttctgtgtt tatgtattgt tgttatagtt    120
gtgtttcctg cgtgggctgg gatttattgg ggtttgtgct tgtttgttag gctctggtgt    180
atgttctttg tgtggtttat tgatttattt ttccggcccc atgcgcttct tgctccgctc    240
ggtctccttg tccgccttgg gcgggaaggt ttgtgtattg cgtggtgaag gctccgtgat    300
gt    302

<210> SEQ ID NO 48
<211> LENGTH: 86
<212> TYPE: DNA
<213> ORGANISM: Artificial
<220> FEATURE:
<223> OTHER INFORMATION: Aptamer

<400> SEQUENCE: 48
cggtggccgt ggtttcttcg tgtggttgtg tttttcgtcc ttggcggggg cagtgttaag    60
tcgtttaggt ggtggtcgtg tggtgg    86

<210> SEQ ID NO 49
<211> LENGTH: 43
<212> TYPE: DNA
<213> ORGANISM: Artificial
<220> FEATURE:
<223> OTHER INFORMATION: Aptamer

<400> SEQUENCE: 49
cccgctgtgt ttccttctgt gatgtttcgt tcgtttgttt gcc    43

<210> SEQ ID NO 50
<211> LENGTH: 42
<212> TYPE: DNA

```
<213> ORGANISM: Artificial
<220> FEATURE:
<223> OTHER INFORMATION: Aptamer

<400> SEQUENCE: 50
gccagtattt tgatttcttt gggcgggggg gaatttatgt gg                    42

<210> SEQ ID NO 51
<211> LENGTH: 214
<212> TYPE: DNA
<213> ORGANISM: Artificial
<220> FEATURE:
<223> OTHER INFORMATION: Aptamer

<400> SEQUENCE: 51
cagtccacga ggggaggtgg gaatttttt gggtggtttt gtcgccgggt gggagtgctc   60
tctgttgcat gtgggtgggt agcgtgggcg ccacgcttgt tgtgggcggg agtggtggga 120
aactacgtgt gcaatctagc tgacaatggg ggggaagaat gtgggtgggt gccgtgggtg 180
ggtgggaatt gggaggatgc ggaattaact cagg                             214

<210> SEQ ID NO 52
<211> LENGTH: 42
<212> TYPE: DNA
<213> ORGANISM: Artificial
<220> FEATURE:
<223> OTHER INFORMATION: Aptamer

<400> SEQUENCE: 52
cgcaatctag ctgacaatgg gggggaagaa tgtgggtggg tg                    42

<210> SEQ ID NO 53
<211> LENGTH: 172
<212> TYPE: DNA
<213> ORGANISM: Artificial
<220> FEATURE:
<223> OTHER INFORMATION: Aptamer

<400> SEQUENCE: 53
cgagatgggg gggaaggatg tgggtgggtg atcttcgttg ggtcgttgtg gggggaagg   60 atgtgggtgg gtctgtttca ggagcacggt actgtggggg ggtgggtcgg aagaacggc  120 gccaggcgtc gtggggggt tgatgagcat tgggtgggag ttcagggttt gg          172

<210> SEQ ID NO 54
<211> LENGTH: 43
<212> TYPE: DNA
<213> ORGANISM: Artificial
<220> FEATURE:
<223> OTHER INFORMATION: Aptamer

<400> SEQUENCE: 54
ccgtgcgtgg gagggtgtga ttttcctggg gtgggagcat ggg                   43

<210> SEQ ID NO 55
<211> LENGTH: 85
<212> TYPE: DNA
<213> ORGANISM: Artificial
<220> FEATURE:
<223> OTHER INFORMATION: Aptamer

<400> SEQUENCE: 55
cgtactgatg cgtgggtggg tgggtacttt cttgatttgg gacgagcgtg gggggtggg   60 tttcgggagc tccgggagca ctttg                                       85
```

<210> SEQ ID NO 56
<211> LENGTH: 346
<212> TYPE: DNA
<213> ORGANISM: Artificial
<220> FEATURE:
<223> OTHER INFORMATION: Aptamer

<400> SEQUENCE: 56

```
cactggattc gttggggttc ttttgggggga tattccgggg tgggcaccgt gggcgggcta     60
tacttctttt catttgggtg ggaggtgcag gtccaatcgt tggggtttgg ggcgttcact    120
tcatcggggc ggctgtgggt ggggggggatt tgggaggatg cagggtaggt tgtcccaggg    180
gaggtgggtt ttttgggtag ttttggatca atggcccggc atgtttgggt gggatattgg    240
cgtgtttggg ttgggactgc tgcatgtttg ggtgggatat tggcgtgttt gggttgggac    300
tgctcgcatt tgggtgggat tgttatttgg gtcgggattg gcagtt                   346
```

<210> SEQ ID NO 57
<211> LENGTH: 84
<212> TYPE: DNA
<213> ORGANISM: Artificial
<220> FEATURE:
<223> OTHER INFORMATION: Aptamer

<400> SEQUENCE: 57

```
cgcatttggg tgggattgtt atttgggtcg ggattggcag ttgtgggcgg gtttatattc     60
ggtggtggtg ggggtggttc tgtt                                            84
```

<210> SEQ ID NO 58
<211> LENGTH: 129
<212> TYPE: DNA
<213> ORGANISM: Artificial
<220> FEATURE:
<223> OTHER INFORMATION: Aptamer

<400> SEQUENCE: 58

```
cgtgggtggg tttatattcg gtggtggtgg gggtggtact gttcgtgggc gggtttatat     60
ttggtggtgg tgggggtggt actgttcgtg ggtgggttta tattcggtgg tggtgggggt    120
ggtactgtt                                                            129
```

<210> SEQ ID NO 59
<211> LENGTH: 172
<212> TYPE: DNA
<213> ORGANISM: Artificial
<220> FEATURE:
<223> OTHER INFORMATION: Aptamer

<400> SEQUENCE: 59

```
ccccaccaac tcgaccaagt cgctgctcct cttccttgtg ttgcaacgga ccctgggatg     60
tattcgtctc tctcgccgcc cacccccgt ccccccgtt gtgttcctac tctcgcccta     120
cacgaaccgc cgttctcgtc gtcctgtatg cgcctgttcg tctcctgttc ct           172
```

<210> SEQ ID NO 60
<211> LENGTH: 43
<212> TYPE: DNA
<213> ORGANISM: Artificial
<220> FEATURE:
<223> OTHER INFORMATION: Aptamer

<400> SEQUENCE: 60
gacggggcgg ttgtttttc tggttttcgg tatgttgtgt gtg    43

<210> SEQ ID NO 61
<211> LENGTH: 43
<212> TYPE: DNA
<213> ORGANISM: Artificial
<220> FEATURE:
<223> OTHER INFORMATION: Aptamer

<400> SEQUENCE: 61
cctcctcatt gcttgttctc gccttgatcg tccctggccc gtt    43

<210> SEQ ID NO 62
<211> LENGTH: 430
<212> TYPE: DNA
<213> ORGANISM: Artificial
<220> FEATURE:
<223> OTHER INFORMATION: Aptamer

<400> SEQUENCE: 62
ccctcactgt agtcctgact tgtcgtattc ccggttttct tgtccctggc cccctcactc    60
cccgtcattt gttctatgcc cgcgccccg gctctcccca ttggtctgtg ctctttcctc    120
cgttcgcccc ccccgcctct cgagcattta ccacccgggc gcttcacgtt tgcccgtttg    180
gtatatcgcg cattttggtc ccgttccttg tttgtcaggg gaggtgggtt tctttgggtt    240
gtttgtgaag tggggtgtcc cgaccccatc cggtattttg tgtaatctag tctctttgtg    300
tcccgaccga cgctgtattt tcgccaccac gctcgaccac ccctcccgac ccgccgcttt    360
ttccctcttc cgtcacctcc tttcgatgcg tcggattggt gttgtggtct ttgggttttg    420
gtttgtgtgt    430

<210> SEQ ID NO 63
<211> LENGTH: 258
<212> TYPE: DNA
<213> ORGANISM: Artificial
<220> FEATURE:
<223> OTHER INFORMATION: Aptamer

<400> SEQUENCE: 63
ccaggggagg atgggcgggc ttttcgttgt cttctgtgtc gctgcggttc tgtgtgtggg    60
tgggtgggtg gtaatattgt ctcgcttccc tctttgcatc tcccgtatac cccgcccttt    120
aaccgtgtgt gggggttggg tgggttgggt gtcgattgcg tctctcttct tgcaggggag    180
gagggtgggc agaggtgttt agtgtgtccg ggtttccacc gcgctgatct tgctcccttc    240
cgtccgtccg ttcctccc    258

<210> SEQ ID NO 64
<211> LENGTH: 42
<212> TYPE: DNA
<213> ORGANISM: Artificial
<220> FEATURE:
<223> OTHER INFORMATION: Aptamer

<400> SEQUENCE: 64
ccctcgacag ccttctcgtc ctctgtattg ggccatcctc cc    42

<210> SEQ ID NO 65
<211> LENGTH: 43
<212> TYPE: DNA
<213> ORGANISM: Artificial
<220> FEATURE:
<223> OTHER INFORMATION: Aptamer

```
<400> SEQUENCE: 65
cctagtacat tcatccgcc tcgttgtcgc cccttcccgc cgt                43

<210> SEQ ID NO 66
<211> LENGTH: 43
<212> TYPE: DNA
<213> ORGANISM: Artificial
<220> FEATURE:
<223> OTHER INFORMATION: Aptamer

<400> SEQUENCE: 66
cggtttggtg tgtggttcgc gagtacgttt ccttctcgac ttg              43

<210> SEQ ID NO 67
<211> LENGTH: 43
<212> TYPE: DNA
<213> ORGANISM: Artificial
<220> FEATURE:
<223> OTHER INFORMATION: Aptamer

<400> SEQUENCE: 67
cgggtgcttt gttgtatgtt gtgtgtgggc tttttggtg tgg               43

<210> SEQ ID NO 68
<211> LENGTH: 24
<212> TYPE: RNA
<213> ORGANISM: Artificial
<220> FEATURE:
<223> OTHER INFORMATION: Aptamer

<400> SEQUENCE: 68
ggaggugcuc cgaaaggaac ucca                                   24

<210> SEQ ID NO 69
<211> LENGTH: 24
<212> TYPE: PRT
<213> ORGANISM: Mus musculus

<400> SEQUENCE: 69

Val Ser Gly Leu Glu Gln Leu Glu Ser Ile Ile Asn Phe Glu Lys Leu
1               5                   10                  15

Thr Glu Trp Thr Ser Ser Asn Val
            20

<210> SEQ ID NO 70
<211> LENGTH: 29
<212> TYPE: PRT
<213> ORGANISM: Mus musculus

<400> SEQUENCE: 70

Ser Ala Glu Ser Leu Lys Ile Ser Gln Ala Val His Ala Ala His Ala
1               5                   10                  15

Glu Ile Asn Glu Ala Gly Arg Glu Val Val Gly Ser Ala
            20                  25

<210> SEQ ID NO 71
<211> LENGTH: 115
<212> TYPE: PRT
<213> ORGANISM: Mus musculus

<400> SEQUENCE: 71

Ile Leu Tyr Gln Ile Asn Ser Lys Ser Ala Leu Thr Trp His Gln Ala
1               5                   10                  15
```

```
Arg Ala Ser Cys Lys Gln Gln Asn Ala Asp Leu Leu Ser Val Thr Glu
                20                  25                  30

Ile His Glu Gln Met Tyr Leu Thr Gly Leu Thr Ser Ser Leu Ser Ser
        35                  40                  45

Gly Leu Trp Ile Gly Leu Asn Ser Leu Ser Val Arg Ser Gly Trp Gln
    50                  55                  60

Trp Ala Gly Gly Ser Pro Phe Arg Tyr Leu Asn Trp Leu Pro Gly Ser
65                  70                  75                  80

Pro Ser Ser Glu Pro Gly Lys Ser Cys Val Ser Leu Asn Pro Gly Lys
                85                  90                  95

Asn Ala Lys Trp Glu Asn Leu Glu Cys Val Gln Lys Leu Gly Tyr Ile
            100                 105                 110

Cys Lys Lys
        115

<210> SEQ ID NO 72
<211> LENGTH: 117
<212> TYPE: PRT
<213> ORGANISM: Mus musculus

<400> SEQUENCE: 72

His Cys Tyr Arg Ile His Arg Glu Glu Lys Lys Ile Gln Lys Tyr Ala
1               5                   10                  15

Leu Gln Ala Cys Arg Lys Glu Gly Gly Asp Leu Ala Ser Ile His Ser
                20                  25                  30

Ile Glu Glu Phe Asp Phe Ile Phe Ser Gln Leu Gly Tyr Glu Pro Asn
        35                  40                  45

Asp Glu Leu Trp Ile Gly Leu Asn Asp Ile Lys Ile Gln Met Tyr Phe
    50                  55                  60

Glu Trp Ser Asp Gly Thr Pro Val Thr Phe Thr Lys Trp Leu Pro Gly
65                  70                  75                  80

Glu Pro Ser His Glu Asn Asn Arg Gln Glu Asp Cys Val Val Met Lys
                85                  90                  95

Gly Lys Asp Gly Tyr Trp Ala Asp Arg Ala Cys Glu Gln Pro Leu Gly
            100                 105                 110

Tyr Ile Cys Lys Met
        115

<210> SEQ ID NO 73
<211> LENGTH: 114
<212> TYPE: PRT
<213> ORGANISM: Mus musculus

<400> SEQUENCE: 73

Tyr Cys Tyr Leu Ile Gly Ser Thr Leu Ser Thr Phe Thr Asp Ala Asn
1               5                   10                  15

His Thr Cys Thr Asn Glu Lys Ala Tyr Leu Thr Thr Val Glu Asp Arg
                20                  25                  30

Tyr Glu Gln Ala Phe Leu Thr Ser Leu Val Gly Leu Arg Pro Glu Lys
        35                  40                  45

Tyr Phe Trp Thr Gly Leu Ser Asp Val Gln Asn Lys Gly Thr Phe Arg
    50                  55                  60

Trp Thr Val Asp Glu Gln Val Gln Phe Thr His Trp Asn Ala Asp Met
65                  70                  75                  80

Pro Gly Arg Lys Ala Gly Cys Val Ala Met Lys Thr Gly Val Ala Gly
                85                  90                  95
```

```
Gly Leu Trp Asp Val Leu Ser Cys Glu Glu Lys Ala Lys Phe Val Cys
            100                 105                 110
Lys His

<210> SEQ ID NO 74
<211> LENGTH: 119
<212> TYPE: PRT
<213> ORGANISM: Mus musculus

<400> SEQUENCE: 74

Lys Leu Tyr Ala Lys Gly Lys His Glu Lys Lys Thr Trp Phe Glu Ser
1               5                   10                  15

Arg Asp Phe Cys Lys Ala Ile Gly Gly Glu Leu Ala Ser Ile Lys Ser
            20                  25                  30

Lys Asp Glu Gln Gln Val Ile Trp Arg Leu Ile Thr Ser Ser Gly Ser
        35                  40                  45

Tyr His Glu Leu Phe Trp Leu Gly Leu Thr Tyr Gly Ser Pro Ser Glu
    50                  55                  60

Gly Phe Thr Trp Ser Asp Gly Ser Pro Val Ser Tyr Glu Asn Trp Ala
65                  70                  75                  80

Tyr Gly Glu Pro Asn Asn Thr Gln Asn Val Glu Tyr Cys Gly Glu Leu
                85                  90                  95

Lys Gly Asp Pro Gly Met Ser Trp Asn Asp Ile Asn Cys Glu His Leu
            100                 105                 110

Asn Asn Trp Ile Cys Gln Ile
        115

<210> SEQ ID NO 75
<211> LENGTH: 113
<212> TYPE: PRT
<213> ORGANISM: Mus musculus

<400> SEQUENCE: 75

Tyr Tyr Phe Ser Lys Glu Lys Glu Thr Met Asp Asn Ala Arg Arg Phe
1               5                   10                  15

Cys Lys Lys Asn Phe Gly Asp Leu Ala Thr Ile Lys Ser Glu Ser Glu
            20                  25                  30

Lys Lys Phe Leu Trp Lys Tyr Ile Asn Lys Asn Gly Gly Gln Ser Pro
        35                  40                  45

Tyr Phe Ile Gly Met Leu Ile Ser Met Asp Lys Lys Phe Ile Trp Met
    50                  55                  60

Asp Gly Ser Lys Val Asp Phe Val Ala Trp Ala Thr Gly Glu Pro Asn
65                  70                  75                  80

Phe Ala Asn Asp Asp Glu Asn Cys Val Thr Met Tyr Thr Asn Ser Gly
                85                  90                  95

Phe Trp Asn Asp Ile Asn Cys Gly Tyr Pro Asn Asn Phe Ile Cys Gln
            100                 105                 110

Arg

<210> SEQ ID NO 76
<211> LENGTH: 122
<212> TYPE: PRT
<213> ORGANISM: Mus musculus

<400> SEQUENCE: 76

Phe Gly Phe Ala Asn Glu Glu Lys Lys Ser Trp Gln Asp Ala Arg Gln
1               5                   10                  15
```

```
Ala Cys Lys Gly Leu Lys Gly Asn Leu Val Ser Ile Glu Asn Ala Gln
                20                  25                  30

Glu Gln Ala Phe Val Thr Tyr His Met Arg Asp Ser Thr Phe Asn Ala
            35                  40                  45

Trp Thr Gly Leu Asn Asp Ile Asn Ala Glu His Met Phe Leu Trp Thr
 50                  55                  60

Ala Gly Gln Gly Val His Tyr Thr Asn Trp Gly Lys Gly Tyr Pro Gly
 65                  70                  75                  80

Gly Arg Arg Ser Ser Leu Ser Tyr Glu Asp Ala Asp Cys Val Val Val
                85                  90                  95

Ile Gly Gly Asn Ser Arg Glu Ala Gly Thr Trp Met Asp Thr Cys
                100                 105                 110

Asp Ser Lys Gln Gly Tyr Ile Cys Gln Thr
                115                 120
```

<210> SEQ ID NO 77
<211> LENGTH: 110
<212> TYPE: PRT
<213> ORGANISM: Mus musculus

<400> SEQUENCE: 77

```
Ser Ser Tyr Ser Leu Met Lys Leu Lys Leu Pro Trp His Glu Ala Gly
 1               5                  10                  15

Thr Tyr Cys Lys Asp His Thr Ser Leu Ala Ser Ile Leu Asp Pro
                20                  25                  30

Tyr Ser Asn Ala Phe Ala Trp Met Lys Met His Pro Phe Asn Val Pro
            35                  40                  45

Ile Trp Ile Ala Leu Asn Ser Asn Leu Thr Asn Asn Glu Tyr Thr Trp
 50                  55                  60

Thr Asp Arg Trp Arg Val Arg Tyr Thr Asn Trp Gly Ala Asp Glu Pro
 65                  70                  75                  80

Lys Leu Lys Ser Ala Cys Val Tyr Met Asp Val Asp Gly Tyr Trp Arg
                85                  90                  95

Thr Ser Tyr Cys Asn Glu Ser Phe Tyr Phe Leu Cys Lys Lys
                100                 105                 110
```

<210> SEQ ID NO 78
<211> LENGTH: 114
<212> TYPE: PRT
<213> ORGANISM: Mus musculus

<400> SEQUENCE: 78

```
His Cys Tyr Tyr Phe Glu Ser Ser Phe Thr Arg Ser Trp Gly Gln Ala
 1               5                  10                  15

Ser Leu Glu Cys Leu Arg Met Gly Ala Ser Leu Val Ser Ile Glu Thr
                20                  25                  30

Ala Ala Glu Ser Ser Phe Leu Ser Tyr Arg Val Glu Pro Leu Lys Ser
            35                  40                  45

Lys Thr Asn Phe Trp Ile Gly Met Phe Arg Asn Val Glu Gly Lys Trp
 50                  55                  60

Leu Trp Leu Asn Asp Asn Pro Val Ser Phe Val Asn Trp Lys Thr Gly
 65                  70                  75                  80

Asp Pro Ser Gly Glu Arg Asn Asp Cys Val Val Leu Ala Ser Ser Ser
                85                  90                  95

Gly Leu Trp Asn Asn Ile His Cys Ser Ser Tyr Lys Gly Phe Ile Cys
                100                 105                 110
```

Lys Met

<210> SEQ ID NO 79
<211> LENGTH: 43
<212> TYPE: PRT
<213> ORGANISM: Artificial
<220> FEATURE:
<223> OTHER INFORMATION: Aptamer

<400> SEQUENCE: 79

Gly Cys Ala Thr Gly Thr Thr Thr Gly Gly Thr Gly Gly Ala
1               5                   10                  15

Thr Ala Thr Thr Gly Gly Cys Gly Thr Gly Thr Thr Gly Gly Gly
            20                  25                  30

Thr Thr Gly Gly Gly Ala Cys Thr Gly Cys Thr
        35                  40

<210> SEQ ID NO 80
<211> LENGTH: 43
<212> TYPE: DNA
<213> ORGANISM: Artificial
<220> FEATURE:
<223> OTHER INFORMATION: Aptamer

<400> SEQUENCE: 80
cgtgggcggg tttatattcg gtggtggtgg gggtggtact gtt                    43

<210> SEQ ID NO 81
<211> LENGTH: 43
<212> TYPE: DNA
<213> ORGANISM: Artificial
<220> FEATURE:
<223> OTHER INFORMATION: Aptamer

<400> SEQUENCE: 81
gcggttctgt gtgtgggtgg gtgggtggta atattgtctc gct                    43

<210> SEQ ID NO 82
<211> LENGTH: 42
<212> TYPE: DNA
<213> ORGANISM: Artificial
<220> FEATURE:
<223> OTHER INFORMATION: Aptamer

<400> SEQUENCE: 82
gggaggtggg tgggttggcc ttcacgttat cttttggtgg tt                     42

<210> SEQ ID NO 83
<211> LENGTH: 42
<212> TYPE: DNA
<213> ORGANISM: Artificial
<220> FEATURE:
<223> OTHER INFORMATION: Aptamer

<400> SEQUENCE: 83
cgcatttggg tgggattgtt atttgggtcg ggattggcag tt                     42

<210> SEQ ID NO 84
<211> LENGTH: 43
<212> TYPE: DNA
<213> ORGANISM: Artificial
<220> FEATURE:
<223> OTHER INFORMATION: Aptamer

<400> SEQUENCE: 84

```
ccaggggagg atgggagggt tttttttcgga ttcttgtcgt gct            43
```

<210> SEQ ID NO 85
<211> LENGTH: 43
<212> TYPE: DNA
<213> ORGANISM: Artificial
<220> FEATURE:
<223> OTHER INFORMATION: Aptamer

<400> SEQUENCE: 85

```
cgtggtatgt ggtgggtggt ggggtggtag ttgggtggac ggt             43
```

<210> SEQ ID NO 86
<211> LENGTH: 43
<212> TYPE: DNA
<213> ORGANISM: Artificial
<220> FEATURE:
<223> OTHER INFORMATION: Aptamer

<400> SEQUENCE: 86

```
cagggggaggt gggtgattgg gttgtttttc gcggacgtga ggt            43
```

<210> SEQ ID NO 87
<211> LENGTH: 43
<212> TYPE: DNA
<213> ORGANISM: Artificial
<220> FEATURE:
<223> OTHER INFORMATION: Aptamer

<400> SEQUENCE: 87

```
gcgtgttggg tggggtggg aggtggtttc ttctacttgg tgg              43
```

<210> SEQ ID NO 88
<211> LENGTH: 43
<212> TYPE: DNA
<213> ORGANISM: Artificial
<220> FEATURE:
<223> OTHER INFORMATION: Aptamer

<400> SEQUENCE: 88

```
cgagtttctg agggtgggtg ggtggttatt agtcgaggtt gca             43
```

<210> SEQ ID NO 89
<211> LENGTH: 43
<212> TYPE: DNA
<213> ORGANISM: Artificial
<220> FEATURE:
<223> OTHER INFORMATION: Aptamer

<400> SEQUENCE: 89

```
tggggtgggt ggtcggggtt gtggttggtt tctctttaag ggt             43
```

<210> SEQ ID NO 90
<211> LENGTH: 43
<212> TYPE: DNA
<213> ORGANISM: Artificial
<220> FEATURE:
<223> OTHER INFORMATION: Aptamer

<400> SEQUENCE: 90

```
ccagggtggg atgggtattt tgaggtggag gtggggttg gtt              43
```

<210> SEQ ID NO 91
<211> LENGTH: 43
<212> TYPE: DNA

```
<213> ORGANISM: Artificial
<220> FEATURE:
<223> OTHER INFORMATION: Aptamer

<400> SEQUENCE: 91
gggtgttgtg gggtggggcg gtgggtgtga gtgtcggcag ctg                      43

<210> SEQ ID NO 92
<211> LENGTH: 43
<212> TYPE: DNA
<213> ORGANISM: Artificial
<220> FEATURE:
<223> OTHER INFORMATION: Aptamer

<400> SEQUENCE: 92
tgtggttcgg taggtcgggg agggtggtgg gttatgcggc ggg                      43

<210> SEQ ID NO 93
<211> LENGTH: 43
<212> TYPE: DNA
<213> ORGANISM: Artificial
<220> FEATURE:
<223> OTHER INFORMATION: Aptamer

<400> SEQUENCE: 93 cacagggag gtcgggcggg ttgtctgctt tcttgggtcg gtt                       43

<210> SEQ ID NO 94
<211> LENGTH: 20
<212> TYPE: DNA
<213> ORGANISM: Artificial
<220> FEATURE:
<223> OTHER INFORMATION: Aptamer

<400> SEQUENCE: 94
ggtgcatcga tgcagggggg                                                20

<210> SEQ ID NO 95
<211> LENGTH: 22
<212> TYPE: DNA
<213> ORGANISM: Aptamer

<400> SEQUENCE: 95
tccatggacg ttcctgagcg tt                                             22

<210> SEQ ID NO 96
<211> LENGTH: 22
<212> TYPE: DNA
<213> ORGANISM: Aptamer

<400> SEQUENCE: 96
tcgtcgttcg aacgacgttg at                                             22

<210> SEQ ID NO 97
<211> LENGTH: 23
<212> TYPE: DNA
<213> ORGANISM: Artificial
<220> FEATURE:
<223> OTHER INFORMATION: Aptamer

<400> SEQUENCE: 97
tcgtcgacga tcggcgcgcg ccg                                            23

<210> SEQ ID NO 98
<211> LENGTH: 38
```

```
<212> TYPE: DNA
<213> ORGANISM: Artificial
<220> FEATURE:
<223> OTHER INFORMATION: Aptamer
<220> FEATURE:
<221> NAME/KEY: misc_feature
<222> LOCATION: (19)..(19)
<223> OTHER INFORMATION: n is a, c, g, or t

<400> SEQUENCE: 98
gctgtgtgac tcctgcaang cagctgtatc ttgtctcc                                   38

<210> SEQ ID NO 99
<211> LENGTH: 18
<212> TYPE: DNA
<213> ORGANISM: Artificial
<220> FEATURE:
<223> OTHER INFORMATION: PCR Primer

<400> SEQUENCE: 99
gctgtgtgac tcctgcaa                                                         18

<210> SEQ ID NO 100
<211> LENGTH: 19
<212> TYPE: DNA
<213> ORGANISM: Artificial
<220> FEATURE:
<223> OTHER INFORMATION: PCR Primer

<400> SEQUENCE: 100
ggagacaaga tacagctgc                                                        19

<210> SEQ ID NO 101
<211> LENGTH: 79
<212> TYPE: DNA
<213> ORGANISM: Artificial
<220> FEATURE:
<223> OTHER INFORMATION: Aptamer

<400> SEQUENCE: 101
gctgtgtgac tcctgcaatg caatctagct gacaatgggg gggaagaatg tgggtgggtg           60
gcagctgtat cttgtctcc                                                        79

<210> SEQ ID NO 102
<211> LENGTH: 79
<212> TYPE: DNA
<213> ORGANISM: Artificial
<220> FEATURE:
<223> OTHER INFORMATION: Aptamer

<400> SEQUENCE: 102
gctgtgtgac tcctgcaacg catttgggtg ggattgttat ttgggtcggg attggcagtt           60
gcagctgtat cttgtctcc                                                        79

<210> SEQ ID NO 103
<211> LENGTH: 80
<212> TYPE: DNA
<213> ORGANISM: Artificial
<220> FEATURE:
<223> OTHER INFORMATION: Aptamer

<400> SEQUENCE: 103
gctgtgtgac tcctgcaacg tgggtgggtt tatattcggt ggtggtgggg gtggtactgt           60
tgcagctgta tcttgtctcc                                                       80
```

<210> SEQ ID NO 104
<211> LENGTH: 79
<212> TYPE: DNA
<213> ORGANISM: Artificial
<220> FEATURE:
<223> OTHER INFORMATION: Aptamer

<400> SEQUENCE: 104
gctgtgtgac tcctgcaagt ggtgttaaga ggtgaggtat aacgcggaat ggtgcgaggc    60
gcagctgtat cttgtctcc                                                 79

<210> SEQ ID NO 105
<211> LENGTH: 24
<212> TYPE: DNA
<213> ORGANISM: Artificial
<220> FEATURE:
<223> OTHER INFORMATION: PCR Primer

<400> SEQUENCE: 105
atcacggctg tgtgactcct gcaa                                           24

<210> SEQ ID NO 106
<211> LENGTH: 25
<212> TYPE: DNA
<213> ORGANISM: Artificial
<220> FEATURE:
<223> OTHER INFORMATION: PCR Primer

<400> SEQUENCE: 106
atcacgggag acaagataca gctgc                                          25

<210> SEQ ID NO 107
<211> LENGTH: 24
<212> TYPE: DNA
<213> ORGANISM: Artificial
<220> FEATURE:
<223> OTHER INFORMATION: PCR Primer

<400> SEQUENCE: 107
cgatgtgctg tgtgactcct gcaa                                           24

<210> SEQ ID NO 108
<211> LENGTH: 25
<212> TYPE: DNA
<213> ORGANISM: Artificial
<220> FEATURE:
<223> OTHER INFORMATION: PCR Primer

<400> SEQUENCE: 108
cgatgtggag acaagataca gctgc                                          25

<210> SEQ ID NO 109
<211> LENGTH: 24
<212> TYPE: DNA
<213> ORGANISM: Artificial
<220> FEATURE:
<223> OTHER INFORMATION: PCR Primer

<400> SEQUENCE: 109
ttaggcgctg tgtgactcct gcaa                                           24

<210> SEQ ID NO 110
<211> LENGTH: 25
<212> TYPE: DNA
<213> ORGANISM: Artificial

```
<220> FEATURE:
<223> OTHER INFORMATION: PCR Primer

<400> SEQUENCE: 110
ttaggcggag acaagataca gctgc                                              25

<210> SEQ ID NO 111
<211> LENGTH: 24
<212> TYPE: DNA
<213> ORGANISM: Artificial
<220> FEATURE:
<223> OTHER INFORMATION: PCR Primer

<400> SEQUENCE: 111
tgaccagctg tgtgactcct gcaa                                               24

<210> SEQ ID NO 112
<211> LENGTH: 25
<212> TYPE: DNA
<213> ORGANISM: Artificial
<220> FEATURE:
<223> OTHER INFORMATION: PCR Primer

<400> SEQUENCE: 112
tgaccaggag acaagataca gctgc                                              25

<210> SEQ ID NO 113
<211> LENGTH: 24
<212> TYPE: DNA
<213> ORGANISM: Artificial
<220> FEATURE:
<223> OTHER INFORMATION: PCR Primer

<400> SEQUENCE: 113
acagtggctg tgtgactcct gcaa                                               24

<210> SEQ ID NO 114
<211> LENGTH: 25
<212> TYPE: DNA
<213> ORGANISM: Artificial
<220> FEATURE:
<223> OTHER INFORMATION: PCR Primer

<400> SEQUENCE: 114
acagtgggag acaagataca gctgc                                              25

<210> SEQ ID NO 115
<211> LENGTH: 24
<212> TYPE: DNA
<213> ORGANISM: Artificial
<220> FEATURE:
<223> OTHER INFORMATION: PCR Primer

<400> SEQUENCE: 115
gccaatgctg tgtgactcct gcaa                                               24

<210> SEQ ID NO 116
<211> LENGTH: 25
<212> TYPE: DNA
<213> ORGANISM: Artificial
<220> FEATURE:
<223> OTHER INFORMATION: PCR Primer

<400> SEQUENCE: 116
gccaatggag acaagataca gctgc                                              25
```

```
<210> SEQ ID NO 117
<211> LENGTH: 24
<212> TYPE: DNA
<213> ORGANISM: Artificial
<220> FEATURE:
<223> OTHER INFORMATION: PCR Primer

<400> SEQUENCE: 117
cagatcgctg tgtgactcct gcaa                                              24

<210> SEQ ID NO 118
<211> LENGTH: 25
<212> TYPE: DNA
<213> ORGANISM: Artificial
<220> FEATURE:
<223> OTHER INFORMATION: PCR Primer

<400> SEQUENCE: 118
cagatcggag acaagataca gctgc                                             25

<210> SEQ ID NO 119
<211> LENGTH: 24
<212> TYPE: DNA
<213> ORGANISM: Artificial
<220> FEATURE:
<223> OTHER INFORMATION: PCR Primer

<400> SEQUENCE: 119
acttgagctg tgtgactcct gcaa                                              24

<210> SEQ ID NO 120
<211> LENGTH: 25
<212> TYPE: DNA
<213> ORGANISM: Artificial
<220> FEATURE:
<223> OTHER INFORMATION: PCR Primer

<400> SEQUENCE: 120
acttgaggag acaagataca gctgc                                             25

<210> SEQ ID NO 121
<211> LENGTH: 24
<212> TYPE: DNA
<213> ORGANISM: Artificial
<220> FEATURE:
<223> OTHER INFORMATION: PCR Primer

<400> SEQUENCE: 121
gatcaggctg tgtgactcct gcaa                                              24

<210> SEQ ID NO 122
<211> LENGTH: 25
<212> TYPE: DNA
<213> ORGANISM: Artificial
<220> FEATURE:
<223> OTHER INFORMATION: PCR Primer

<400> SEQUENCE: 122
gatcagggag acaagataca gctgc                                             25

<210> SEQ ID NO 123
<211> LENGTH: 24
<212> TYPE: DNA
<213> ORGANISM: Artificial
<220> FEATURE:
<223> OTHER INFORMATION: PCR Primer
```

```
<400> SEQUENCE: 123
tagcttgctg tgtgactcct gcaa                                           24

<210> SEQ ID NO 124
<211> LENGTH: 25
<212> TYPE: DNA
<213> ORGANISM: Artificial
<220> FEATURE:
<223> OTHER INFORMATION: PCR Primer

<400> SEQUENCE: 124
tagcttggag acaagataca gctgc                                          25

<210> SEQ ID NO 125
<211> LENGTH: 24
<212> TYPE: DNA
<213> ORGANISM: Artificial
<220> FEATURE:
<223> OTHER INFORMATION: PCR Primer

<400> SEQUENCE: 125
ggctacgctg tgtgactcct gcaa                                           24

<210> SEQ ID NO 126
<211> LENGTH: 25
<212> TYPE: DNA
<213> ORGANISM: Artificial
<220> FEATURE:
<223> OTHER INFORMATION: PCR Primer

<400> SEQUENCE: 126
ggctacggag acaagataca gctgc                                          25

<210> SEQ ID NO 127
<211> LENGTH: 24
<212> TYPE: DNA
<213> ORGANISM: Artificial
<220> FEATURE:
<223> OTHER INFORMATION: PCR Primer

<400> SEQUENCE: 127
cttgtagctg tgtgactcct gcaa                                           24

<210> SEQ ID NO 128
<211> LENGTH: 25
<212> TYPE: DNA
<213> ORGANISM: Artificial
<220> FEATURE:
<223> OTHER INFORMATION: PCR Primer

<400> SEQUENCE: 128
cttgtaggag acaagataca gctgc                                          25

<210> SEQ ID NO 129
<211> LENGTH: 116
<212> TYPE: DNA
<213> ORGANISM: Artificial
<220> FEATURE:
<223> OTHER INFORMATION: Aptamer Library
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (95)..(95)
```

```
<223> OTHER INFORMATION: n is a, c, g, t or u

<400> SEQUENCE: 129
atagctaata cgactcacta tagggagagg agggaagtct acatcttntt tctggagttg      60
acgaagcttg ggagaggagg gaagucuaca ucuunuuucu ggaguugacg aagcuu         116

<210> SEQ ID NO 130
<211> LENGTH: 47
<212> TYPE: DNA
<213> ORGANISM: Artificial
<220> FEATURE:
<223> OTHER INFORMATION: PCR Primer

<400> SEQUENCE: 130
atagctaata cgactcacta tagggagagg agggaagtct acatctt                    47

<210> SEQ ID NO 131
<211> LENGTH: 21
<212> TYPE: DNA
<213> ORGANISM: Artificial
<220> FEATURE:
<223> OTHER INFORMATION: PCR Primer

<400> SEQUENCE: 131
aagcttcgtc aactccagaa a                                                21

<210> SEQ ID NO 132
<211> LENGTH: 8
<212> TYPE: PRT
<213> ORGANISM: Mus musculus

<400> SEQUENCE: 132

Ser Ile Ile Asn Phe Glu Lys Leu
1               5

<210> SEQ ID NO 133
<211> LENGTH: 17
<212> TYPE: PRT
<213> ORGANISM: Mus musculus

<400> SEQUENCE: 133

Ile Ser Gln Ala Val His Ala Ala His Ala Glu Ile Asn Glu Ala Gly
1               5                   10                  15
Arg
```